US012436462B2

(12) United States Patent
Hatakeyama et al.

(10) Patent No.: US 12,436,462 B2
(45) Date of Patent: Oct. 7, 2025

(54) POSITIVE RESIST COMPOSITION AND PATTERN FORMING PROCESS

(71) Applicant: Shin-Etsu Chemical Co., Ltd., Tokyo (JP)

(72) Inventors: Jun Hatakeyama, Joetsu (JP); Kousuke Ohyama, Joetsu (JP); Shun Kikuchi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 432 days.

(21) Appl. No.: 17/986,233

(22) Filed: Nov. 14, 2022

(65) Prior Publication Data

US 2023/0152696 A1 May 18, 2023

(30) Foreign Application Priority Data

Nov. 17, 2021 (JP) ................................ 2021-187306
Aug. 5, 2022 (JP) ................................ 2022-125391

(51) Int. Cl.

*G03F 7/039* (2006.01)
*C07C 381/12* (2006.01)
*C08F 212/14* (2006.01)
*C08F 220/18* (2006.01)
*C08F 220/22* (2006.01)
*C08F 220/36* (2006.01)

(52) U.S. Cl.

CPC ............ *G03F 7/039* (2013.01); *C07C 381/12* (2013.01); *C08F 212/24* (2020.02); *C08F 220/1806* (2020.02); *C08F 220/1807* (2020.02); *C08F 220/1808* (2020.02); *C08F 220/1811* (2020.02); *C08F 220/22* (2013.01); *C08F 220/36* (2013.01)

(58) Field of Classification Search

CPC ............................ C07C 381/12; C08F 220/36
See application file for complete search history.

(56) References Cited

U.S. PATENT DOCUMENTS

| | | | | |
|---|---|---|---|---|
| 7,482,108 | B2 | 1/2009 | Matsumaru et al. | |
| 9,910,354 | B2 * | 3/2018 | Sakaida | G03F 7/2006 |
| 2005/0008964 | A1 * | 1/2005 | Takei | C08L 71/00 430/271.1 |
| 2014/0065550 | A1 | 3/2014 | Kramer et al. | |
| 2017/0045820 | A1 * | 2/2017 | Sakaida | C08G 73/0655 |
| 2021/0048746 | A1 | 2/2021 | Hatakeyama et al. | |
| 2024/0241441 | A1 * | 7/2024 | Marangoni | G03F 7/028 |

FOREIGN PATENT DOCUMENTS

| | | | | | |
|---|---|---|---|---|---|
| CN | 109134788 | A | * | 1/2019 | C08F 8/00 |
| JP | 2003140350 | A | * | 5/2003 | |
| JP | 2003301006 | A | * | 10/2003 | |
| JP | 2006-45311 | A | | 2/2006 | |
| JP | 2006-178317 | A | | 7/2006 | |
| JP | 2008102506 | A | * | 5/2008 | C08F 2/38 |
| JP | 4132783 | B2 | | 8/2008 | |
| JP | 2013-1850 | A | | 1/2013 | |
| JP | 2014-65896 | A | | 4/2014 | |
| TW | 202113478 | A | | 4/2021 | |

OTHER PUBLICATIONS

Hutchinson, "The Shot Noise Impact on Resist Roughness in EUV Lithography", SPIE, 1998, vol. 3331, pp. 531-536, cited in Specification (7 pages).
Office Action dated Jul. 3, 2025, issued in counterpart CN Application No. 202211439146.7, with English translation. (14 pages).

* cited by examiner

*Primary Examiner* — Amanda C. Walke
(74) *Attorney, Agent, or Firm* — WHDA, LLP

(57) ABSTRACT

A positive resist composition is provided comprising a base polymer end-capped with a sulfonium salt containing a carboxylate anion having a sulfide group linked thereto. Because of controlled acid diffusion, a resist film of the composition forms a pattern of good profile with a high resolution and reduced edge roughness or dimensional variation.

12 Claims, No Drawings

POSITIVE RESIST COMPOSITION AND PATTERN FORMING PROCESS

CROSS-REFERENCE TO RELATED APPLICATION

This non-provisional application claims priority under 35 U.S.C. § 119(a) on Patent Application Nos. 2021-187306 and 2022-125391 filed in Japan on Nov. 17, 2021 and Aug. 5, 2022, respectively, the entire contents of which are hereby incorporated by reference.

TECHNICAL FIELD

This invention relates to a positive resist composition and a pattern forming process.

BACKGROUND ART

To meet the demand for higher integration density and operating speed of LSIs, the effort to reduce the pattern title is in rapid progress. As the use of 5G high-speed communications and artificial intelligence (AI) is widely spreading, high-performance devices are needed for their processing. As the advanced miniaturization technology, manufacturing of microelectronic devices at the 5-nm node by the lithography using EUV of wavelength 13.5 nm has been implemented in a mass scale. Studies are made on the application of EUV lithography to 3-nm node devices of the next generation and 2-nm node devices of the next-but-one generation.

As the feature size reduces, image blurs due to acid diffusion become a problem. To insure resolution for fine patterns with a sub-45 nm size, not only an improvement in dissolution contrast is important as previously reported, but the control of acid diffusion is also important as reported in Non-Patent Document 1. Since chemically amplified resist compositions are designed such that sensitivity and contrast are enhanced by acid diffusion, an attempt to minimize acid diffusion by reducing the temperature and/or time of post-exposure bake (PEB) fails, resulting in drastic reductions of sensitivity and contrast.

The addition of an acid generator capable of generating a bulky acid is an effective means for suppressing acid diffusion. It was then proposed to incorporate in a polymer repeat units derived from an opium salt having a polymerizable unsaturated bond. Since the resulting polymer functions as an acid generator, it is referred to as polymer-bound acid generator. Patent Document 1 discloses a sulfonium or iodonium salt having a polymerizable unsaturated bond, capable of generating a specific sulfonic acid. Patent Document 2 discloses a sulfonium salt having a sulfonic acid directly attached to the backbone.

There are proposed resist materials comprising terminally modified polymers. For example, Patent Document 3 discloses a resist material comprising a polymer terminated with an acid labile group, resulting from living anion polymerization using an alkyl lithium initiator. Patent Document 4 discloses a resist material comprising a polymer resulting from living radical polymerization (RAFT), the polymer being end-capped with a sulfonium salt to become an acid generator capable of generating fluorosulfonic acid. Patent Document 5 discloses a resist material comprising a polymer which is polymerized with the aid of an azo type polymerization initiator provided on both sides with a sulfonium salt to become an acid generator capable of generating fluorosulfonic acid so that the polymer has the acid generator attached at both ends. The polymer capped with the acid generator, however, has the drawback that the end is so mobile as to promote acid diffusion.

CITATION LIST

Patent Document 1: JP-A 2006-045311 (U.S. Pat. No. 7,482,108)
Patent Document 2: JP-A 2006-178317
Patent Document 3: JP 4132783
Patent Document 4: JP-A 2014-065896
Patent Document 5: JP-A 2013-001850
Non-Patent Document 1: SPIE Vol. 3331 p 531 (1998)

SUMMARY OF INVENTION

An object of the present invention is to provide a positive resist composition which is controlled in acid diffusion, exhibits a high resolution surpassing conventional positive resist compositions, and forms a pattern of good profile having reduced edge roughness or dimensional variation after exposure and development, and a patterning process using the resist composition.

Making extensive investigations in search for a positive resist material capable of meeting the current requirements including high resolution, low edge roughness and small dimensional variation, the inventors have found the following. To meet the requirements, the acid diffusion distance should be minimized and the swell in alkaline developer be suppressed. When a polymer is end-capped with a sulfonium salt containing a carboxylate anion to become a quencher, acid diffusion is minimized, and a swell-reducing effect is exerted. Satisfactory results are obtained using the polymer as a base in a chemically amplified positive resist composition.

Further, for improving the dissolution contrast, repeat units having a carboxy or phenolic hydroxy group whose hydrogen is substituted by an acid labile group are incorporated into the base polymer. There is then obtained a positive resist composition having a significantly increased contrast of alkaline dissolution rate before and after exposure, a remarkable acid diffusion-suppressing effect, a high resolution, a good pattern profile after exposure, reduced edge roughness (LWR), and improved dimensional uniformity (CDU). The composition is thus suitable as a fine pattern forming material for the manufacture of VLSIs and photomasks.

In one aspect, the invention provides a positive resist composition comprising a base polymer which is end-capped with a sulfonium salt containing a carboxylate anion having a sulfide group linked thereto.

In a preferred embodiment the base polymer has a terminal structure represented by the formula (a).

(a)

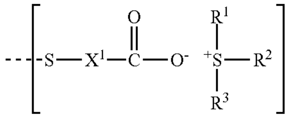

Herein $X^1$ is a $C_1$-$C_{20}$ hydrocarbylene group which may contain at least one moiety selected from hydroxy, ether bond, sulfide, ester bond, carbonate bond, urethane bond, lactone ring, sultone ring, and halogen. $R^1$ to $R^3$ are each independently a $C_1$-$C_{20}$ hydrocarbyl group which may contain at least one atom selected from oxygen, sulfur, nitrogen and halogen. $R^1$ and $R^2$ may bond together to form a ring with the sulfur atom to which they are attached. The broken line designates a valence bond.

In a preferred embodiment, the base polymer comprises repeat units (b1) having a carboxy group whose hydrogen is substituted by an acid labile group or repeat units (b2) having a phenolic hydroxy group whose hydrogen is substituted by an acid labile group. More preferably, the repeat units (b1) are represented by the formula (b1) and the repeat units (b2) are represented by the formula (b2).

(b1)

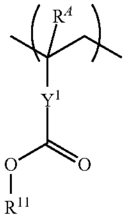

(b2)

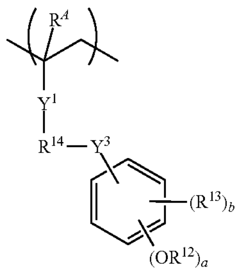

Herein $R^A$ is each independently hydrogen or methyl; $Y^1$ is a single bond, phenylene group, naphthylene group, or a $C_1$-$C_{12}$ linking group containing at least one moiety selected from an ester bond, ether bond and lactone ring; $Y^2$ is a single bond, ester bond or amide bond; $Y^3$ is a single bond, ether bond or ester bond; $R^{11}$ and $R^{12}$ are each independently an acid labile group; $R^{13}$ is fluorine, trifluoromethyl, cyano or a $C_1$-$C_6$ saturated hydrocarbyl group; $R^{14}$ is a single bond or a $C_1$-$C_6$ alkanediyl group which may contain an ether bond or ester bond; a is 1 or 2, b is an integer of 0 to 4, and the sum of a+b is from 1 to 5.

In a preferred embodiment, the base polymer further comprises repeat units (c) having an adhesive group which is selected from a hydroxy moiety, carboxy moiety, lactone ring, carbonate bond, thiocarbonate bond, carbonyl moiety, cyclic acetal moiety, ether bond, ester bond, sulfonic ester bond, cyano moiety, amide bond, —O—C(═O)—S—, and —O—C(═O)—NH—.

In a preferred embodiment, the base polymer further comprises repeat units having the formula (d1), (d2) or (d3).

(d1)

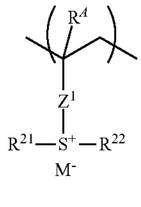

-continued (d2)

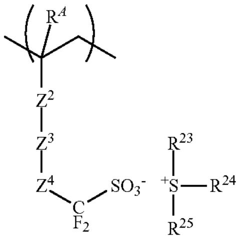

(d3)

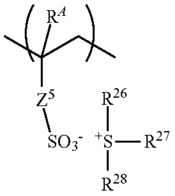

Herein $R^A$ is each independently hydrogen or methyl. $Z^1$ is a single bond, a $C_1$-$C_6$ aliphatic hydrocarbylene group, phenylene group, naphthylene group, or $C_7$-$C_{18}$ group obtained by combining the foregoing, or —O—$Z^{11}$—, —C(═O)—O—$Z^{11}$— or —C(═O)—NH—$Z^{11}$—, wherein $Z^{11}$ is a $C_1$-$C_6$ aliphatic hydrocarbylene group, phenylene group, naphthylene group, or $C_7$-$C_{18}$ group obtained by combining the foregoing, which may contain a carbonyl moiety, ester bond, ether bond or hydroxy moiety. $Z^2$ is a single bond or ester bond. $Z^3$ is a single bond, —$Z^{31}$—C(═O)—O—, —$Z^{31}$—O— or —$Z^{31}$—O—C(═O)—, wherein $Z^{31}$ is a $C_1$-$C_{12}$ aliphatic hydrocarbylene group, phenylene group, or $C_7$-$C_{18}$ group obtained by combining the foregoing, which may contain a carbonyl moiety, ester bond, ether bond, bromine or iodine. $Z^4$ is methylene, 2,2,2-trifluoro-1,1-ethanediyl, or carbonyl. $Z^5$ is a single bond, methylene, ethylene, phenylene, fluorinated phenylene, trifluoromethyl-substituted phenylene group, —O—$Z^{51}$—, —C(O)—O—$Z^{51}$—, or —C(═O)—NH—$Z^{51}$—, wherein $Z^{51}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond, halogen or hydroxy moiety. $R^{21}$ to $R^{26}$ are each independently halogen or a $C_1$-$C_{20}$ hydrocarbyl group which may contain a heteroatom, a pair of $R^{23}$ and $R^{24}$ or $R^{26}$ and $R^{27}$ may bond together to form a ring with the sulfur atom to which they are attached. M is a non-nucleophilic counter ion.

The positive resist composition may further comprise an acid generator, organic solvent, quencher, and/or surfactant.

In another aspect, the invention provides a pattern forming process comprising the steps of applying the positive resist composition defined herein onto a substrate to form a resist film thereon, exposing the resist film to high-energy radiation, and developing the exposed resist film in a developer.

Typically, the high-energy radiation is i-line, KrF excimer laser, ArF excimer laser. EB, or EUV of wavelength 3 to 15 inn.

Advantageous Effects of Invention

The positive resist composition has a remarkable acid diffusion-suppressing effect, a significantly increased contrast of alkaline dissolution rate before and after exposure, and a high resolution, and forms a pattern of good profile with reduced edge roughness and improved CDU after exposure and development. By virtue of these properties, the resist composition is fully useful in commercial application and best suited as a micropatterning material for photomasks by EB lithography or for VLSIs by EB or EUV lithography. The resist composition may be used not only in the lithography for forming semiconductor circuits, but also in the formation of mask circuit patterns, micromachines, and thin-film magnetic head circuits.

DESCRIPTION OF EMBODIMENTS

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. In chemical formulae, the broken line designates a valence bond; Me stands for methyl, and Ac for acetyl. As used herein, the term "fluorinated" refers to a fluorine-substituted or fluorine-containing compound or group. The terms "group" and "moiety" are interchangeable.

The abbreviations and acronyms have the following meaning.

EB: electron beam
EUV: extreme ultraviolet
Mw: weight average molecular weight
Mn: number average molecular weight
Mw/Mn: molecular weight distribution or dispersity
GPC: gel permeation chromatography
PEB: post-exposure bake
PAG: photoacid generator
LWR: line width roughness
CDU: critical dimension uniformity Positive Resist Composition Base Polymer One embodiment of the invention is a positive resist composition comprising a base polymer end-capped with a sulfonium salt containing a carboxylate anion having a sulfide group linked thereto.

Preferably, the base polymer has a terminal structure represented by the following formula (a), which is also referred to as terminal structure (a), hereinafter.

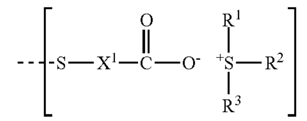

(a)

In formula (a), $X^1$ is a $C_1$-$C_{20}$ hydrocarbylene group which may contain at least one moiety selected from hydroxy, ether bond, sulfide, ester bond, carbonate bond, urethane bond, lactone ring, sultone ring, and halogen. The hydrocarbylene group may be saturated or unsaturated and straight, branched or cyclic. Examples thereof include $C_1$-$C_{20}$ alkanediyl groups such as methanediyl, ethane-1,1-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, and dodecane-1,12-diyl; $C_3$-$C_{20}$ cyclic saturated hydrocarbylene groups such as cyclopentanediyl, cyclohexanediyl, norbornanediyl, and adamantanediyl; $C_2$-$C_{20}$ unsaturated aliphatic hydrocarbylene groups such as vinylene, propene-1,3-diyl, ethyne-1,2-diyl, and propyne-1,3-diyl; $C_6$-$C_{20}$ arylene groups such as phenylene, naphthylene and biphenylylene; substituted forms of the foregoing groups in which some or all of the hydrogen atoms are substituted by a $C_1$-$C_{12}$ hydrocarbyl moiety; and combinations thereof. The $C_1$-$C_{12}$ hydrocarbyl substituent may be saturated or unsaturated and straight, branched or cyclic, and examples thereof are as will be exemplified later for the $C_1$-$C_{20}$ hydrocarbyl groups represented by $R^{101}$ to $R^{105}$ in formulae (1-1) and (1-2), but of 1 to 12 carbon atoms.

In formula (a), $R^1$ to $R^3$ are each independently a $C_1$-$C_{20}$ hydrocarbyl group which may contain at least one atom selected from oxygen, sulfur, nitrogen and halogen. The hydrocarbyl group may be saturated or unsaturated and straight, branched or cyclic, and examples thereof are as will be exemplified later for the $C_1$-$C_{20}$ hydrocarbyl groups represented by $R^{101}$ to $R^{105}$ in formulae (1-1) and (1-2). $R^1$ and $R^2$ may bond together to form a ring with the sulfur atom to which they are attached. Examples of the ring are as will be exemplified later for the ring that $R^{101}$ and $R^{102}$ in formula (1-1), taken together, form with the sulfur atom to which they are attached.

In order that a sulfonium salt containing a carboxylate anion having a sulfide group linked thereto be attached to the end of a polymer, a thiol compound having the formula (a1) shown below is used as a chain transfer agent. The compound having formula (a1) is added prior to or during polymerization reaction. A polymerization initiator is decomposed to generate radicals, which chain transfer to the thiol compound to initiate polymerization, whereby a polymer end-capped with a sulfonium salt is formed.

(a1)

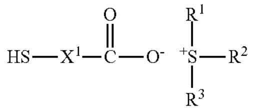

Herein $X^1$ and $R^1$ to $R^3$ are as defined above.

Examples of the anion in the compound having formula (a1) are shown below, but not limited thereto.

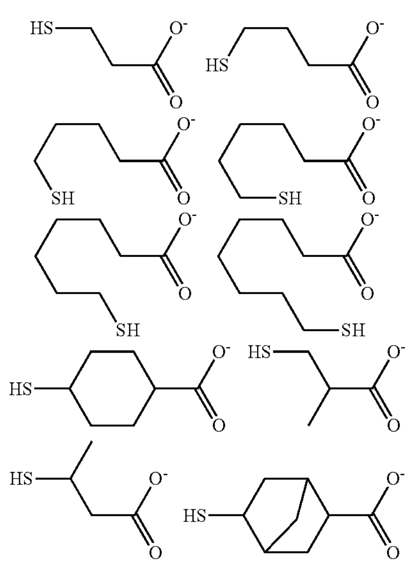

-continued
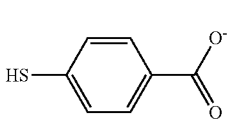
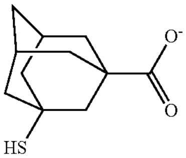
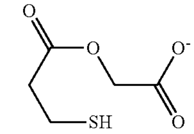
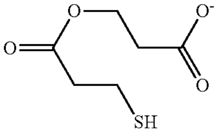
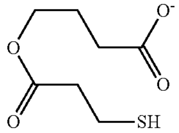
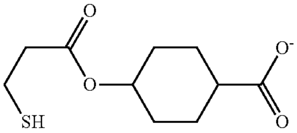
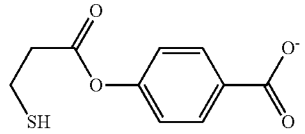
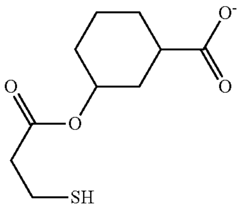
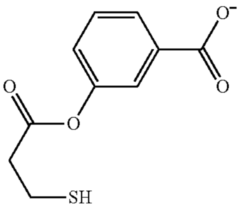
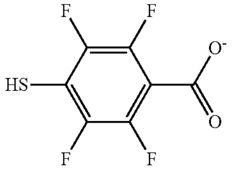
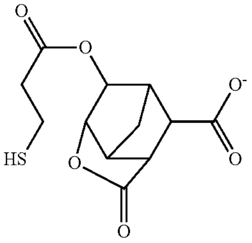
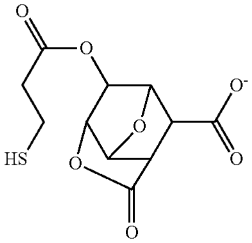
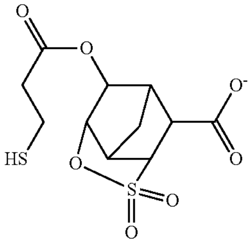
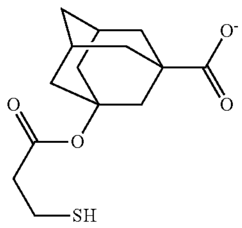
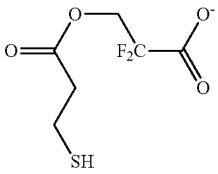
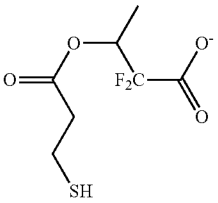
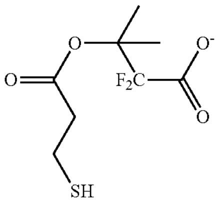
-continued
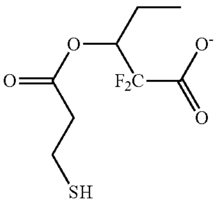
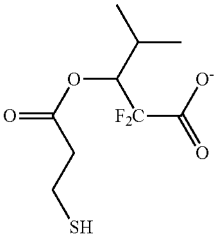
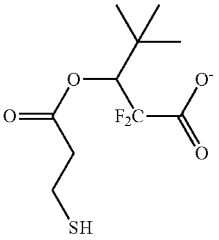
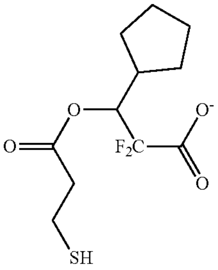
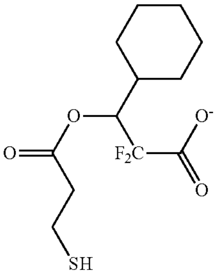
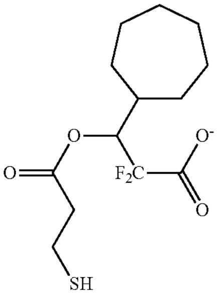
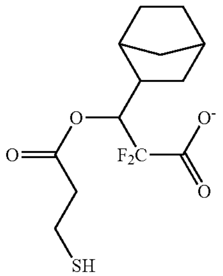
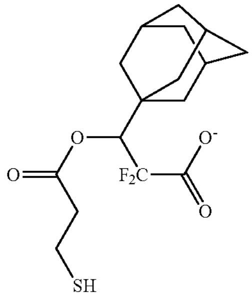
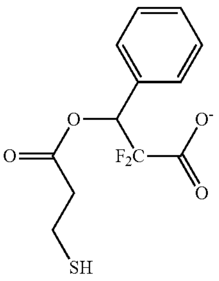
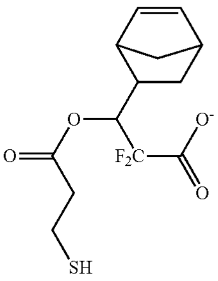
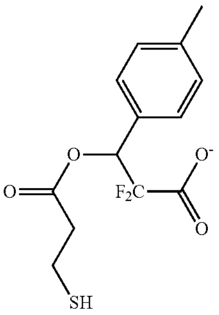
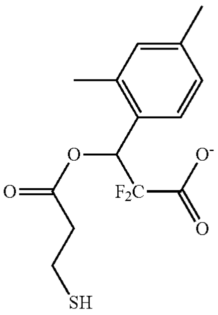

-continued
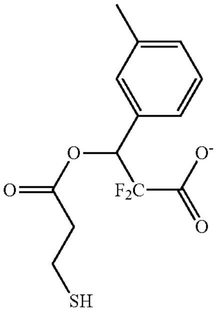
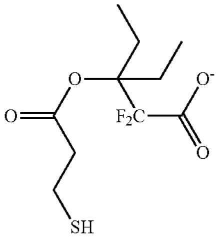
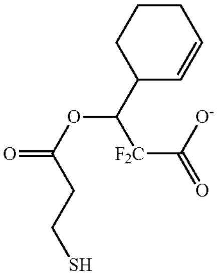
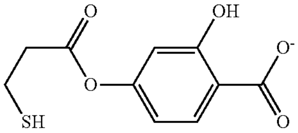
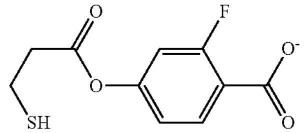
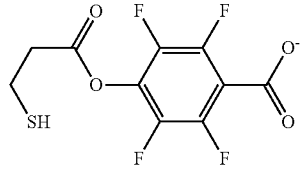
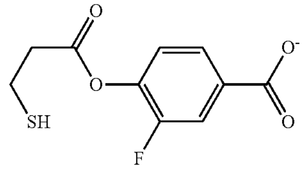
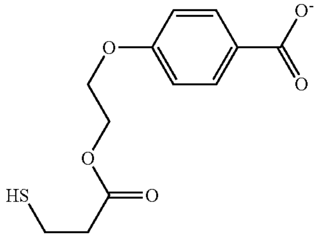
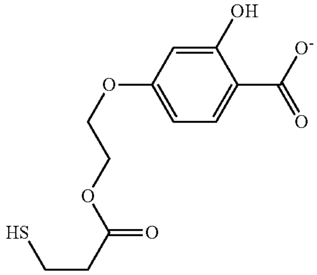
-continued
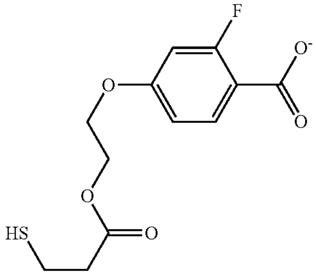
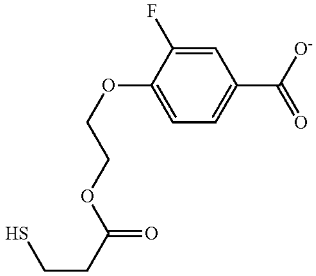
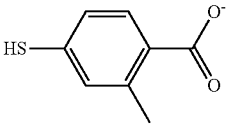
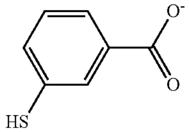
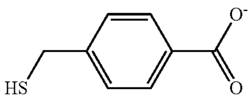
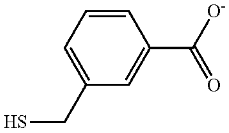
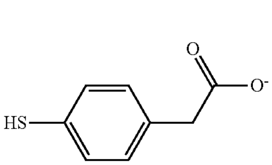
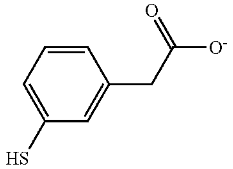
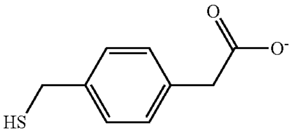
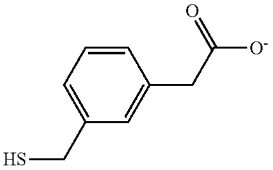
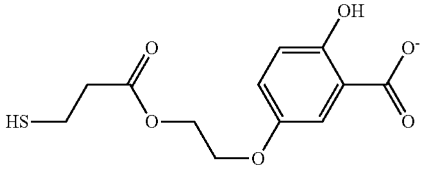
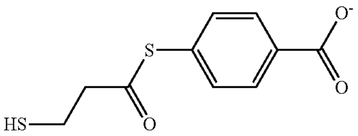
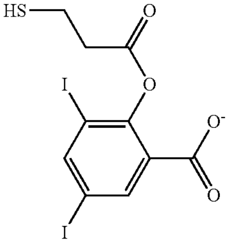
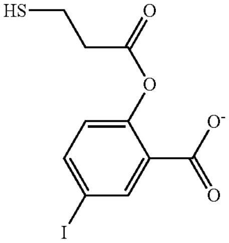

-continued
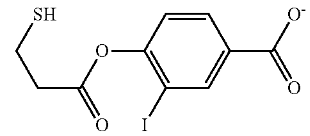
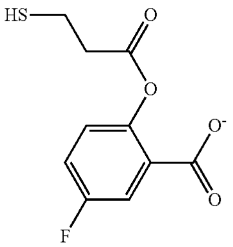
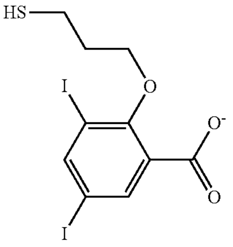
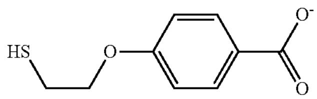
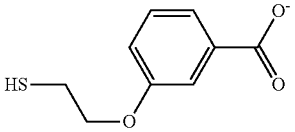
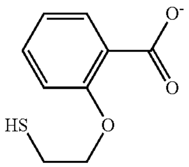
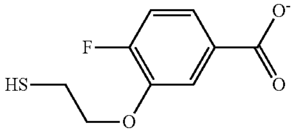
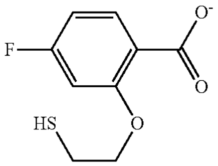
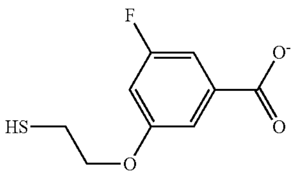
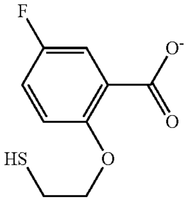
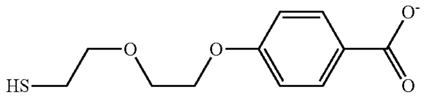
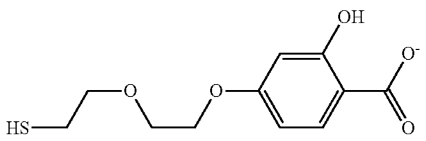
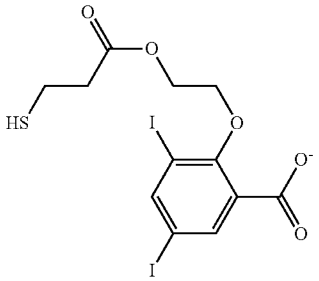
-continued
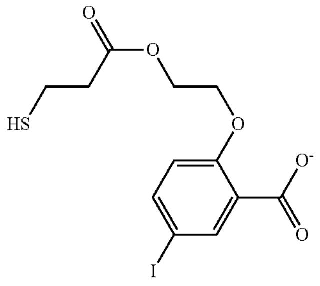
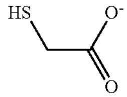
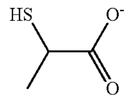
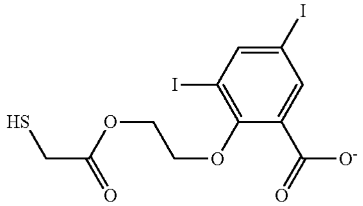
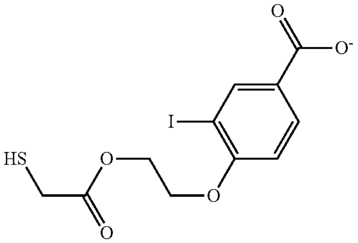
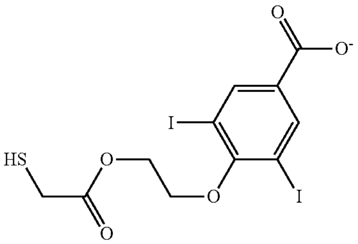
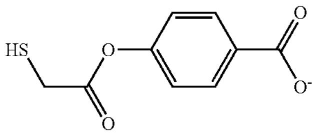
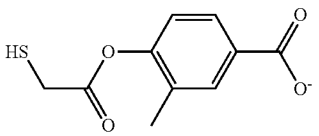
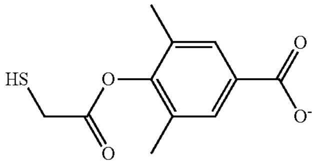
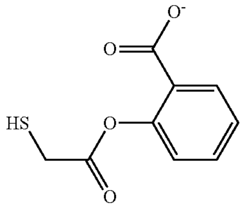
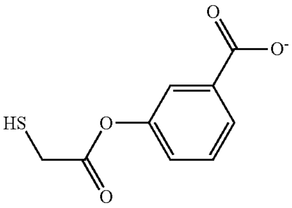

-continued
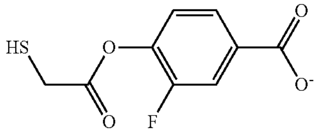
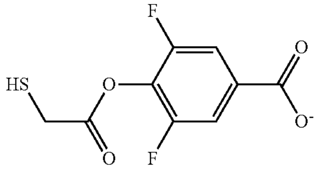
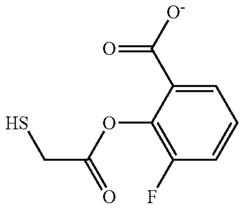
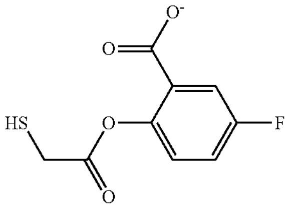
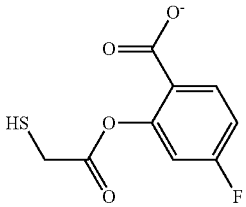
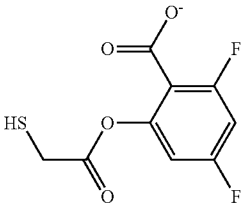
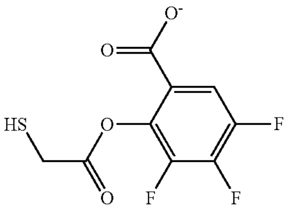
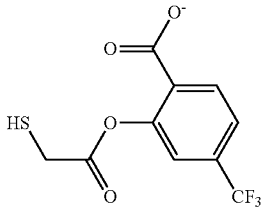
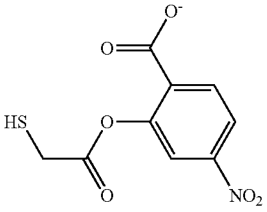
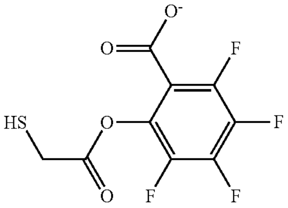
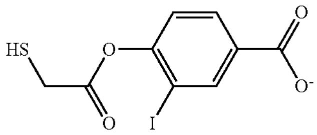
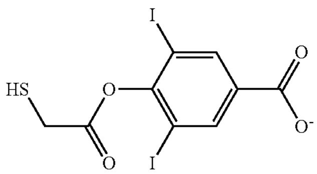
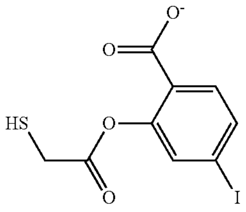
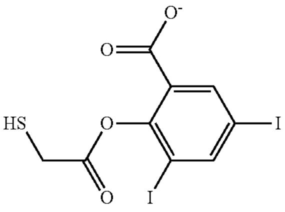
-continued
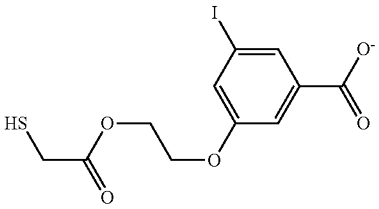
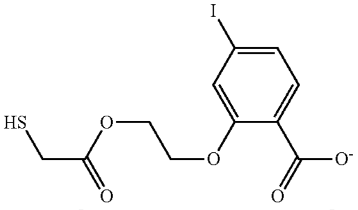
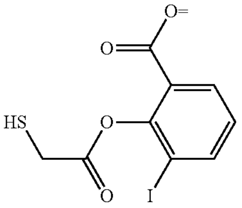
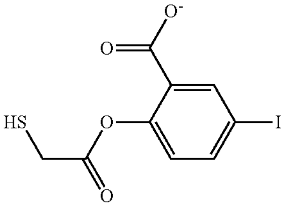
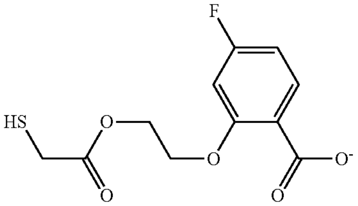
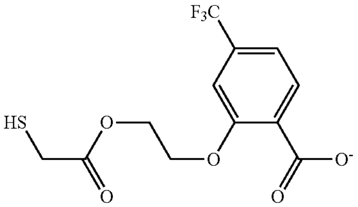
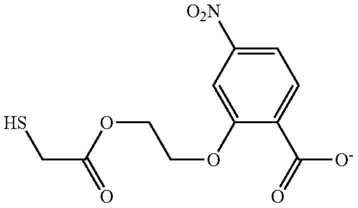
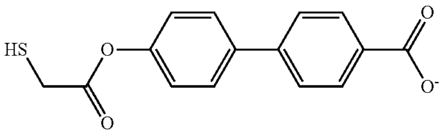
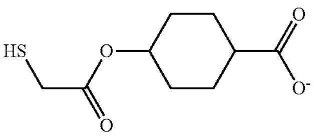
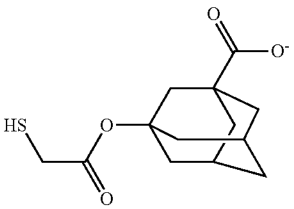

-continued
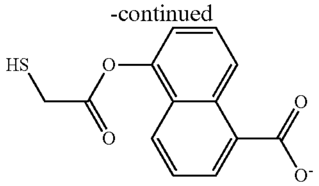
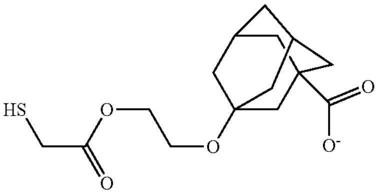
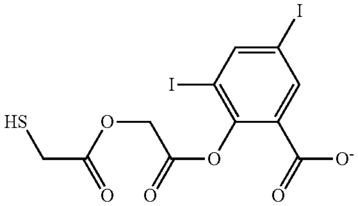
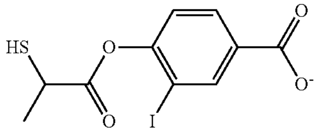
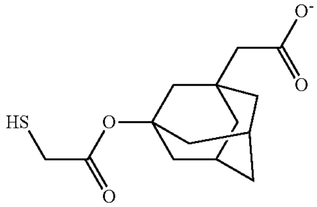
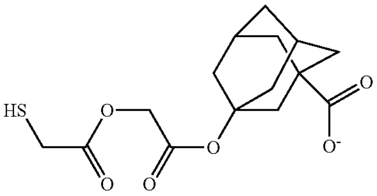
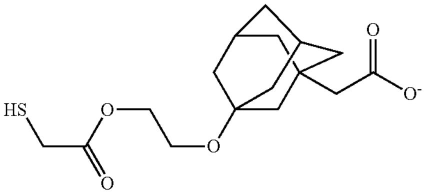
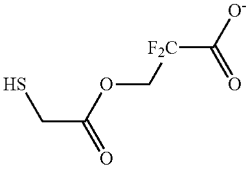
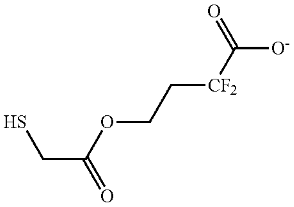
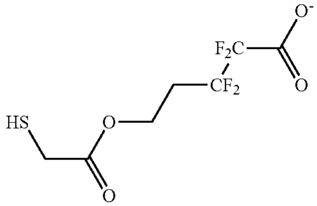
-continued
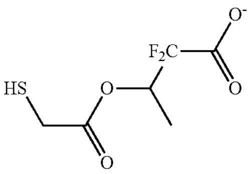
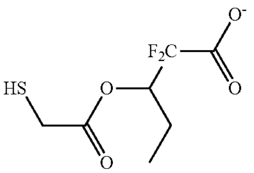
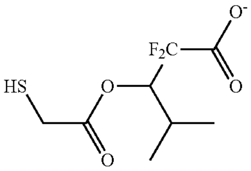
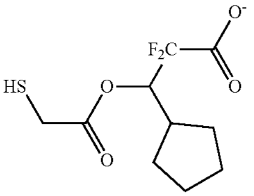
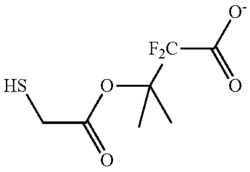
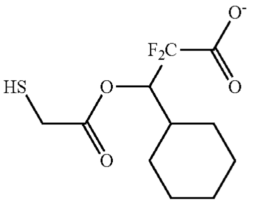
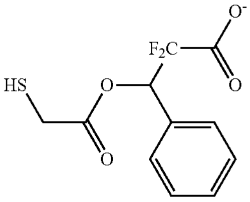
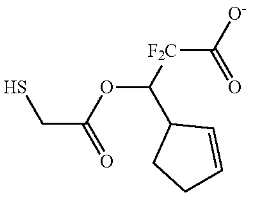
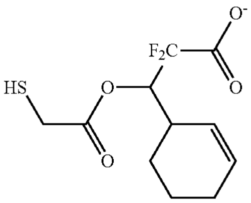
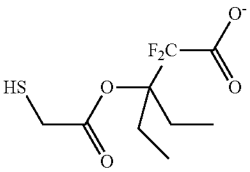
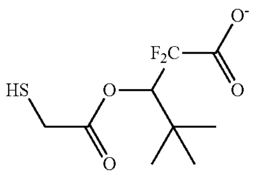
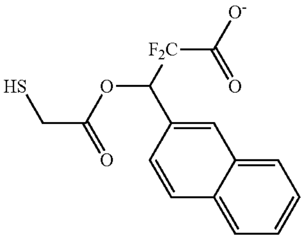
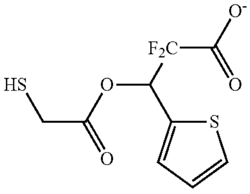
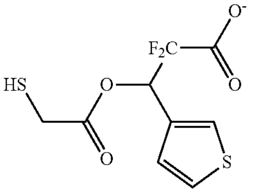
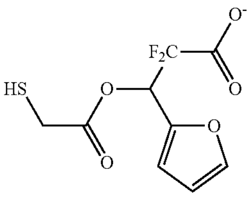
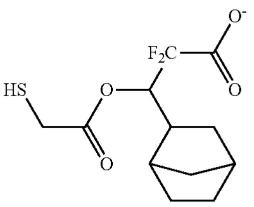

-continued

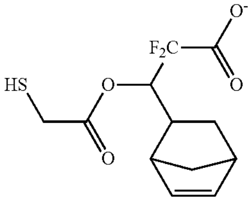
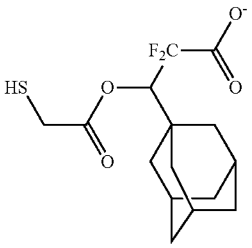
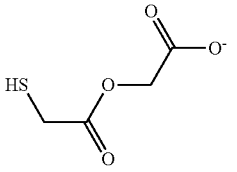
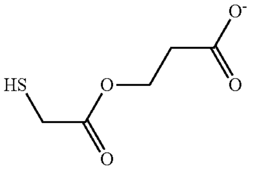
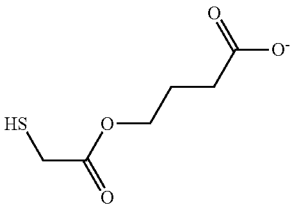
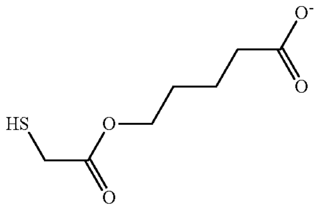
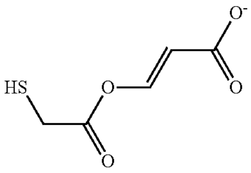
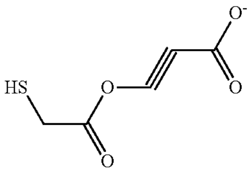
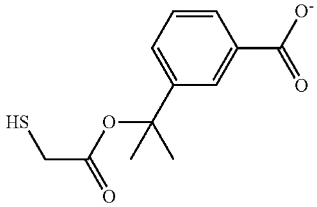
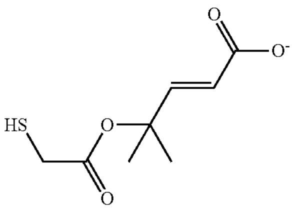
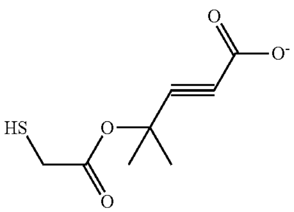

-continued

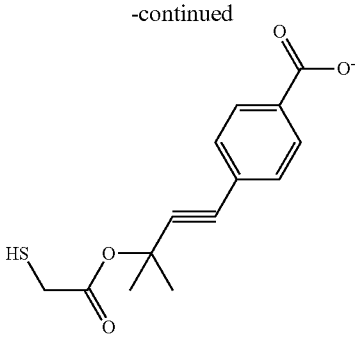
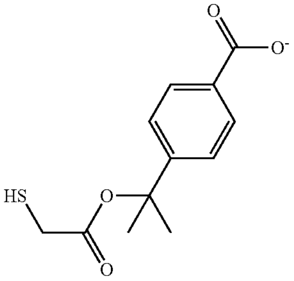
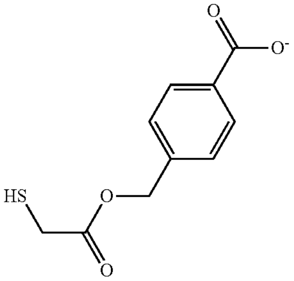
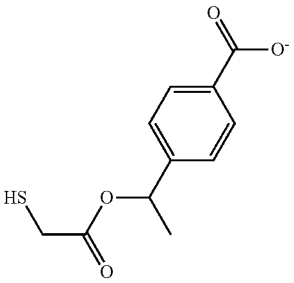
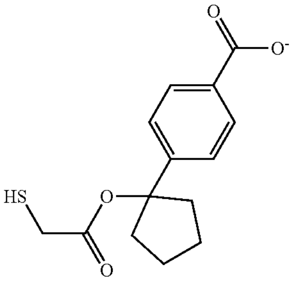

Examples of the cation in terminal structure (a) or the cation in the compound having formula (a1) are as will be exemplified later for the cation in a sulfonium salt having formula (1-1).

The compound having formula (a1) is synthesized, for example, via ion exchange reaction between a carboxylic acid having a sulfide group linked thereto and a carbonic acid or hydrochloric acid salt of a sulfonium salt.

In a preferred embodiment, the base polymer comprises repeat units (b1) having a carboxy group whose hydrogen is substituted by an acid labile group or repeat units (b2)

having a phenolic hydroxy group whose hydrogen is substituted by an acid labile group.

In a preferred embodiment, the repeat units (b1) and (b2) are represented by the formulae (b1) and (b2), respectively.

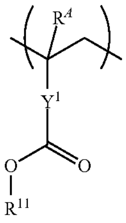

(b1)

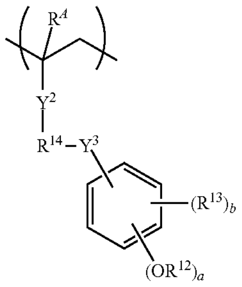

(b2)

In formulae (b1) and (b2), $R^A$ is each independently hydrogen or methyl. $Y^1$ is a single bond, phenylene group, naphthylene group, or a $C_1$-$C_{12}$ linking group containing at least one moiety selected from an ester bond, ether bond and lactone ring. $Y^2$ is a single bond ester bond or amide bond. $Y^3$ is a single bond, ether bond or ester bond. $R^{11}$ and $R^{12}$ are each independently an acid labile group. $R^{13}$ is fluorine, trifluoromethyl, cyano or a $C_1$-$C_6$ saturated hydrocarbyl group. $R^{14}$ is a single bond or a $C_1$-$C_6$ alkanediyl group which may contain an ether bond or ester bond. The subscript "a" is 1 or 2, "b" is an integer of 0 to 4, and the sum of a+b is from 1 to 5.

Examples of the monomer from which repeat unit (b1) is derived are shown below, but not limited thereto. Herein $R^A$ and $R^{11}$ are as defined above.

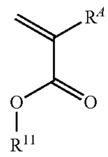

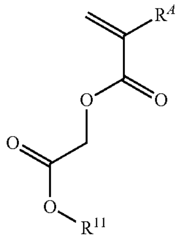

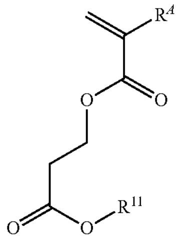

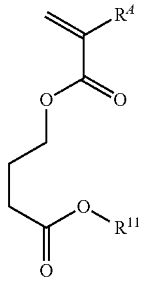

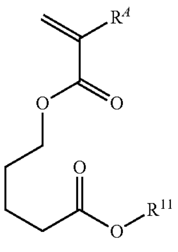

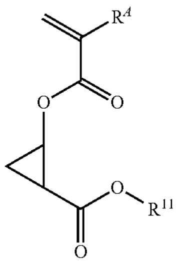

-continued

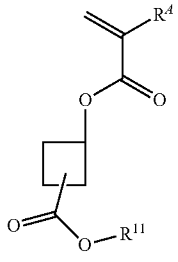

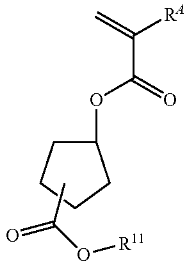

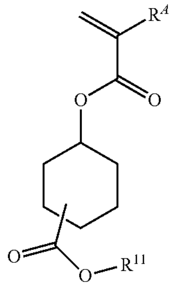

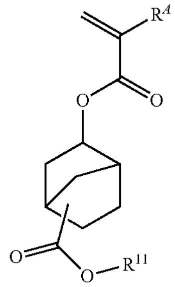

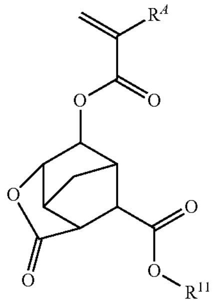

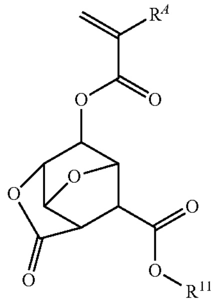

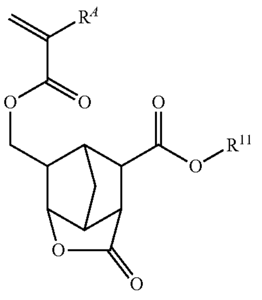

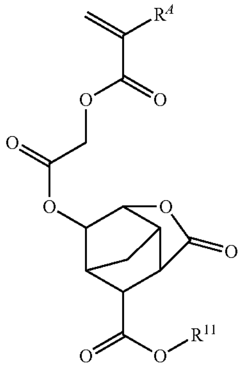

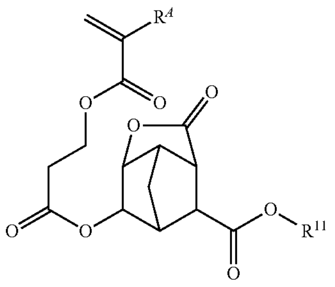

-continued
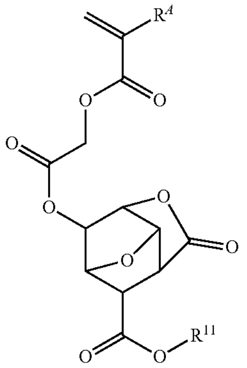
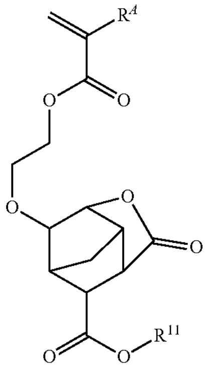
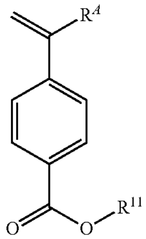
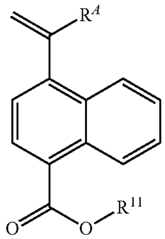
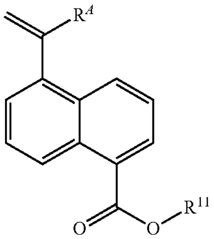
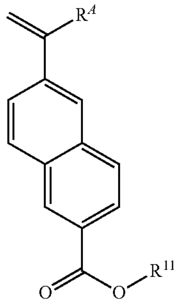
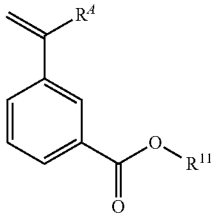
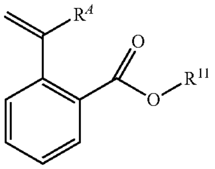
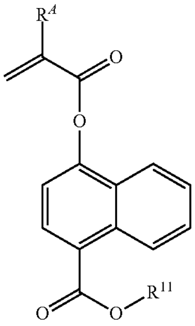
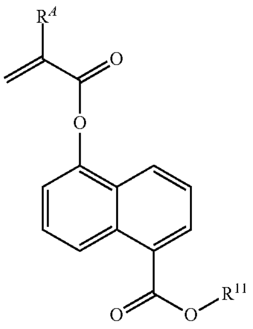
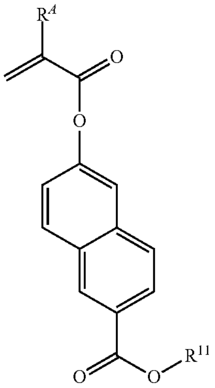
-continued
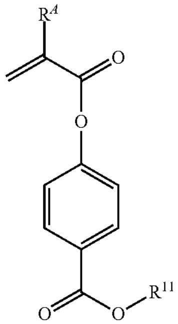
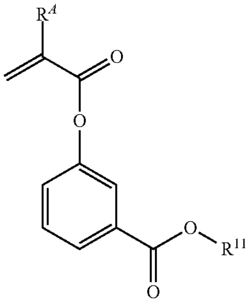
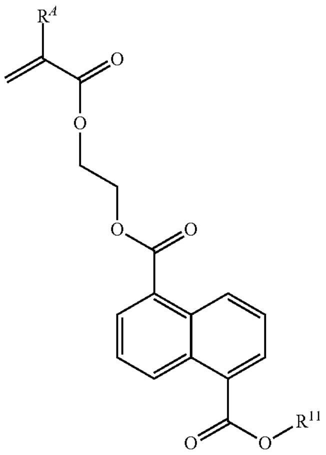
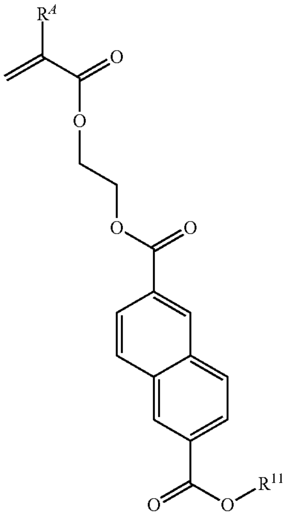
Examples of the monomer from which repeat unit (b2) is derived are shown below, but not limited thereto. Herein $R^A$ and $R^{12}$ are as defined above.
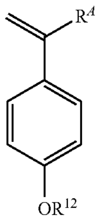
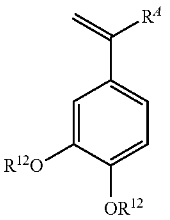
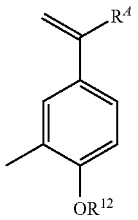

-continued

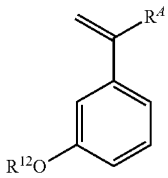

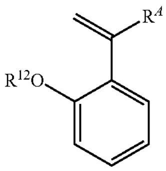

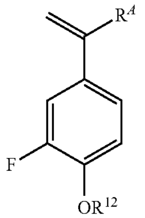

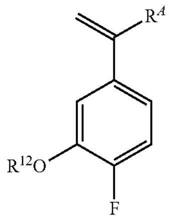

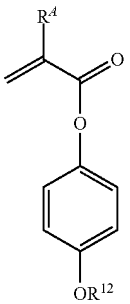

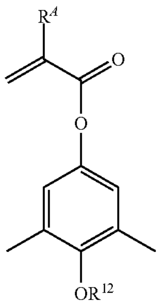

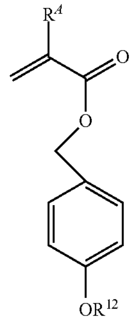

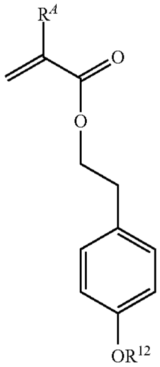

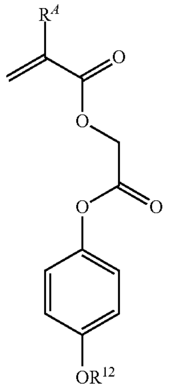

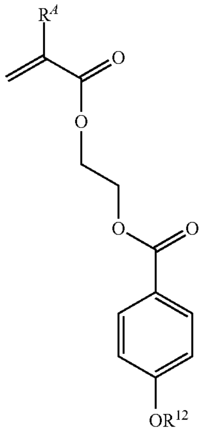

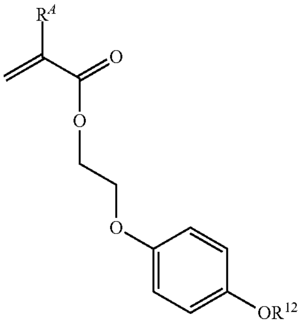

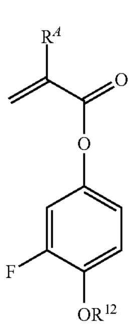

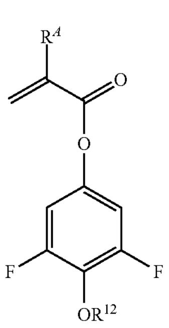

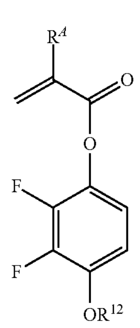

-continued

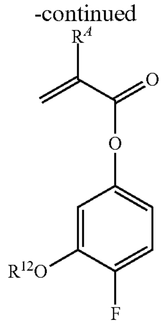

The acid labile groups represented by $R^{11}$ and $R^{12}$ may be selected from a variety of such groups, for example, groups of the following formulae (AL-1) to (AL-3).

(AL-1)

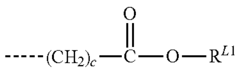

(AL-2)

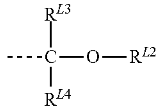

(AL-3)

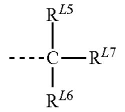

In formula (AL-1), c is an integer of 0 to 6. $R^{L1}$ is a $C_4$-$C_{20}$, preferably $C_4$-$C_{15}$ tertiary hydrocarbyl group, a trihydrocarbylsilyl group in which each hydrocarbyl moiety is a $C_1$-$C_6$ saturated one, a $C_4$-$C_{20}$ saturated hydrocarbyl group containing a carbonyl moiety, ether bond or ester bond, or a group of formula (AL-3). Notably, the tertiary hydrocarbyl group is a group obtained by eliminating hydrogen from the tertiary carbon in a tertiary hydrocarbon.

The tertiary hydrocarbyl group $R^{L1}$ may be saturated or unsaturated and branched or cyclic. Examples thereof include tert-butyl, tert-pentyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, and 2-methyl-2-adamantyl. Examples of the trihydrocarbylsilyl group include trimethylsilyl, triethylsilyl, and dimethyl-tert-butylsilyl. The saturated hydrocarbyl group containing a carbonyl moiety, ether bond or ester bond may be straight, branched or cyclic, preferably cyclic and examples thereof include 3-oxocyclohexyl, 4-methyl-2-oxooxan-4-yl, 5-methyl-2-oxooxolan-5-yl, 2-tetrahydropyranyl, and 2-tetrahydrofuranyl.

Examples of the acid labile group having formula (AL-1) include tert-butoxycarbonyl, tert-butoxycarbonylmethyl, tert-pentyloxycarbonyl, tert pentyloxycarbonylmethyl, 1,1-diethylpropyloxycarbonyl, 1,1-diethylpropyloxycarbonylmethyl 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl and 2-tetrahydrofuranyloxycarbonylmethyl.

Other examples of the acid labile group having formula (AL-1) include groups having the formulae (AL-1)-1 to (AL-1)-10.

(AL-1)-1

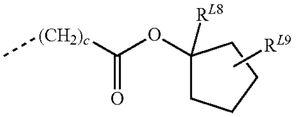

(AL-1)-2

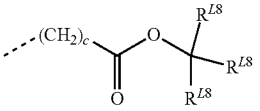

(AL-1)-3

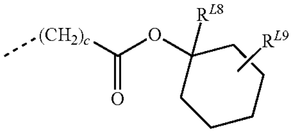

(AL-1)-4

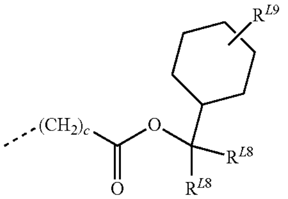

(AL-1)-5

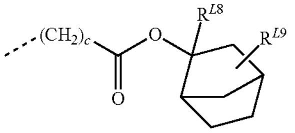

(AL-1)-6

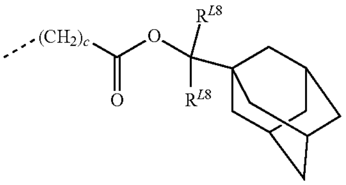

(AL-1)-7

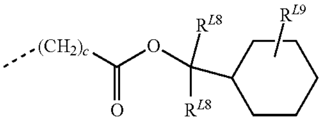

(AL-1)-8

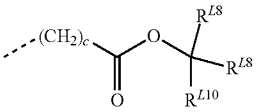

(AL-1)-9

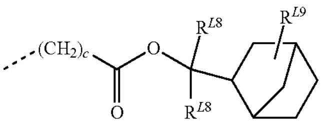

(AL-1)-10

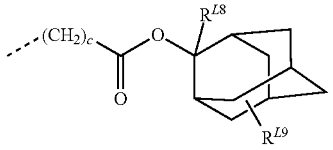

In formulae (AL-1)-1 to (AL-1)-10, c is as defined above. $R^{L8}$ is each independently a $C_1$-$C_{10}$ saturated hydrocarbyl group or $C_6$-$C_{20}$ aryl group. $R^{L9}$ is hydrogen or a $C_1$-$C_{10}$ saturated hydrocarbyl group. $R^{L10}$ is a $C_2$-$C_{10}$ saturated hydrocarbyl group or $C_6$-$C_{20}$ aryl group. The saturated hydrocarbyl group may be straight, branched or cyclic.

In formula (AL-2), $R^{L2}$ and $R^{L3}$ are each independently hydrogen or a $C_1$-$C_{18}$, preferably $C_1$-$C_{10}$ saturated hydrocarbyl group. The saturated hydrocarbyl group may be straight, branched or cyclic and examples thereof include methyl, ethyl, n-propyl, isopropyl, n-butyl, isobutyl, sec-butyl, tert-butyl, cyclopentyl, cyclohexyl, 2-ethylhexyl and n-octyl.

$R^{L4}$ is a $C_1$-$C_{18}$, preferably $C_1$-$C_{10}$ hydrocarbyl group which may contain a heteroatom. The hydrocarbyl group may be saturated or unsaturated and straight, branched or cyclic. Typical are $C_1$-$C_{18}$ saturated hydrocarbyl groups, in which some hydrogen may be substituted by hydroxy, alkoxy, oxo, amino or alkylamino Examples of the substituted saturated hydrocarbyl group are shown below.

$—(CH_2)_4OH$ $\quad$ $-----(CH_2)_2O(CH_2)_3CH_3$

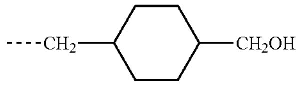 $-----(CH_2)_2O(CH_2)_2OH$ $—(CH_2)_6OH$

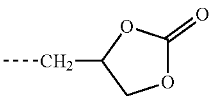

A pair of $R^{L2}$ and $R^{L3}$, $R^{L2}$ and $R^{L4}$, or $R^{L3}$ and $R^{L4}$ may bond together to form a ring with the carbon atom or carbon and oxygen atoms to which they are attached. $R^{L2}$ and $R^{L3}$, $R^{L2}$ and $R^{L4}$, or $R^{L3}$ and $R^{L4}$ that form a ring are each independently a $C_1$-$C_{18}$, preferably $C_1$-$C_{10}$ alkanediyl group. The ring thus formed is preferably of 3 to 10, more preferably 4 to 10 carbon atoms.

Of the acid labile groups having formula (AL-2), suitable straight or branched groups include those having formulae (AL-2)-1 to (AL-2)-69, but are not limited thereto.

(AL-2)-1

$----CH_2—O—CH_3$ (AL-2)-2

$----CH_2—O—CH_2—CH_3$ (AL-2)-3

$----CH_2—O—(CH_2)_2—CH_3$ (AL-2)-4

$----CH_2—O—(CH_2)_3—CH_3$ (AL-2)-5

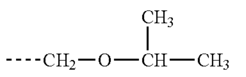

(AL-2)-6

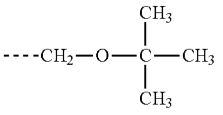

(AL-2)-7

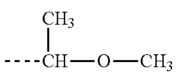

(AL-2)-8

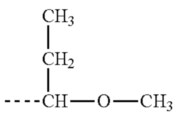

-continued
(AL-2)-9
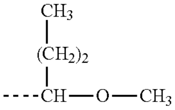
(AL-2)-10
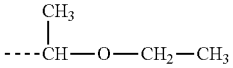
(AL-2)-11
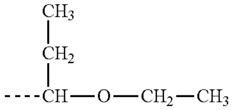
(AL-2)-12
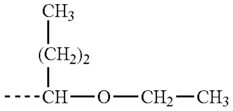
(AL-2)-13
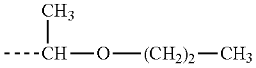
(AL-2)-14
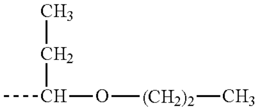
(AL-2)-15
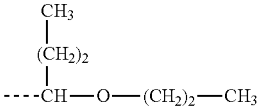
(AL-2)-16
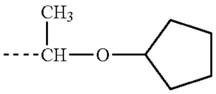
(AL-2)-17
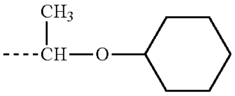
(AL-2)-18
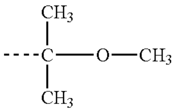
(AL-2)-19
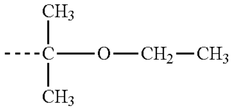
(AL-2)-20
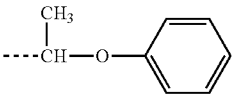
(AL-2)-21
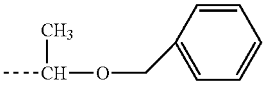
(AL-2)-22
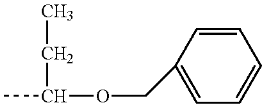
-continued
(AL-2)-23
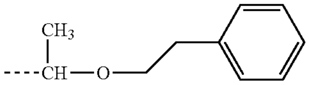
(AL-2)-24
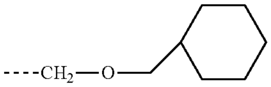
(AL-2)-25
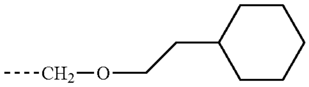
(AL-2)-26
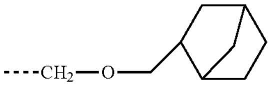
(AL-2)-27
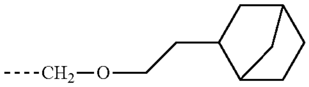
(AL-2)-28
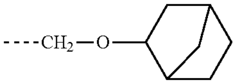
(AL-2)-29
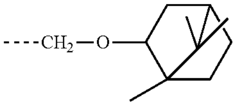
(AL-2)-30
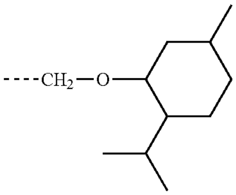
(AL-2)-31
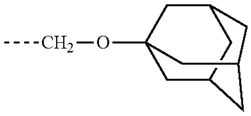
(AL-2)-32
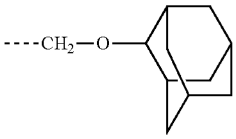
(AL-2)-33
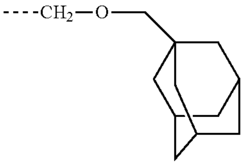
(AL-2)-34
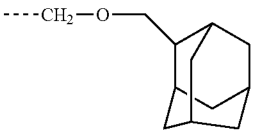

-continued
(AL-2)-35
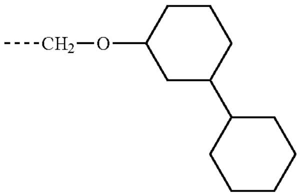
(AL-2)-36
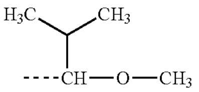
(AL-2)-37
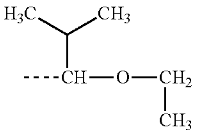
(AL-2)-38
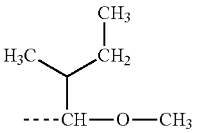
(AL-2)-39
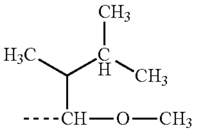
(AL-2)-40
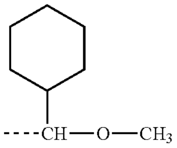
(AL-2)-41
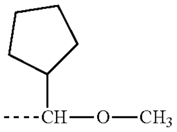
(AL-2)-42
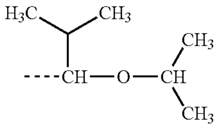
(AL-2)-43
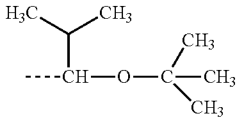
(AL-2)-44
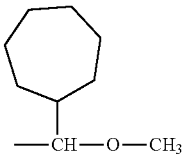
-continued
(AL-2)-45
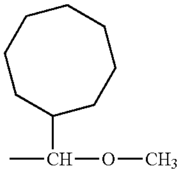
(AL-2)-46
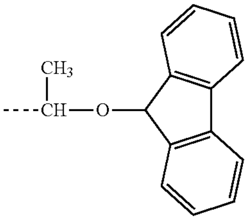
(AL-2)-47
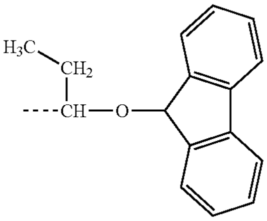
(AL-2)-48
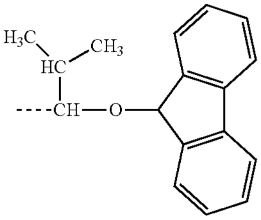
(AL-2)-49
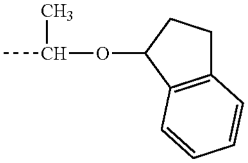
(AL-2)-50
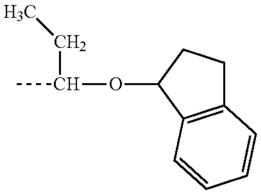
(AL-2)-51
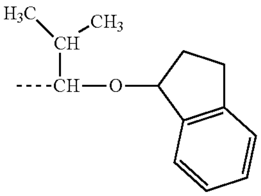
(AL-2)-52
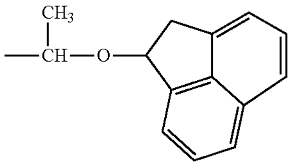

-continued
(AL-2)-53
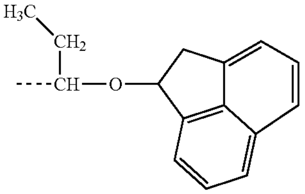
(AL-2)-54
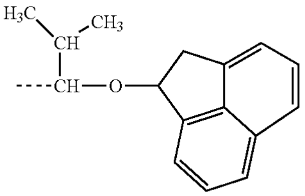
(AL-2)-55
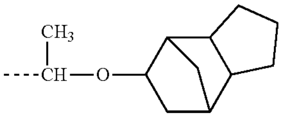
(AL-2)-56
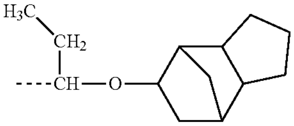
(AL-2)-57
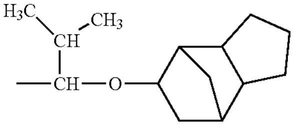
(AL-2)-58
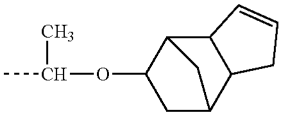
(AL-2)-59
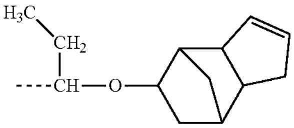
(AL-2)-60
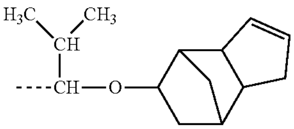
(AL-2)-61
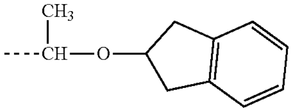
(AL-2)-62
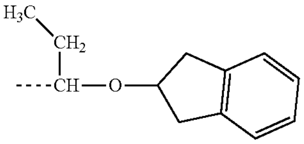
-continued
(AL-2)-63
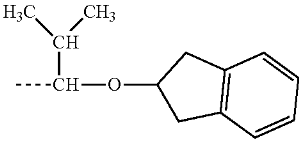
(AL-2)-64
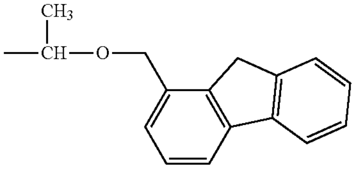
(AL-2)-65
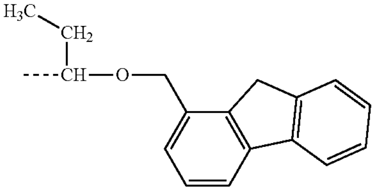
(AL-2)-66
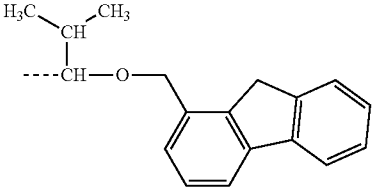
(AL-2)-67
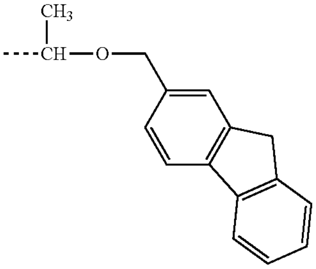
(AL-2)-68
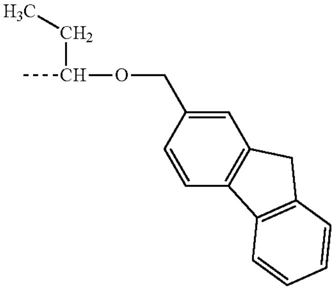
(AL-2)-69
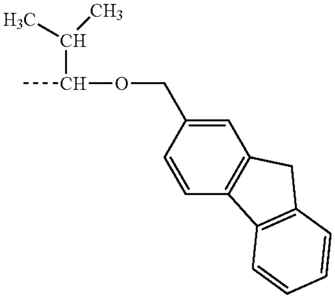

Of the acid labile groups having formula (AL-2), suitable cyclic groups include tetrahydrofuran-2-yl, 2-methyltetrahydrofuran-2 yl, tetrahydropyran-2-yl, and 2-methyltetrahydropyran-2-yl.

Also included are acid labile groups having the following formulae (AL-2a) and (AL-2b). The base polymer may be crosslinked within the molecule or between molecules with these acid labile groups.

(AL-2a)

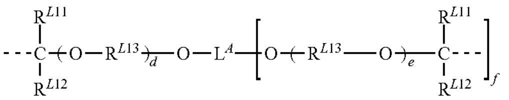

(AL-2b)

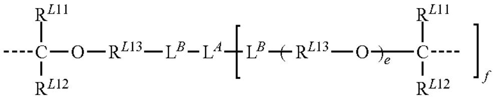

In formulae (AL-2a) and (AL-2b), $R^{L11}$ and $R^{L12}$ are each independently hydrogen or a $C_1$-$C_8$ saturated hydrocarbyl group which may be straight, branched or cyclic. Also, $R^{L11}$ and $R^{L12}$ may bond together to form a ring with the carbon atom to which they are attached, and in this case, $R^{L11}$ and $R^{L12}$ are each independently a $C_1$-$C_8$ alkanediyl group. $R^{L13}$ is each independently a $C_1$-$C_{10}$ saturated hydrocarbylene group which may be straight, branched or cyclic. The subscripts d and e are each independently an integer of 0 to 10, preferably 0 to 5, and f is an integer of 1 to 7, preferably 1 to 3.

In formulae (AL-2a) and (AL-2b), $L^A$ is a (f+1)-valent $C_1$-$C_{50}$ aliphatic saturated hydrocarbon group, (f+1)-valent $C_6$-$C_{50}$ alicyclic saturated hydrocarbon group, (f+1)-valent $C_6$-$C_{50}$ aromatic hydrocarbon group or (f+1)-valent $C_3$-$C_{50}$ heterocyclic group. In these groups, some constituent —$CH_2$— may be replaced by a heteroatom-containing moiety, or some hydrogen may be substituted by a hydroxy, carboxy, acyl moiety or fluorine. $L^A$ is preferably a $C_1$-$C_{20}$ saturated hydrocarbylene, saturated hydrocarbon group (e.g., tri- or tetravalent saturated hydrocarbon group), or $C_6$-$C_{30}$ arylene group. The saturated hydrocarbon group may be straight, branched or cyclic. $L^B$ is —C(═O)—O—, NH—C(═O)—O— or —NH—C(═O)—NH—.

Examples of the crosslinking acetal groups having formulae (AL-2a) and (AL-2b) include groups having the formulae (AL-2)-70 to (AL-2)-77.

(AL-2)-70

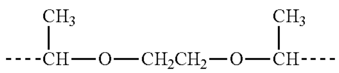

(AL-2)-71

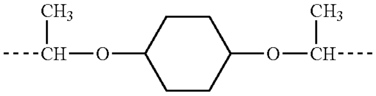

(AL-2)-72

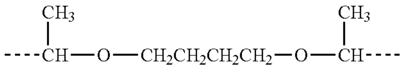

(AL-2)-73

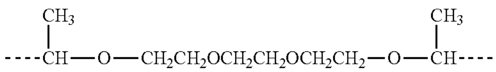

-continued (AL-2)-74

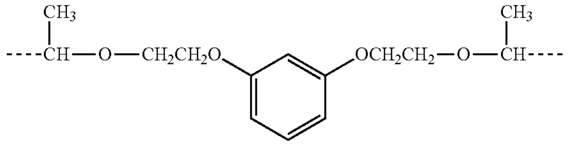

(AL-2)-75

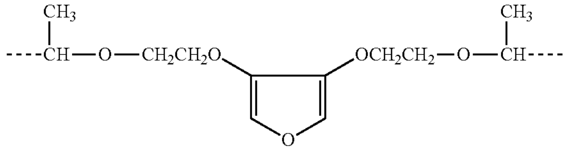

(AL-2)-76

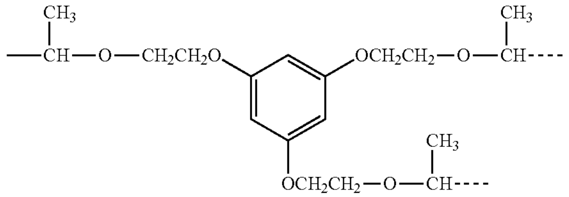

(AL-2)-77

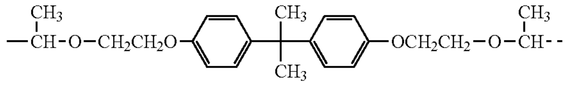

In formula (AL-3), $R^{L5}$, $R^{L6}$ and $R^{L7}$ are each independently a $C_1$-$C_{20}$ hydrocarbyl group which may contain a heteroatom such as oxygen, sulfur, nitrogen or fluorine. The hydrocarbyl group may be saturated or unsaturated and straight, branched or cyclic. Examples thereof include $C_1$-$C_{20}$ alkyl groups, $C_3$-$C_{20}$ cyclic saturated hydrocarbyl groups. $C_2$-$C_{20}$ alkenyl groups, $C_3$-$C_{20}$ cyclic unsaturated hydrocarbyl groups, and $C_6$-$C_{10}$ aryl groups. A pair of $R^{L5}$ and $R^{L6}$, $R^{L5}$ and $R^{L7}$, or $R^{L6}$ and $R^{L7}$ may bond together to form a $C_3$-$C_{20}$ aliphatic ring with the carbon atom to which they are attached.

Examples of the group having formula (AL-3) include tert-butyl, 1,1-diethylpropyl, 1-ethylnorbornyl, 1-methylcyclopentyl, 1-ethylcyclopentyl, 1-isopropylcyclopentyl, 1-methylcyclohexyl, 2-(2-methyl)adamantyl, 2-(2-ethyl) adamantyl, and tert-pentyl.

Examples of the group having formula (AL-3) also include groups having the formulae (AL-3)-1 to (AL-3)-19.

(AL-3)-1

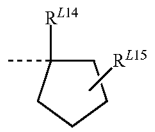

(AL-3)-2

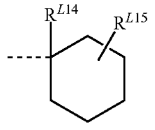

(AL-3)-3

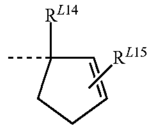

-continued
(AL-3)-4
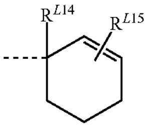
(AL-3)-5
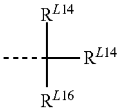
(AL-3)-6
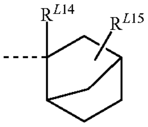
(AL-3)-7
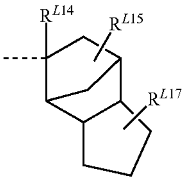
(AL-3)-8
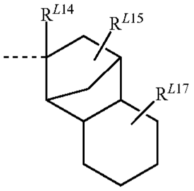
(AL-3)-9
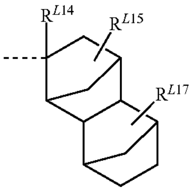
(AL-3)-10
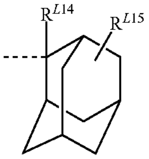
(AL-3)-11
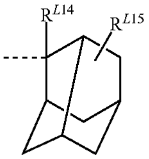
(AL-3)-12
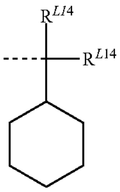
-continued
(AL-3)-13
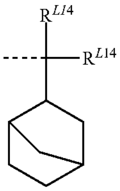
(AL-3)-14
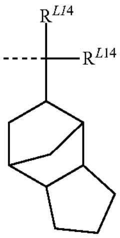
(AL-3)-15
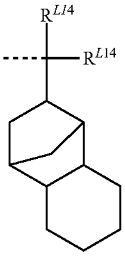
(AL-3)-16
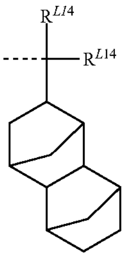
(AL-3)-17
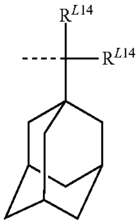
(AL-3)-18
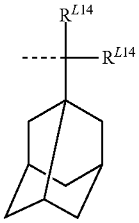

-continued (AL-3)-19

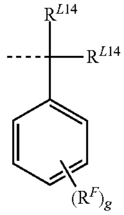

In formulae (AL-3)-1 to (AL-3)-19, $R^{L14}$ is each independently a $C_1$-$C_8$ saturated hydrocarbyl group or $C_6$-$C_{20}$ aryl group. $R^{L15}$ and $R^{L17}$ are each independently hydrogen or a $C_1$-$C_{20}$ saturated hydrocarbyl group. $R^{L16}$ is a $C_6$-$C_{20}$ aryl group. The saturated hydrocarbyl group may be straight, branched or cyclic. Typical of the aryl group is phenyl. $R^F$ is fluorine, trifluoromethyl or nitro, and g is an integer of 1 to 5.

Other examples of the acid labile group having formula (AL-3) include groups having the formulae (AL-3)-20 and (AL-3)-21. The base polymer may be crosslinked within the molecule or between molecules with these acid labile groups.

(AL-3)-20

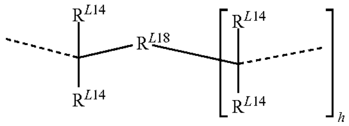

(AL-3)-21

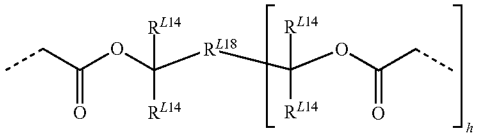

In formulae (AL-3)-20 and (AL-3)-21. $R^{L14}$ is as defined above. $R^{L18}$ is a (h+1)-valent $C_1$-$C_{20}$ saturated hydrocarbylene group or (h+1)-valent $C_6$-$C_{20}$ arylene group, which may contain a heteroatom such as oxygen, sulfur or nitrogen. The saturated hydrocarbylene group may be straight, branched or cyclic. The subscript h is an integer of 1 to 3.

Examples of the monomer from which repeat units containing an acid labile group of formula (AL-3) are derived include (meth)acrylates (inclusive of exo-form structure) having the formula (AL-3)-22.

(AL-3)-22

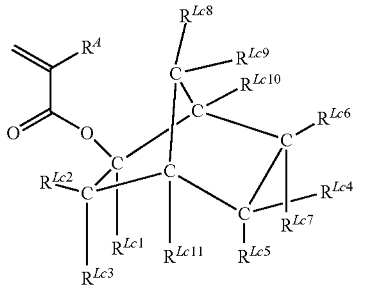

In formula (AL-3)-22, $R^A$ is as defined above. $R^{Lc1}$ is a $C_1$-$C_6$ saturated hydrocarbyl group or an optionally substituted $C_6$-$C_{20}$ aryl group; the saturated hydrocarbyl group may be straight, branched or cyclic. $R^{Lc2}$ to $R^{Lc11}$ are each independently hydrogen or a $C_1$-$C_{15}$ hydrocarbyl group which may contain a heteroatom; oxygen is a typical heteroatom. Suitable hydrocarbyl groups include $C_1$-$C_{15}$ alkyl groups and $C_6$-$C_{15}$ aryl groups. Alternatively, a pair of $R^{Lc2}$ and $R^{Lc3}$, $R^{Lc4}$ and $R^{Lc6}$, $R^{Lc4}$ and $R^{Lc7}$, $R^{Lc5}$ and $R^{Lc7}$, $R^{Lc5}$ and $R^{Lc11}$, $R^{Lc6}$ and $R^{Lc10}$, $R^{Lc8}$ and $R^{Lc9}$, or $R^{Lc9}$ and $R^{Lc10}$, taken together, may form a ring with the carbon atom to which they are attached, and in this event, the ring-forming group is a $C_1$-$C_{15}$ hydrocarbylene group which may contain a heteroatom. Also, a pair of $R^{Lc2}$ and $R^{Lc11}$, $R^{Lc8}$ and $R^{Lc11}$, or $R^{Lc4}$ and $R^{Lc6}$ which are attached to vicinal carbon atoms may bond together directly to form a double bond. The formula also represents an enantiomer.

Examples of the monomer having formula (AL-3)-22 are described in U.S. Pat. No. 6,448,420 (JP-A 2000-327633). Illustrative non-limiting examples of suitable monomers are given below. $R^A$ is as defined above.

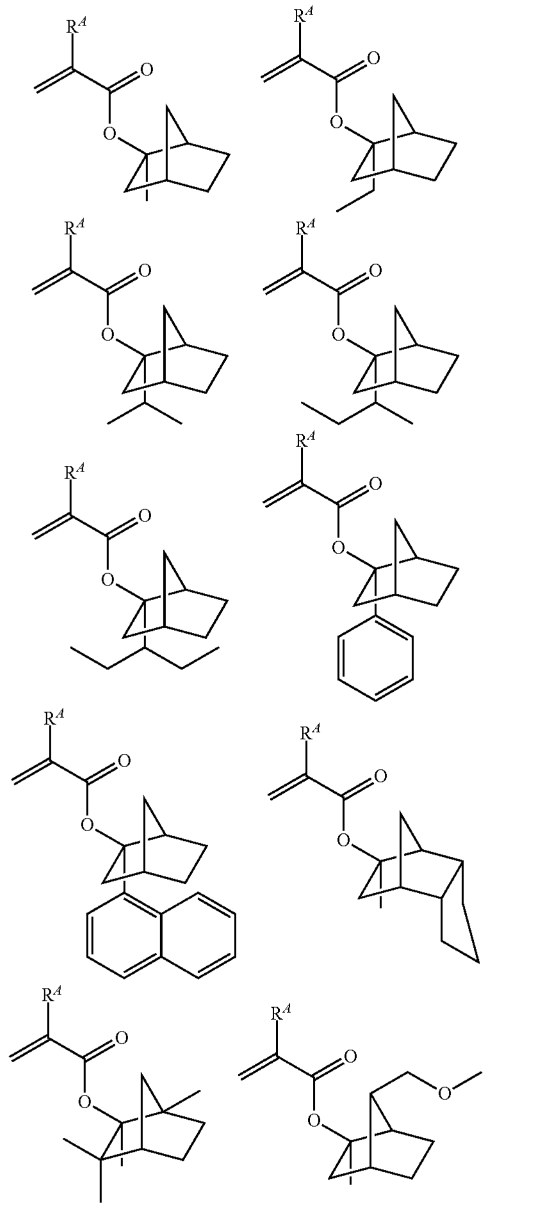

-continued

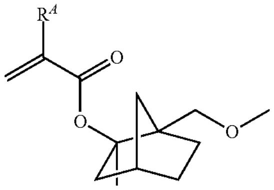

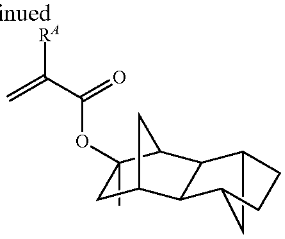

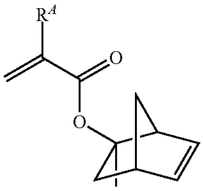

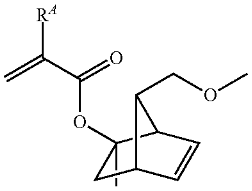

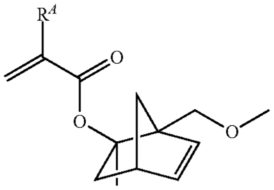

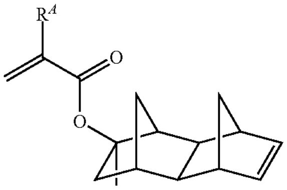

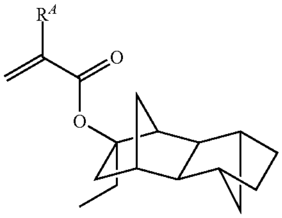

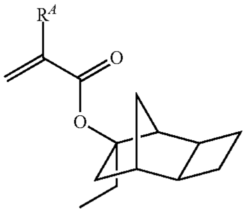

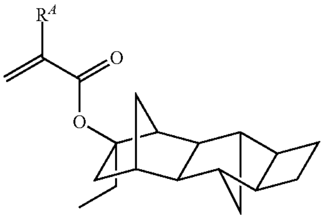

Examples of the monomer from which the repeat units having an acid labile group of formula (AL-3) are derived also include (meth)acrylate monomers having a furandiyl, tetrahydrofurandiyl or oxanorbornanediyl group as represented by the following formula (AL-3)-23.

(AL-3)-23

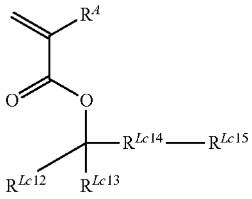

In formula (AL-3)-23, $R^A$ is as defined above. $R^{Lc12}$ and $R^{Lc13}$ are each independently a $C_1$-$C_{10}$ hydrocarbyl group, or $R^{Lc12}$ and $R^{Lc13}$, taken together, may form an aliphatic ring with the carbon atom to which they are attached. $R^{Lc14}$ is furandiyl, tetrahydrofurandiyl or oxanorbornanediyl. $R^{Lc15}$ is hydrogen or a $C_1$-$C_{10}$ hydrocarbyl group which may contain a heteroatom. The hydrocarbyl group may be straight, branched or cyclic, and examples thereof include $C_1$-$C_{10}$ saturated hydrocarbyl groups.

Examples of the monomer having formula (AL-3)-23 are shown below, but not limited thereto. Herein $R^A$ is as defined above.

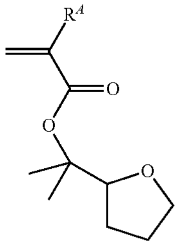

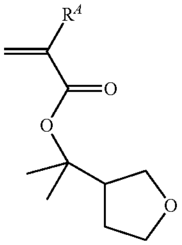

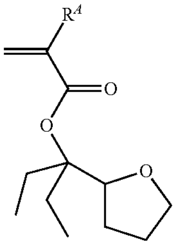

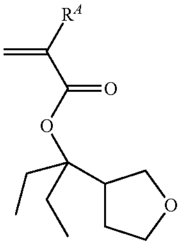

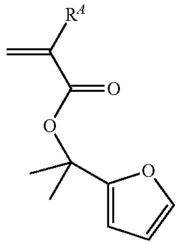

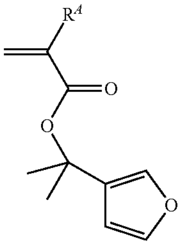

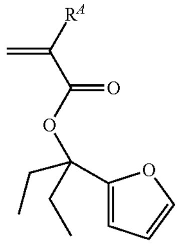

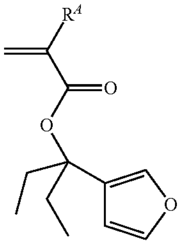

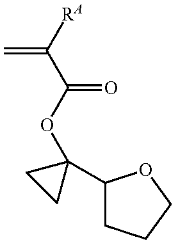

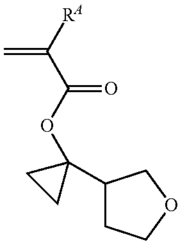

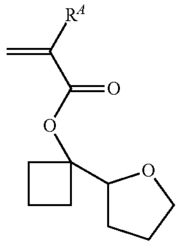

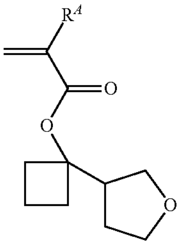

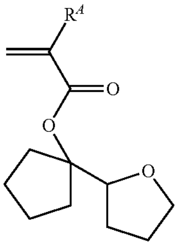

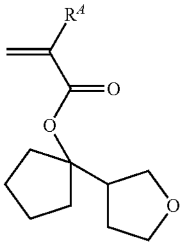

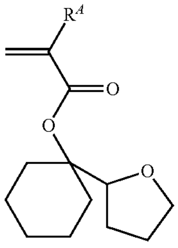

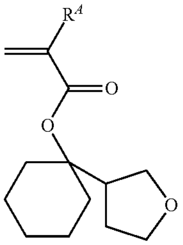

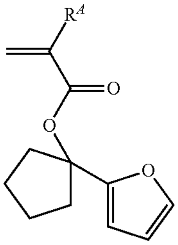

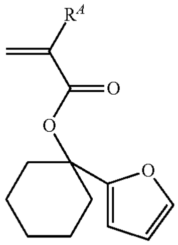

-continued
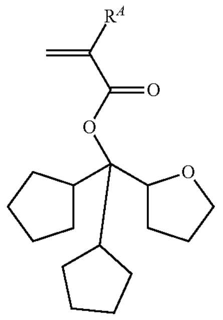
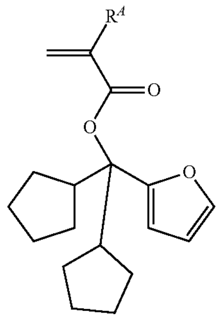
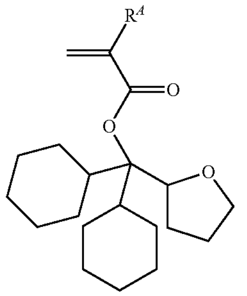
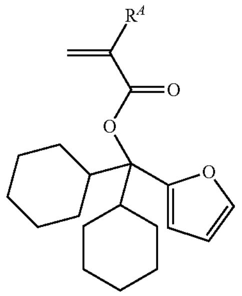
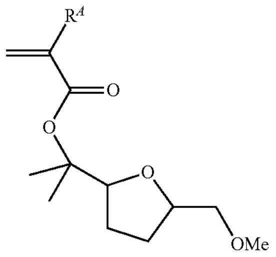
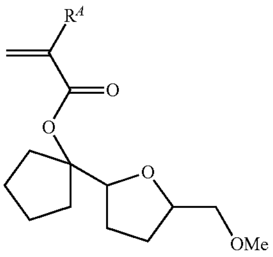
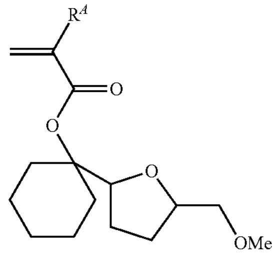
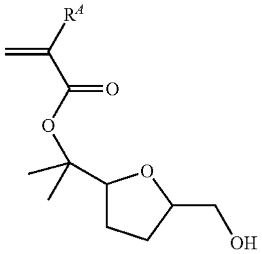
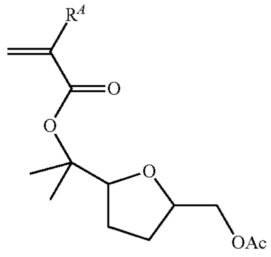
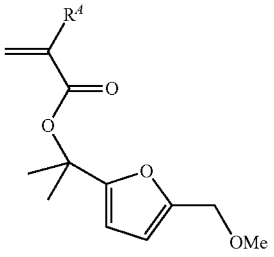
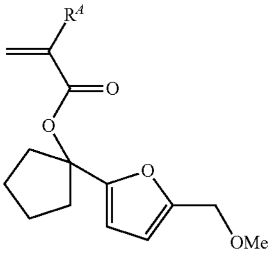
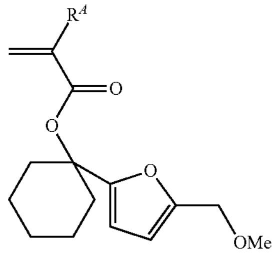
-continued
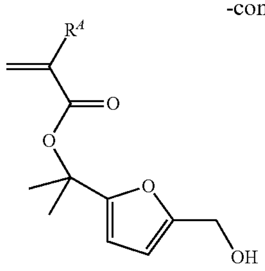
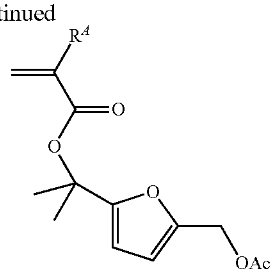
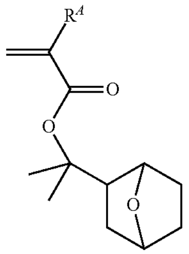
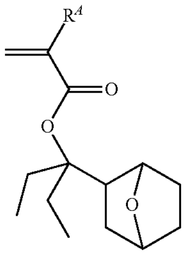
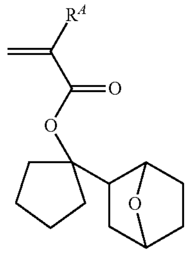
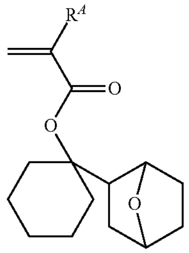
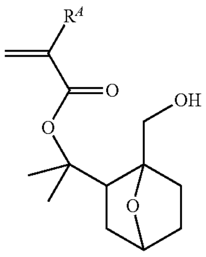
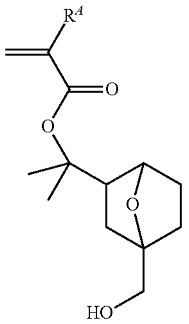
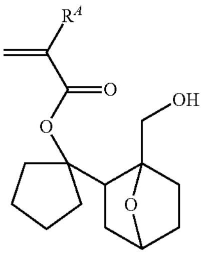
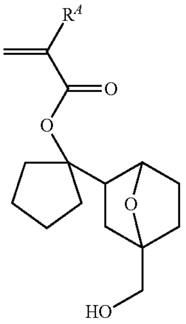
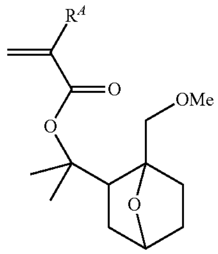
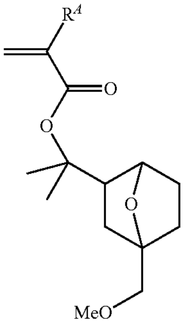

-continued

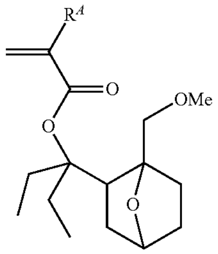
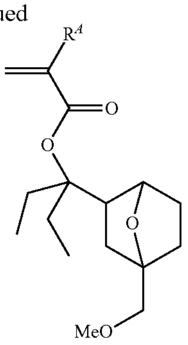
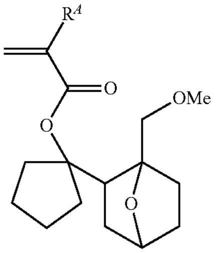
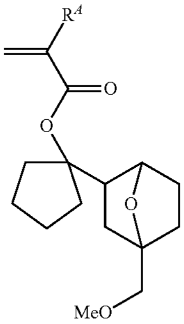
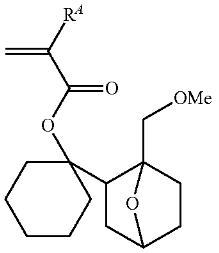
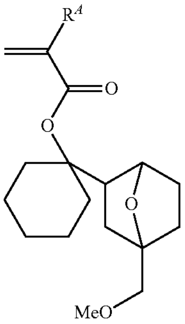
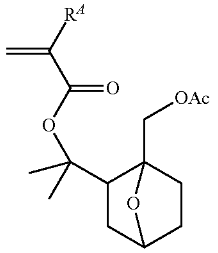
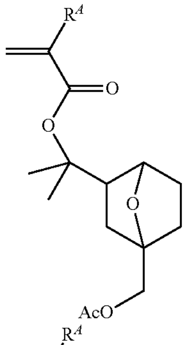
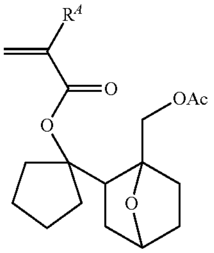
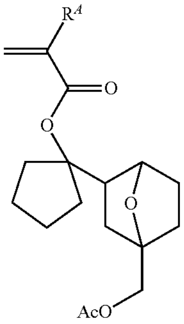

In addition to the foregoing acid labile groups, aromatic moiety-containing acid labile groups as described in JP 5565293, JP 5434983, JP 5407941, JP 5655756, and JP 5655755 are also useful.

The base polymer may further comprise a repeat unit (c) having an adhesive group. The adhesive group is selected from hydroxy, carboxy, lactone ring, carbonate bond, thiocarbonate bond, carbonyl, cyclic acetal, ether bond, ester bond, sulfonic ester bond, cyano, amide bond, —O—C(═O)—S— and —O—C(═O)—NH—.

Examples of the monomer from which repeat unit (c) is derived are given below, but not limited thereto. Herein $R^A$ is as defined above.

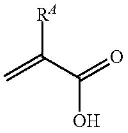
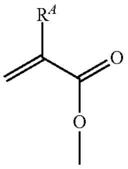
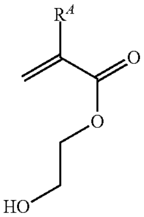
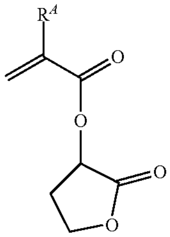
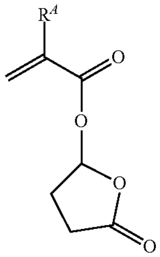
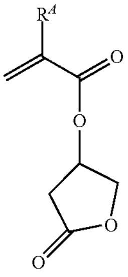

-continued
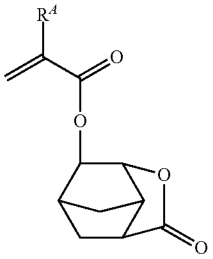
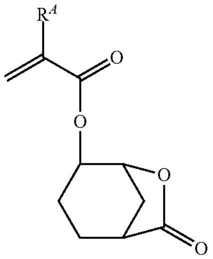
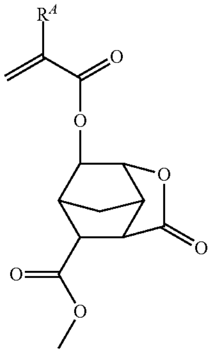
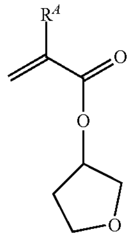
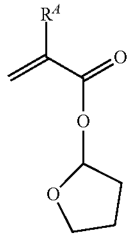
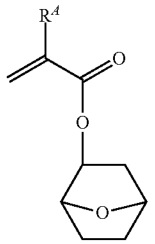
-continued
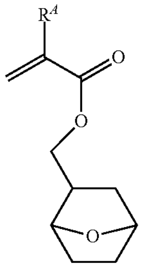
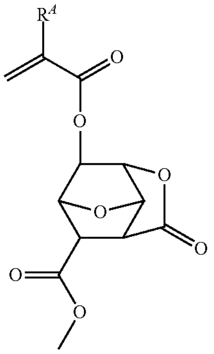
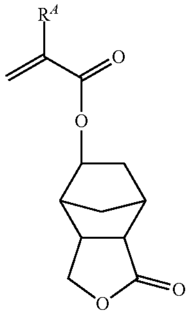
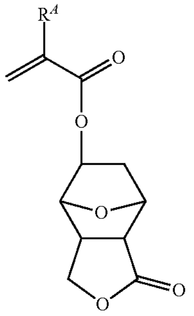
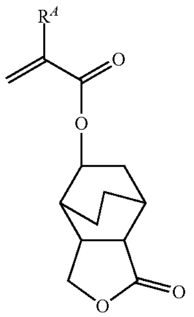

-continued
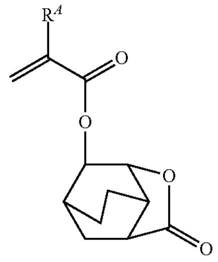
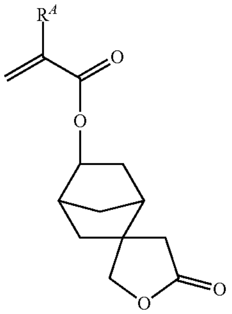
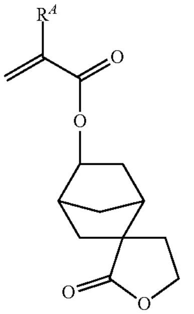
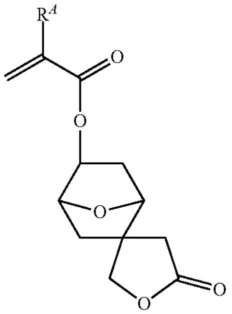
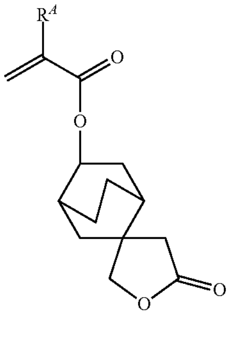
-continued
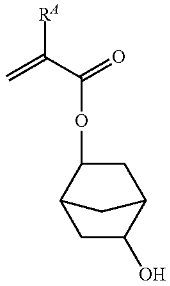
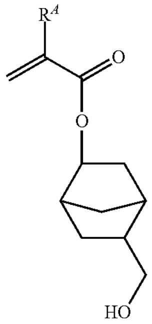
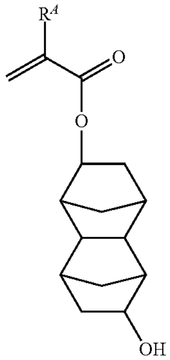
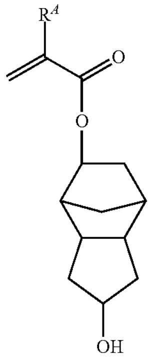
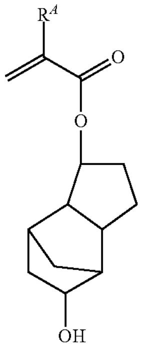

-continued
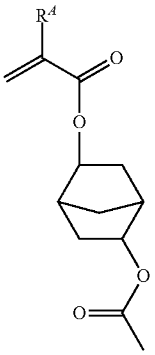
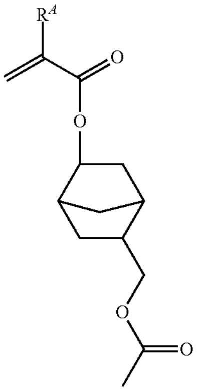
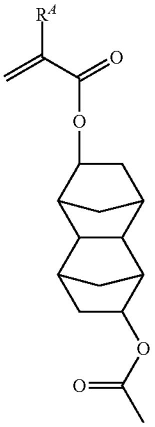
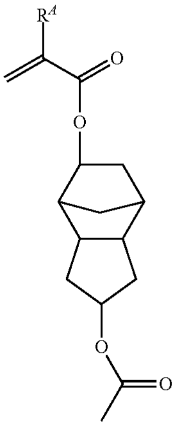
-continued
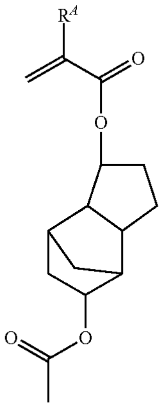
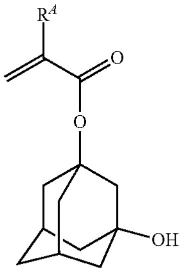
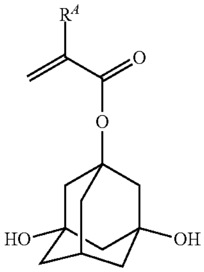
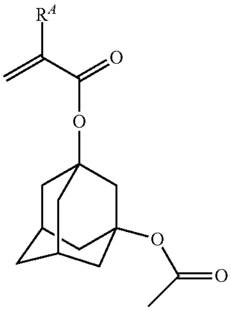
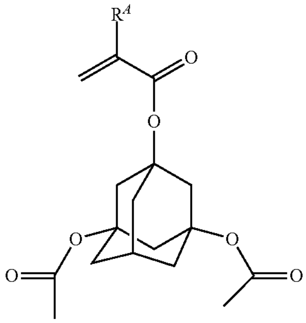

-continued
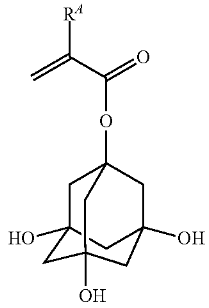
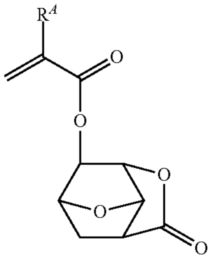
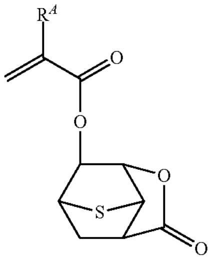
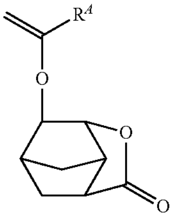
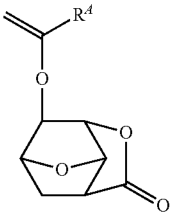
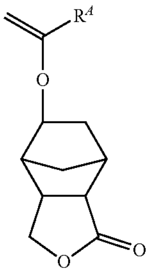
-continued
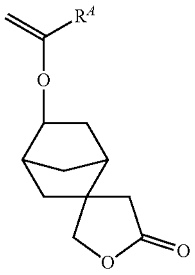
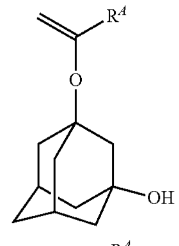
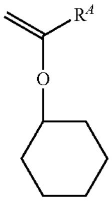
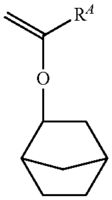
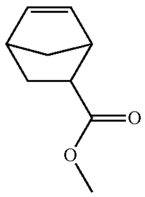
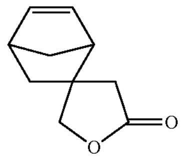
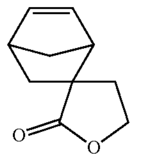
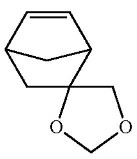

-continued
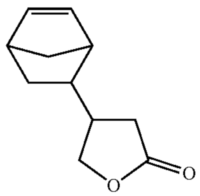
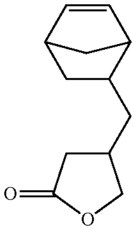
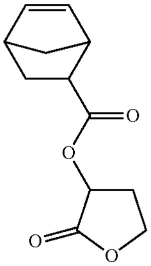
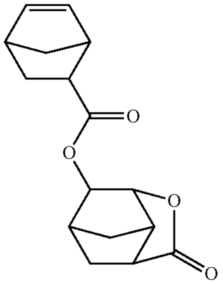
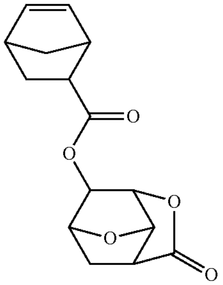
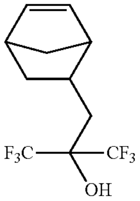
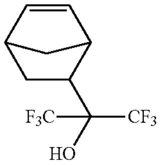
-continued
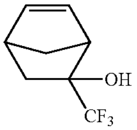
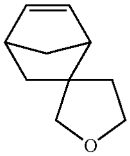
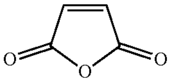
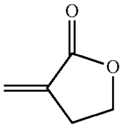
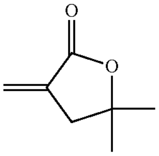
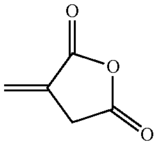
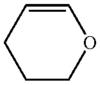
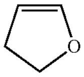
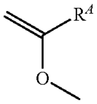
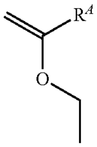
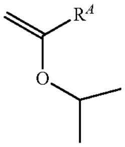
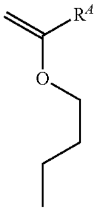
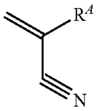

-continued
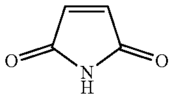
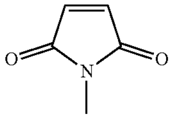
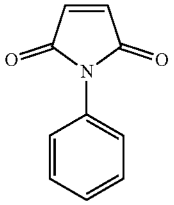
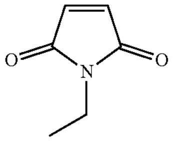
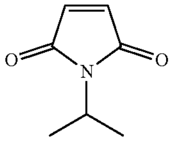
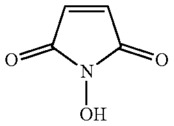
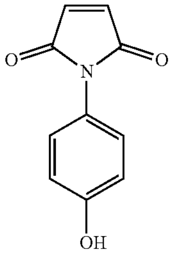
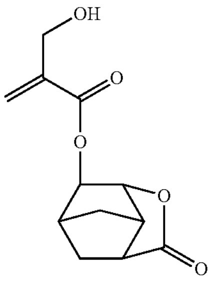
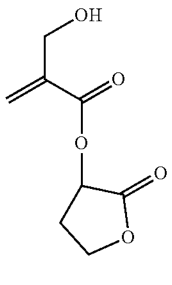
-continued
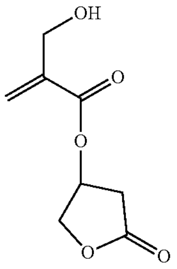
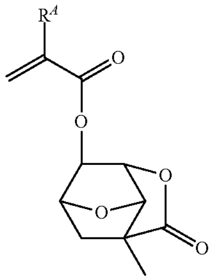
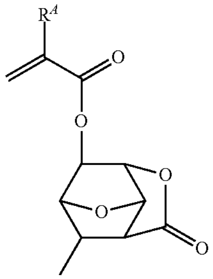
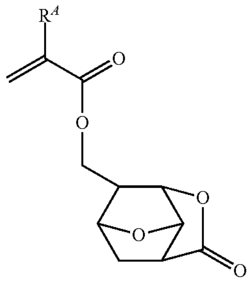
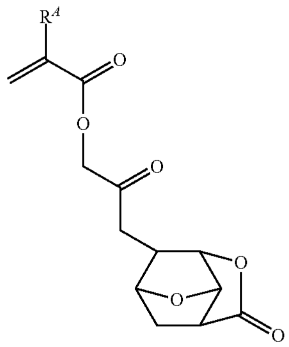

-continued
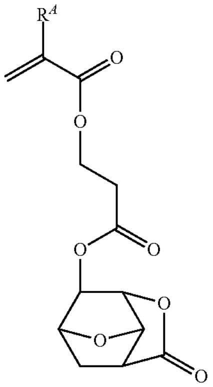
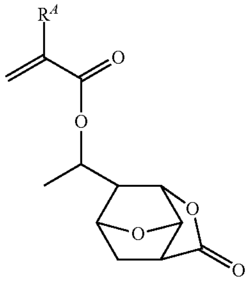
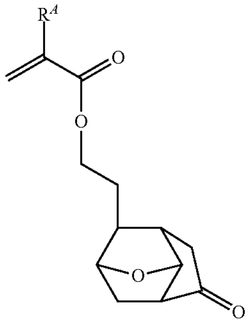
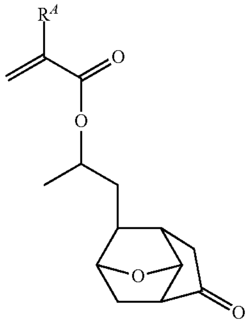
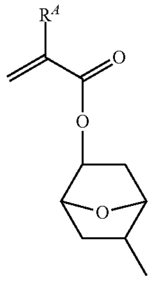
-continued
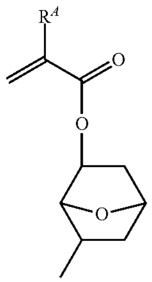
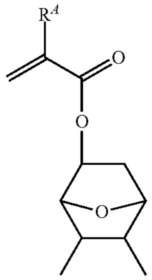
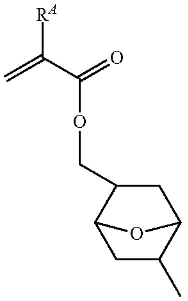
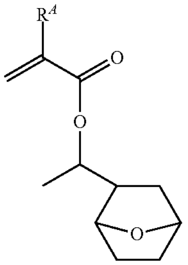
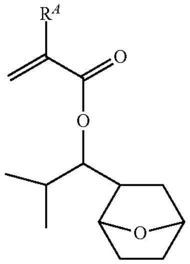
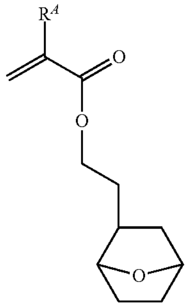

-continued
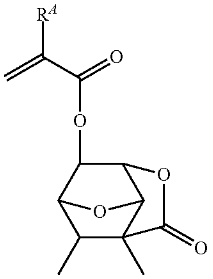
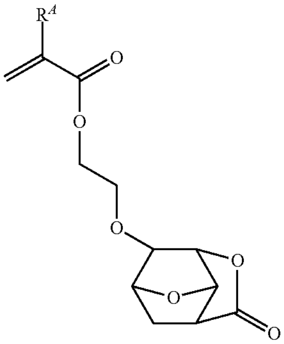
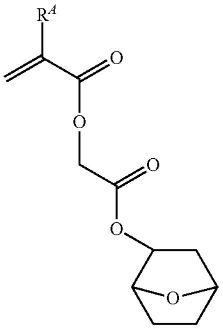
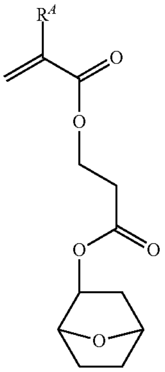
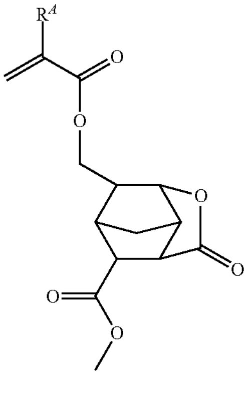
-continued
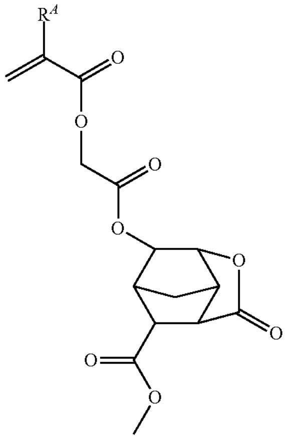
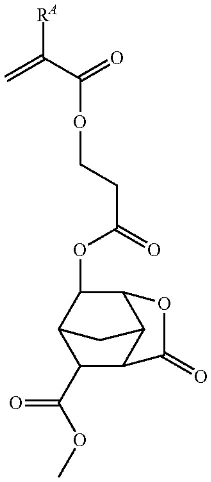
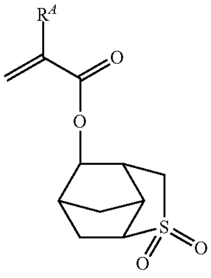
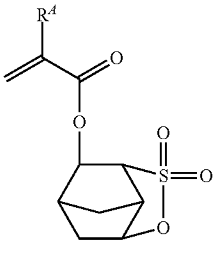

-continued
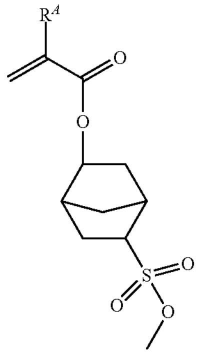
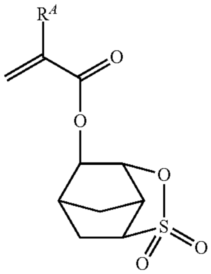
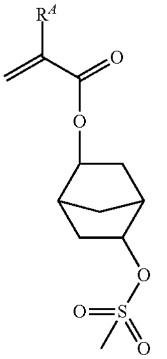
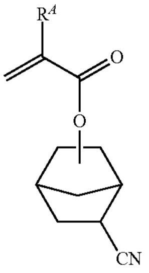
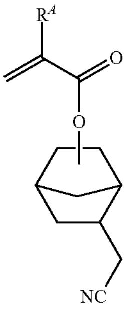
-continued
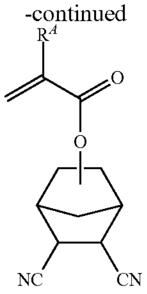
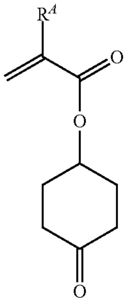
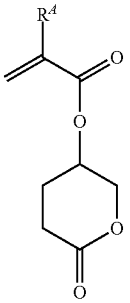
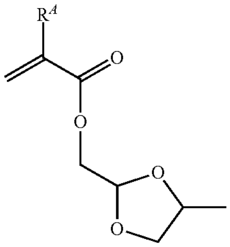
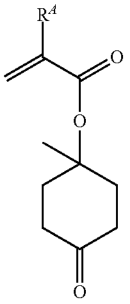
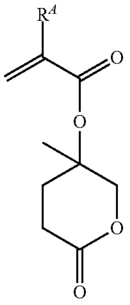

-continued
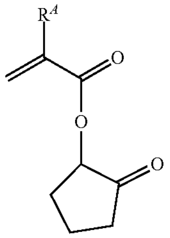
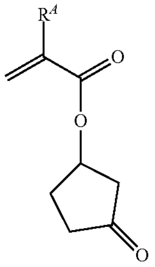
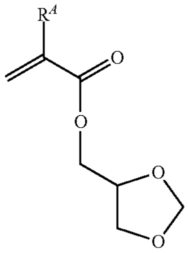
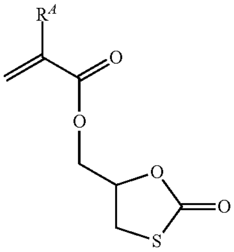
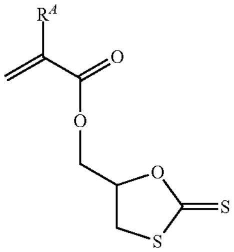
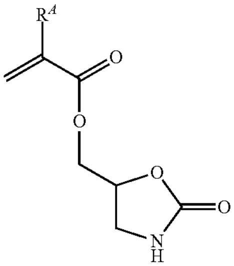
-continued
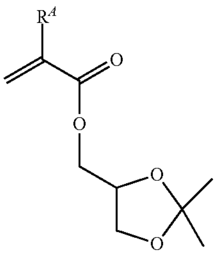
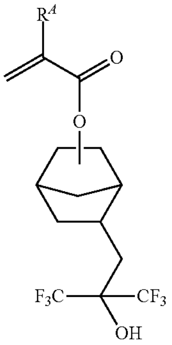
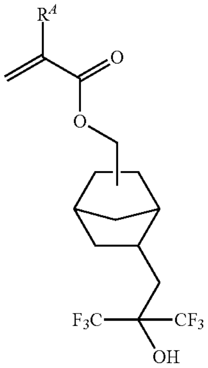
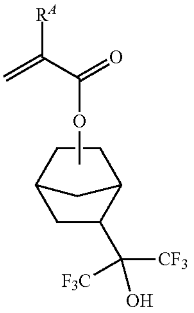
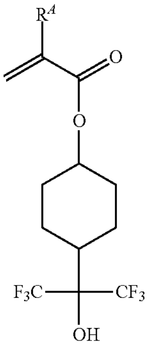

-continued
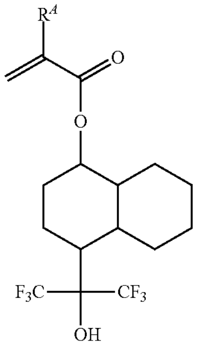
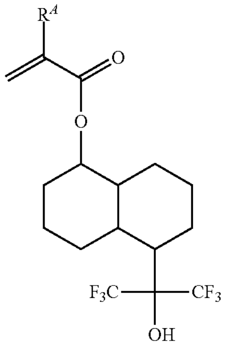
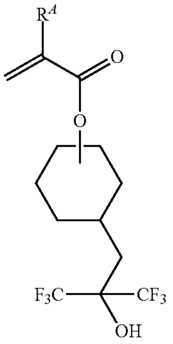
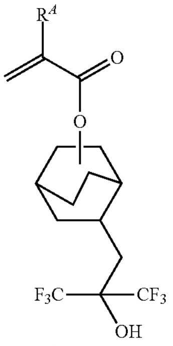
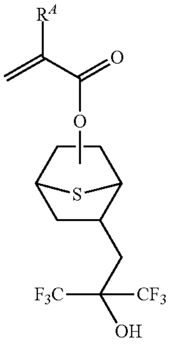
-continued
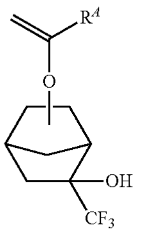
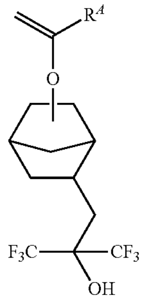
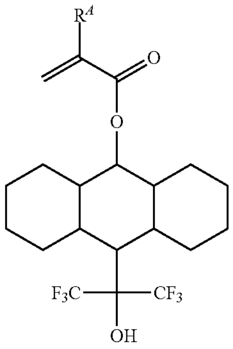
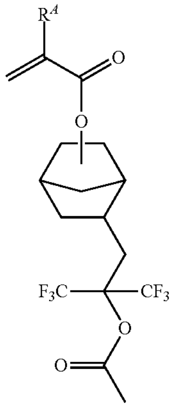
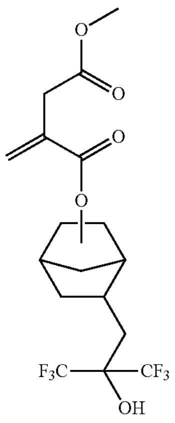

-continued
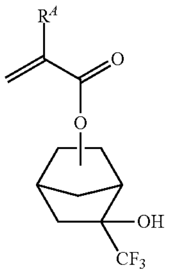
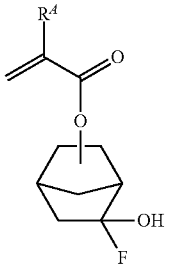
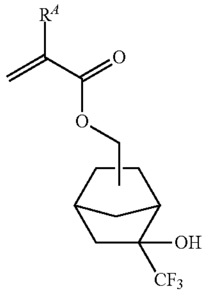
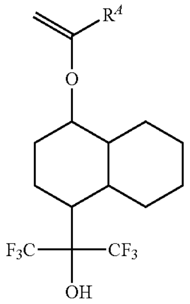
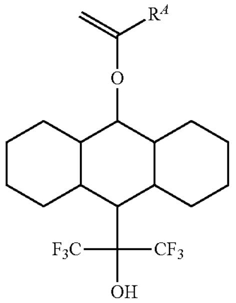
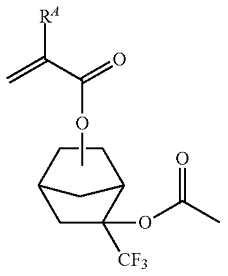
-continued
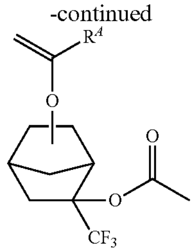
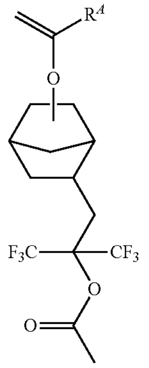
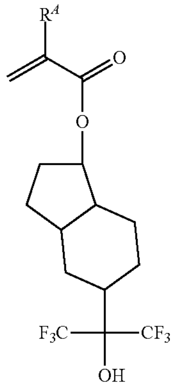
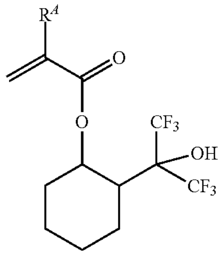
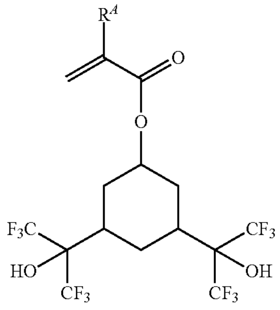

-continued
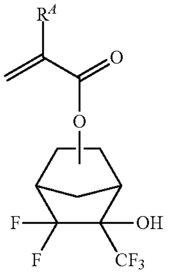
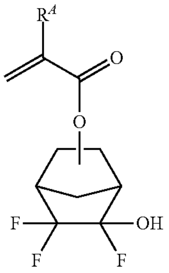
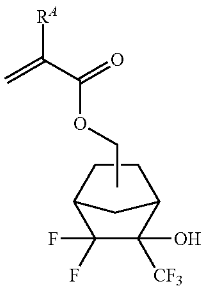
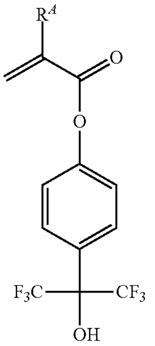
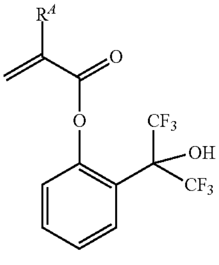
-continued
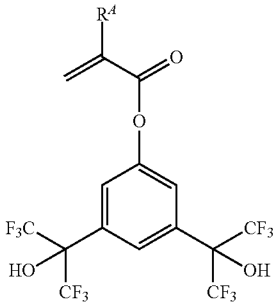
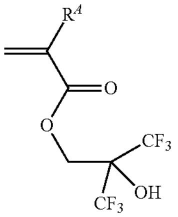
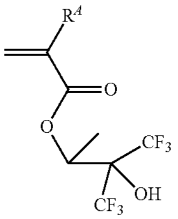
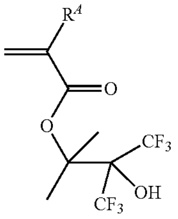
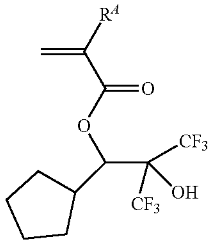
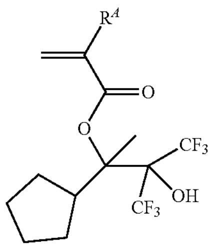
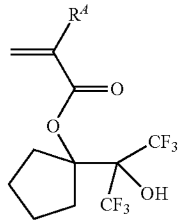

-continued
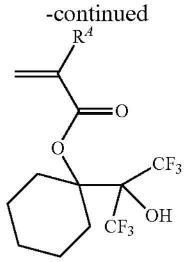
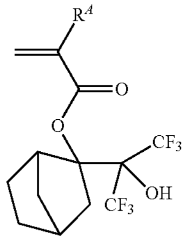
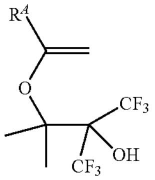
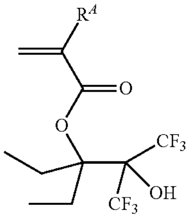
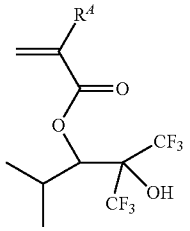
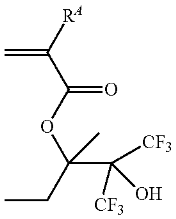
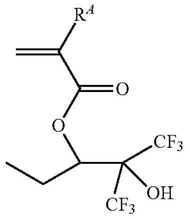
-continued
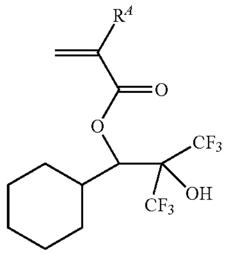
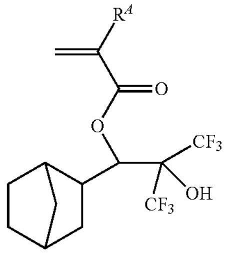
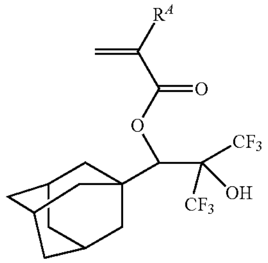
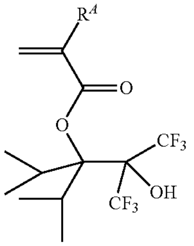
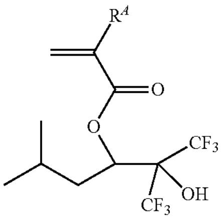
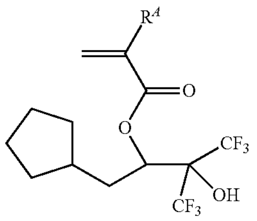
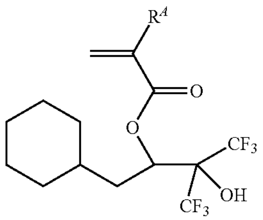

-continued
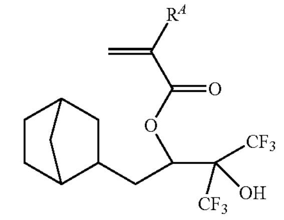
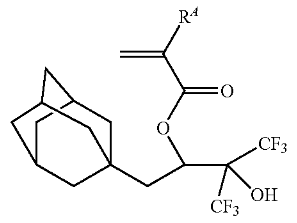
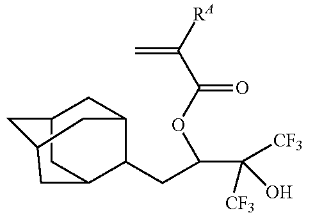
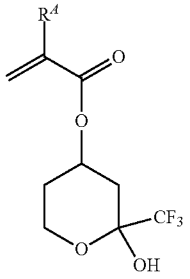
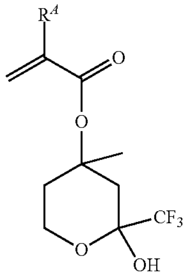
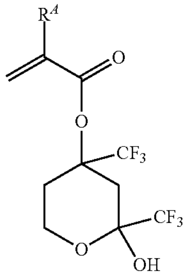
-continued
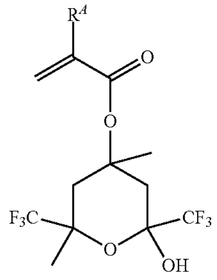
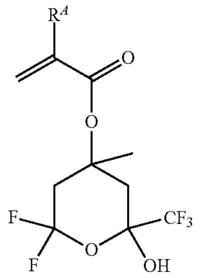
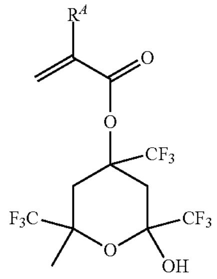
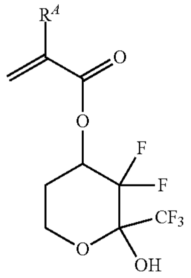
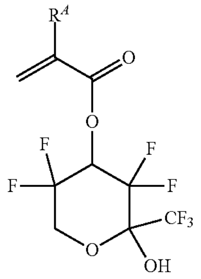
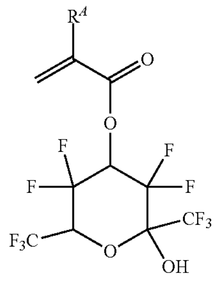

-continued
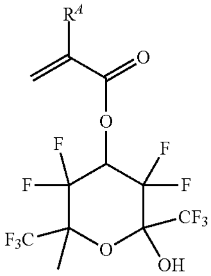
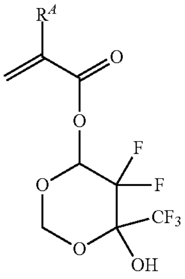
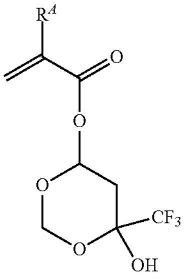
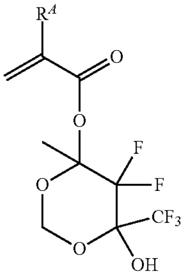
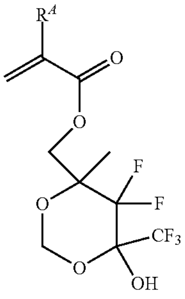
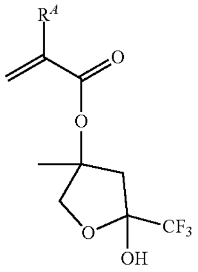
-continued
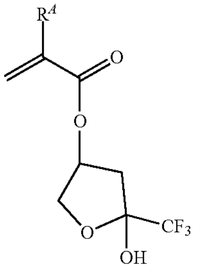
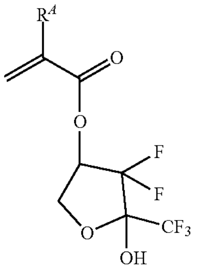
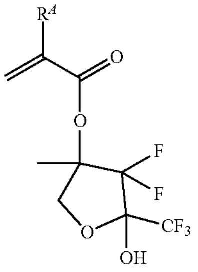
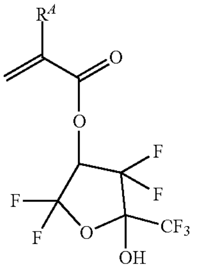
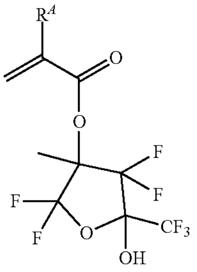
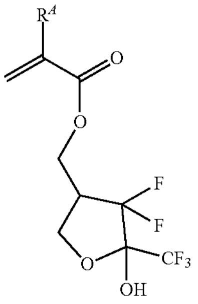

-continued
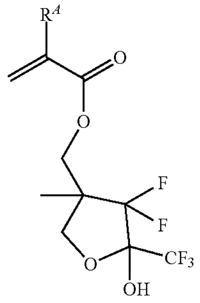
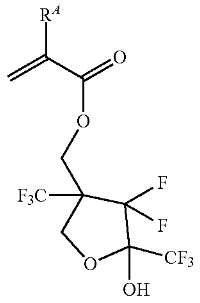
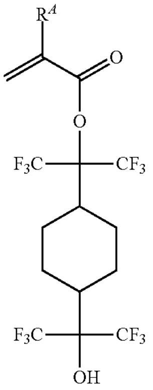
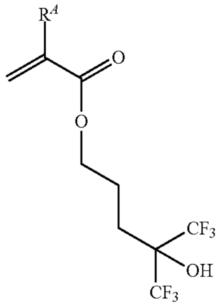
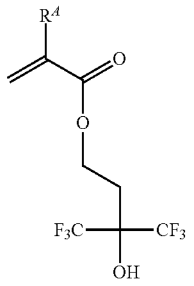
-continued
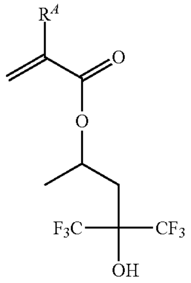
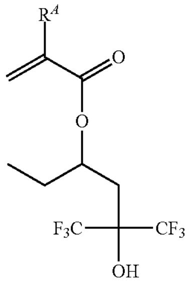
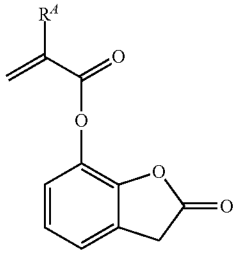
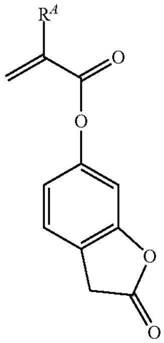
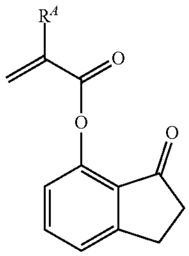
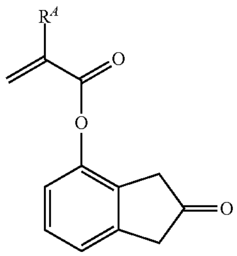

-continued
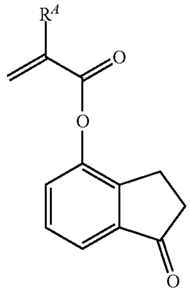
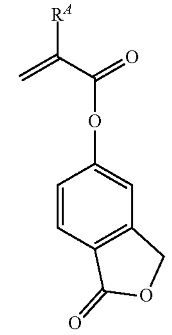
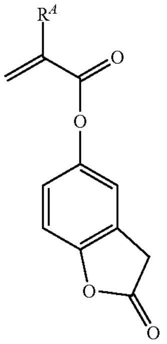
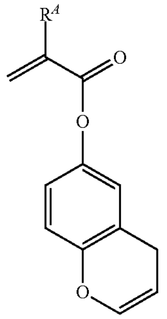
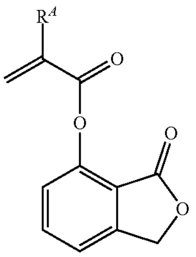
-continued
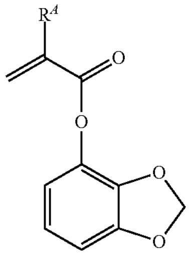
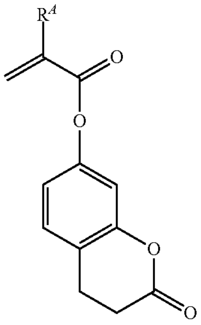
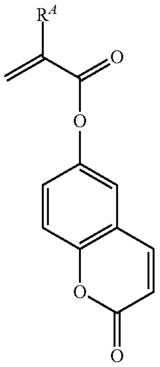
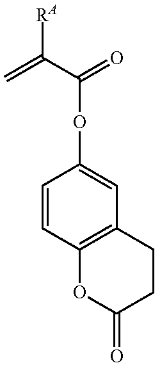
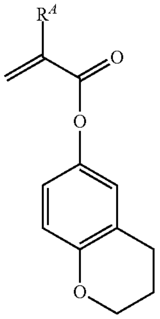

-continued
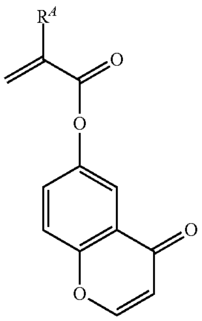
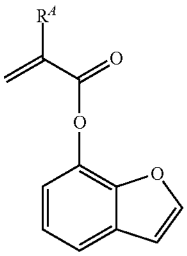
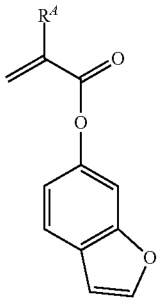
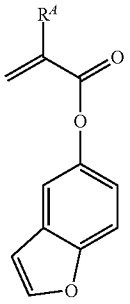
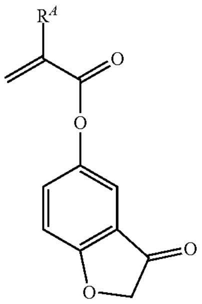
-continued
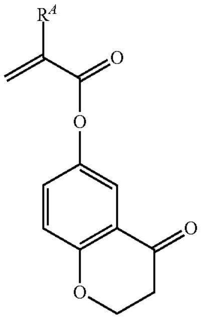
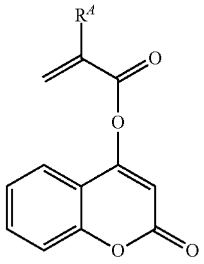
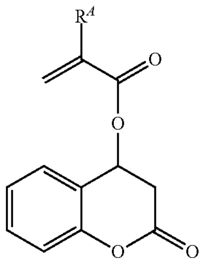
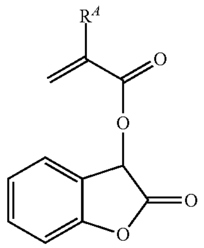
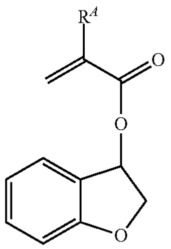
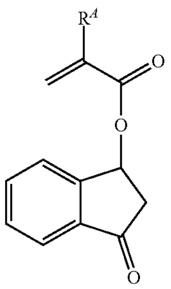

-continued
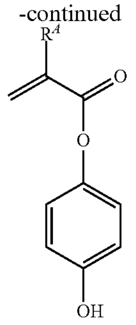
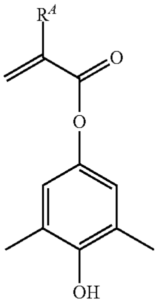
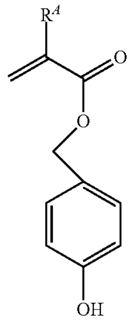
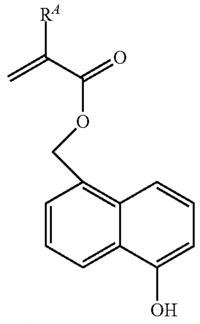
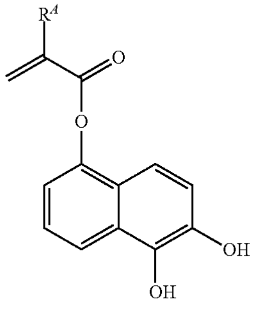
-continued
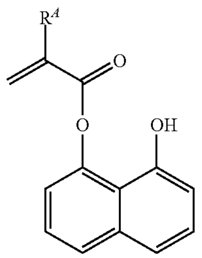
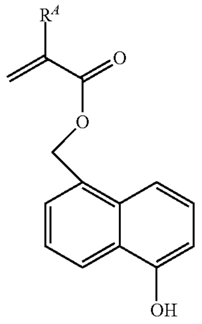
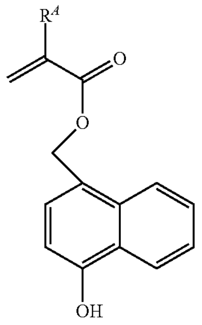
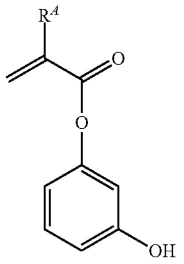
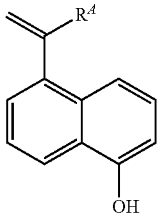
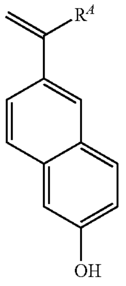

-continued
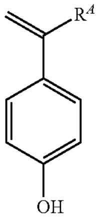
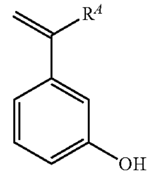
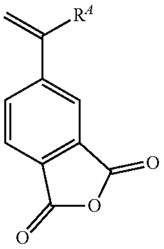
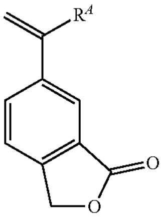
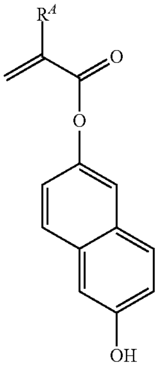
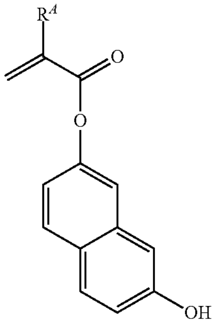
-continued
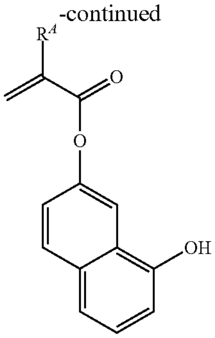
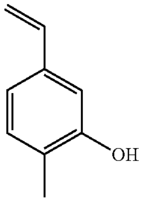
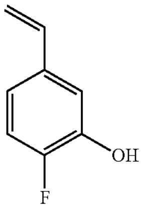
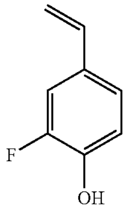
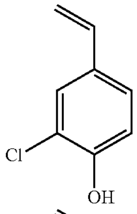
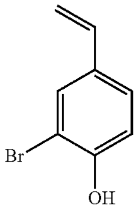
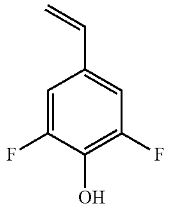

-continued
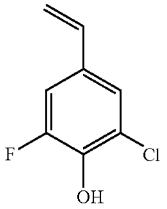
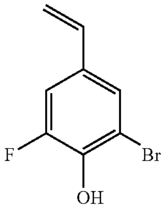
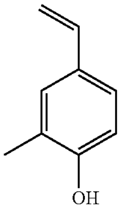
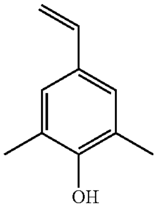
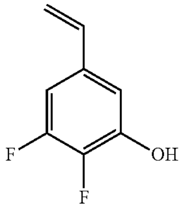
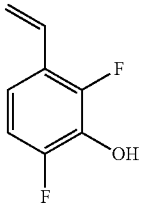
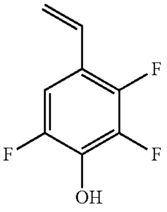
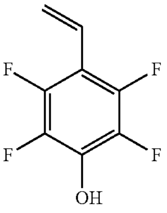
-continued
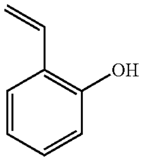
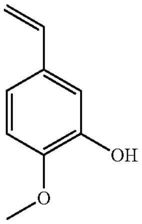
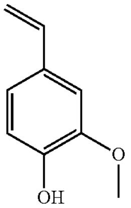
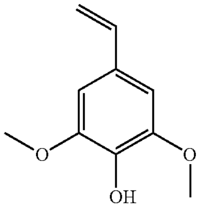
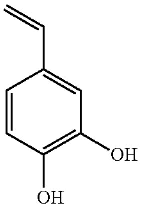
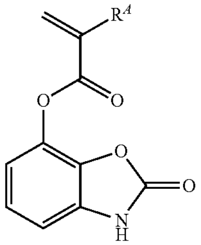
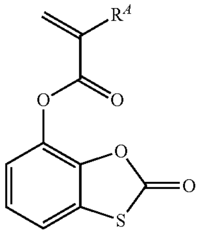

-continued
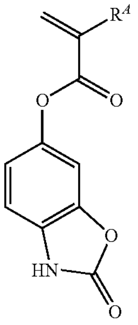
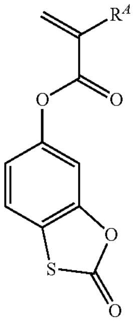
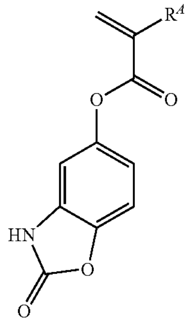
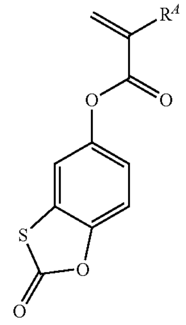
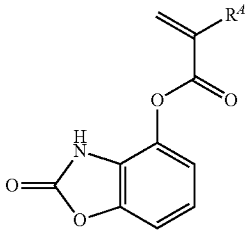
-continued
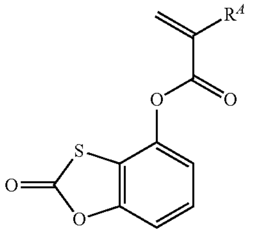
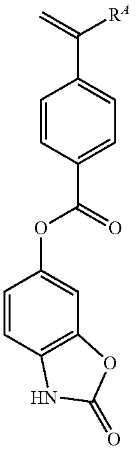
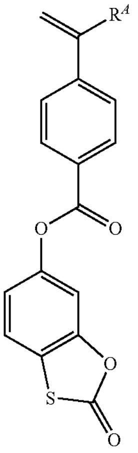
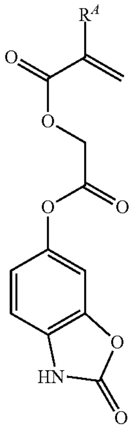

-continued
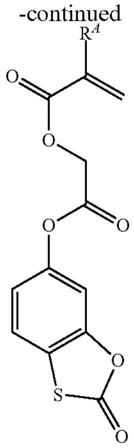
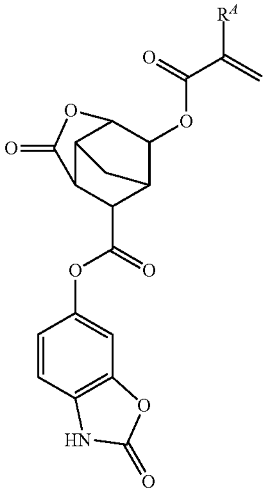
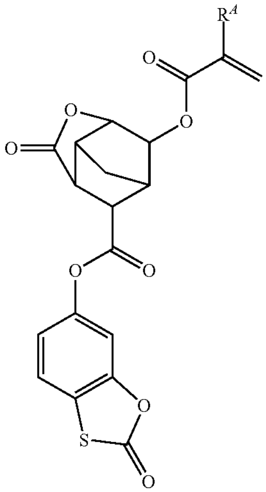
-continued
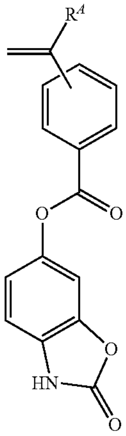
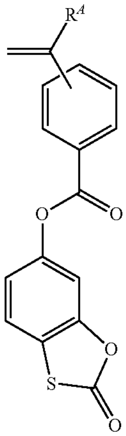
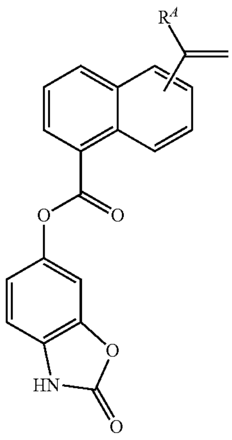

-continued

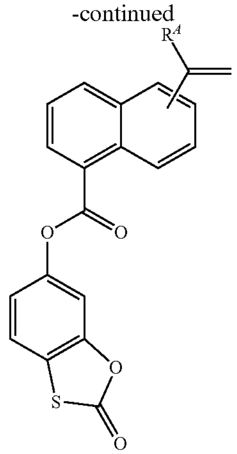

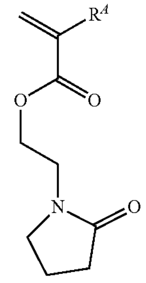

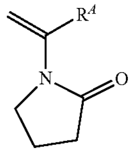

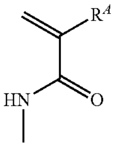

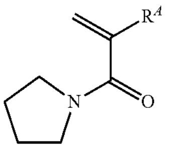

In a further embodiment, the base polymer may comprise repeat units (d) of at least one type selected from repeat units having the following formulae (d1), (d2) and (d3). These units are also referred to as repeat units (d1), (d2) and (d3).

(d1)

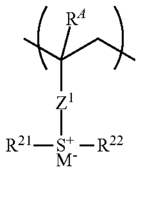

-continued (d2)

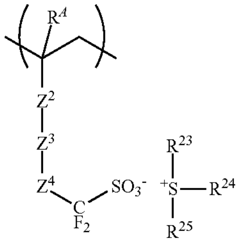

(d3)

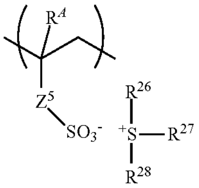

In formulae (d1) to (d3), $R^A$ is each independently hydrogen or methyl. $Z^1$ is a single bond, $C_1$-$C_6$ aliphatic hydrocarbylene group, phenylene, naphthylene, or a $C_7$-$C_{18}$ group obtained by combining the foregoing, or —O—$Z^{11}$—, —C(═O)—O—$Z^{11}$— or —C(═O)—NH—$Z^{11}$—, wherein $Z^{11}$ is a $C_1$-$C_6$ aliphatic hydrocarbylene group, phenylene, naphthylene, or a $C_7$-$C_{18}$ group obtained by combining the foregoing, which may contain a carbonyl moiety, ester bond, ether bond or hydroxy moiety. $Z^2$ is a single bond or ester bond. $Z^3$ is a single bond, —$Z^{31}$—C(═O)—O—, —$Z^{31}$—O—, or —$Z^{31}$—O—C(═O)—, wherein $Z^{31}$ is a $C_1$-$C_{12}$ aliphatic hydrocarbylene group, phenylene group, or a $C_7$-$C_{18}$ group obtained by combining the foregoing, which may contain a carbonyl moiety, ester bond, ether bond, bromine or iodine. $Z^4$ is methylene, 2,2,2-trifluoro-1,1-ethanediyl or carbonyl. $Z^5$ is a single bond methylene, ethylene, phenylene, fluorinated phenylene, trifluoromethyl-substituted phenylene, —O—$Z^{51}$—, —C(═O)—O—$Z^{51}$—, or —C(═O)—NH—$Z^{51}$—, wherein $Z^{51}$ is a $C_1$-$C_6$ aliphatic hydrocarbylene group, phenylene, fluorinated phenylene, or trifluoromethyl-substituted phenylene group, which may contain a carbonyl moiety, ester bond, ether bond, halogen or hydroxy moiety. The aliphatic hydrocarbylene group represented by $Z^1$, $Z^{11}$, $Z^{31}$ and $Z^{51}$ may be saturated or unsaturated and straight, branched or cyclic.

In formulae (d1) to (d3), $R^{21}$ to $R^{28}$ are each independently halogen or a $C_1$-$C_{20}$ hydrocarbyl group which may contain a heteroatom. Suitable halogen atoms include fluorine, chlorine, bromine and iodine. The hydrocarbyl group may be saturated or unsaturated and straight, branched or cyclic. Examples thereof are as will be exemplified later for $R^{101}$ to $R^{105}$ in formulae (1-1) and (1-2).

A pair of $R^{23}$ and $R^{24}$, or $R^{26}$ and $R^{27}$ may bond together to form a ring with the sulfur atom to which they are attached. Examples of the ring are as will be exemplified later for the ring that $R^{101}$ and $R^{102}$ in formula (1-1), taken together, form with the sulfur atom to which they are attached.

In formula (d1), $M^-$ is a non-nucleophilic counter ion. Examples of the non-nucleophilic counter ion include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesuulfonate: alkylsulfonate ions such as mesylate and butanesulfonate: imide ions such as bis(trifluorowethylsulfonyl)imide, bis(perfluoroethylsulfonyl)imide and bis(perfluorobutylsulfonyl)imide; methide ions such as tris(trifluoromethylsulfonyl)methide and tris(perfluoroethylsulfonyl)methide.

Also included are sulfonate ions having fluorine substituted at α-position as represented by the formula (d1-1) and sulfonate ions having fluorine substituted at α-position and trifluoromethyl at β-position as represented by the formula (d1-2).

$$R^{31}—CF_2—SO_3^- \quad (d1\text{-}1)$$

(d1-2)

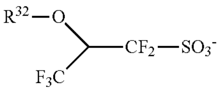

In formula (d1-1), $R^{31}$ is hydrogen or a $C_1$-$C_{20}$ hydrocarbyl group which may contain an ether bond, ester bond, carbonyl moiety, lactone ring, or fluorine atom. The hydrocarbyl group may be saturated or unsaturated and straight, branched or cyclic. Examples thereof are as will be exemplified later for the hydrocarbyl group $R^{111}$ in formula (1A').

In formula (d1-2), $R^{32}$ is hydrogen, or a $C_1$-$C_{30}$ hydrocarbyl group or $C_2$-$C_{30}$ hydrocarbylcarbonyl group, which may contain an ether bond, ester bond, carbonyl moiety or lactone ring. The hydrocarbyl group and the hydrocarbyl moiety in the hydrocarbylcarbonyl group may be saturated or unsaturated and straight, branched or cyclic. Examples thereof are as will be exemplified later for the hydrocarbyl group $R^{111}$ in formula (1A').

Examples of the cation in the monomer from which repeat unit (d1) is derived are shown below, but not limited thereto. $R^A$ is as defined above.

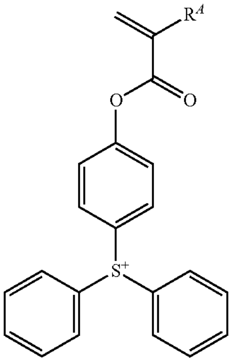

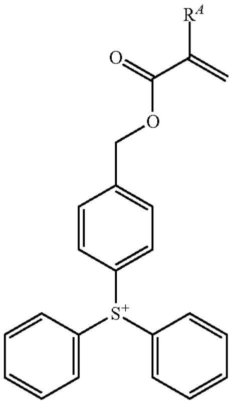

-continued

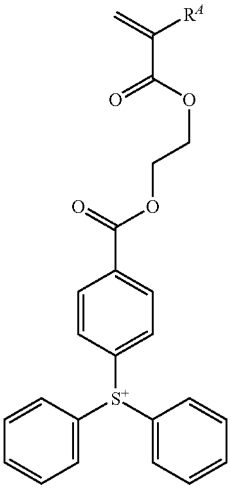

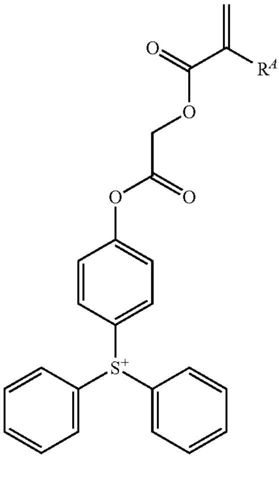

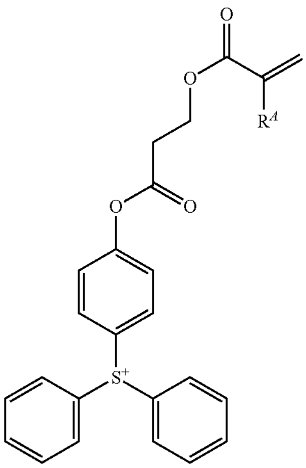

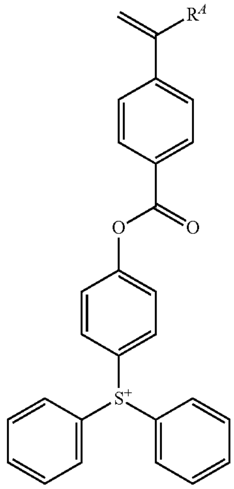

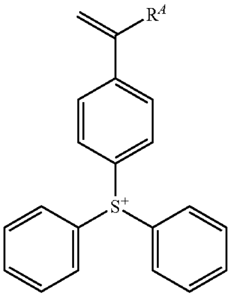

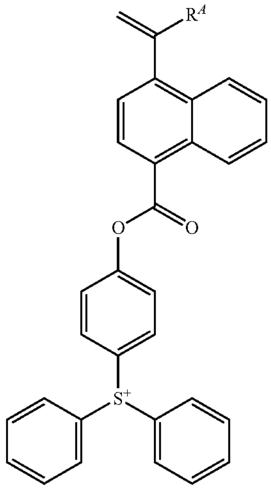

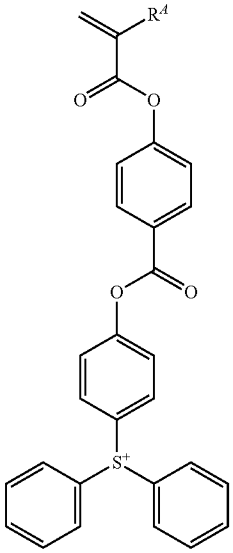
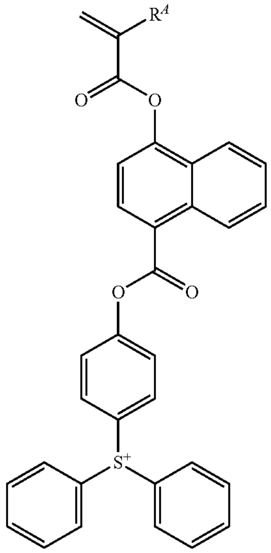
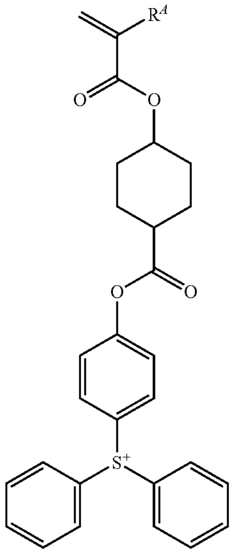
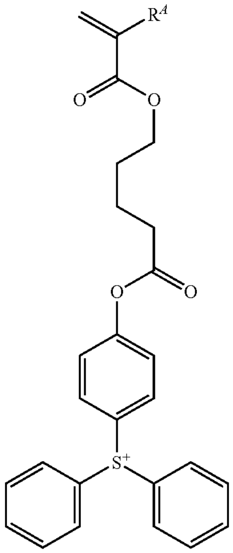
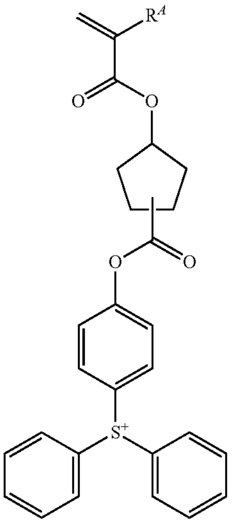
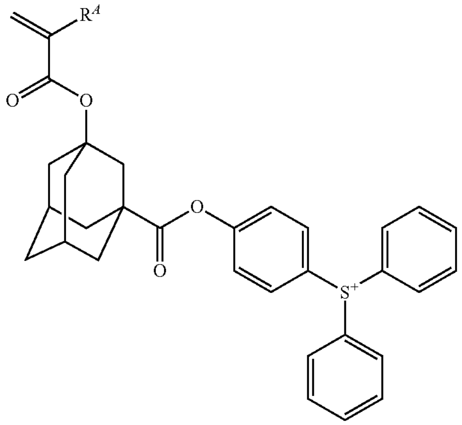
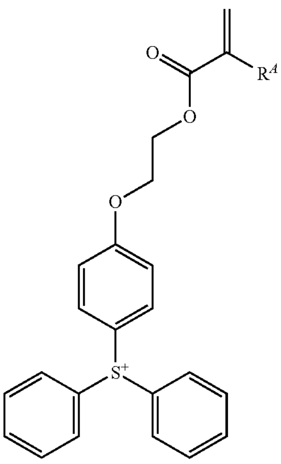
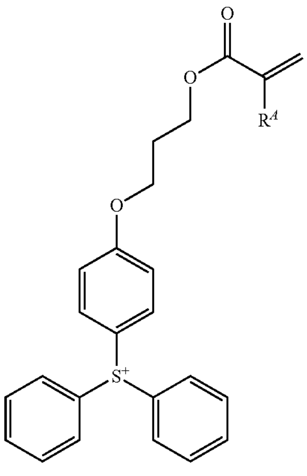

-continued
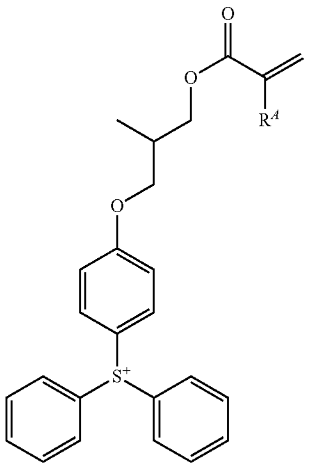
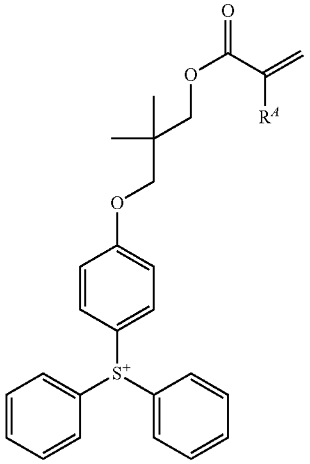
Examples of the cation in the monomer from which repeat unit (d2) or (d3) is derived are as will be exemplified later for the cation in the sulfonium salt having formula (1-1).
Examples of the anion in the monomer from which repeat unit (d2) is derived are shown below, but not limited thereto. $R^A$ is as defined above.
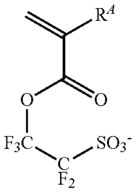
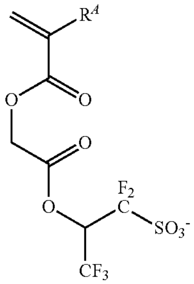
-continued
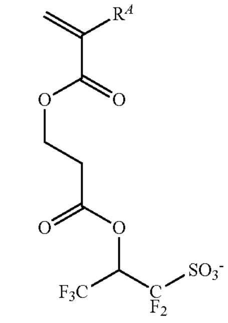
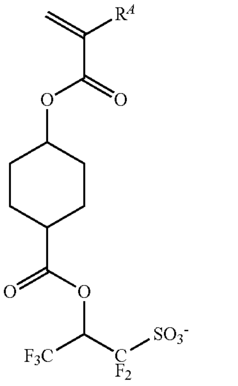
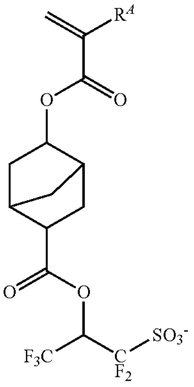
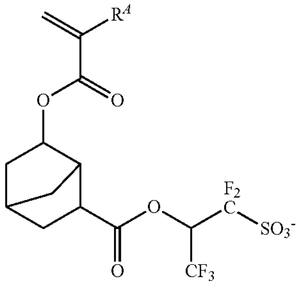
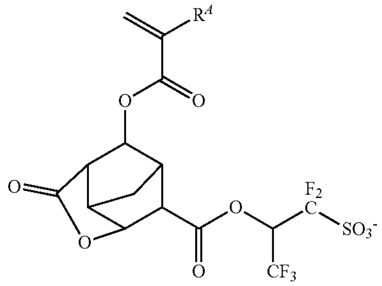
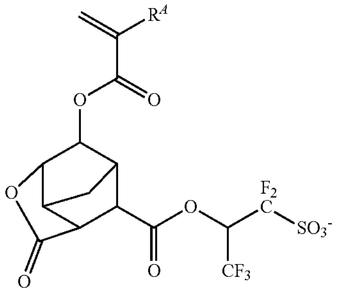
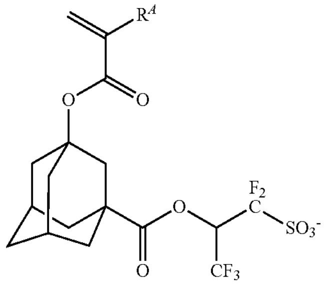

-continued
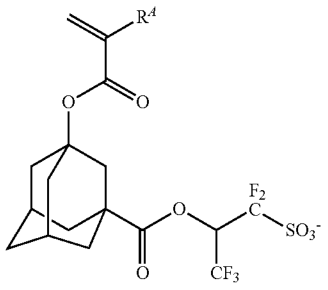
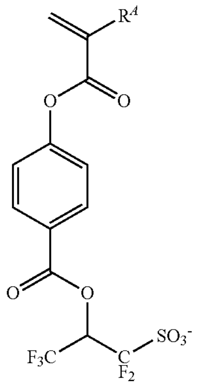
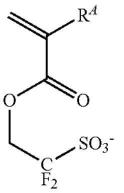
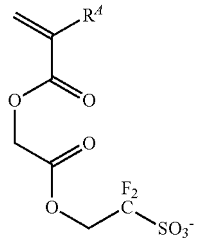
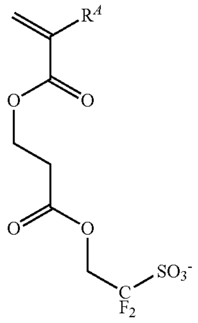
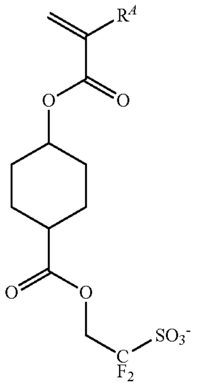
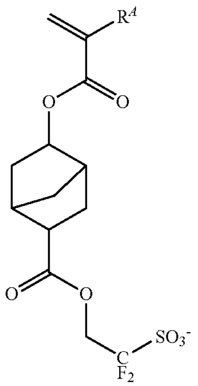
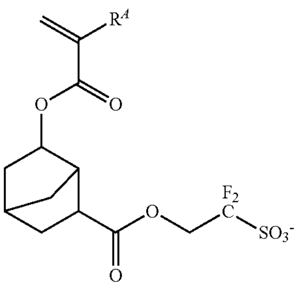
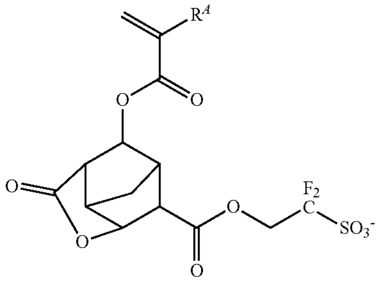
-continued
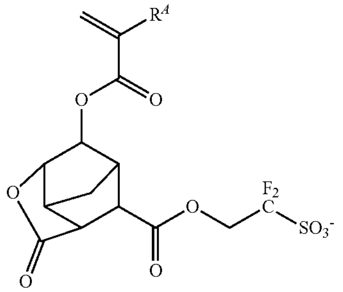
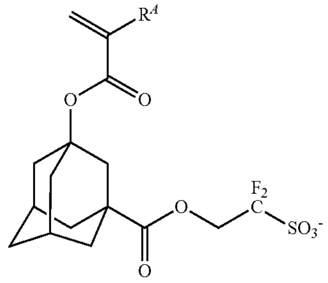
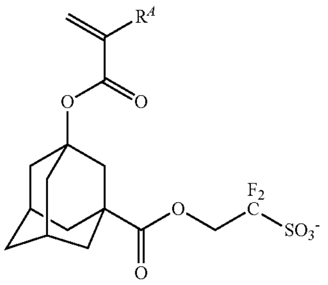
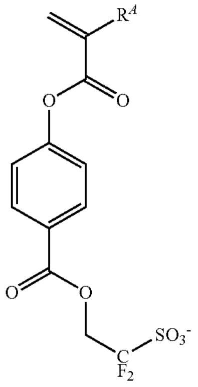
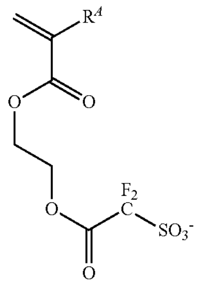
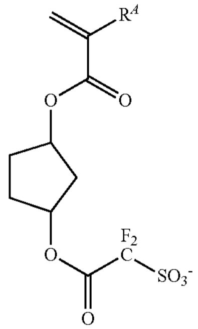
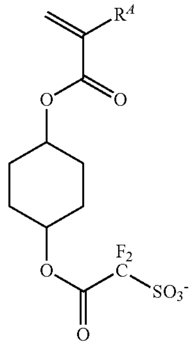
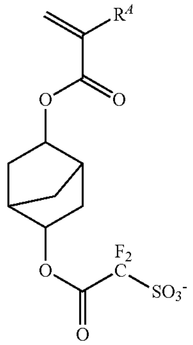

-continued
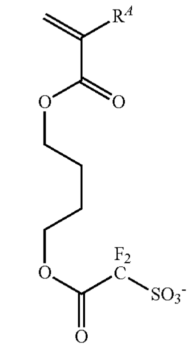
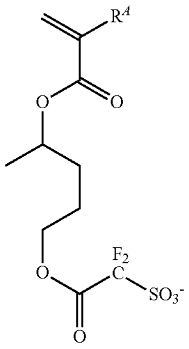
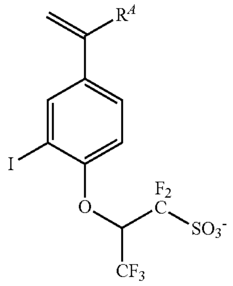
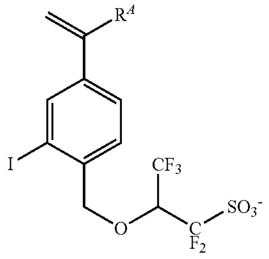
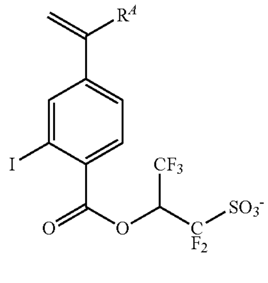
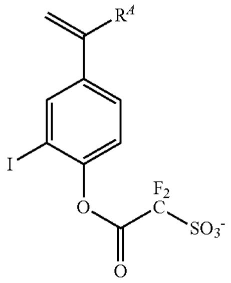
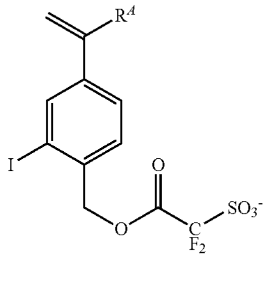
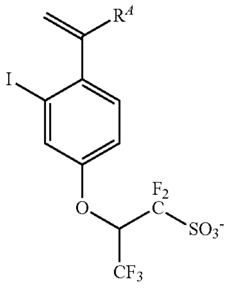
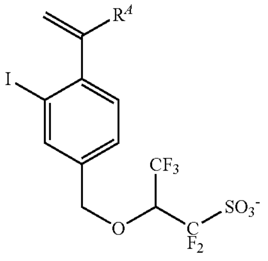
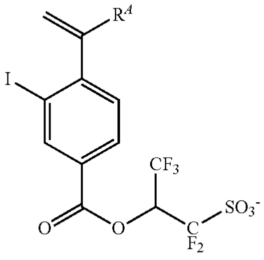
-continued
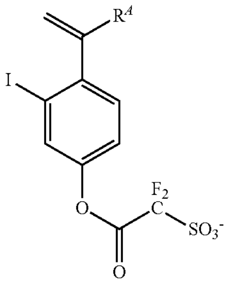
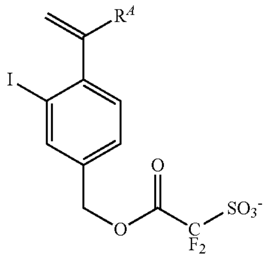
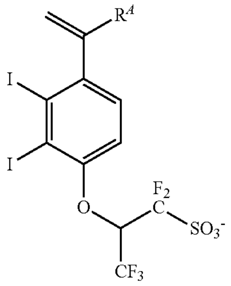
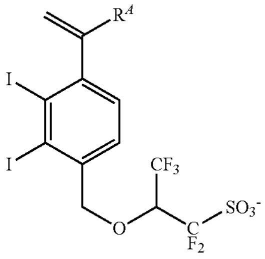
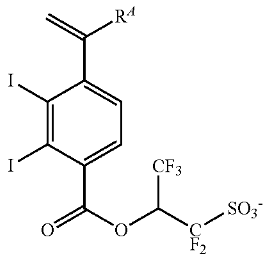
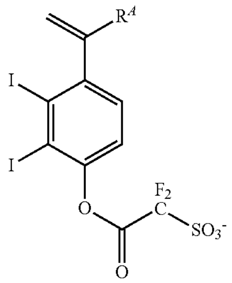
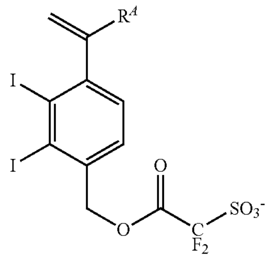
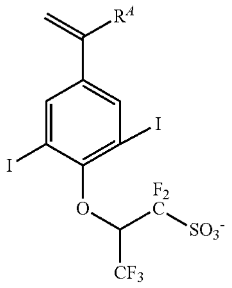
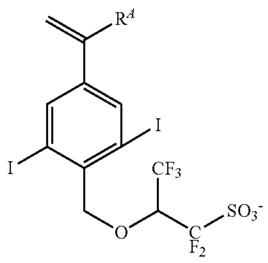
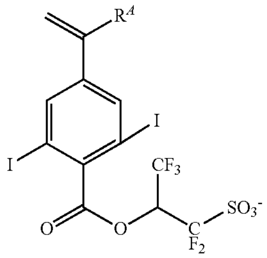
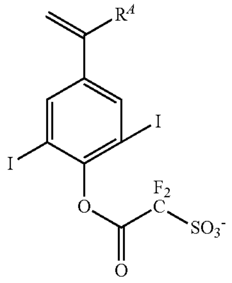
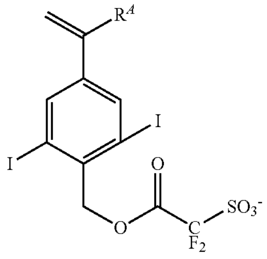

-continued
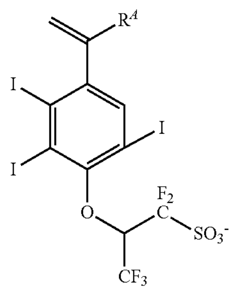
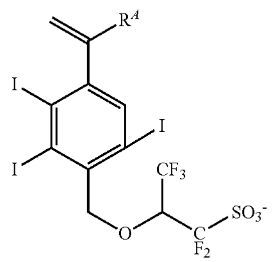
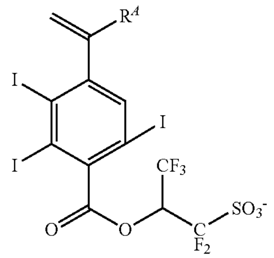
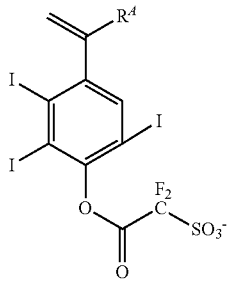
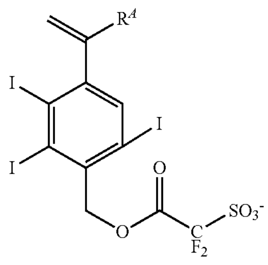
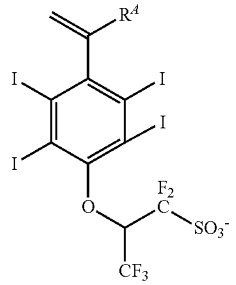
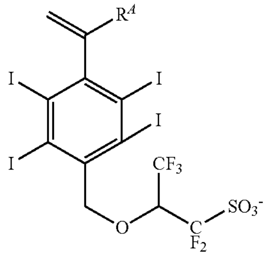
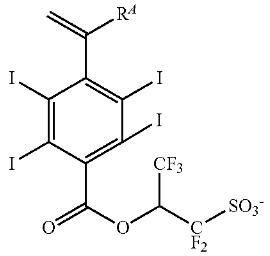
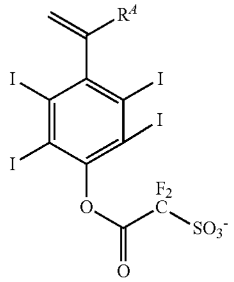
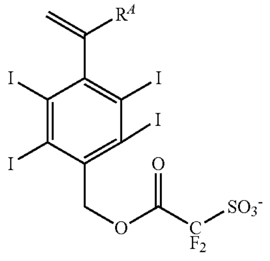
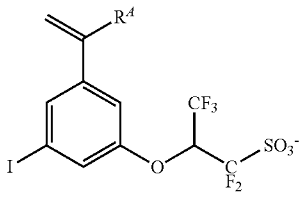
-continued
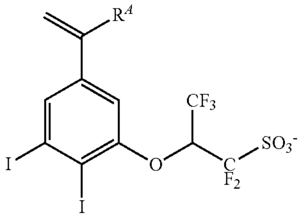
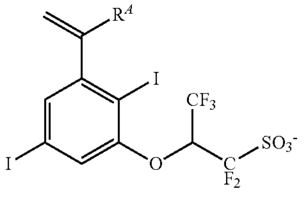
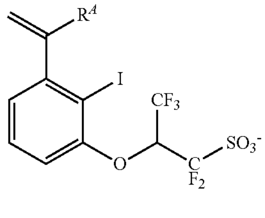
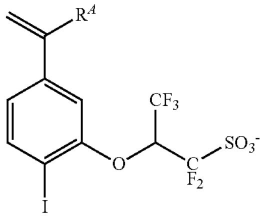
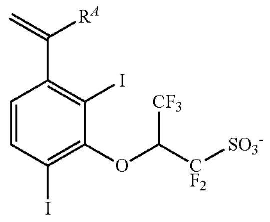
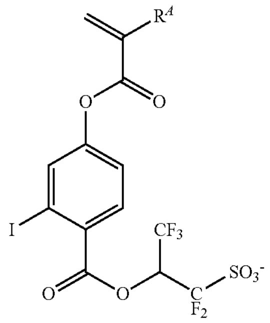
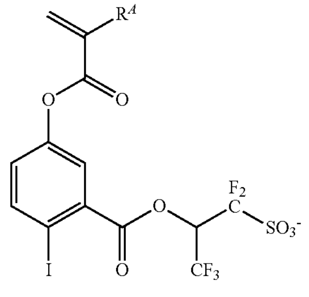

-continued
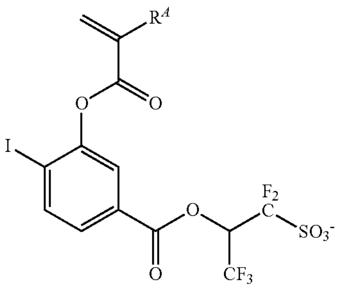
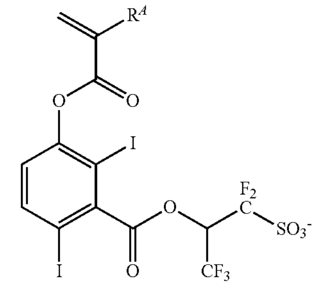
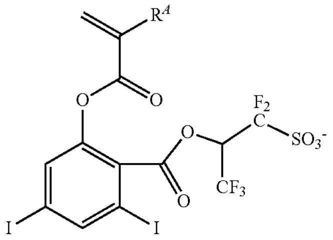
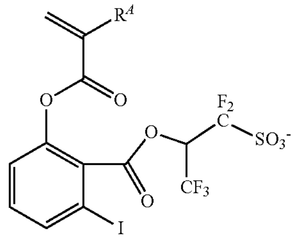
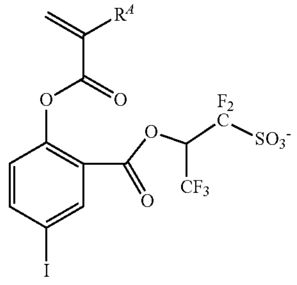
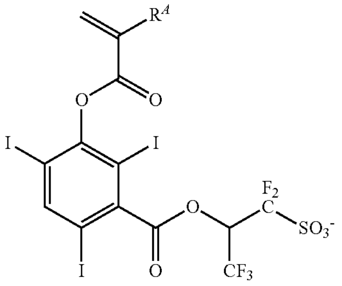
-continued
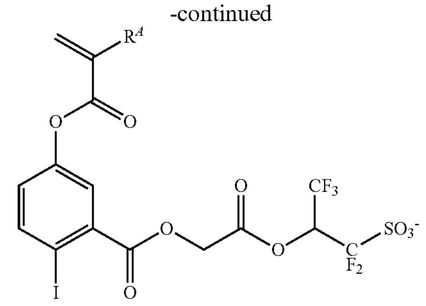
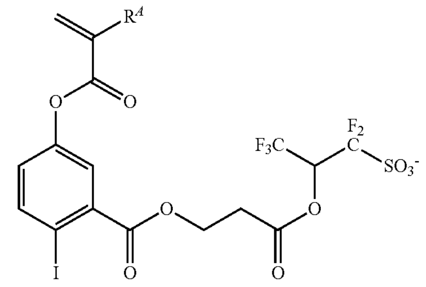
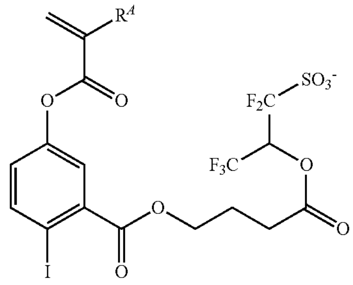
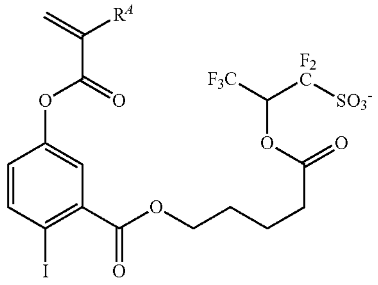
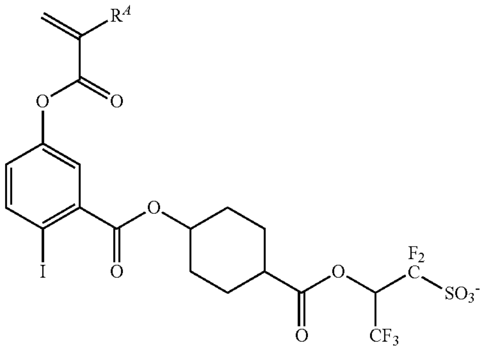

-continued
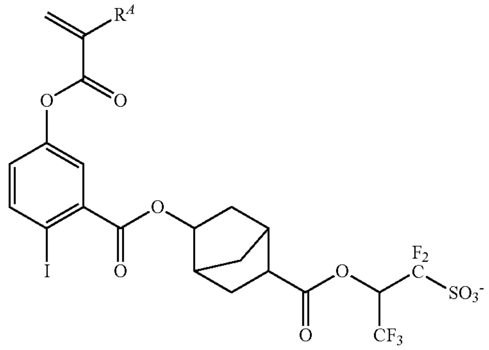
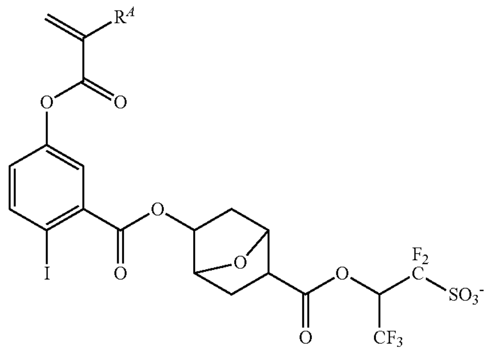
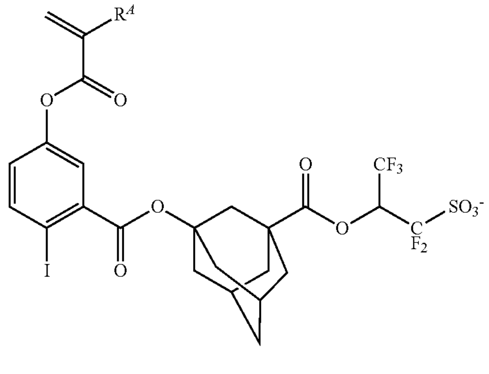
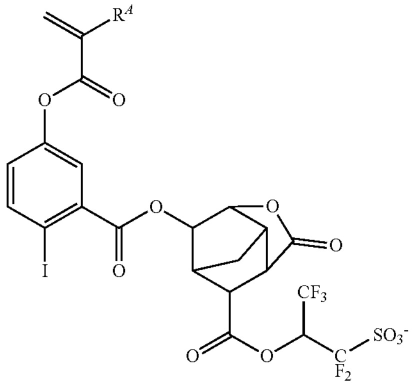
-continued
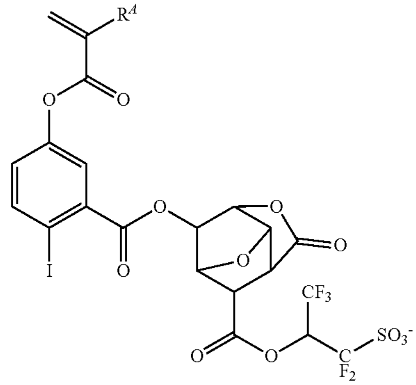
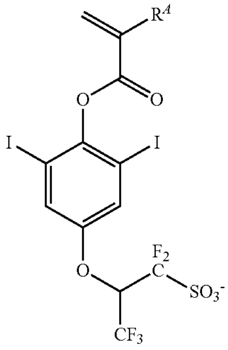
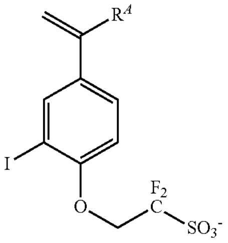
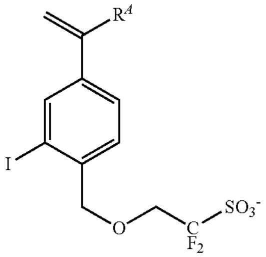
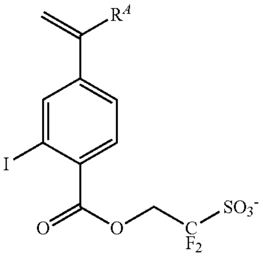
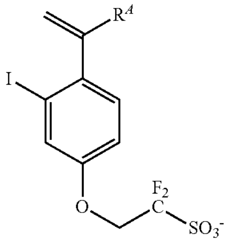
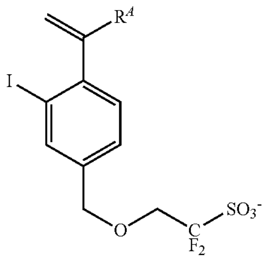
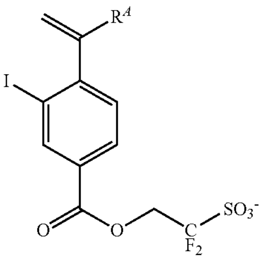

-continued
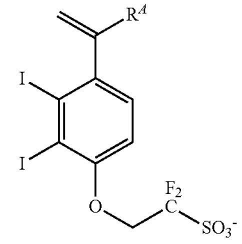
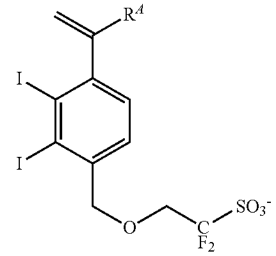
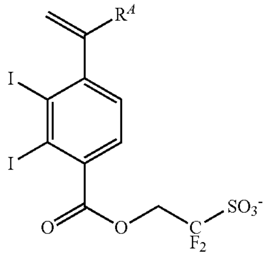
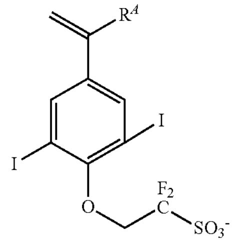
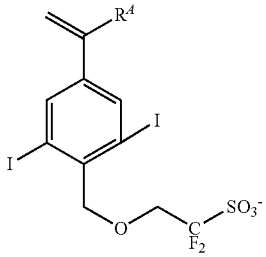
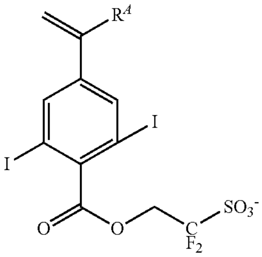
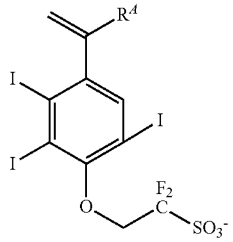
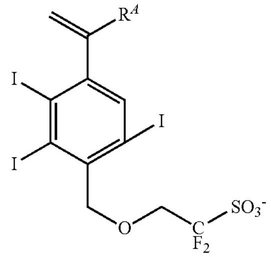
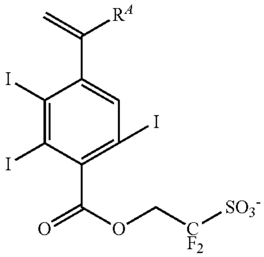
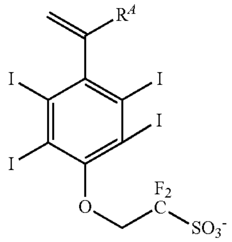
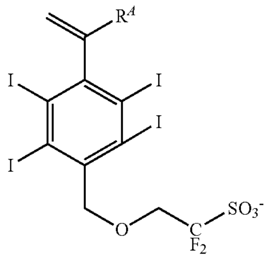
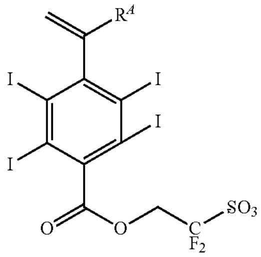
-continued
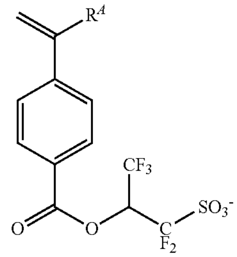
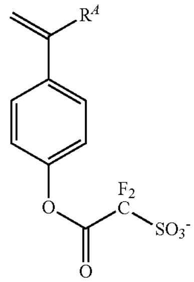
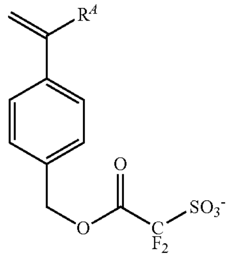
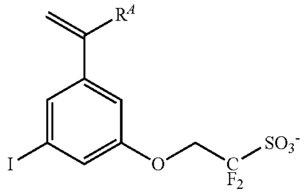
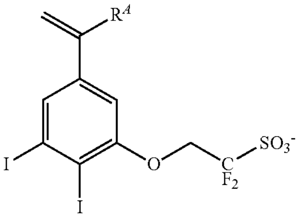
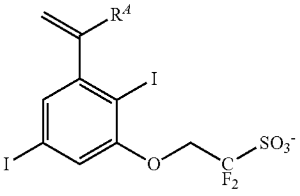
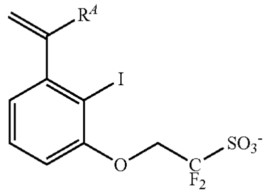
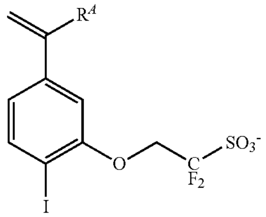
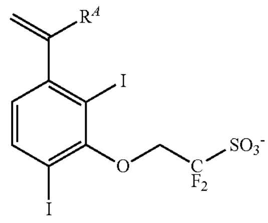
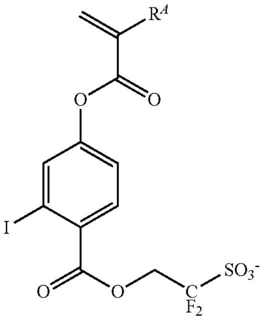

-continued
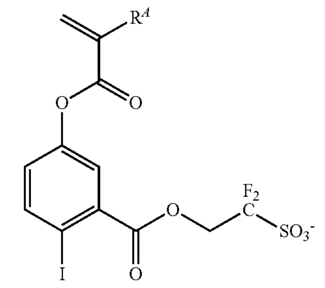
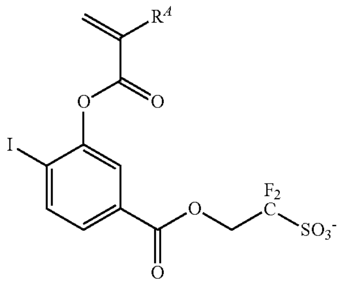
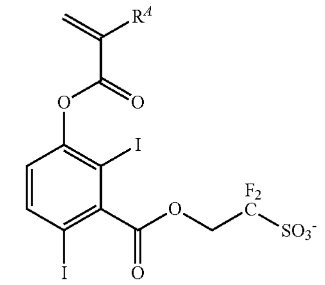
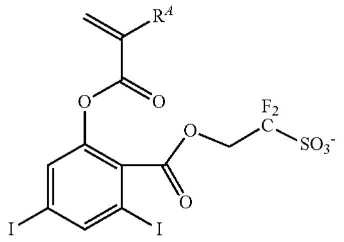
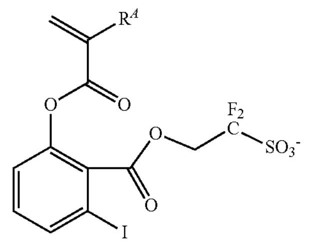
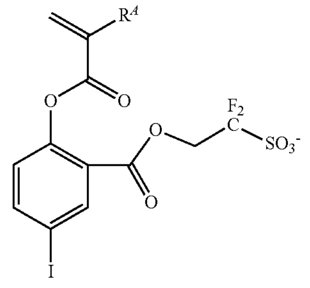
-continued
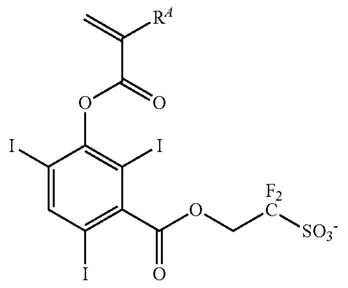
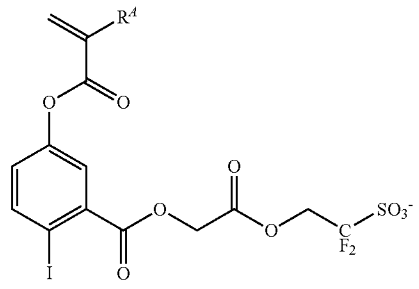
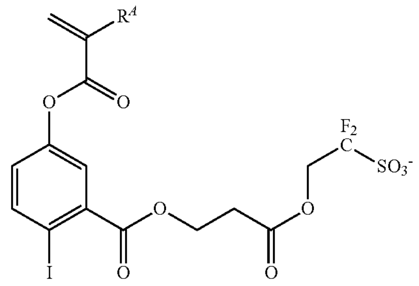
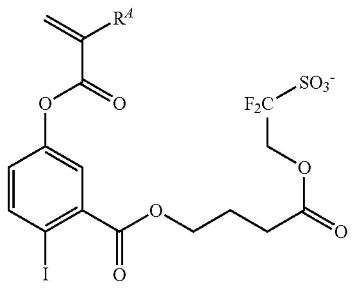
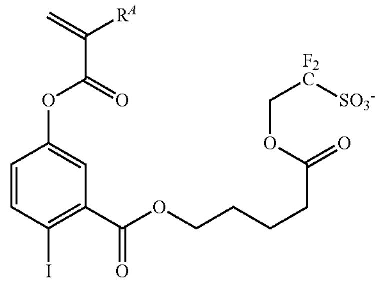

-continued
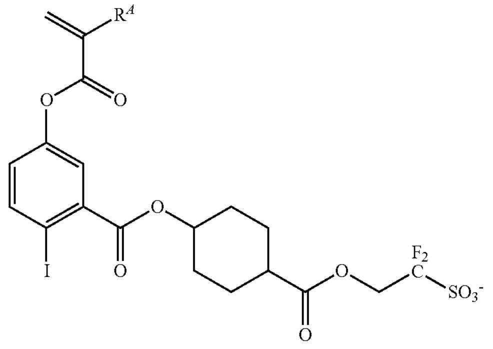
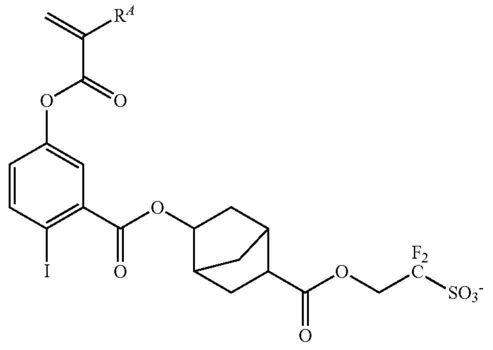
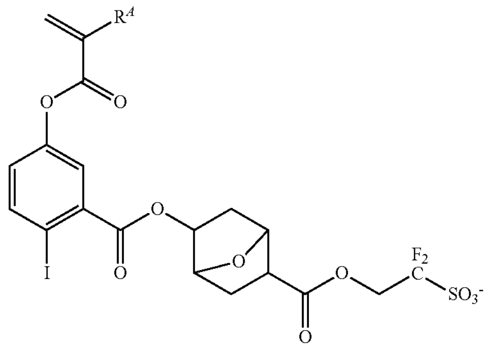
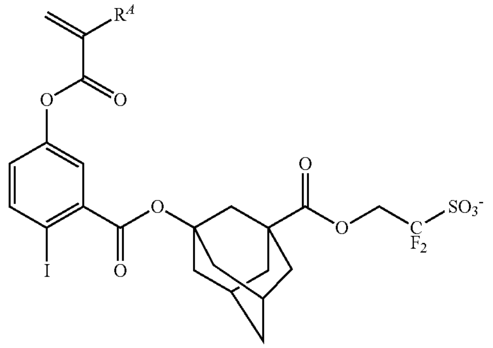
-continued
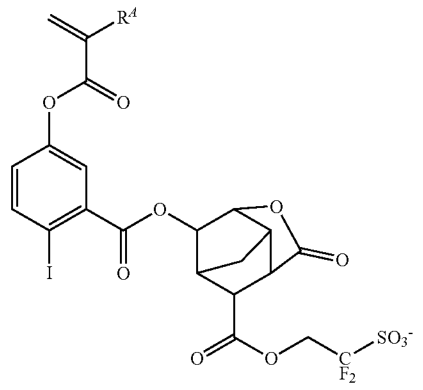
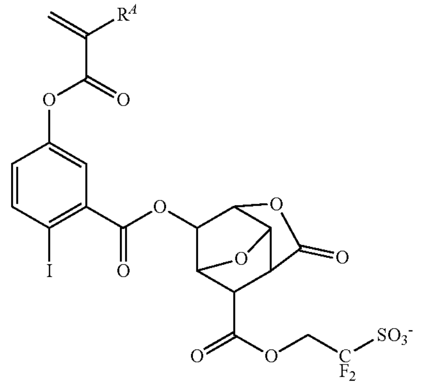
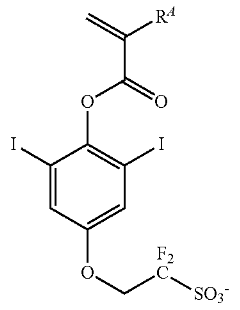
Examples of the anion in the monomer from which repeat unit (d3) is derived are shown below, but not limited thereto. $R^A$ is as defined above.
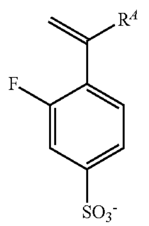
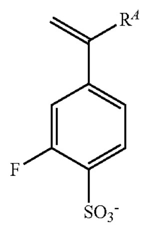
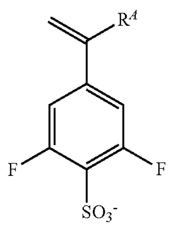
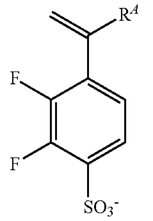
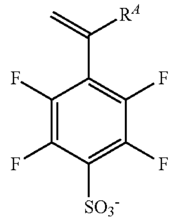
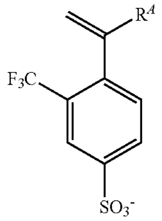

-continued
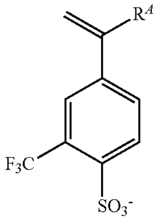
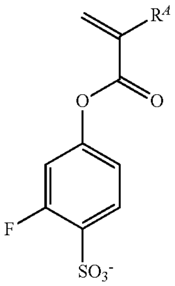
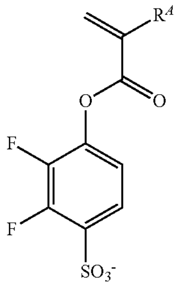
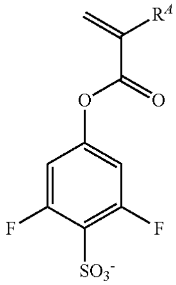
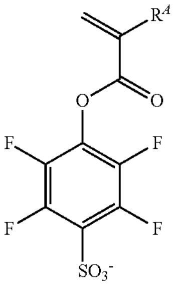
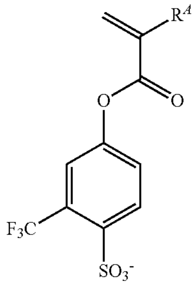
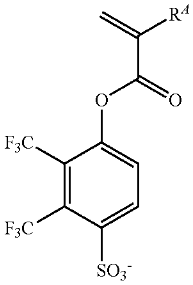
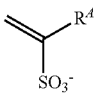
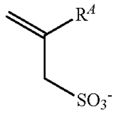
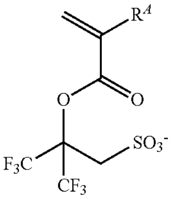
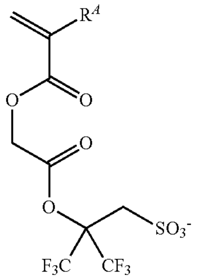
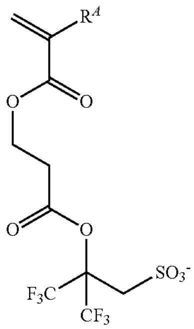
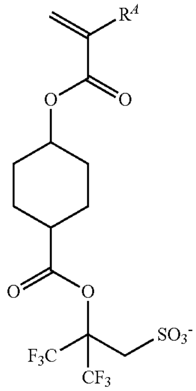
-continued
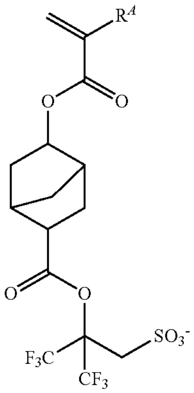
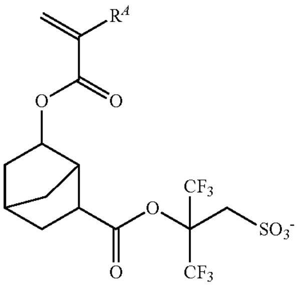
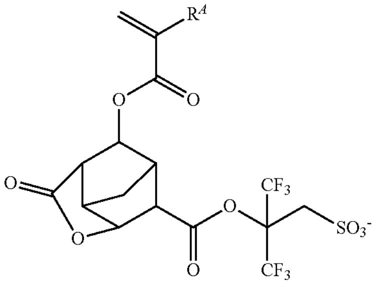
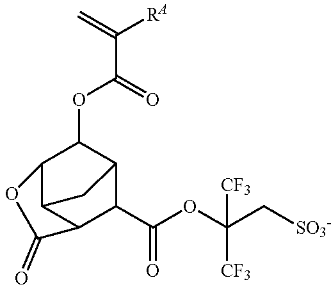
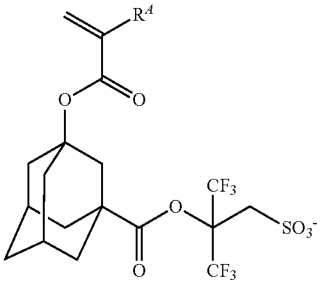
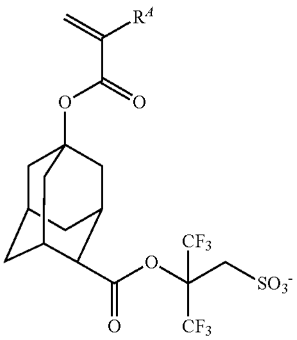
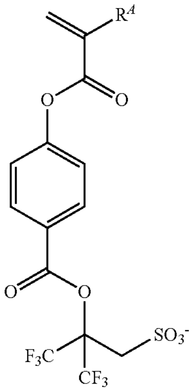

-continued

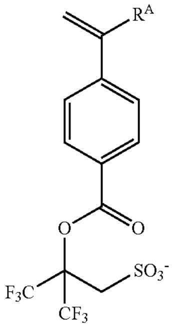

Repeat units (d1) to (d3) have the function of acid generator. The attachment of an acid generator to the polymer main chain is effective in restraining acid diffusion, thereby preventing a reduction of resolution due to blur by acid diffusion. Also, LWR and CDU are improved since the acid generator is uniformly distributed. When a base polymer comprising repeat units (d) is used, that is, in the case of polymer-bound acid generator, an acid generator of addition type (to be described later) may be omitted.

The base polymer may further comprise a repeat unit (e) containing iodine. Examples of the monomer from which repeat unit (e) is derived are shown below, but not limited thereto. Herein $R^A$ is as defined above.

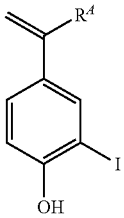 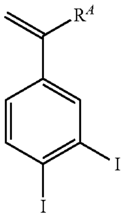 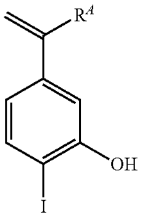 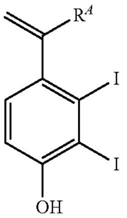

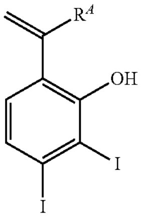 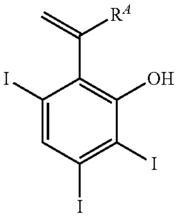 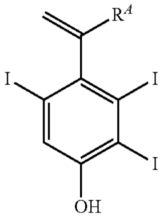

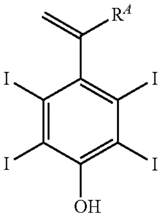 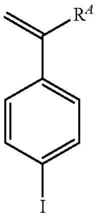 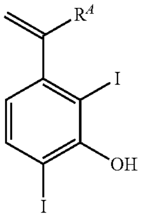

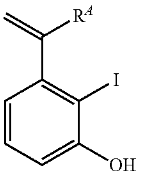 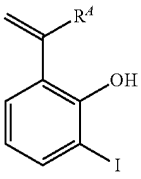 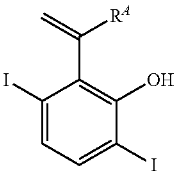

-continued

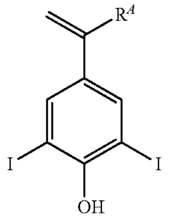 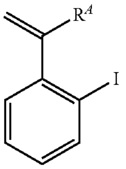 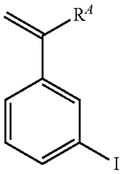

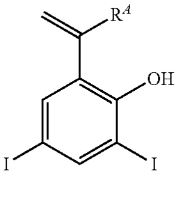 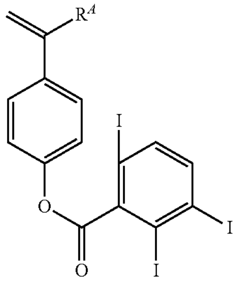

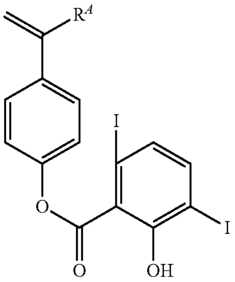 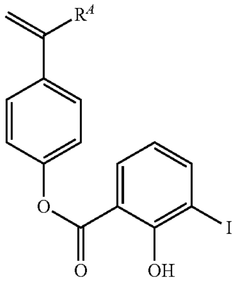

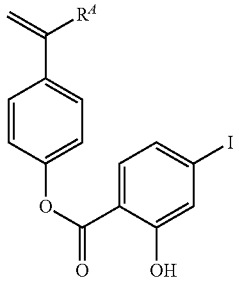 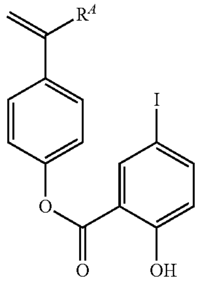

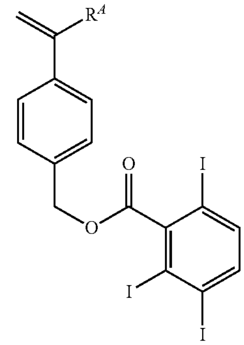 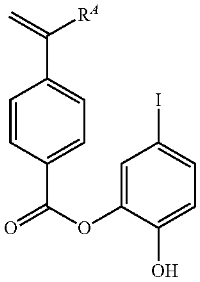

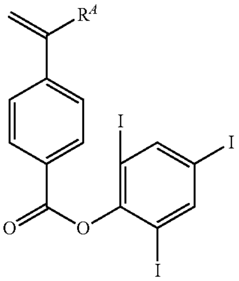 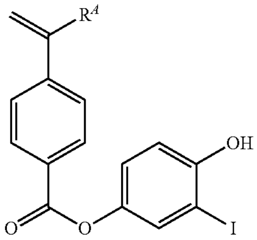

-continued

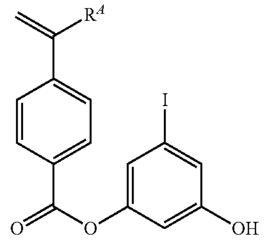
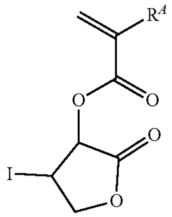
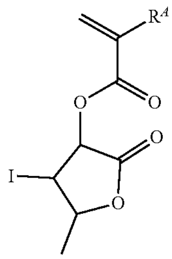
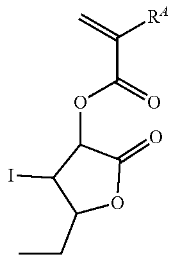
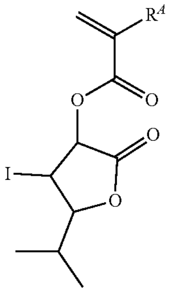
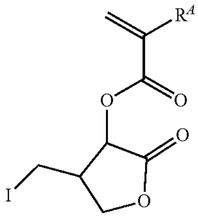
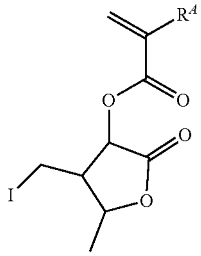
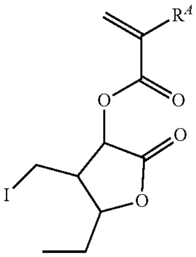
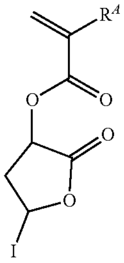
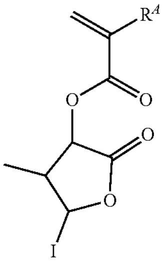
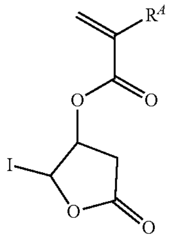
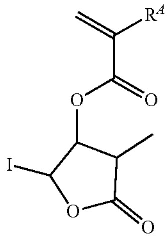
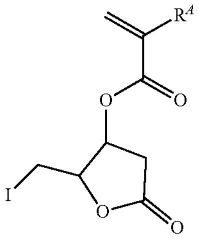
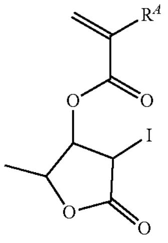
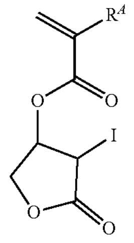

Besides the repeat units described above, the base polymer may further comprise a repeat unit (f) which is derived from styrene, vinylnaphthalene, indene, acenaphthylene, coumarin, and coumarone compounds.

In the base polymer comprising repeat units (b1), (b2), (c), (d1), (d2), (d3), (e) and (f), a fraction of these units is: preferably $0 \le b1 \le 0.9$, $0 \le b2 \le 0.9$, $0.1 \le b1+b2 \le 0.9$, $0 \le c \le 0.9$, $0 \le d1 \le 0.5$, $0 \le d2 \le 0.5$, $0 \le d3 \le 0.5$, $0 \le d1+d2+d3 \le 0.5$, $0 \le e \le 0.5$, and $0 \le f \le 0.5$;

more preferably $0 \le b1 \le 0.8$, $0 \le b2 \le 0.8$, $0.2 \le b1+b2 \le 0.8$, $0 \le c \le 0.8$, $0 \le d1 \le 0.4$, $0 \le d2 \le 0.4$, $0 \le d3 \le 0.4$, $0 \le d1+d2+d3 \le 0.4$, $0 \le e \le 0.4$, and $0 \le f \le 0.4$; and even more preferably $0 \le b1 \le 0.7$, $0 \le b2 \le 0.7$, $0.25 \le b1+b2 \le 0.7$, $0 \le c \le 0.7$, $0 \le d1 \le 0.3$, $0 \le d2 \le 0.3$, $0 \le d3 \le 0.3$, $0 \le d1+d2+d3 \le 0.3$, $0 \le e \le 0.3$, and $0 \le f \le 0.3$. Notably, $b1+b2+c+d1+d2+d3+e+f=1.0$.

The base polymer may be synthesized by any desired methods, for example, by dissolving monomers corresponding to the foregoing repeat units in an organic solvent, adding a radical polymerization initiator and a chain transfer agent in the form of a sulfonium salt containing a carboxylate anion having a thiol group linked thereto to the solution, and heating for polymerization. Using the chain transfer agent, the base polymer can be end-capped with a sulfonium salt containing a carboxylate anion having a thiol group linked thereto. The polymerization initiator and the chain transfer agent may be added at the start of polymerization, during polymerization, or gradually in the course of polymerization.

The chain transfer agent is generally used for the purpose of reducing the molecular weight of a polymer. The polymerization initiator generates radicals, with which polymerization is advanced. Activating radicals transfer to the sulfonium salt containing a carboxylate anion having a thiol group linked thereto, from which polymerization starts. In this way, the sulfonium salt containing a carboxylate anion having a thiol group linked thereto bonds to the polymer at its end.

A lowering of molecular weight brings about the advantage that a polymer is unlikely to swell in a developer. Since the glass transition temperature (Tg) of the polymer is accordingly lowered, there arises a disadvantage that acid diffusion during PEB is promoted. A polymeric quencher has a remarkable acid diffusion-suppressing effect, which is maintained even when the molecular weight of the polymer is lowered. Particularly when a quencher is disposed at the end of a polymer as in the invention, the acid trapping capability can be enhanced. The invention aims to provide a material which can meet both minimal swell in developer and low acid diffusion by reducing the molecular weight.

The amount of the chain transfer agent used may be selected in accordance with the desired molecular weight, monomers or reactants, and preparation conditions including polymerization temperature and mode.

The polymerization initiator used herein may be selected from those commercially available as the radical polymerization initiator. The preferred radical polymerization initiators include azo and peroxide initiators while they may be used alone or in admixture.

The amount of the polymerization initiator used may be selected in accordance with the desired molecular weight, monomers or reactants, and preparation conditions including polymerization temperature and mode.

Examples of the azo initiator include 2,2'-azobisisobutyronitrile (AIBN), 2,2'-azobis(2,4-dimethylvaleronitrile), dimethyl 2,2-azobis(2-methylpropionate), 2,2'-azobis(4-methoxy-2,4-dimethylvaleronitrile), 2,2'-azobis(cyclohexane-1-carbonitrile), 4,4'-azobis(4-cyanovaleric acid), and dimethyl 2,2'-azobis(isobutyrate). Examples of the peroxide initiator include benzoyl peroxide, decanoyl peroxide, lauroyl peroxide, succinic acid peroxide, tert-butyl peroxy-2-ethylhexanoate, tert-butyl peroxypivalate, and 1,1,3,3-tetramethylbutyl peroxy-2-ethylhexanoate.

Examples of the organic solvent which can be used for polymerization include toluene, benzene, tetrahydrofuran (THF), diethyl ether, and dioxane. Preferably the polymerization temperature is 50 to 80° C. and the reaction time is 2 to 100 hours, more preferably 5 to 20 hours.

In the case of a monomer having a hydroxy group, the hydroxy group may be replaced by an acetal group susceptible to deprotection with acid, typically ethoxyethoxy, prior to polymerization, and the polymerization be followed by deprotection with weak acid and water. Alternatively, the hydroxy group may be replaced by an acetyl, formyl, pivaloyl or similar group prior to polymerization, and the polymerization be followed by alkaline hydrolysis.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the polymer product to hydroxystyrene or hydroxyvinylnaphthalene. For alkaline hydrolysis, a base such as aqueous ammonia or triethylamine may be used. Preferably the reaction temperature is −20° C. to 100° C., more preferably 0° C. to 60° C., and the reaction time is 0.2 to 100 hours, more preferably 0.5 to 20 hours.

The base polymer should preferably have a weight average molecular weight (Mw) in the range of 1,000 to 500,000, and more preferably 2,000 to 30,000, as measured by GPC versus polystyrene standards using tetrahydrofuran (THF) solvent. With too low a Mw, the resist composition may become less heat resistant. A polymer with too high a Mw is likely to lose alkaline solubility and give rise to a footing phenomenon after pattern formation. If a base polymer has a wide molecular weight distribution or dispersity (Mw/Mn), which indicates the presence of lower and higher molecular weight polymer fractions, there is a possibility that foreign matter is left on the pattern or the pattern profile is degraded. The influences of Mw and Mw/Mn become stronger as the pattern rule becomes finer. Therefore, the base polymer should preferably have a narrow dispersity (Mw/Mn) of 1.0 to 2.0, especially 1.0 to 1.5, in order to provide a resist composition suitable for micropatterning to a small feature size.

The base polymer may be a blend of two or more polymers which differ in compositional ratio, Mw or Mw/Mn. It may also be a blend of polymers containing different terminal structures (a), or a blend of a polymer containing terminal structure (a) and a polymer free of terminal structure (a).

Acid Generator

The positive resist composition may contain an acid generator capable of generating a strong acid, also referred to as acid generator of addition type. As used herein, the "strong acid" is a compound having a sufficient acidity to induce deprotection reaction of acid labile groups on the base polymer.

The acid generator is typically a compound (PAG) capable of generating an acid upon exposure to actinic ray or radiation. Although the PAG used herein may be any compound capable of generating an acid upon exposure to high-energy radiation, those compounds capable of generating sulfonic acid, imidic acid (imide acid) or methide acid are preferred. Suitable PAGs include sulfonium salts, iodonium salts, sulfonyldiazomethane, N-sulfonyloxyinlide, and oxime-O-sulfonate acid generators. Suitable PAGs are as exemplified in U.S. Pat. No. 7,537,880 (JP-A 2008-111103, paragraphs [0122]-[0142]).

As the PAG used herein, sulfonium salts having the formula (1-1) and iodonium salts having the formula (1-2) are also preferred.

(1-1)

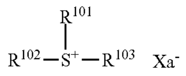

(1-2)

$R^{104}—I^{+}—R^{105}$ $Xa^{-}$

In formulae (1-1) and (1-2), $R^{101}$ to $R^{105}$ are each independently halogen or a $C_1$-$C_{20}$ hydrocarbyl group which may contain a heteroatom.

Suitable halogen atoms include fluorine, chlorine, bromine and iodine.

The $C_1$-$C_{20}$ hydrocarbyl group represented by $R^{101}$ to $R^{105}$ may be saturated or unsaturated and straight, branched or cyclic. Examples thereof include $C_1$-$C_{20}$ alkyl groups such as methyl, ethyl, n-propyl, isopropyl, n-butyl, isobutyl, sec-butyl, tert-butyl, n-pentyl, n-hexyl, n-octyl, n-nonyl, n-decyl, undecyl, dodecyl, tridecyl, tetradecyl, pentadecyl, heptadecyl, octadecyl, nonadecyl and icosyl $C_3$-$C_{20}$ cyclic saturated hydrocarbyl groups such as cyclopropyl, cyclopentyl, cyclohexyl, cyclopropylmethyl, 4-methylcyclohexyl, cyclohexylmethyl, norbornyl, and adamantyl; $C_2$-$C_{20}$ alkenyl groups such as vinyl, propenyl, butenyl and hexenyl; $C_2$-$C_{20}$ alkynyl groups such as ethynyl, propynyl and butynyl; $C_3$-$C_{20}$ cyclic unsaturated aliphatic hydrocarbyl groups such as cyclohexenyl and norbornenyl; $C_6$-$C_{20}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutylnaphthyl, sec-butylnaphthyl, and tert-butylnaphthyl; $C_7$-$C_{20}$ aralkyl groups such as benzyl and phenethyl; and combinations thereof.

In the foregoing hydrocarbyl groups, some or all of the hydrogen atoms may be substituted by a moiety containing a heteroatom such as oxygen, sulfur, nitrogen or halogen, and some constituent —$CH_2$— may be replaced by a moiety containing a heteroatom such as oxygen, sulfur or nitrogen, so that the group may contain a hydroxy, fluorine, chlorine, bromine, iodine, cyano, nitro, carbonyl, ether bond, ester bond, sulfonic ester bond, carbonate bond, lactone ring, sultone ring, carboxylic anhydride or haloalkyl moiety.

$R^{101}$ and $R^{102}$ may bond together to form a ring with the sulfur atom to which they are attached. Preferred examples of the ring are shown below.

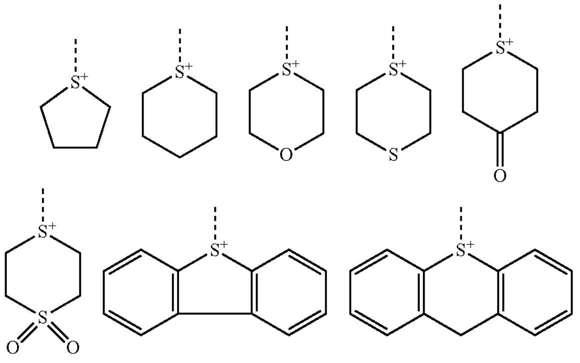

-continued
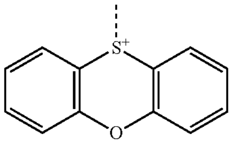
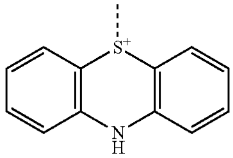
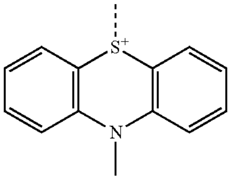
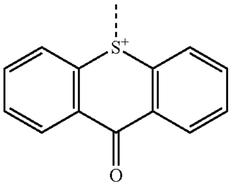
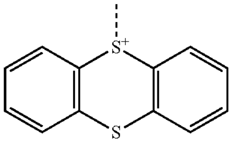
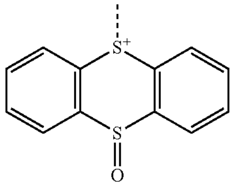
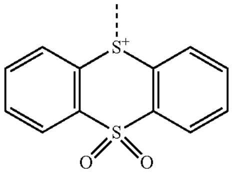
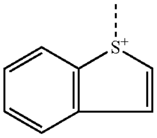
Herein the broken line designates a point of attachment to $R^{103}$.
Examples of the cation in the sulfonium salt having formula (1-1) are shown below, but not limited thereto.
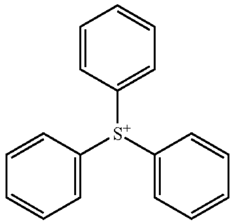
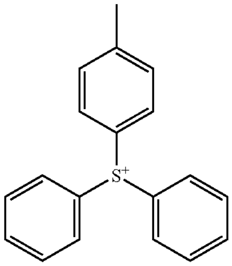
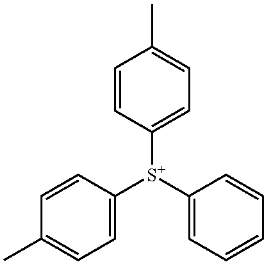
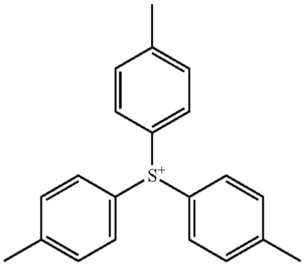
-continued
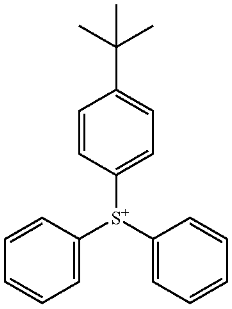
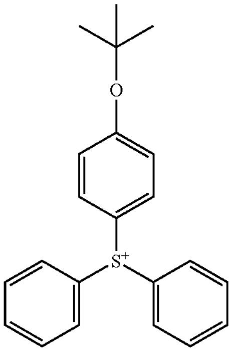
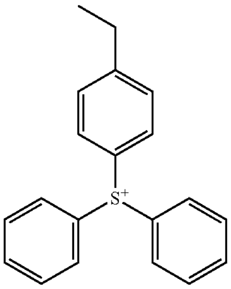
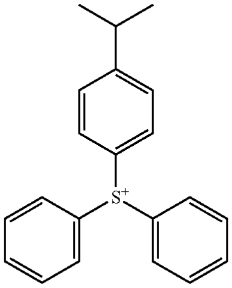
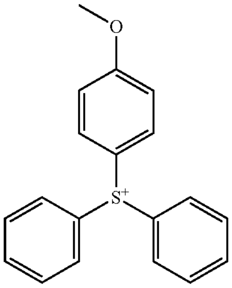
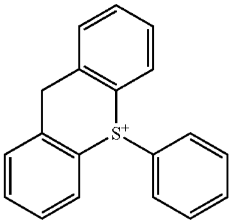
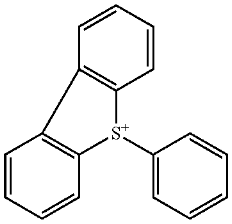
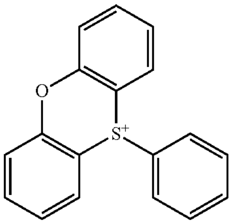
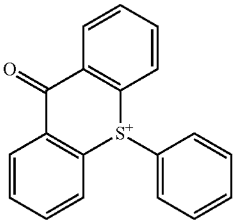
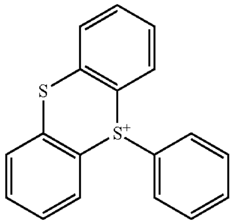
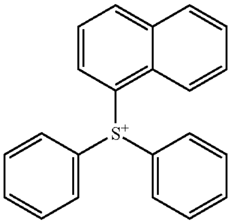
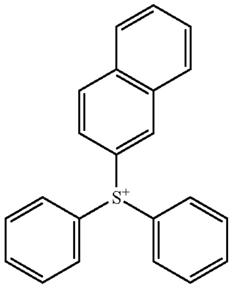

-continued
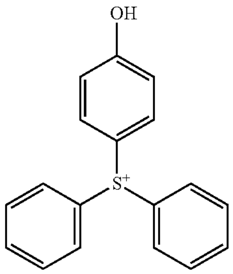
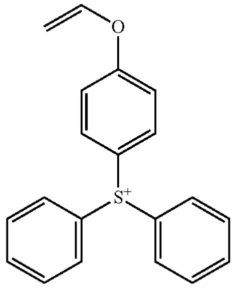
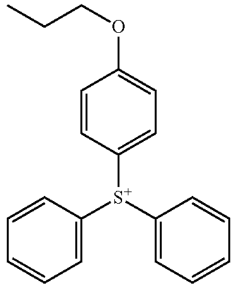
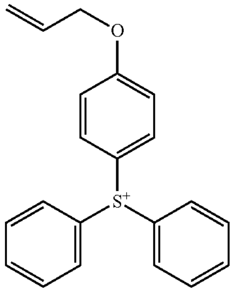
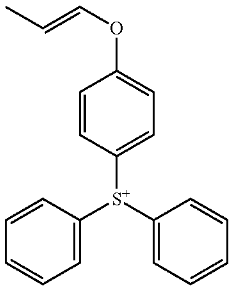
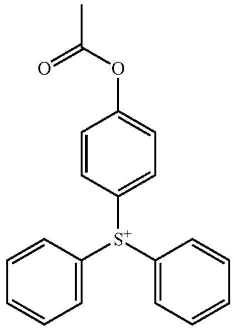
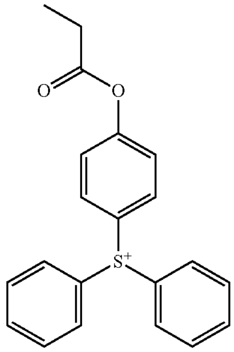
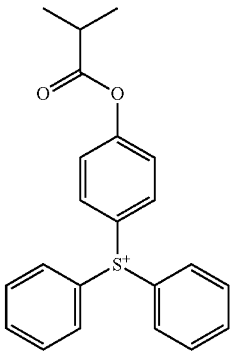
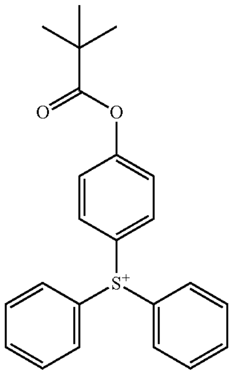
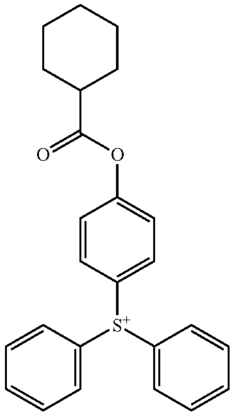
-continued
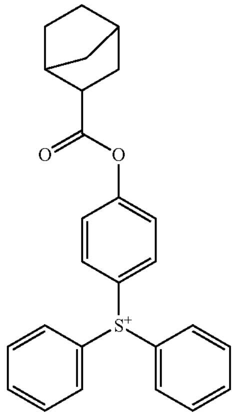
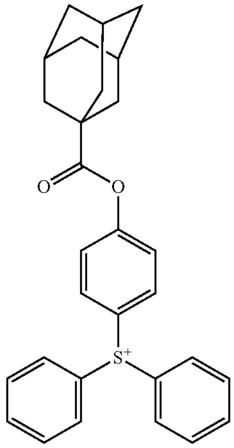
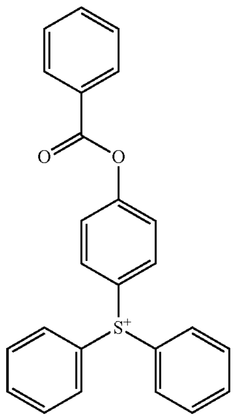
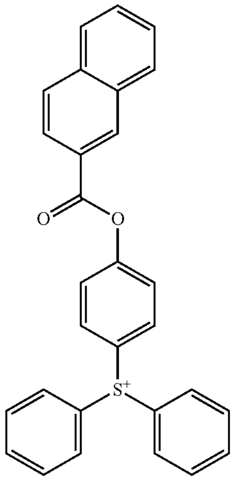
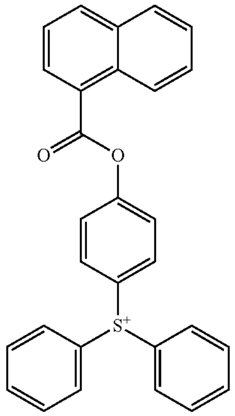
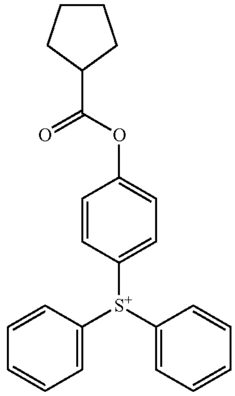

-continued
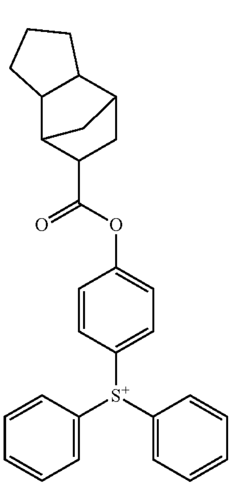
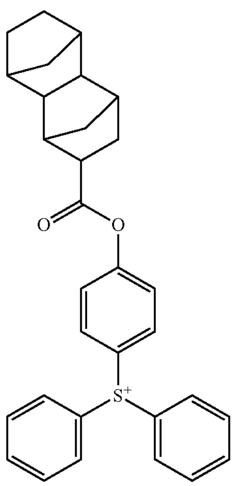
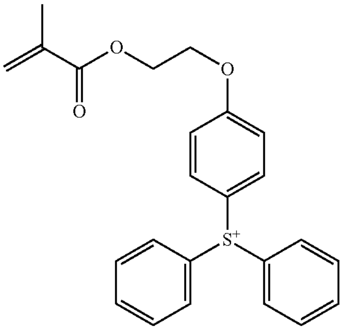
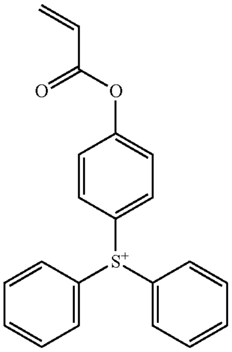
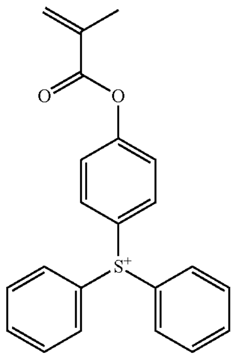
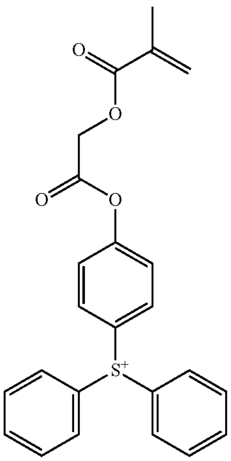
-continued
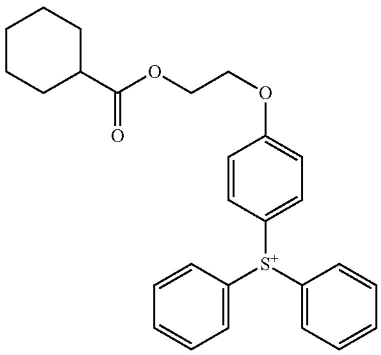
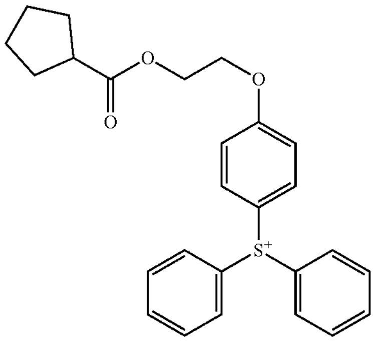
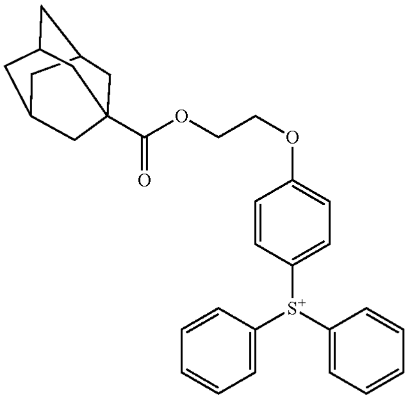
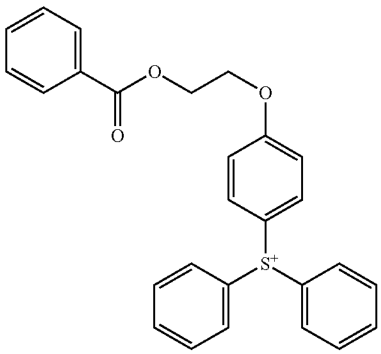

-continued
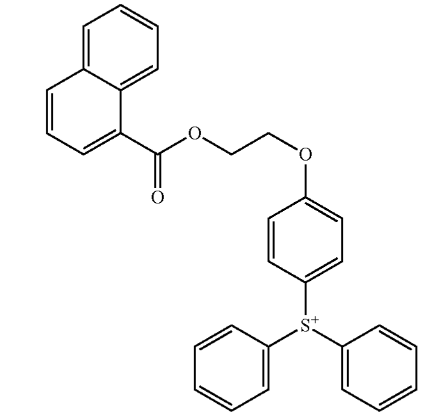
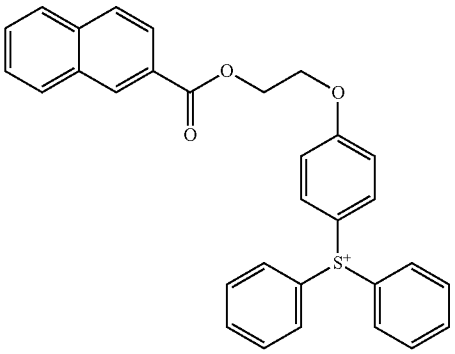
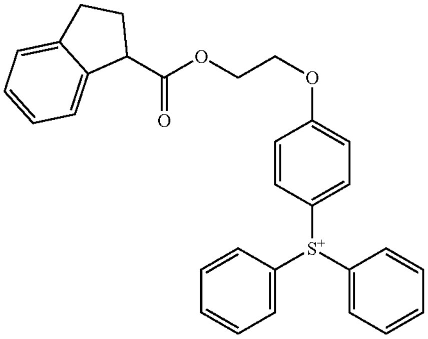
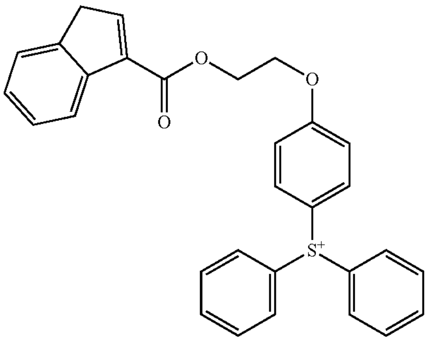
-continued
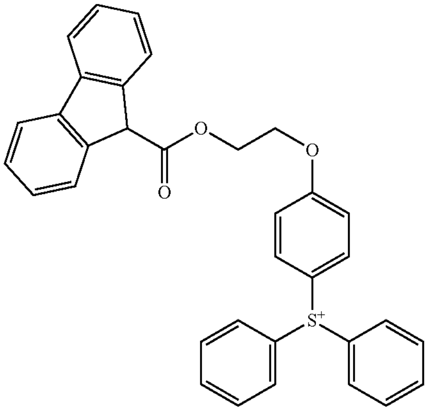
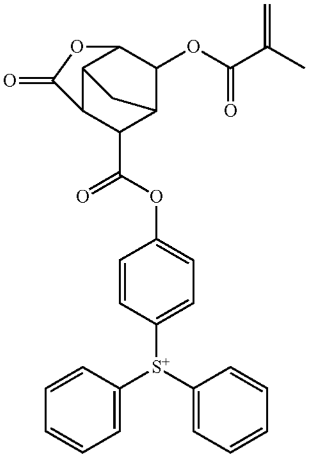
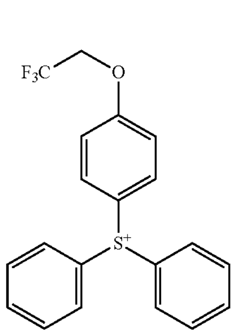
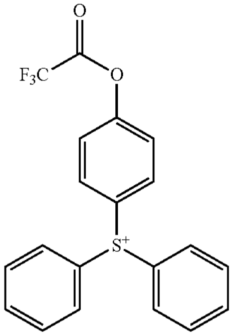
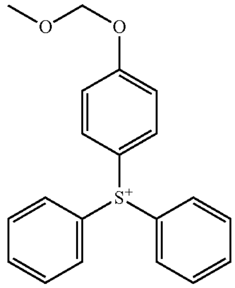
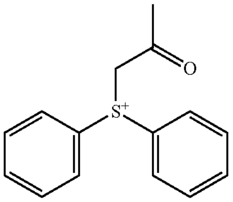

-continued
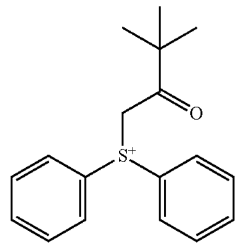
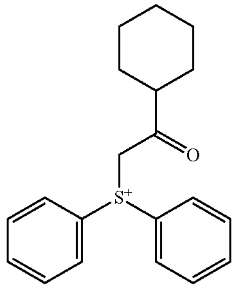
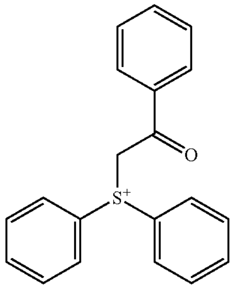
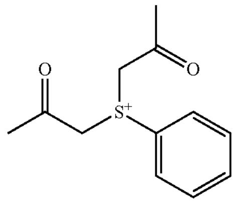
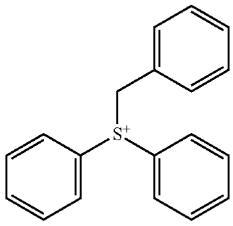
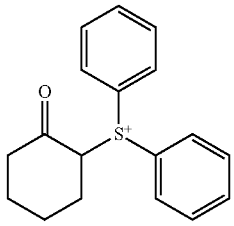
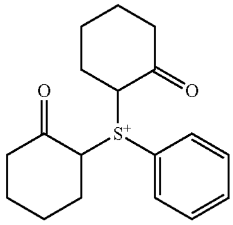
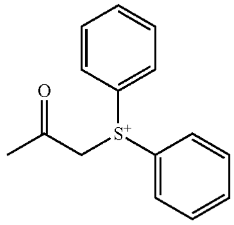
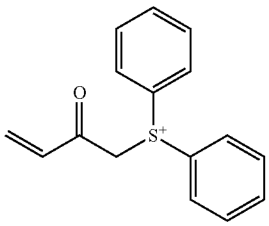
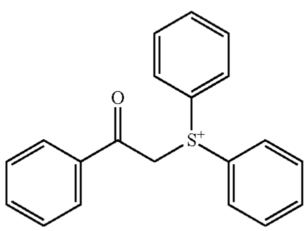
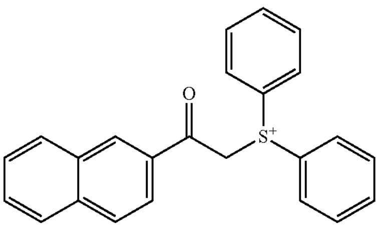
-continued
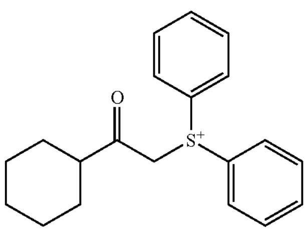
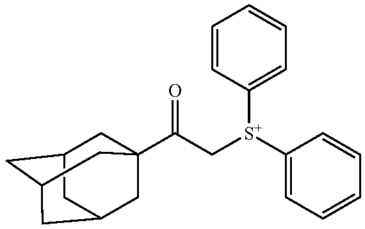
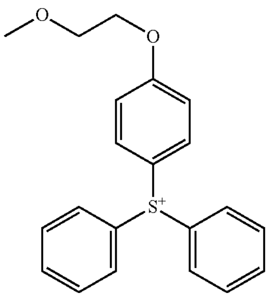
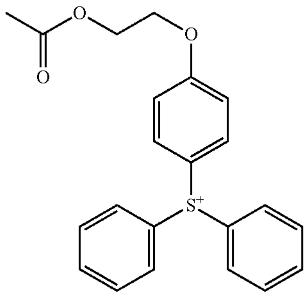
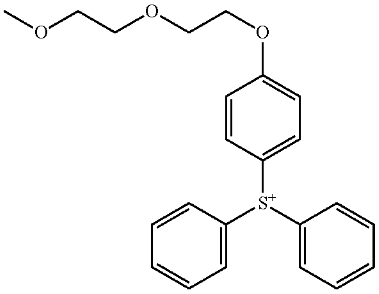
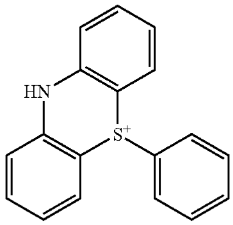
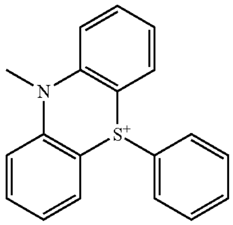

-continued
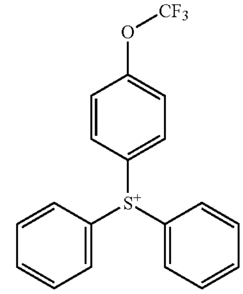
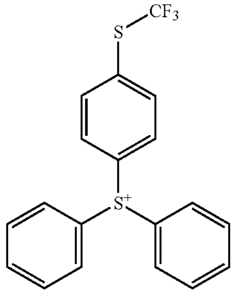
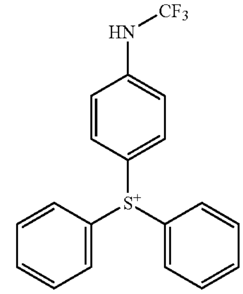
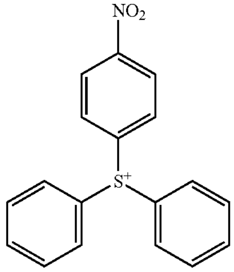
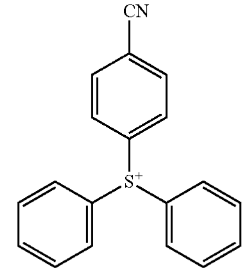
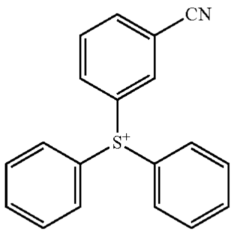
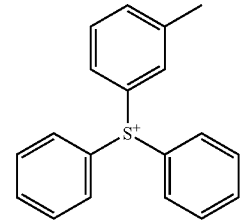
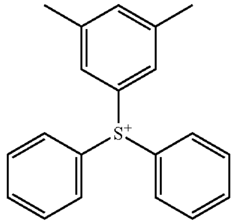
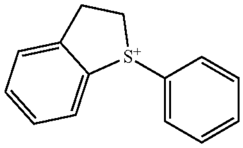
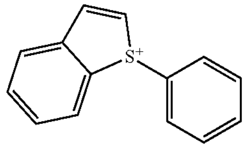
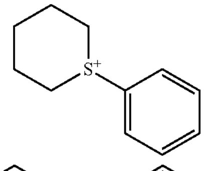
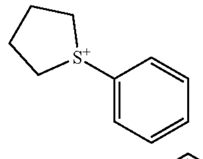
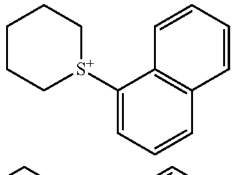
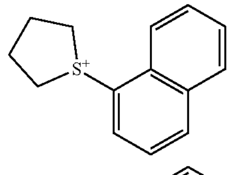
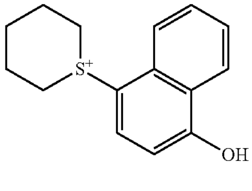
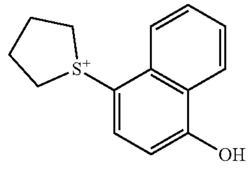
-continued
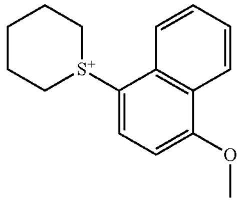
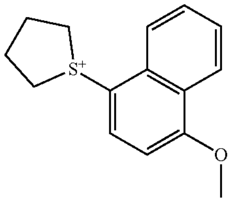
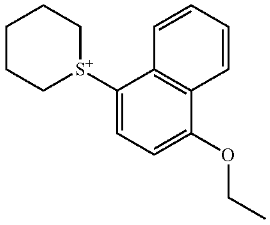
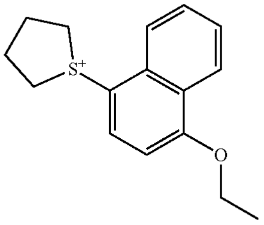
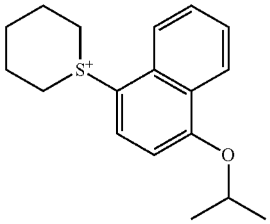
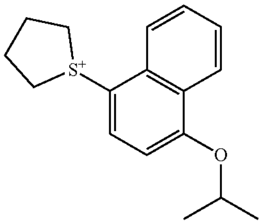
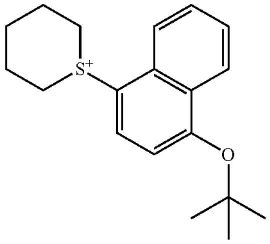
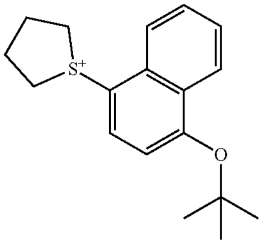
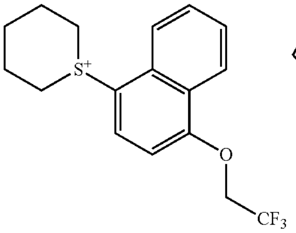
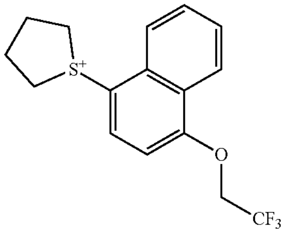
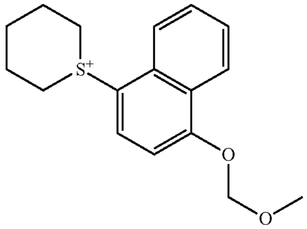
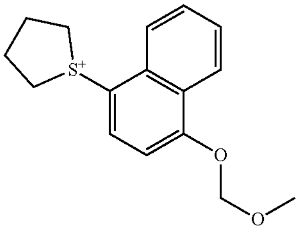

-continued
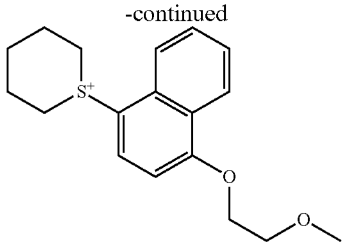
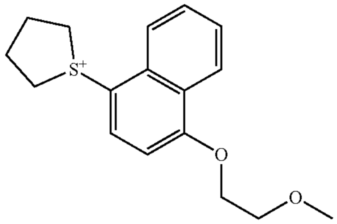
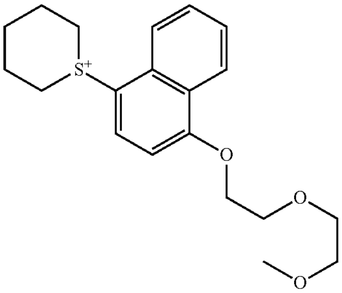
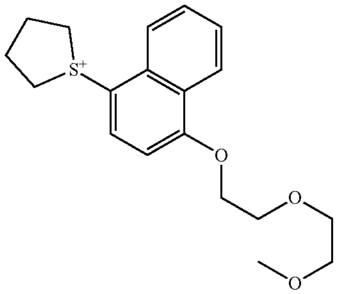
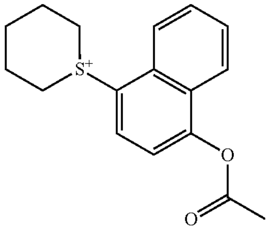
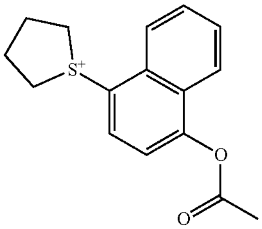
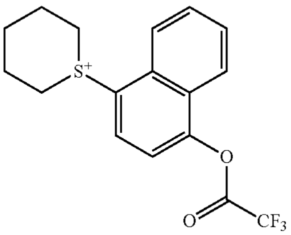
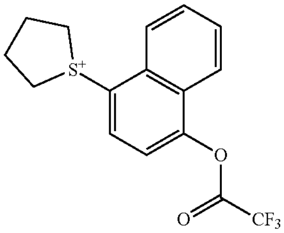
-continued
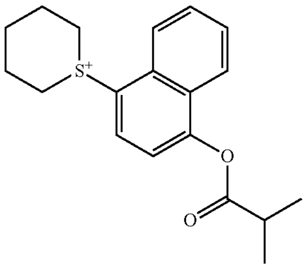
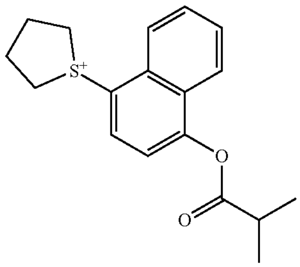
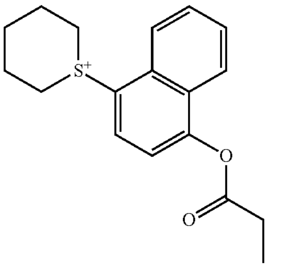
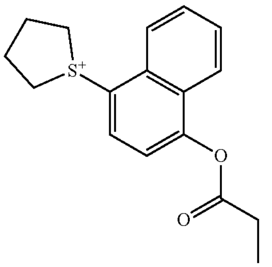
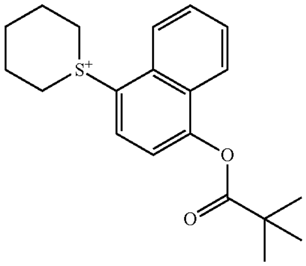
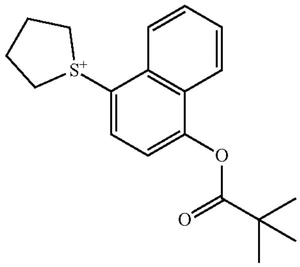
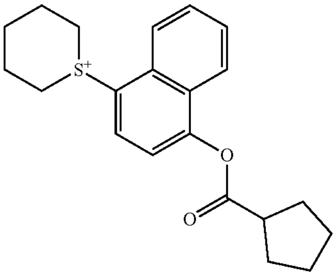

-continued
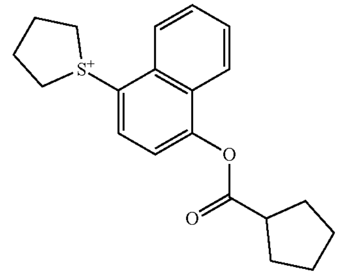
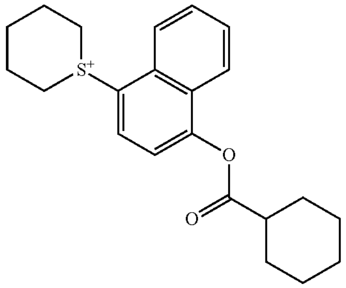
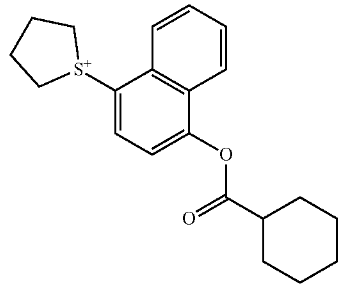
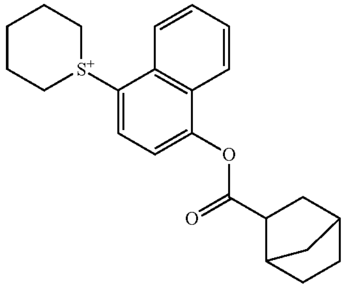
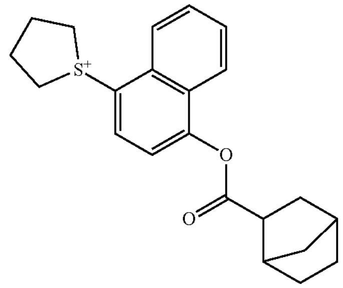
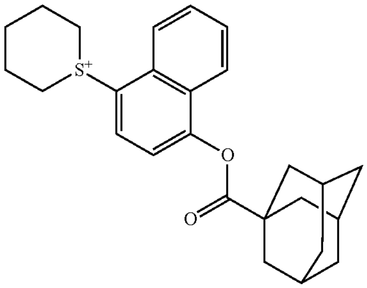
-continued
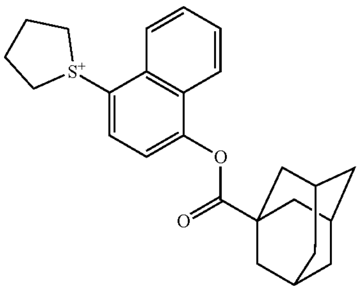
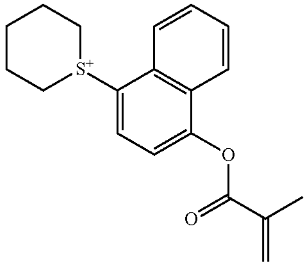
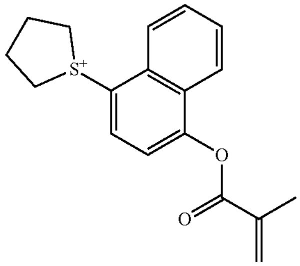
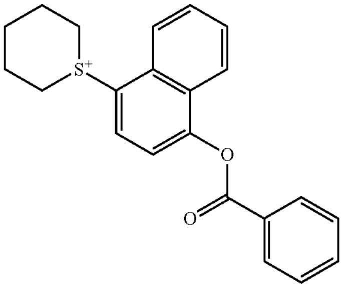
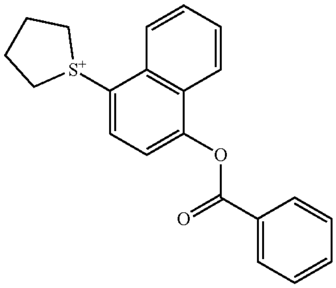
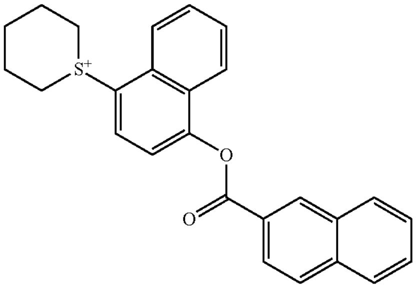

-continued
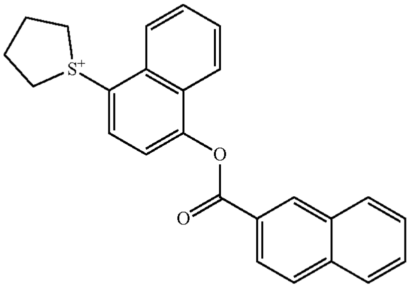
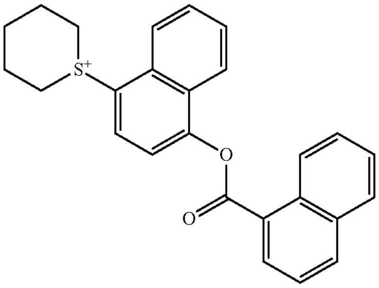
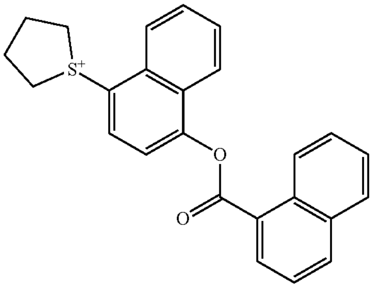
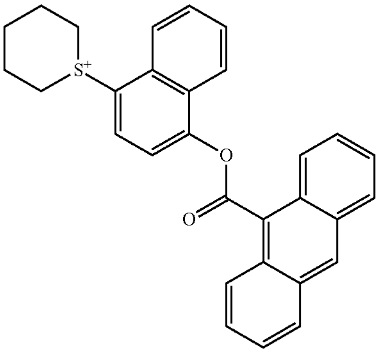
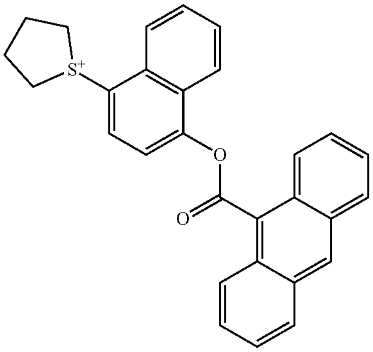
-continued
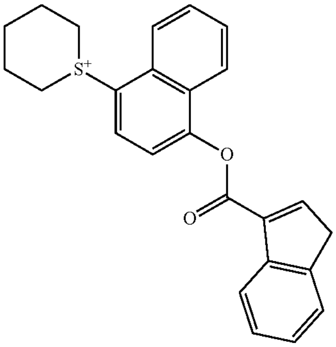
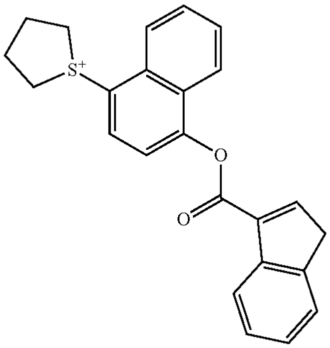
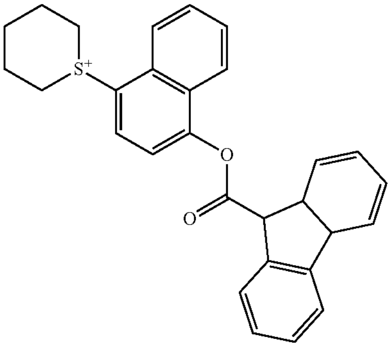
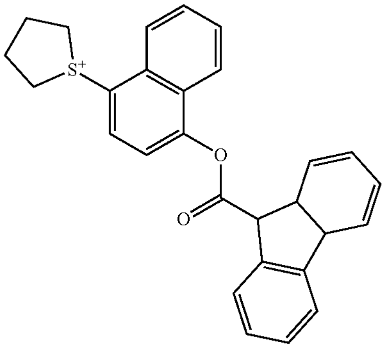
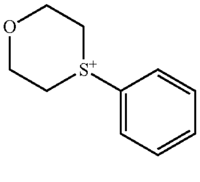
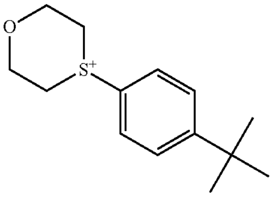

-continued
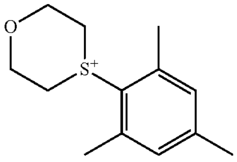
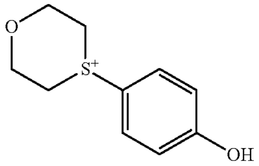
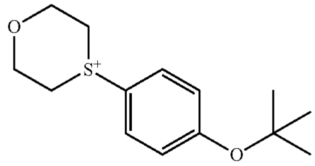
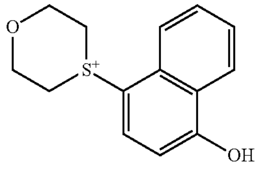
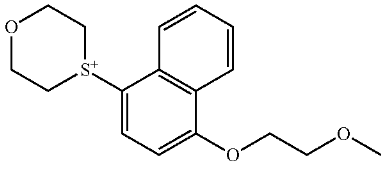
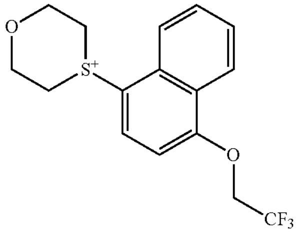
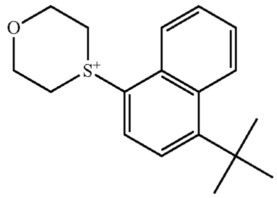
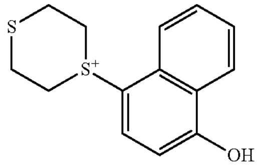
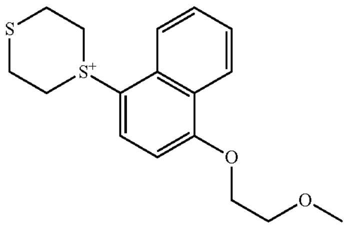
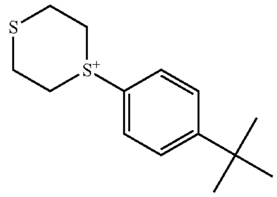
-continued
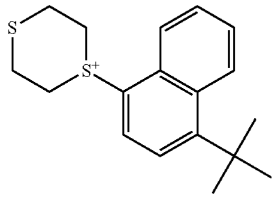
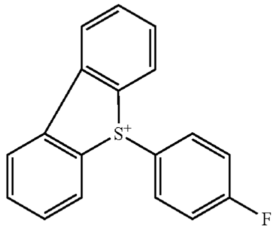
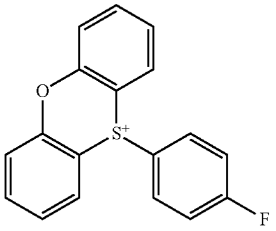
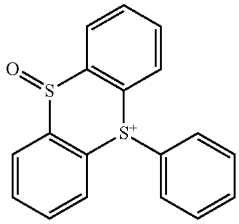
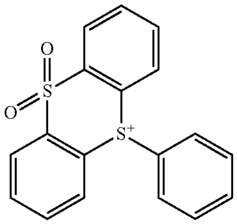
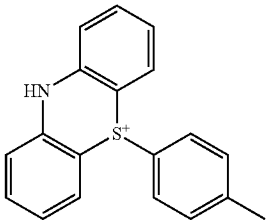
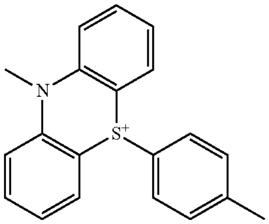
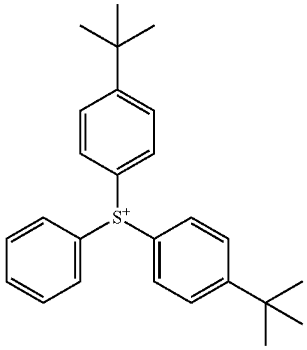

-continued
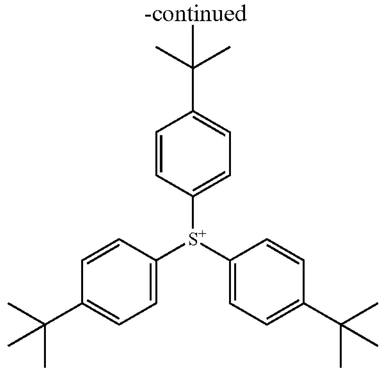
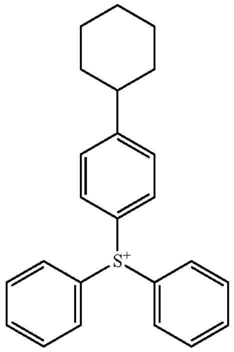
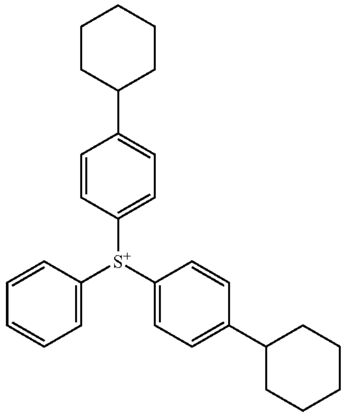
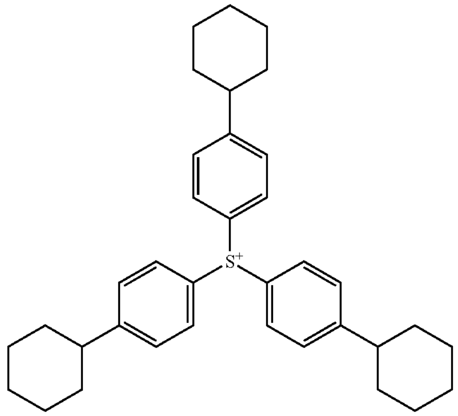
-continued
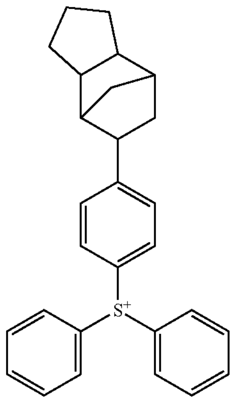
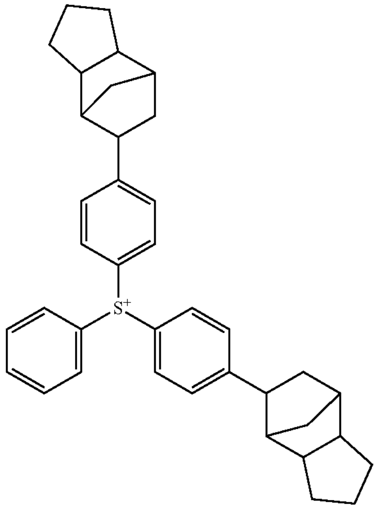
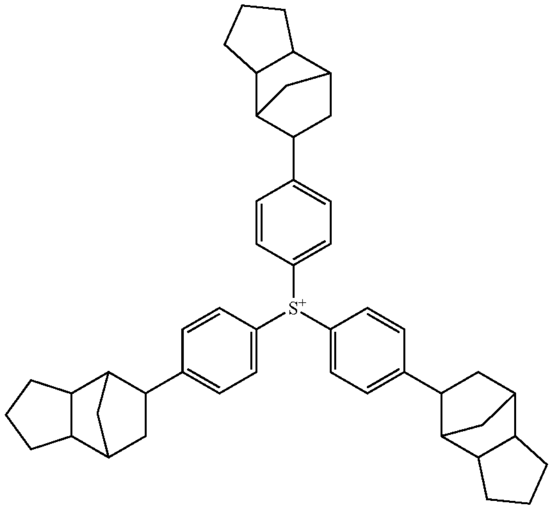

-continued
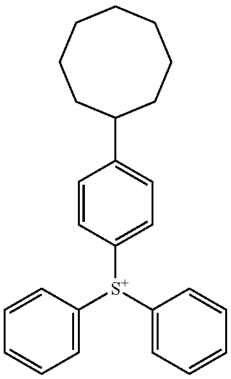
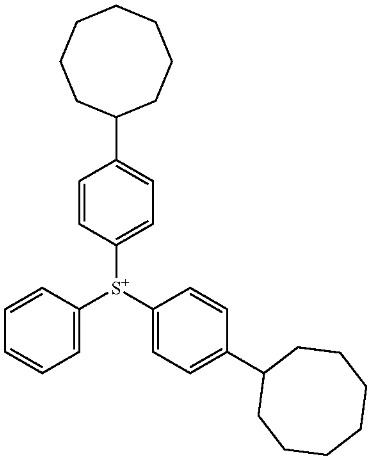
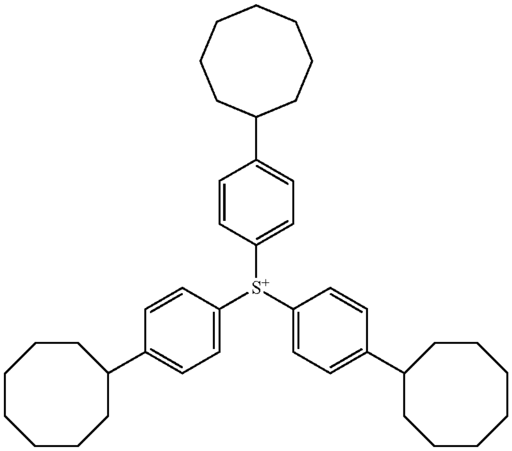
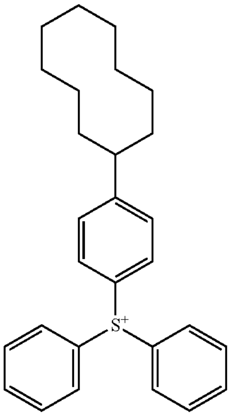
-continued
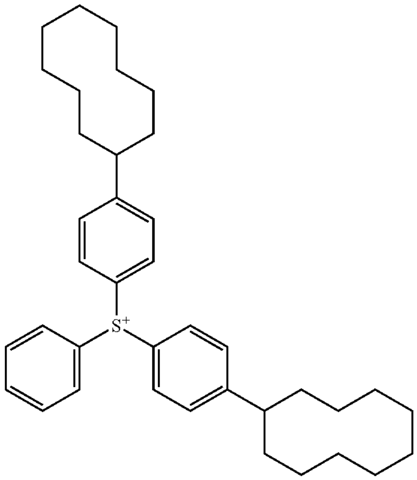
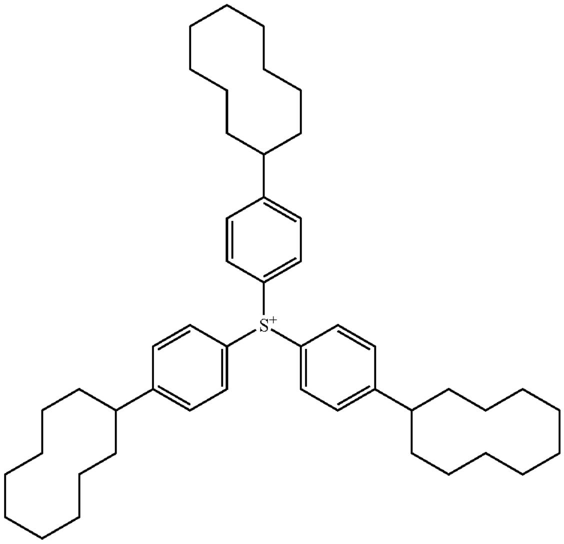
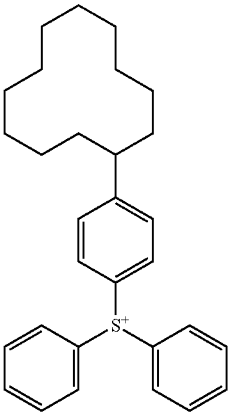

-continued
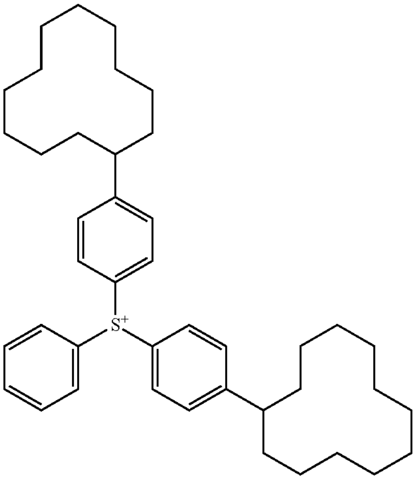
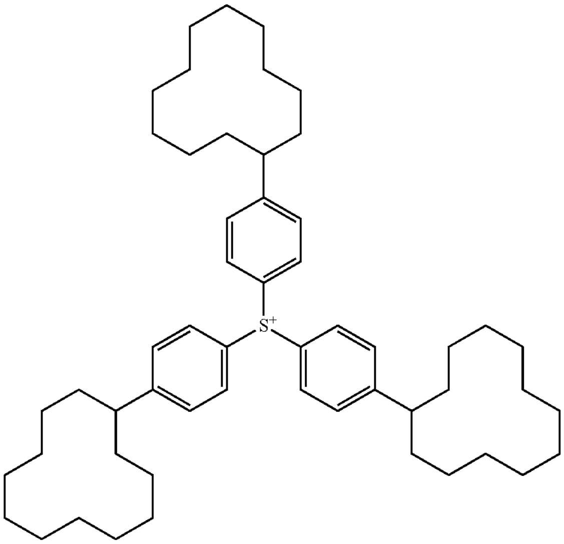
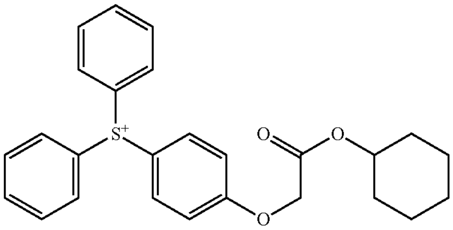
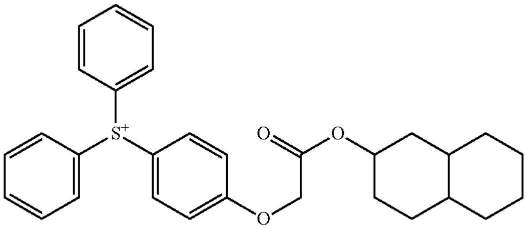
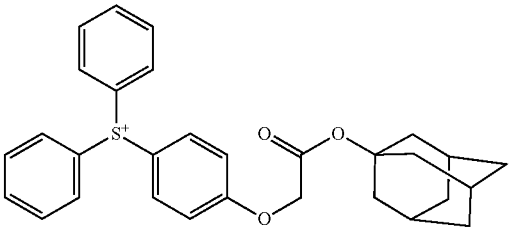
-continued
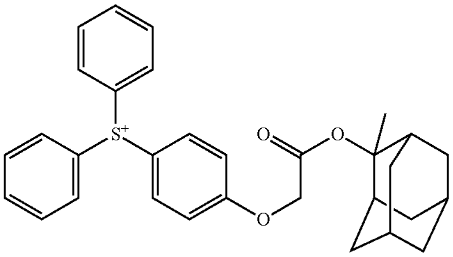
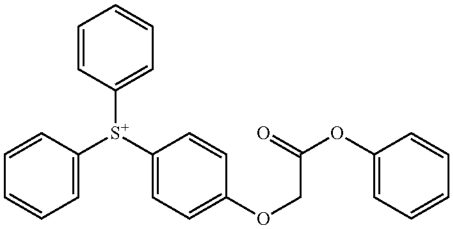
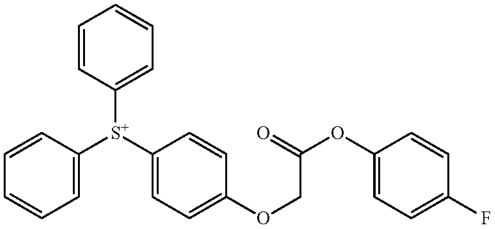
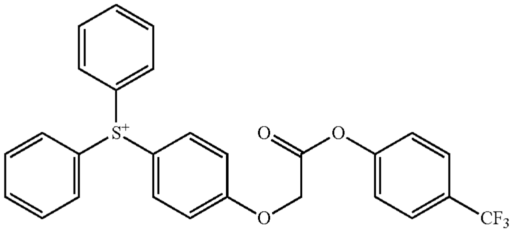
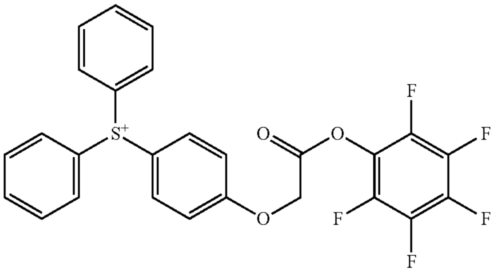
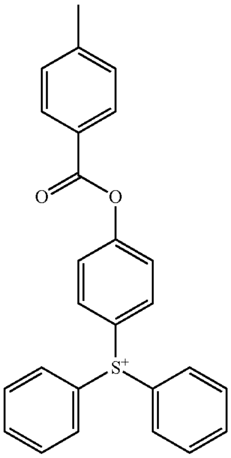

-continued
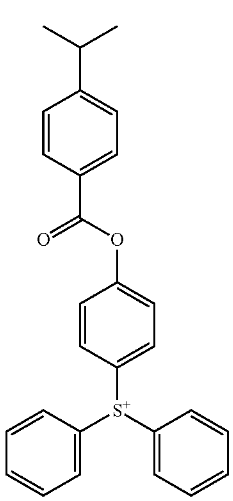
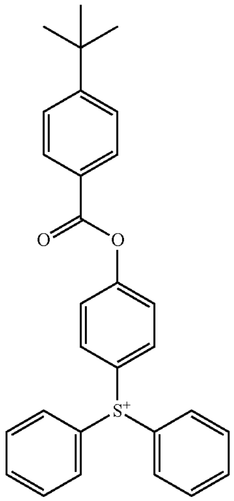
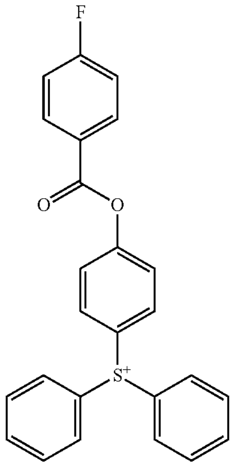
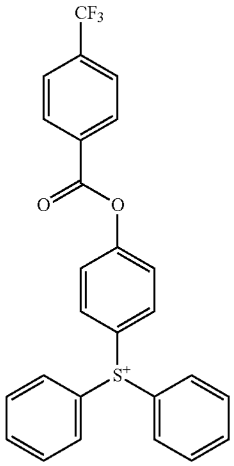
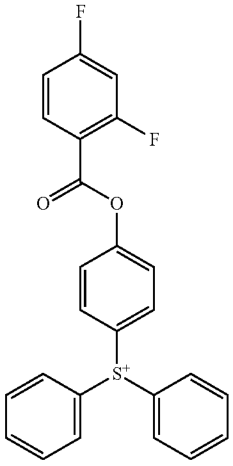
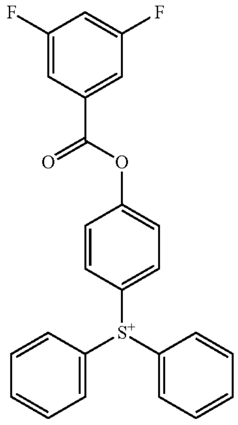
-continued
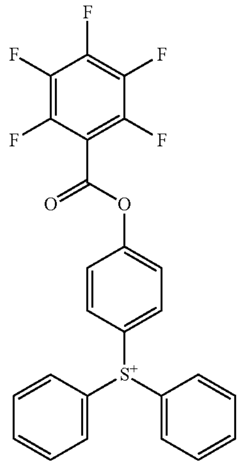
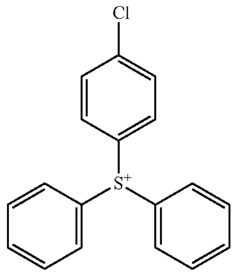
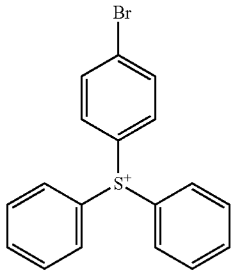
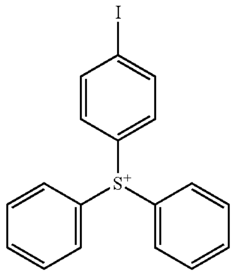
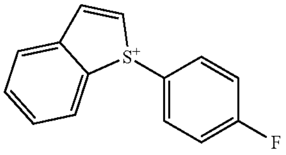
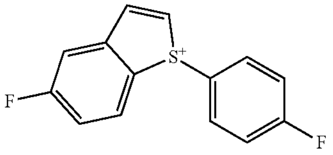
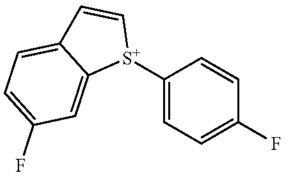
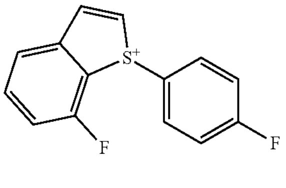
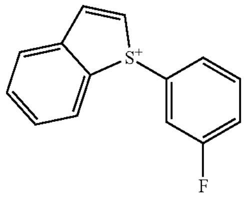
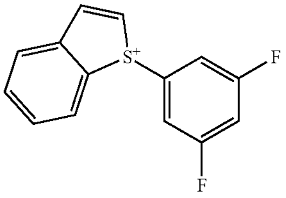
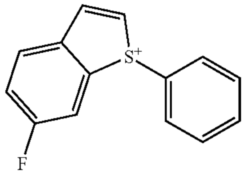

-continued
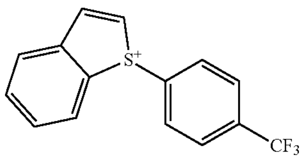
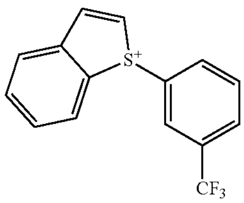
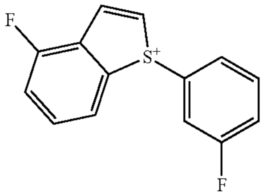
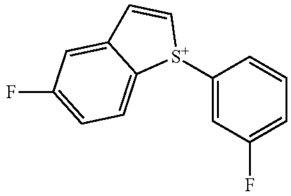
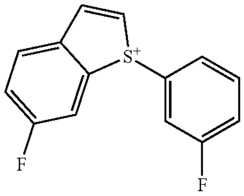
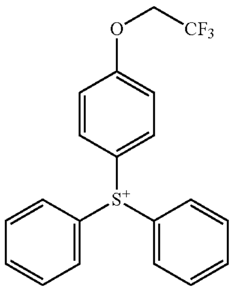
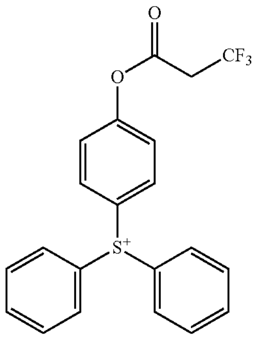
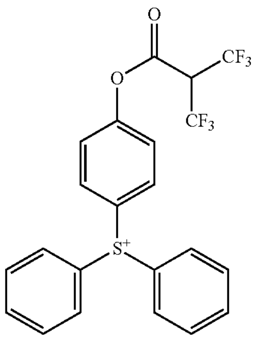
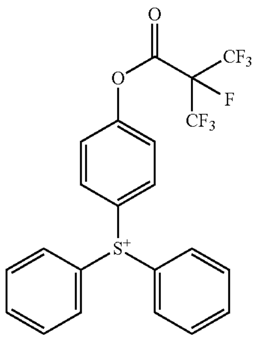
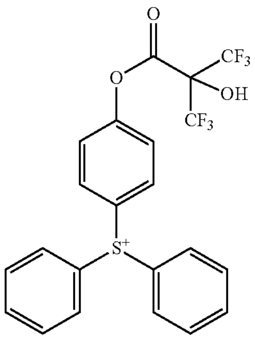
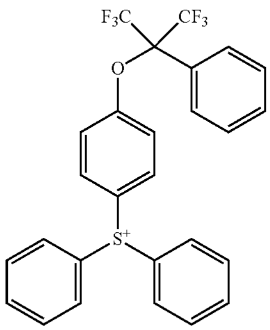
-continued
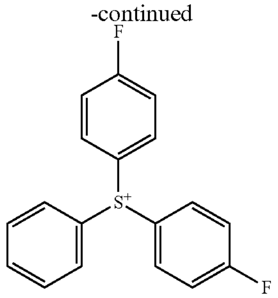
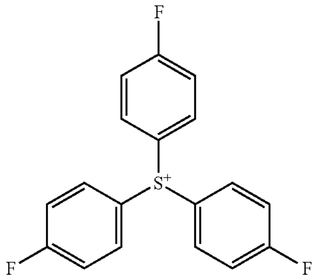
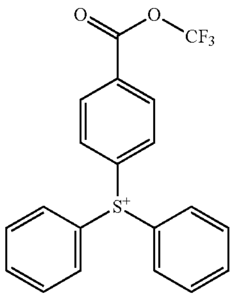
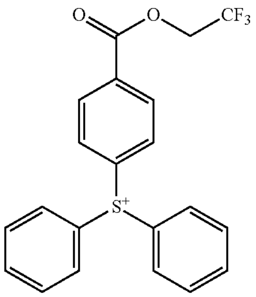
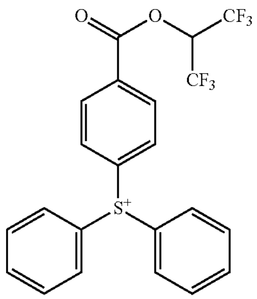
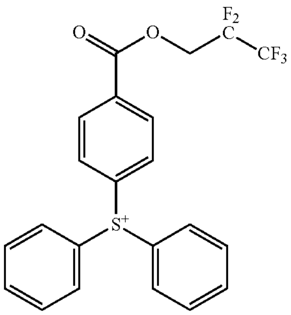

-continued
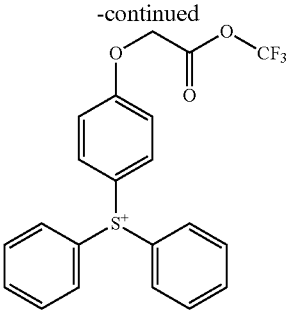
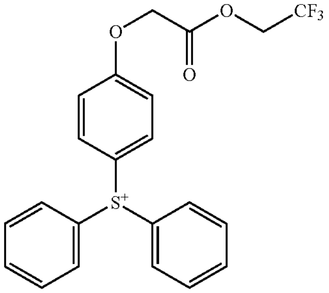
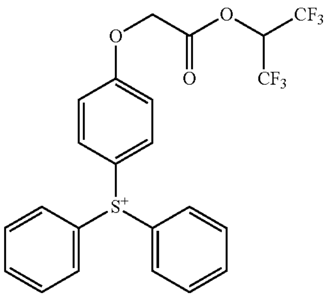
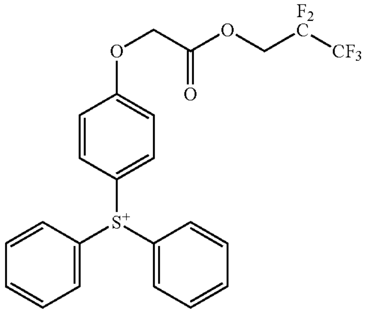
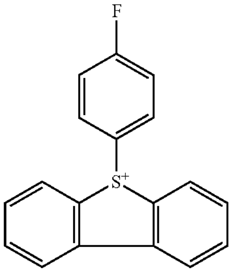
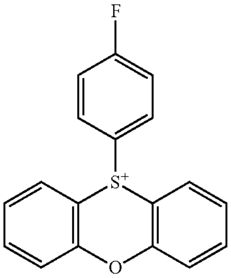
-continued
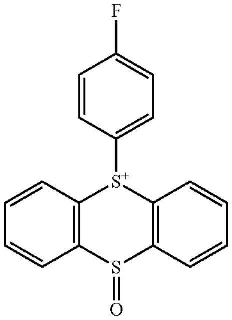
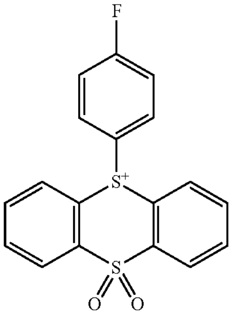
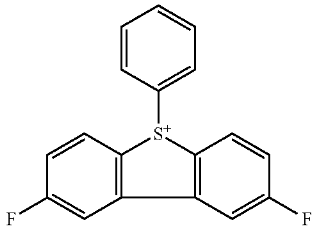
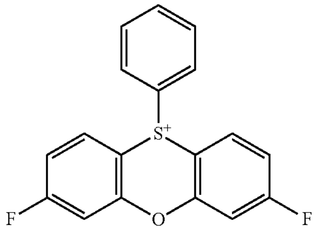
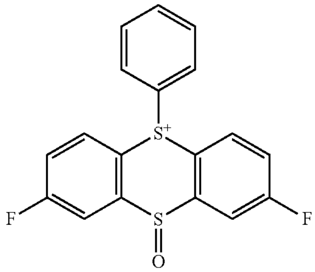
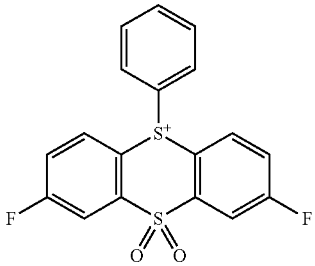
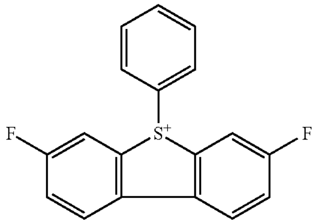

-continued
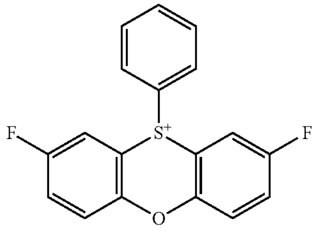
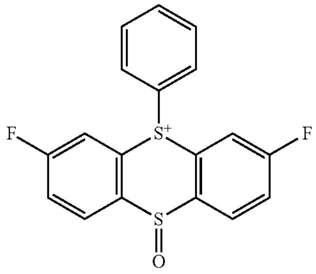
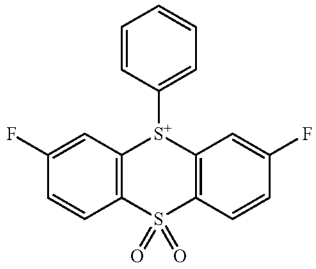
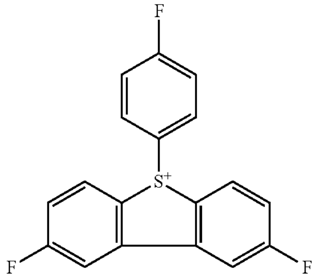
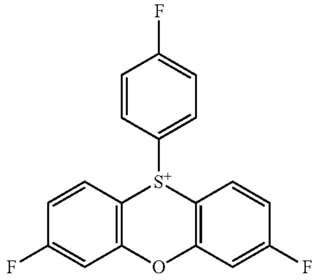
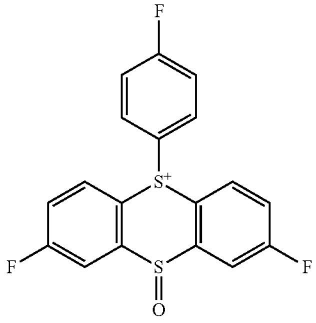
-continued
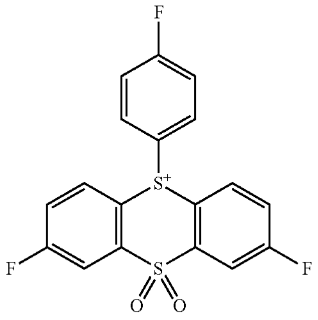
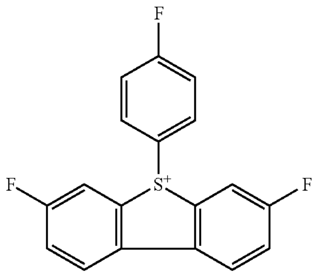
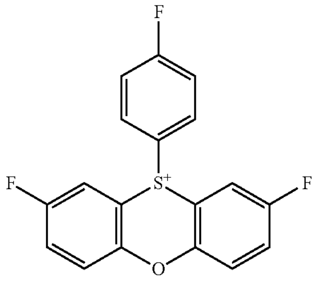
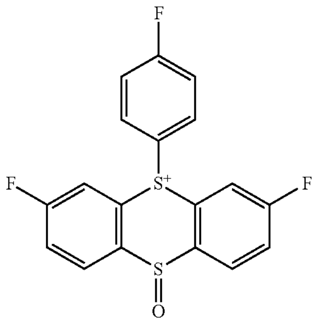
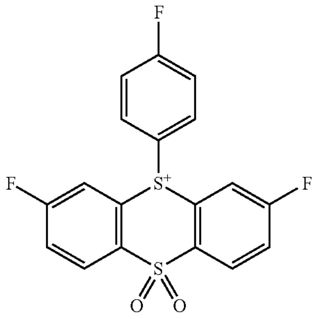
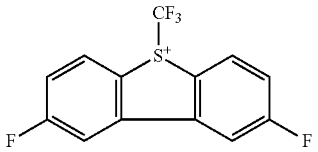

-continued
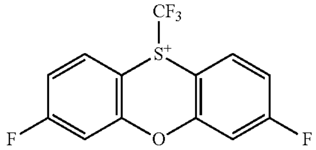
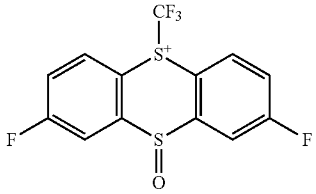
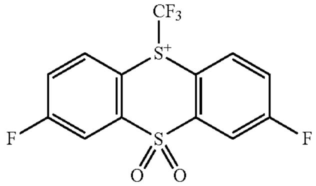
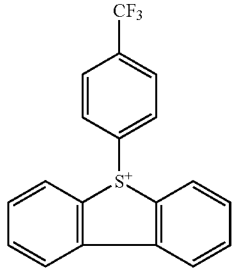
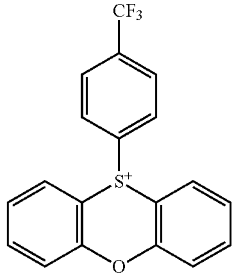
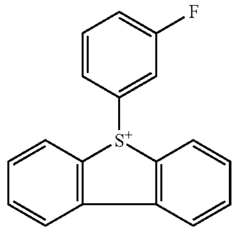
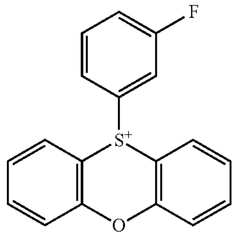
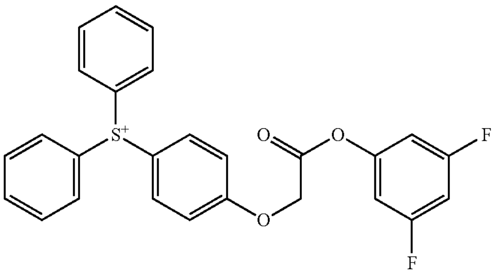
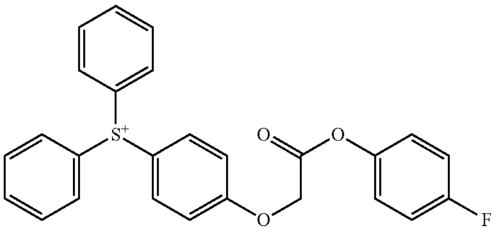
-continued
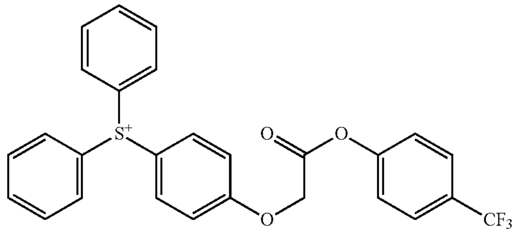
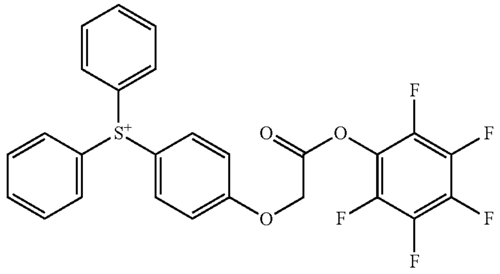
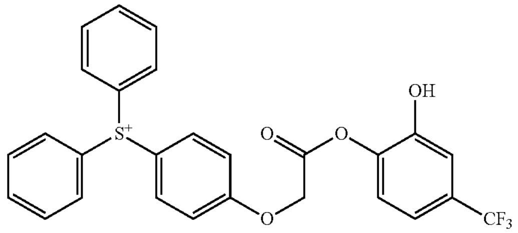
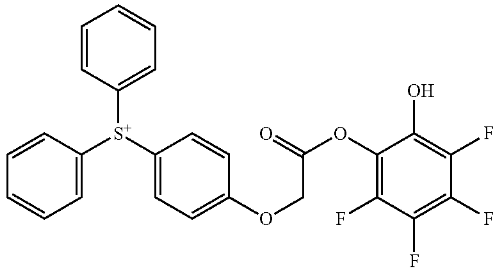
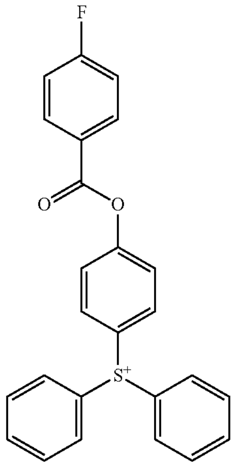
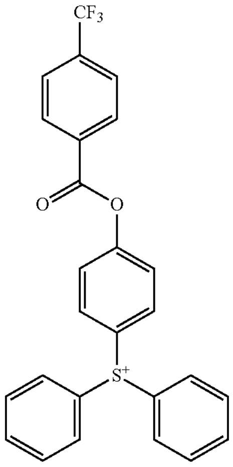

-continued
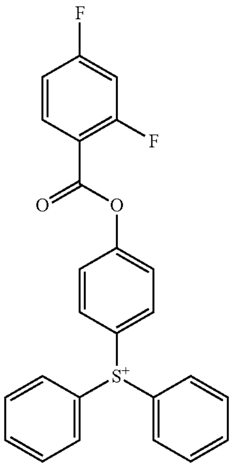
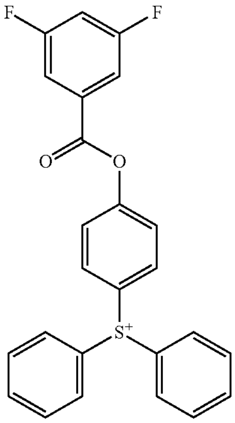
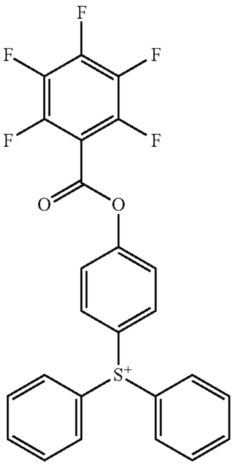
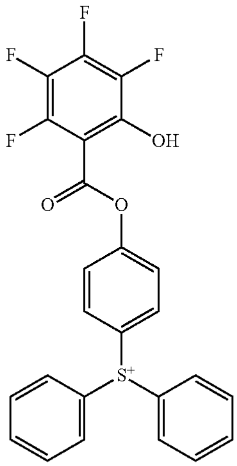
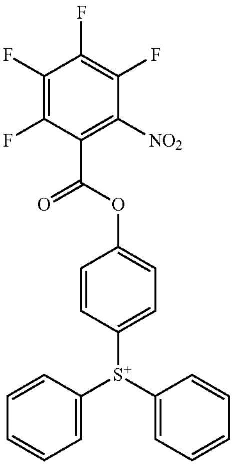
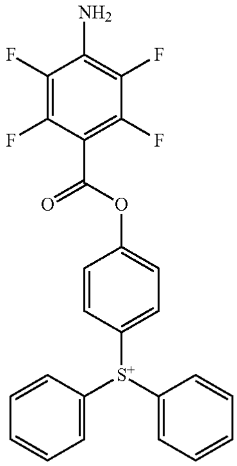
-continued
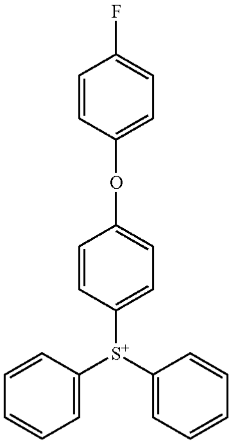
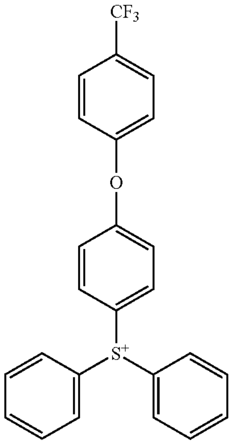
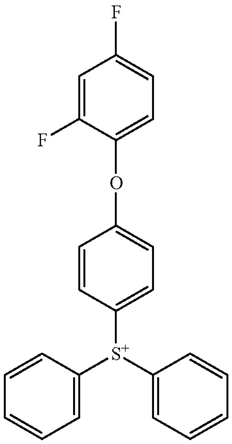
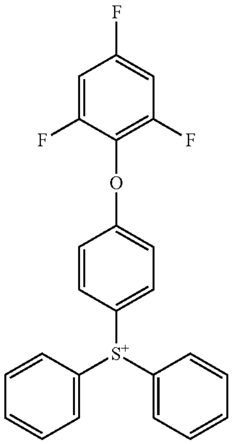
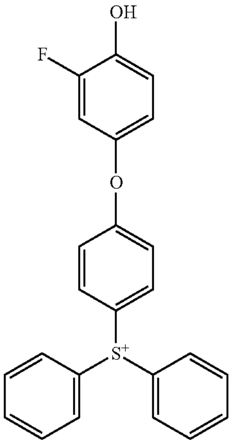
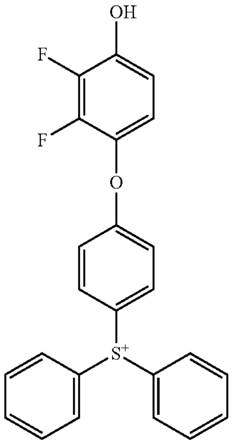

-continued
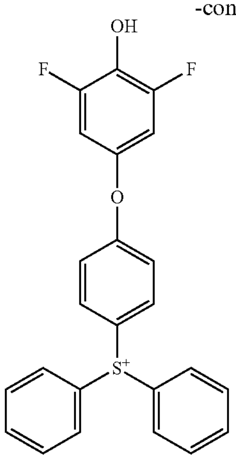
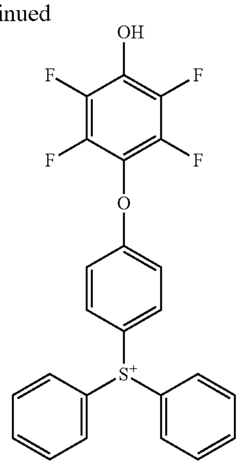
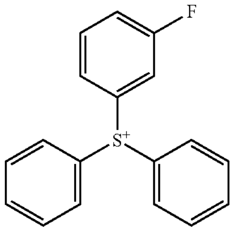
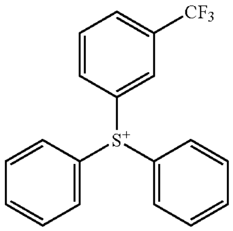
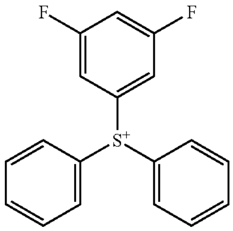
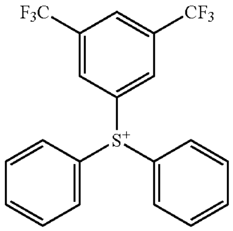
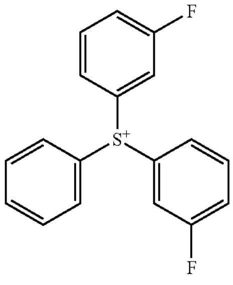
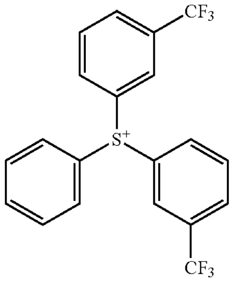
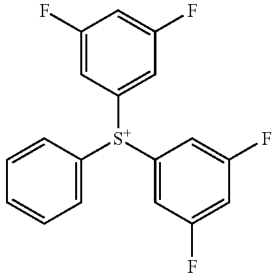
-continued
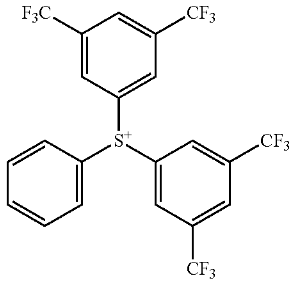
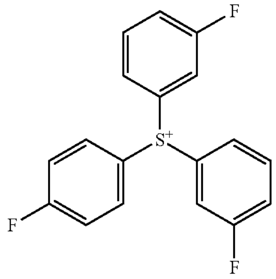
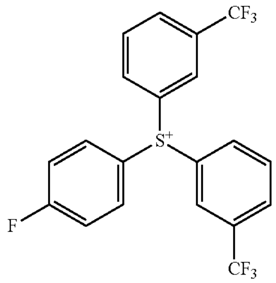
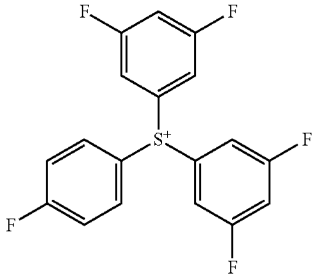
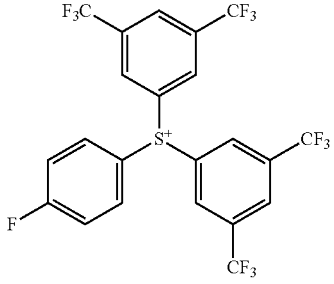
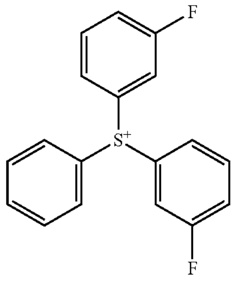
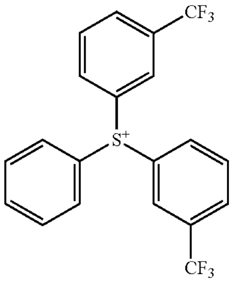

-continued
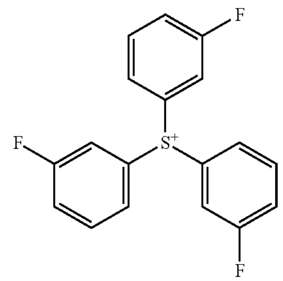
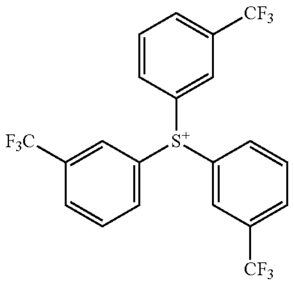
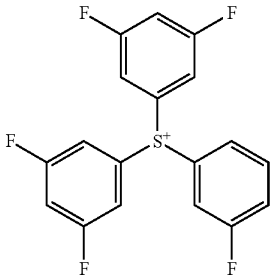
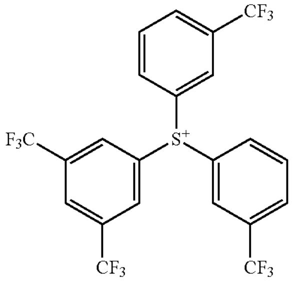
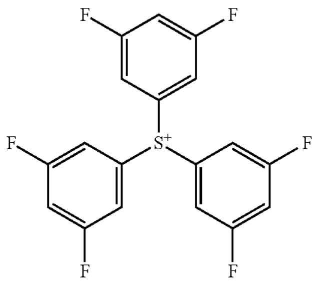
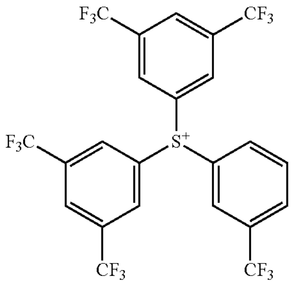
-continued
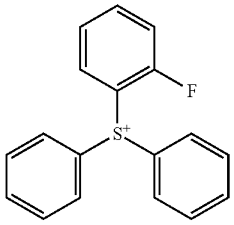
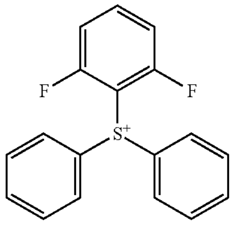
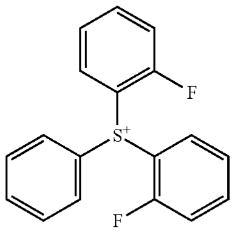
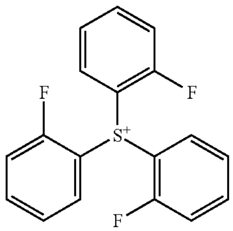
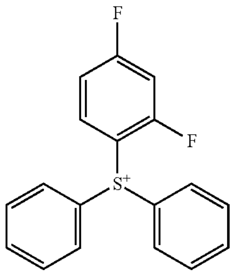
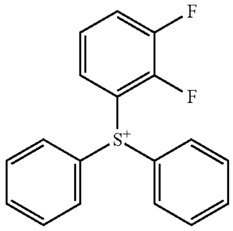
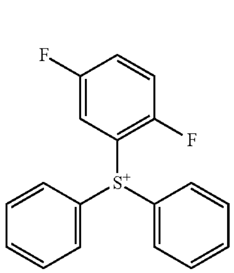
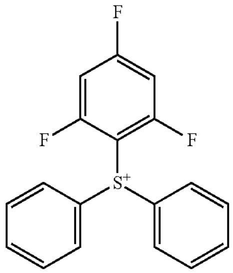
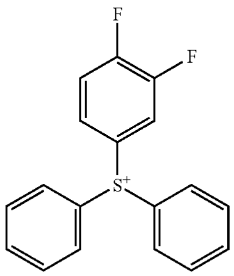
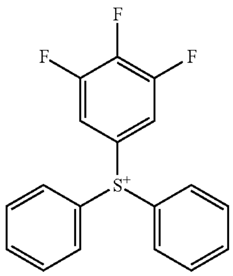
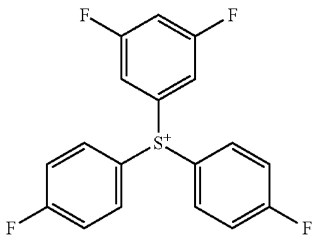

-continued
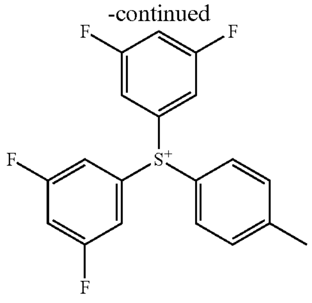
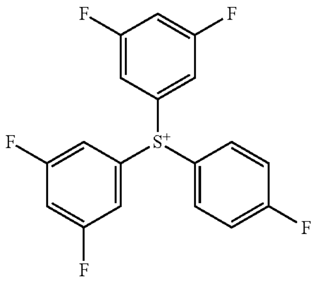
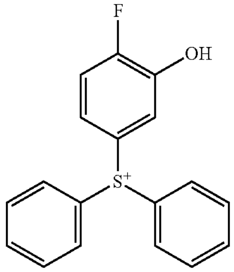
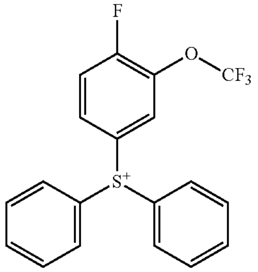
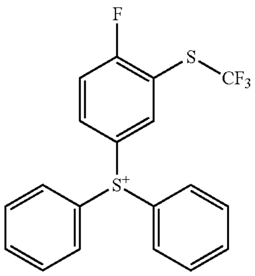
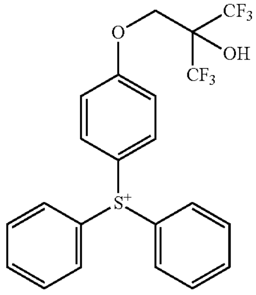
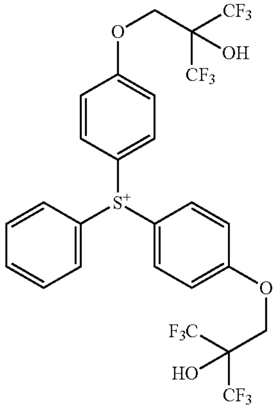
-continued
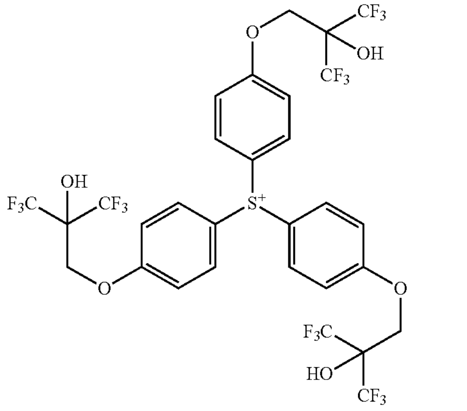
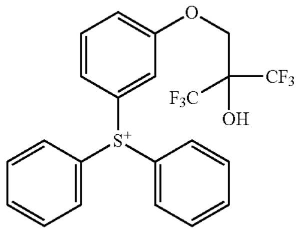
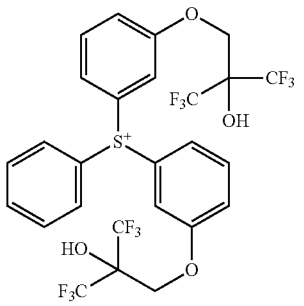
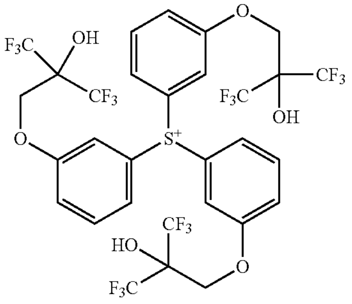
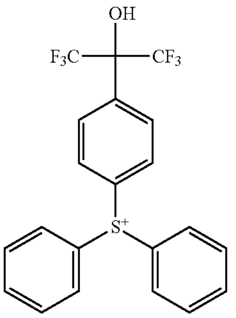
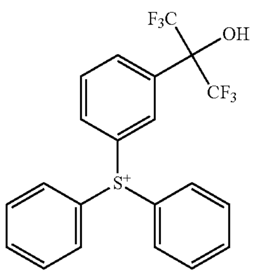

-continued
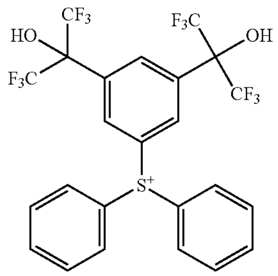
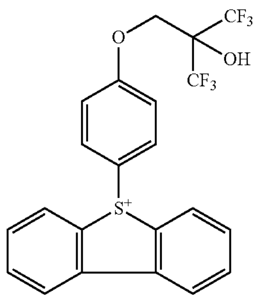
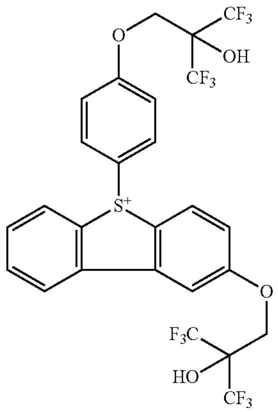
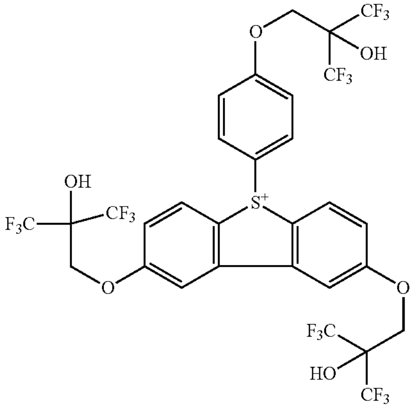
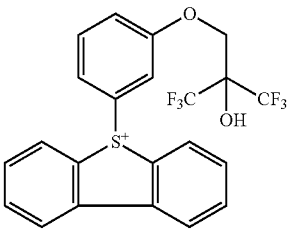
-continued
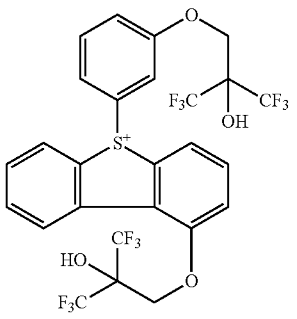
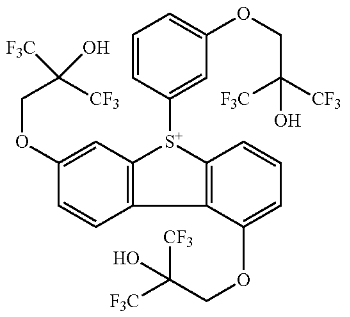
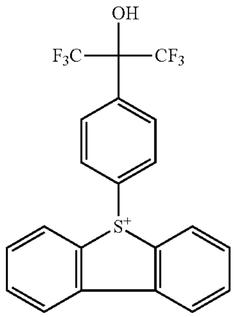
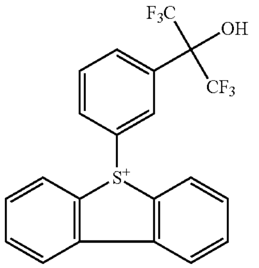
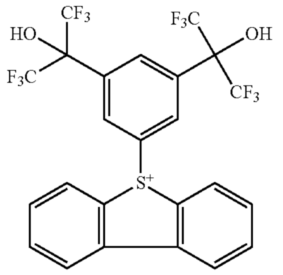
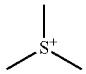
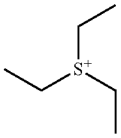
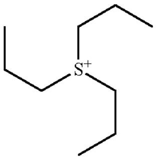
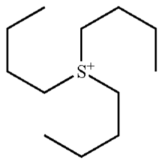
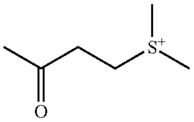
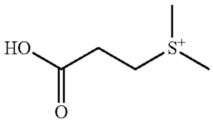
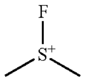
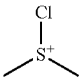
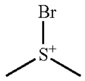

-continued
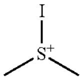
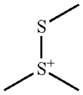
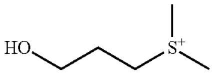
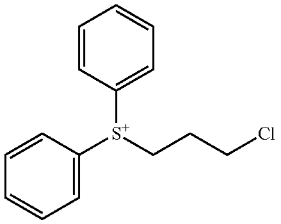
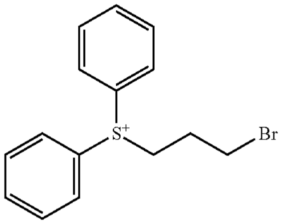
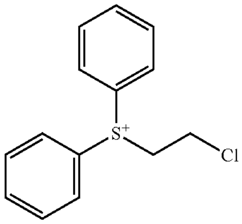
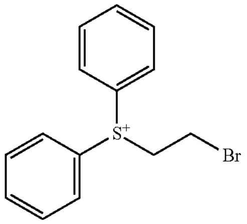
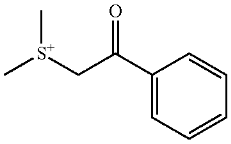
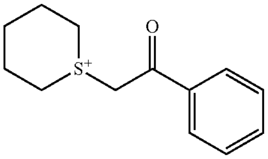
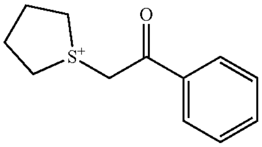
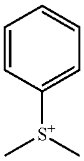
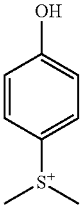
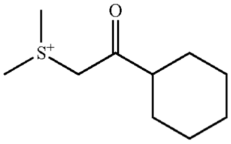
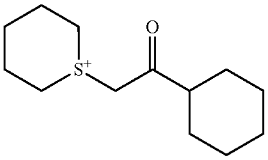
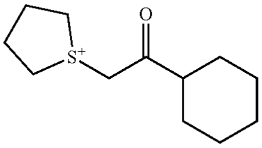
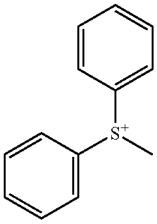
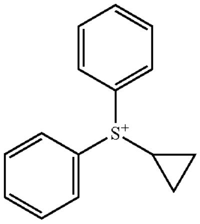
-continued
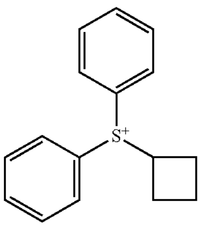
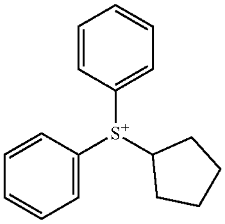
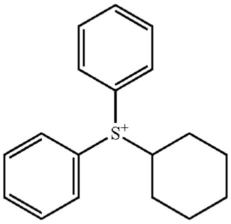
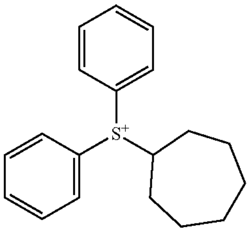
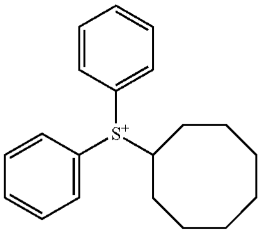
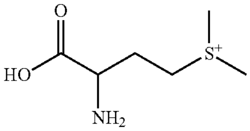
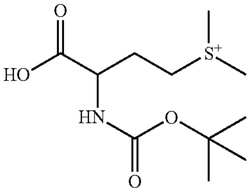
Examples of the cation in the iodonium salt having formula (1-2) are shown below, but not limited thereto.
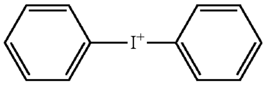
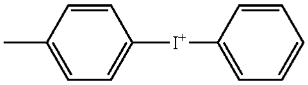
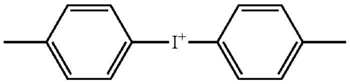
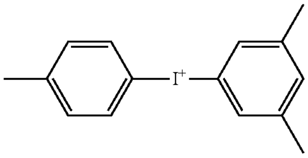
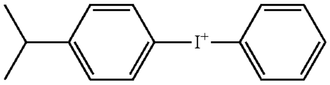
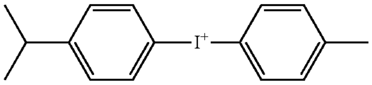

-continued
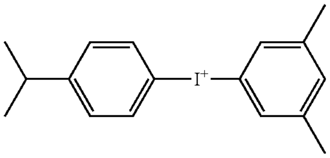
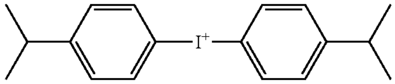
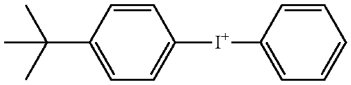
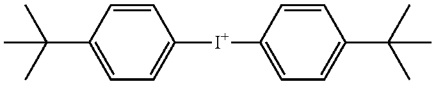
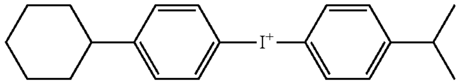
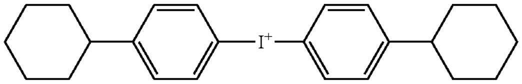
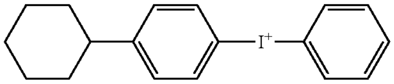
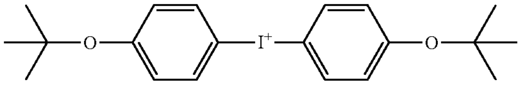
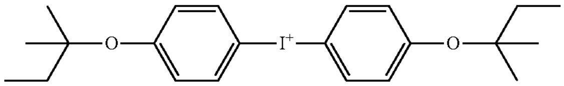
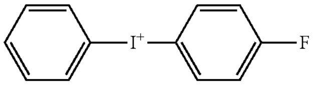
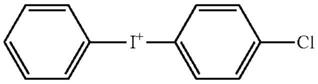
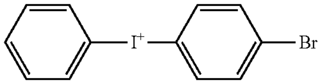
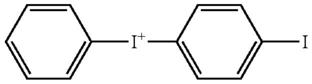
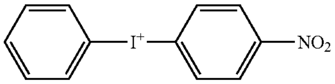
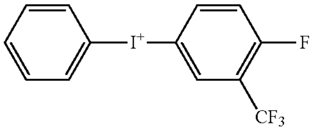
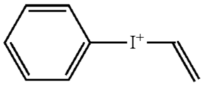
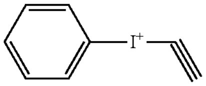
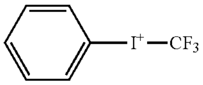
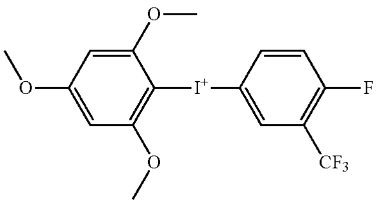
-continued
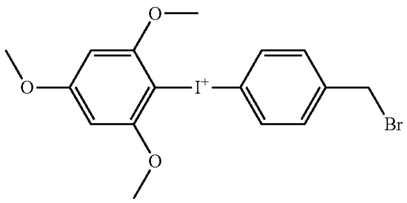
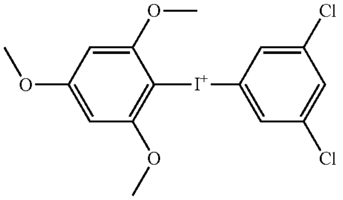
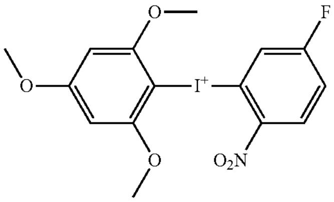
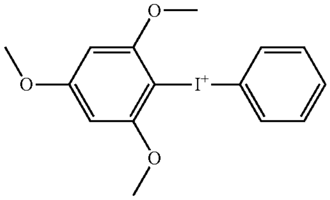
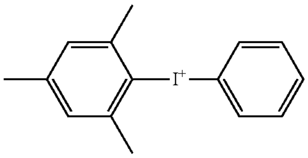
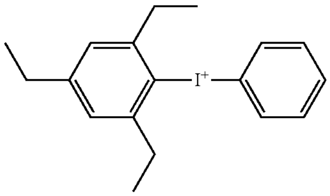
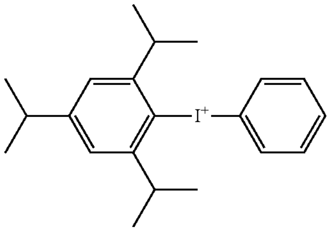
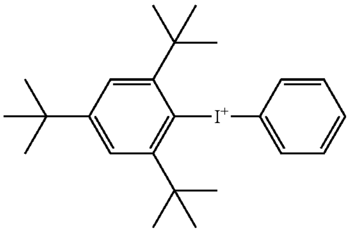

-continued

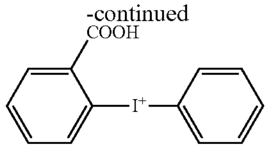

In formulae (1-1) and (1-2), $Xa^-$ is an anion of the following formula (1A), (1B), (1C) or (1D).

(1A)

$$R^{fa}-CF_2-SO_3^-$$

(1B)

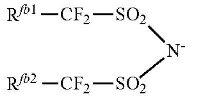

(1C)

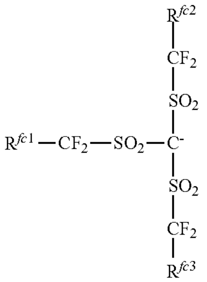

(1D)

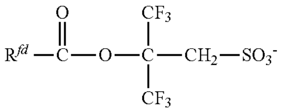

In formula (1A), $R^{fa}$ is fluorine or a $C_1$-$C_{40}$ hydrocarbyl group which may contain a heteroatom. The hydrocarbyl group may be saturated or unsaturated and straight, branched or cyclic. Examples thereof are as will be exemplified later for the hydrocarbyl group $R^{111}$ in formula (1A').

Of the anions having formula (1A), an anion having the formula (1A') is preferred.

(1A')

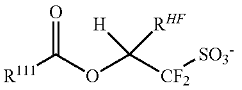

In formula (1A'). $R^{HF}$ is hydrogen or trifluoromethyl, preferably trifluoromethyl.

$R^{111}$ is a $C_1$-$C_{38}$ hydrocarbyl group which may contain a heteroatom. As the heteroatom, oxygen, nitrogen, sulfur and halogen atoms are preferred, with oxygen being most preferred. Of the hydrocarbyl groups represented by $R^{111}$, those groups of 6 to 30 carbon atoms are preferred from the aspect of achieving a high resolution in forming patterns of fine feature size. The hydrocarbyl group may be saturated or unsaturated and straight, branched or cyclic. Examples thereof include $C_1$-$C_{38}$ alkyl groups such as methyl, ethyl, n propyl, isopropyl, butyl, isobutyl, sec-butyl, tert-butyl, pentyl, neopentyl, hexyl, heptyl, 2-ethylhexyl, nonyl, undecyl, tridecyl, pentadecyl, heptadecyl, and icosyl; $C_3$-$C_{38}$ cyclic saturated hydrocarbyl groups such as cyclopentyl, cyclohexyl, 1-adamantyl, 2-adamantyl, 1-adamantylmethyl, norbornyl, norbornylmethyl, tricyclodecanyl, tetracyclododecanyl, tetracyclododecanylmethyl, and dicyclohexylmethyl; $C_2$-$C_{38}$ unsaturated aliphatic hydrocarbyl groups such as ally and 3-cyclohexenyl; $C_6$-$C_{38}$ aryl groups such as phenyl, 1-naphthyl and 2-naphthyl; $C_7$-$C_{38}$ aralkyl groups such as benzyl and diphenylmethyl; and combinations thereof.

In the foregoing hydrocarbyl groups, some or all hydrogen atoms may be substituted by a moiety containing a heteroatom such as oxygen, sulfur, nitrogen or halogen, and some constituent $—CH_2—$ may be replaced by a moiety containing a heteroatom such as oxygen, sulfur or nitrogen, so that the group may contain a hydroxy, fluorine, chlorine, bromine, iodine, cyano, nitro, carbonyl, ether bond, ester bond, sulfonic ester bond, carbonate bond, lactone ring, sultone ring, carboxylic anhydride, or haloalkyl moiety. Examples of the heteroatom-containing hydrocarbyl group include tetrahydrofuryl, methoxymethyl, ethoxymethyl, methylthiomethyl, acetamidemethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl.

With respect to the synthesis of the sulfonium salt having an anion of formula (1A'), reference may be made to JP-A 2007-145797, JP-A 2008-106045, JP-A 2009-007327, and JP A 2009-258695. Also useful are the sulfonium salts described in JP-A 2010-215608, JP A 2012-041320, JP-A 2012-106986, and JP A 2012-153644.

Examples of the anion having formula (1A) include those exemplified as the anion having formula (1A) in JP-A 2018-197853.

In formula (1B), $R^{fb1}$ and $R^{fb2}$ are each independently fluorine or a $C_1$-$C_{40}$ hydrocarbyl group which may contain a heteroatom. The hydrocarbyl group may be saturated or unsaturated and straight, branched or cyclic, and examples thereof are as exemplified above for $R^{111}$ in formula (1A'). Preferably $R^{fb1}$ and $R^{fb2}$ are fluorine or $C_1$-$C_4$ straight fluorinated alkyl groups. Also, $R^{fb1}$ and $R^{fb2}$ may bond together to form a ring with the linkage: $—CF_2—SO_2—N^-—SO_2—CF_2—$ to which they are attached. It is preferred that a combination of $R^{fb1}$ and $R^{fb2}$ be a fluorinated ethylene or fluorinated propylene group.

In formula (1C), $R^{fc1}$, $R^{fc2}$ and $R^{fc3}$ are each independently fluorine or a $C_1$-$C_{40}$ hydrocarbyl group which may contain a heteroatom. The hydrocarbyl group may be saturated or unsaturated and straight, branched or cyclic, and examples thereof are as exemplified above for $R^{111}$ in formula (1A'). Preferably $R^{fc1}$, $R^{fc2}$ and $R^{fc3}$ are fluorine or $C_1$-$C_4$ straight fluorinated alkyl groups. Also, $R^{fc1}$ and $R^{fc2}$ may bond together to form a ring with the linkage: $—CF_2—SO_2—C^-—SO_2—CF_2—$ to which they are attached. It is preferred that a combination of $R^{fc1}$ and $R^{fc2}$ be a fluorinated ethylene or fluorinated propylene group.

In formula (1D), $R^{fd}$ is a $C_1$-$C_{40}$ hydrocarbyl group which may contain a heteroatom. The hydrocarbyl group may be saturated or unsaturated and straight, branched or cyclic, and examples thereof are as exemplified above for $R^{111}$ in formula (1A').

With respect to the synthesis of the sulfonium salt having an anion of formula (1D), reference may be made to JP-A 2010-215608 and JP-A 2014-133723.

Examples of the anion having formula (1D) include those exemplified as the anion having formula (1D) in U.S. Pat. No. 11,022,883 (JP-A 2018-197853).

Notably, the compound having the anion of formula (1D) does not have fluorine at the α-position relative to the sulfo group, but two trifluoromethyl groups at the β-position. For this reason, it has a sufficient acidity to sever the acid labile groups in the base polymer. Thus the compound is an effective PAG.

Another preferred PAG is a compound having the formula (2).

(2)

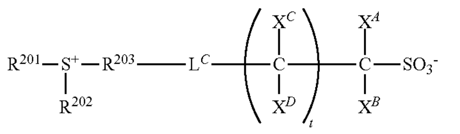

In formula (2), $R^{201}$ and $R^{202}$ are each independently halogen or a $C_1$-$C_{30}$ hydrocarbyl group which may contain a heteroatom. $R^{203}$ is a $C_1$-$C_{30}$ hydrocarbylene group which may contain a heteroatom. Any two of $R^{201}$, $R^{202}$ and $R^{203}$ may bond together to form a ring with the sulfur atom to which they are attached. Examples of the ring are as exemplified above for the ring that $R^{101}$ and $R^{102}$ in formula (1-1), taken together, form with the sulfur atom to which they are attached.

The hydrocarbyl groups $R^{201}$ and $R^{202}$ may be saturated or unsaturated and straight, branched or cyclic. Examples thereof include $C_1$-$C_{30}$ alkyl groups such as methyl, ethyl, n-propyl, isopropyl, n-butyl, isobutyl, sec-butyl, tert-butyl, n-pentyl, tert-pentyl, n-hexyl, n-octyl, 2-ethylhexyl, n-nonyl, and n-decyl; $C_3$-$C_{30}$ cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.$0^{2,6}$]decanyl, and adamantyl; $C_6$-$C_{30}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl isobutylnaphthyl, sec-butylnaphthyl, tert-butylnaphthyl, and anthracenyl: and combinations thereof. In the foregoing hydrocarbyl groups, some or all of the hydrogen atoms may be substituted by a moiety containing a heteroatom such as oxygen, sulfur, nitrogen or halogen, and some constituent —$CH_2$— may be replaced by a moiety containing a heteroatom such as oxygen, sulfur or nitrogen, so that the group may contain a hydroxy, fluorine, chlorine, bromine, iodine, cyano, nitro, carbonyl, ether bond ester bond, sulfonic ester bond, carbonate bond, lactone ring, sultone ring, carboxylic anhydride or haloalkyl moiety.

The hydrocarbylene group $R^{203}$ may be saturated or unsaturated and straight, branched or cyclic. Examples thereof include $C_1$-$C_{30}$ alkanediyl groups such as methanediyl, ethane-1,1-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; $C_3$-$C_{30}$ cyclic saturated hydrocarbylene groups such as cyclopentanediyl, cyclohexanediyl, norbornanediyl and adamantanediyl; $C_6$-$C_{30}$ arylene groups such as phenylene, methylphenylene, ethylphenylene, n-propylphenylene, isopropylphenylene, n-butylphenylene, isobutylphenylene, sec-butylphenylene, test-butylphenylene, naphthylene, methylnaphthylene, ethylnaphthylene, n-propylnaphthylene, isopropylnaphthylene, n-butylnaphthylene, isobutylnaphthylene, sec-butylnaphthylene, and tert-butylnaphthylene; and combinations thereof. In the hydrocarbylene group, some or all of the hydrogen atoms may be substituted by a moiety containing a heteroatom such as oxygen, sulfur, nitrogen or halogen, or some constituent —$CH_2$— may be replaced by a moiety containing a heteroatom such as oxygen, sulfur or nitrogen, so that the group may contain a hydroxy, fluorine, chlorine, bromine, iodine, cyano, nitro, carbonyl, ether bond, ester bond, sulfonic ester bond, carbonate bond, lactone ring, sultone ring, carboxylic anhydride or haloalkyl moiety. Of the heteroatoms, oxygen is preferred.

In formula (2), $L^C$ is a single bond, ether bond or a $C_1$-$C_2$ hydrocarbylene group which may contain a heteroatom. The hydrocarbylene group may be saturated or unsaturated and straight, branched or cyclic. Examples thereof are as exemplified above for $R^{203}$.

In formula (2), $X^A$, $X^B$, $X^C$ and $X^D$ are each independently hydrogen, fluorine or trifluoromethyl, with the proviso that at least one of $X^A$, $X^B$, $X^C$ and $X^D$ is fluorine or trifluoromethyl, and t is an integer of 0 to 3.

Of the PAGs having formula (2), those having formula (2') are preferred.

(2')

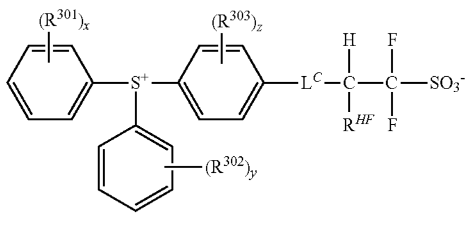

In formula (2'), $L^C$ is as defined above. $R^{HF}$ is hydrogen or trifluoromethyl, preferably trifluoromethyl. $R^{301}$, $R^{302}$ and $R^{303}$ are each independently hydrogen or a $C_1$-$C_{20}$ hydrocarbyl group which may contain a heteroatom. The hydrocarbyl group may be saturated or unsaturated and straight, branched or cyclic. Examples thereof are as exemplified above for $R^{111}$ in formula (1A'). The subscripts x and y are each independently an integer of 0 to 5, and z is an integer of 0 to 4.

Examples of the PAG having formula (2) are as exemplified as the PAG having formula (2) in U.S. Pat. No. 9,720,324 (JP-A 2017-026980).

Of the foregoing PAGs, those having an anion of formula (1A') or (1D) are especially preferred because of reduced acid diffusion and high solubility in the solvent. Also those having formula (2') are especially preferred because of extremely reduced acid diffusion.

A sulfonium or iodonium salt having an iodized or brominated aromatic ring-containing anion may also be used as the PAG. Suitable are sulfonium and iodonium salts having the formulae (3-1) and (3-2).

(3-1)

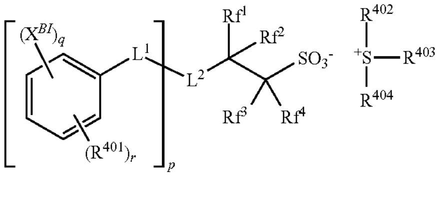

-continued (3-2)

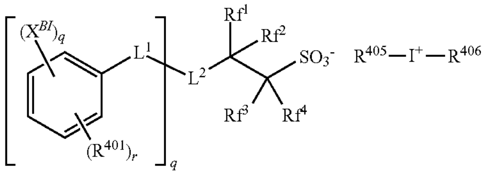

In formulae (3-1) and (3-2), p is an integer of 1 to 3, q is an integer of 1 to 5, r is an integer of 0 to 3, and $1 \leq q+r \leq 5$. Preferably, q is an integer of 1 to 3, more preferably 2 or 3, and r is an integer of 0 to 2.

$X^{B1}$ is iodine or bromine, and may be the same or different when p and/or q is 2 or more.

$L^1$ is a single bond, ether bond, ester bond, or a $C_1$-$C_6$ saturated hydrocarbylene group which may contain an ether bond or ester bond. The saturated hydrocarbylene group may be straight, branched or cyclic.

$L^2$ is a single bond or a $C_1$-$C_{20}$ divalent linking group when p=1, or a $C_1$-$C_{20}$ (p+1)-valent linking group when p=2 or 3, the linking group optionally containing an oxygen, sulfur or nitrogen atom.

$R^{401}$ is a hydroxy group, carboxy group, fluorine, chlorine, bromine, amino group, or a $C_1$-$C_{20}$ hydrocarbyl, $C_1$-$C_{20}$ hydrocarbyloxy, $C_2$-$C_{20}$ hydrocarbylcarbonyl, $C_2$-$C_{20}$ hydrocarbyloxycarbonyl, $C_2$-$C_{20}$ hydrocarbylcarbonyloxy or $C_1$-$C_{20}$ hydrocarbylsulfonyloxy group, which may contain fluorine, chlorine, bromine, hydroxy, amino or ether bond, or —$N(R^{401A})(R^{401B})$, —$N(R^{401C})$—C(═O)—$R^{401D}$ or —$N(R^{401C})$—C(═O)—O—$R^{401D}$. $R^{401A}$ and $R^{401B}$ are each independently hydrogen or a $C_1$-$C_6$ saturated hydrocarbyl group. $R^{401C}$ is hydrogen or a $C_1$-$C_6$ saturated hydrocarbyl group which may contain halogen, hydroxy, $C_1$-$C_6$ saturated hydrocarbyloxy. $C_2$-$C_6$ saturated hydrocarbylcarbonyl or $C_2$-$C_6$ saturated hydrocarbylcarbonyloxy moiety. $R^{401D}$ is a $C_1$-$C_{16}$ aliphatic hydrocarbyl, $C_6$-$C_{12}$ aryl or $C_7$-$C_{15}$ aralkyl group, which may contain halogen, hydroxy, $C_1$-$C_6$ saturated hydrocarbyloxy, $C_2$-$C_6$ saturated hydrocarbylcarbonyl or $C_2$-$C_6$ saturated hydrocarbylcarbonyloxy moiety. The aliphatic hydrocarbyl group may be saturated or unsaturated and straight, branched or cyclic. The hydrocarbyl, hydrocarbyloxy, hydrocarbylcarbonyl, hydrocarbyloxycarbonyl, hydrocarbylcarbonyloxy, and hydrocarbylsulfonyloxy groups may be straight, branched or cyclic. Groups $R^{401}$ may be the same or different when p and/or r is 2 or more. Of these, $R^{401}$ is preferably hydroxy, $N(R^{401C})$—C(═O)—$R^{401D}$, —$N(R^{401C})$—C(═O)—O—$R^{401D}$, fluorine, chlorine, bromine, methyl or methoxy.

In formulae (3-1) and (3-2), $Rf^1$ to $Rf^4$ are each independently hydrogen, fluorine or trifluoromethyl, at least one of $Rf^1$ to $Rf^4$ is fluorine or trifluoromethyl, or $Rf^1$ and $Rf^2$, taken together, may form a carbonyl group. Preferably, both $Rf^3$ and $Rf^4$ are fluorine.

$R^{402}$ to $R^{406}$ are each independently halogen or a $C_1$-$C_{20}$ hydrocarbyl group which may contain a heteroatom. The hydrocarbyl group may be saturated or unsaturated and straight, branched or cyclic. Examples thereof are as exemplified above for the hydrocarbyl groups $R^{101}$ to $R^{105}$ in formulae (1-1) and (1-2). In the hydrocarbyl group, some or all of the hydrogen atoms may be substituted by a hydroxy, carboxy, halogen, cyano, nitro, mercapto, sultone, sulfo, or sulfonium salt-containing moiety, and some constituent —$CH_2$— may be replaced by an ether bond, ester bond, carbonyl moiety, amide bond, carbonate bond or sulfonic ester bond. $R^{402}$ and $R^{403}$ may bond together to form a ring with the sulfur atom to which they are attached. Exemplary rings are the same as described above for the ring that $R^{101}$ and $R^{102}$ in formula (1-1), taken together, form with the sulfur atom to which they are attached.

Examples of the cation in the sulfonium salt having formula (3-1) include those exemplified above as the cation in the sulfonium salt having formula (1-1). Examples of the cation in the iodonium salt having formula (3-2) include those exemplified above as the cation in the iodonium salt having formula (1-2).

Examples of the anion in the opium salts having formulae (3-1) and (3-2) are shown below, but not limited thereto. Herein $X^{B1}$ is as defined above.

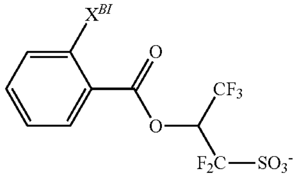

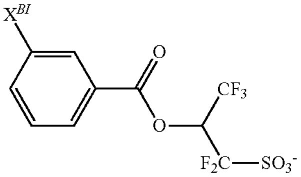

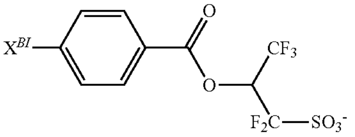

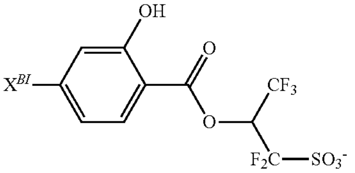

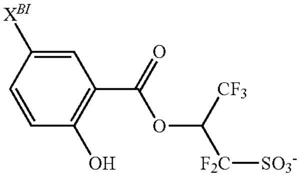

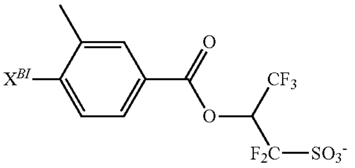

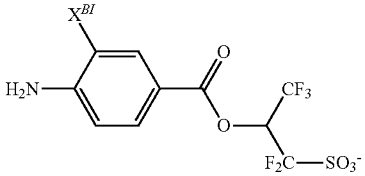

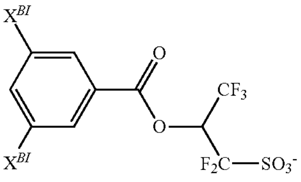

-continued
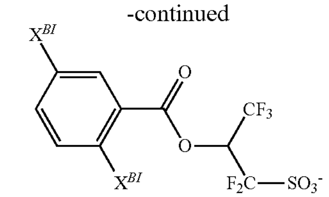
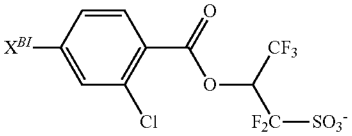
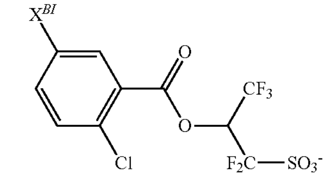
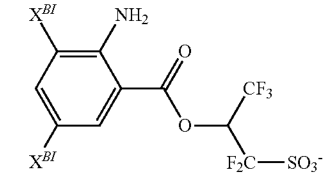
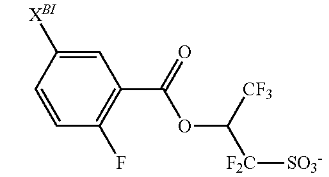
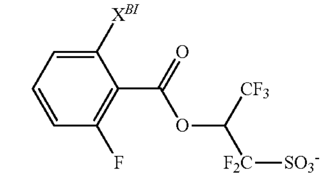
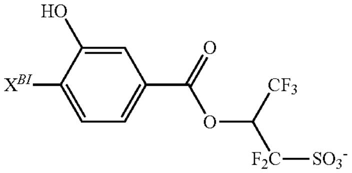
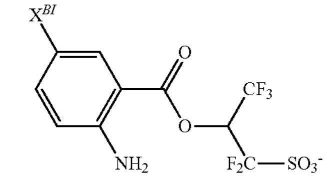
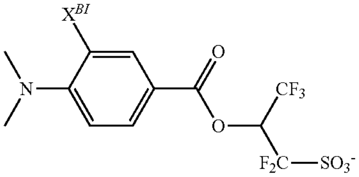
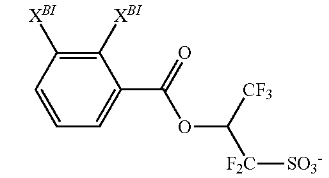
-continued
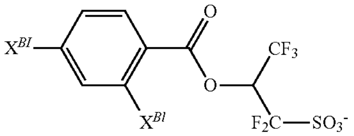
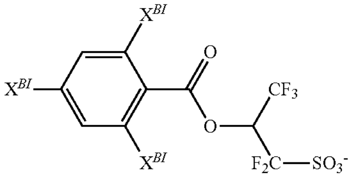
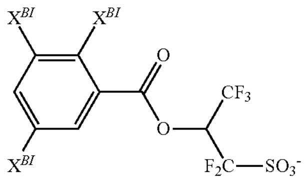
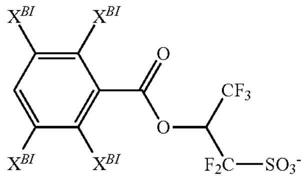
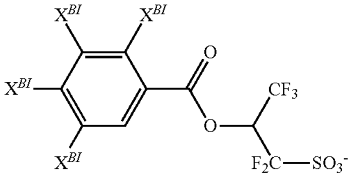
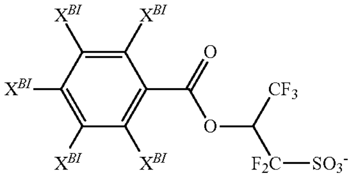
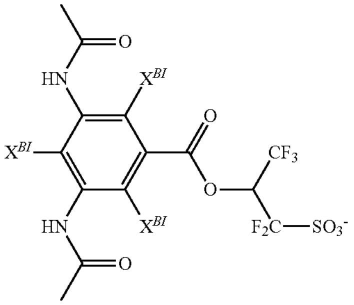
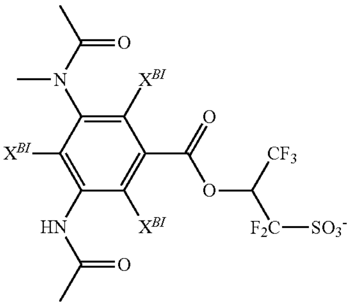

-continued
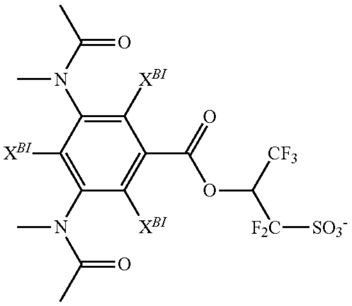
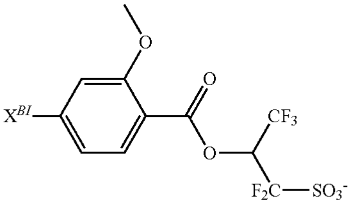
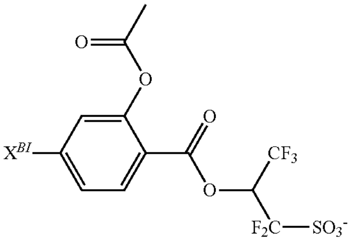
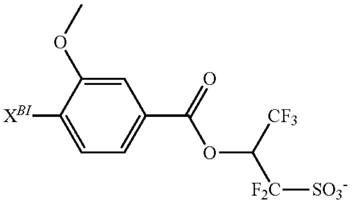
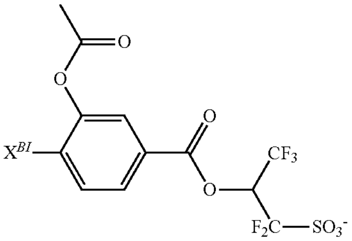
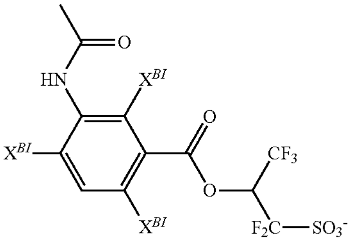
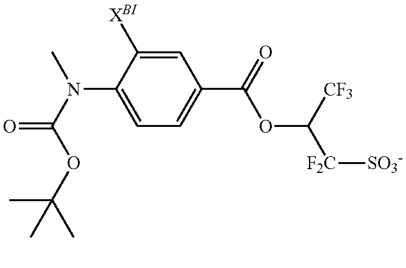
-continued
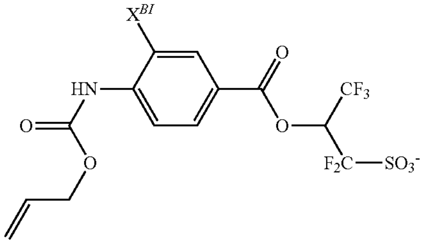
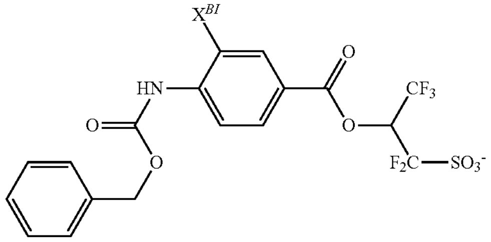
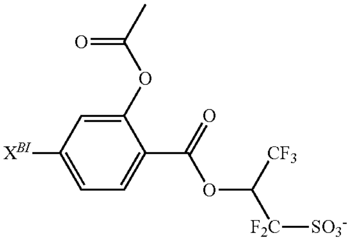
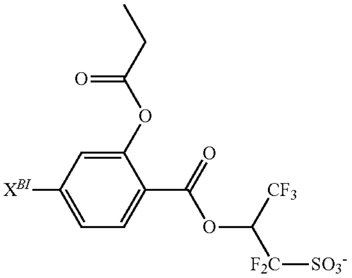
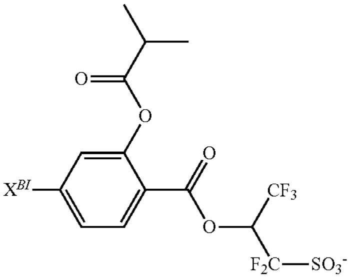
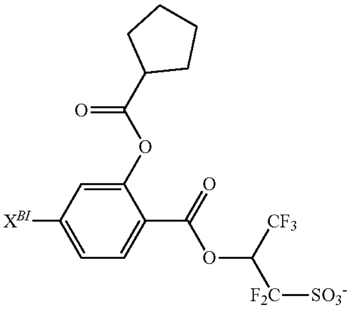

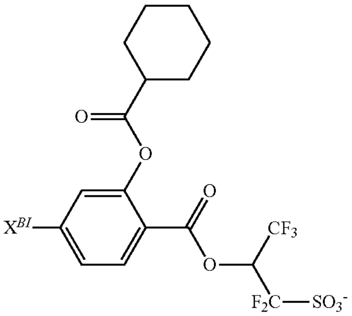
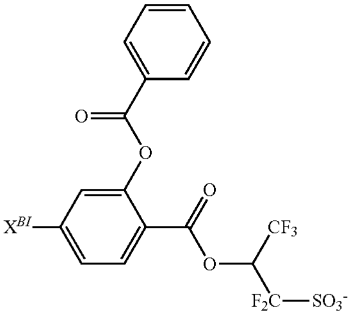
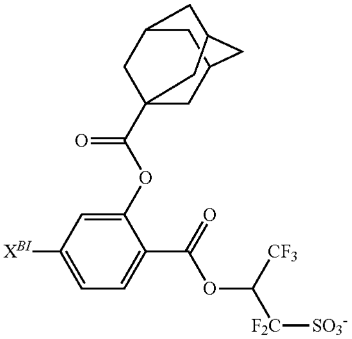
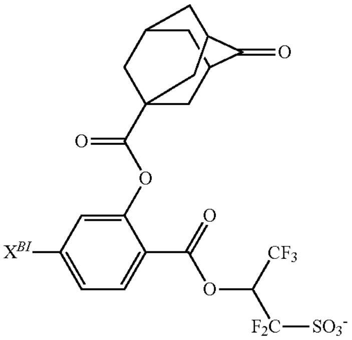
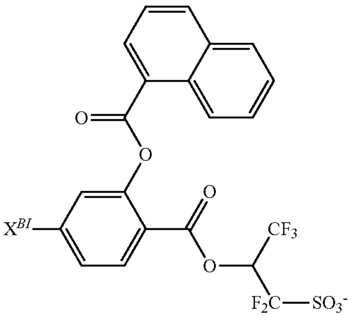
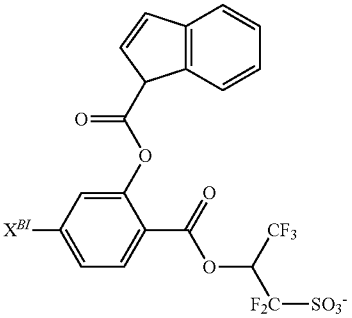
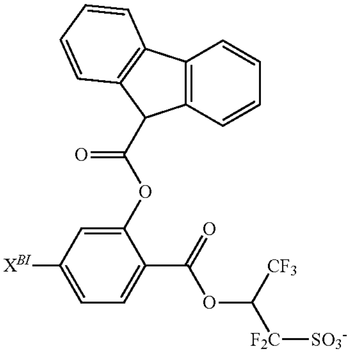
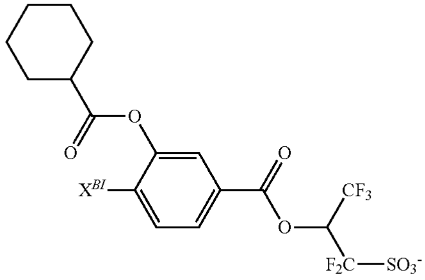
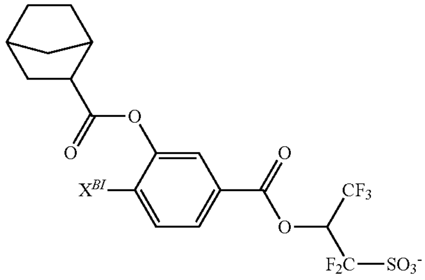
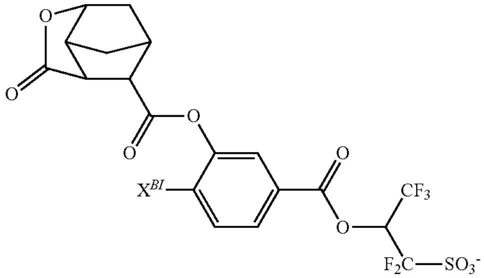
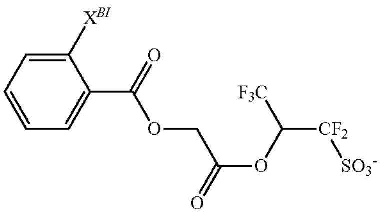

-continued
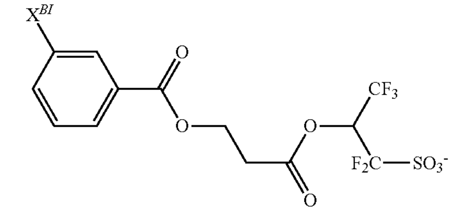
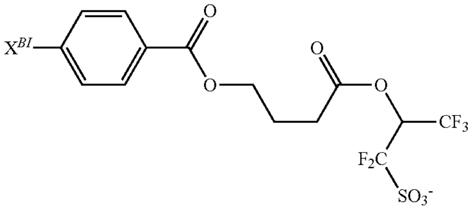
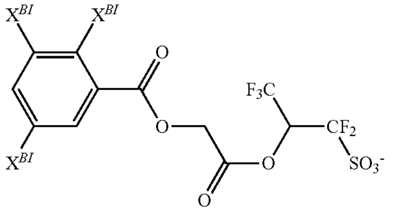
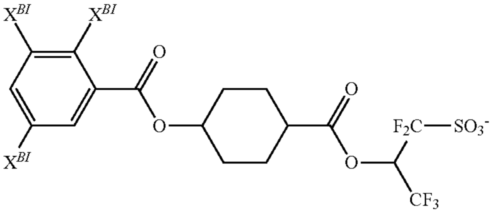
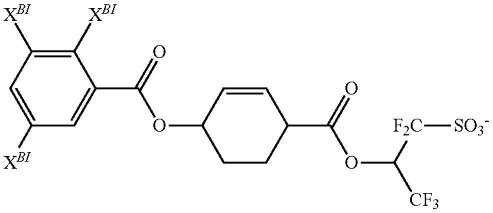
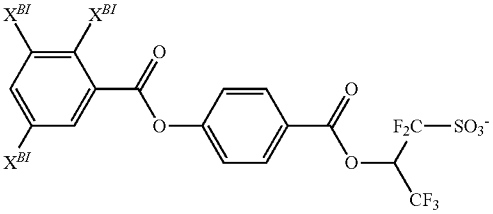
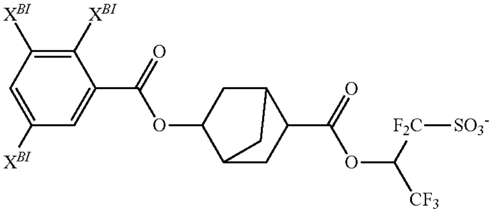
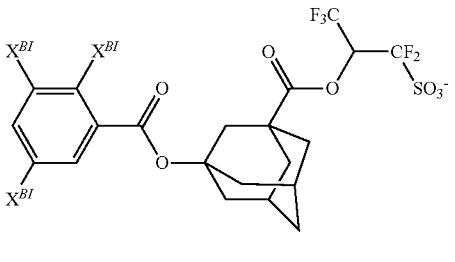
-continued
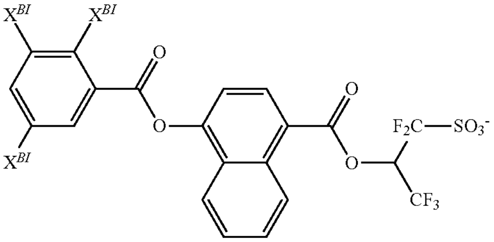
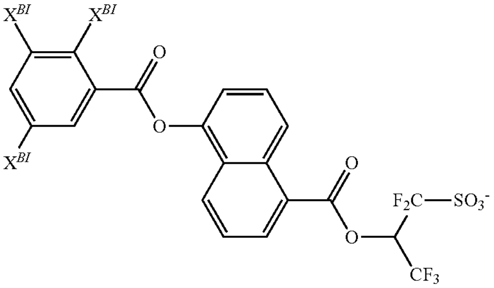
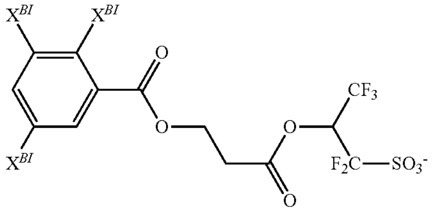
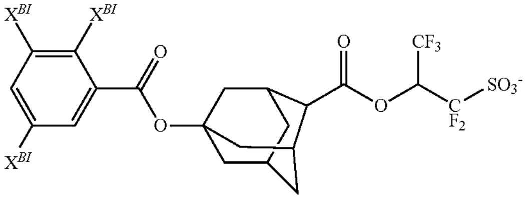
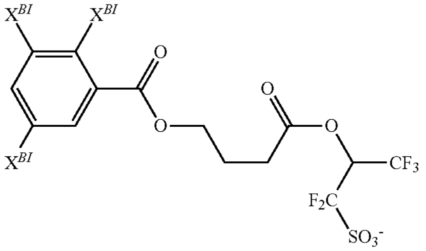
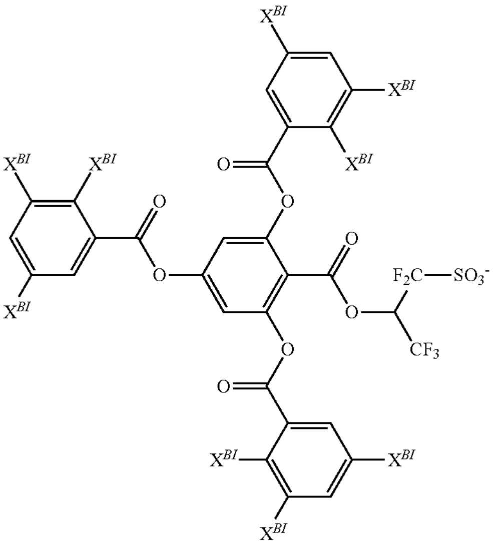

-continued
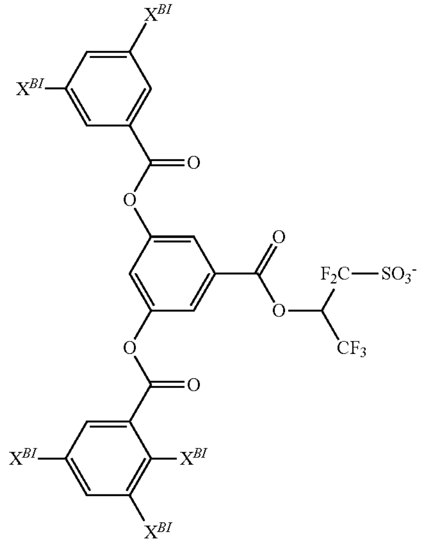
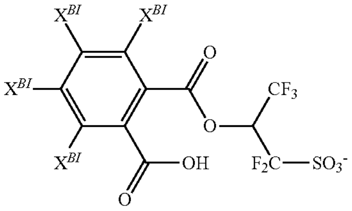
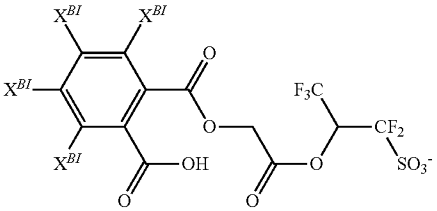
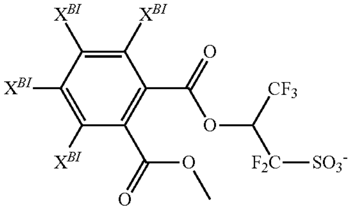
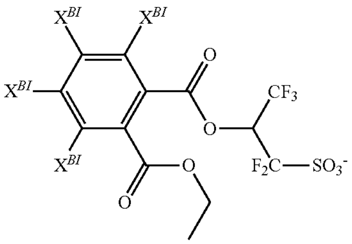
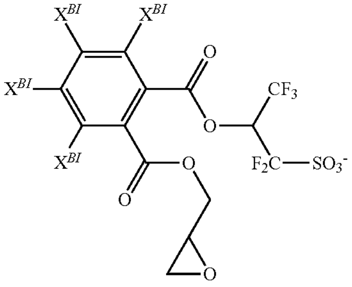
-continued
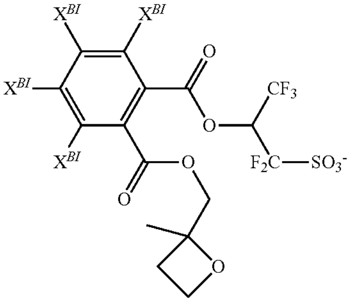
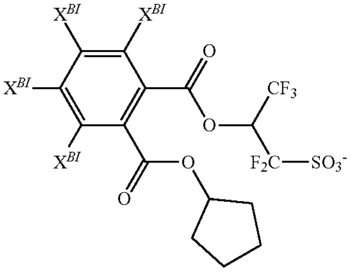
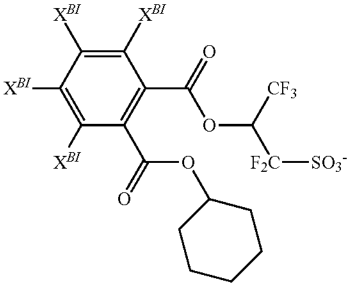
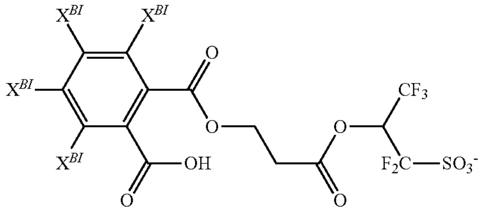
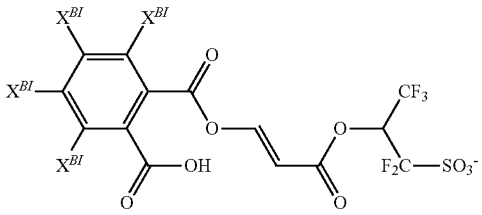
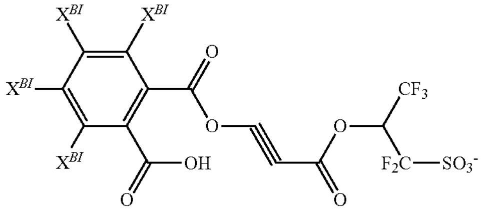
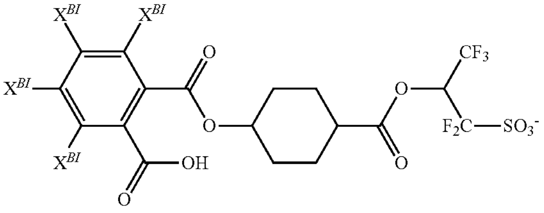

-continued
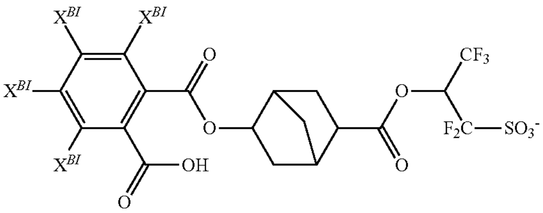
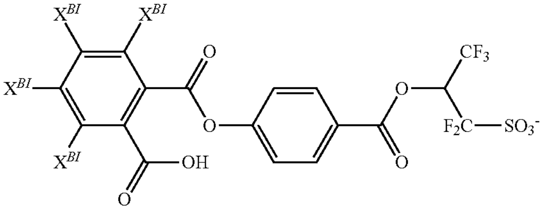
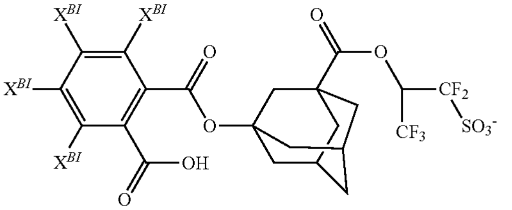
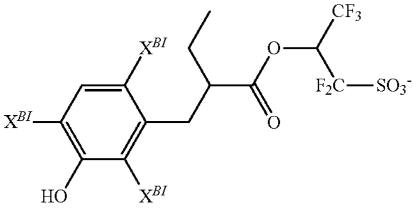
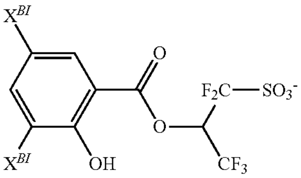
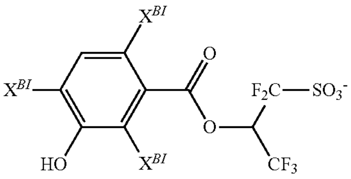
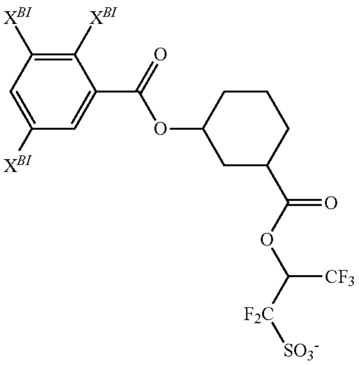
-continued
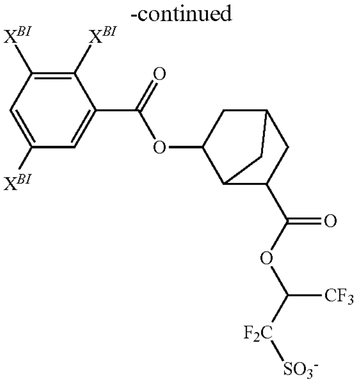
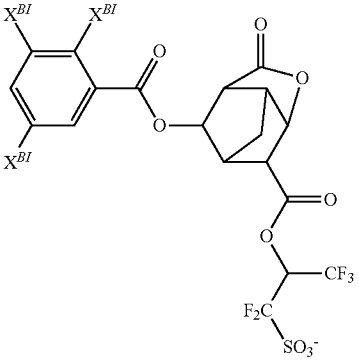
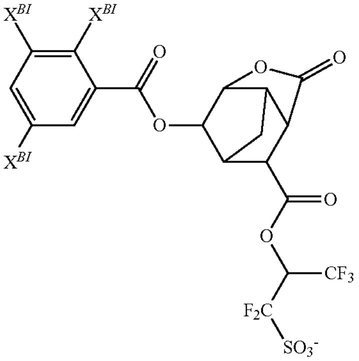
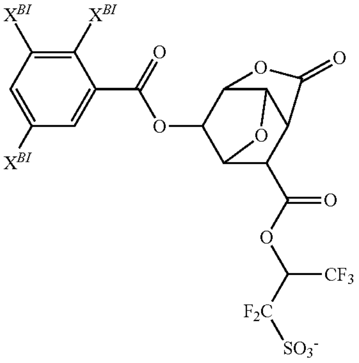

-continued
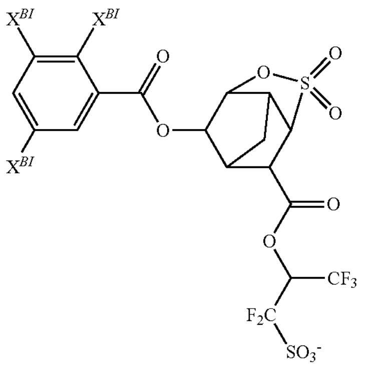
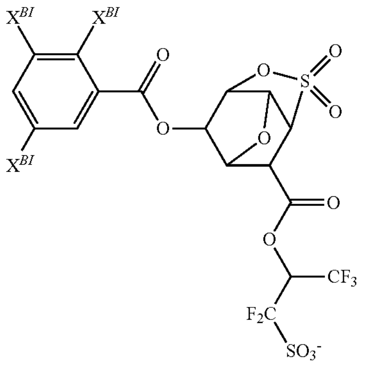
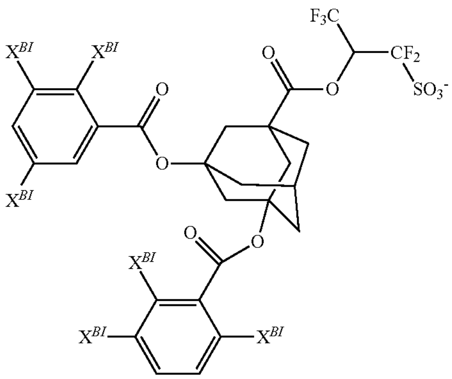
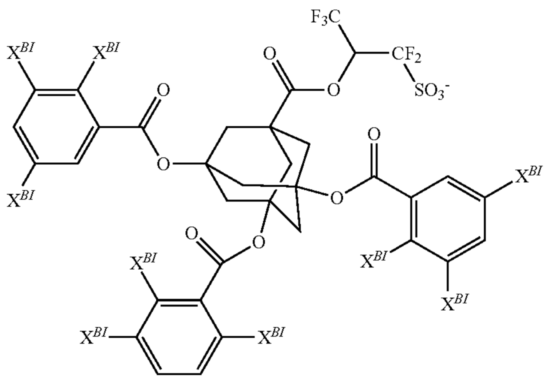
-continued
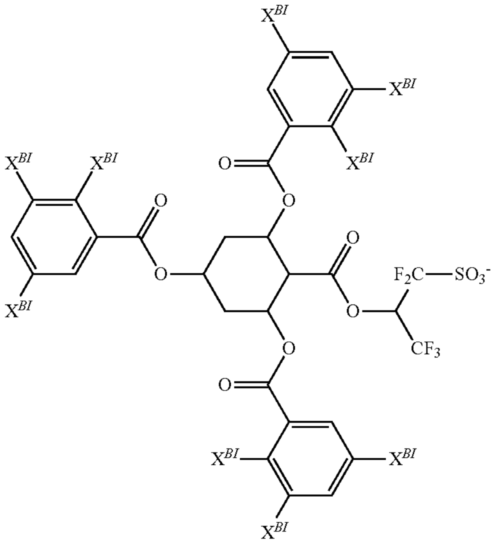
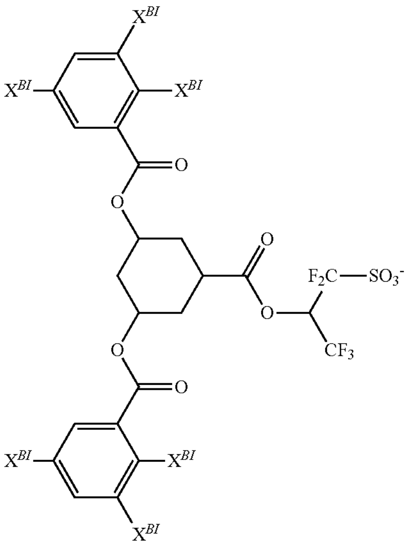
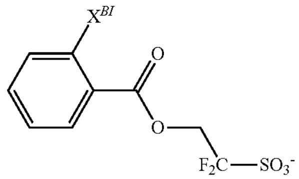
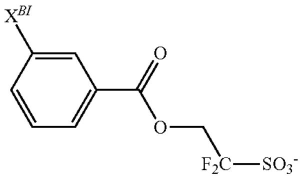
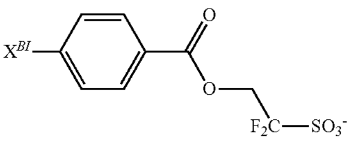

-continued
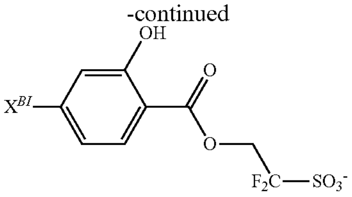
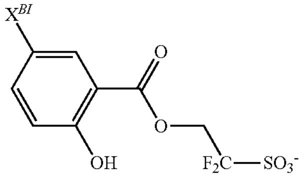
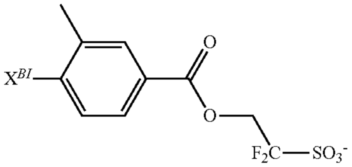
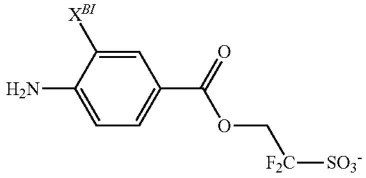
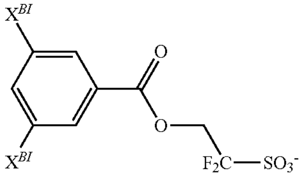
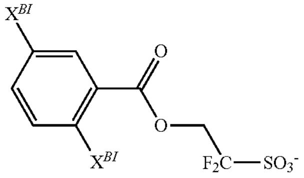
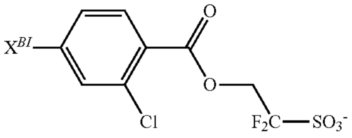
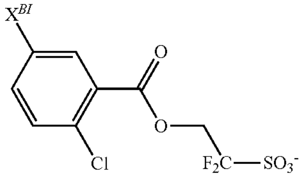
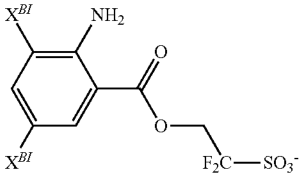
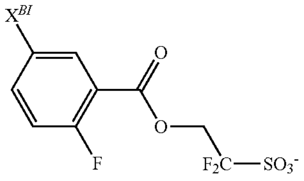
-continued
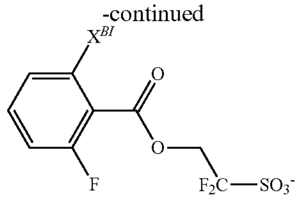
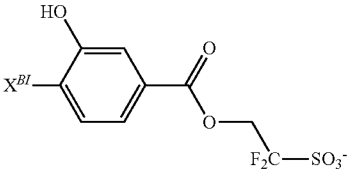
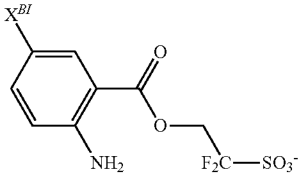
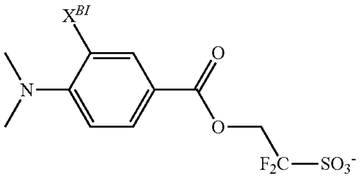
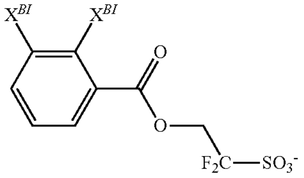
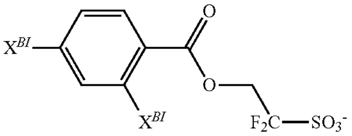
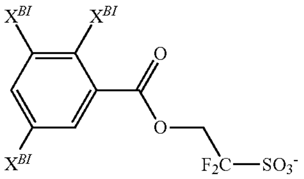
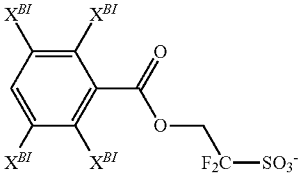
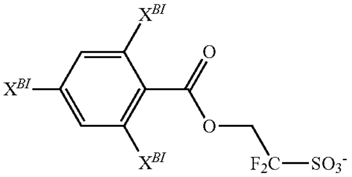
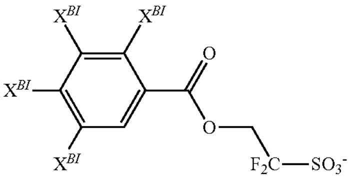

-continued
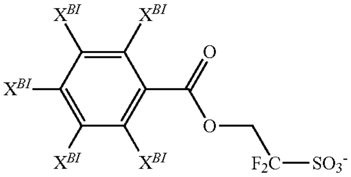
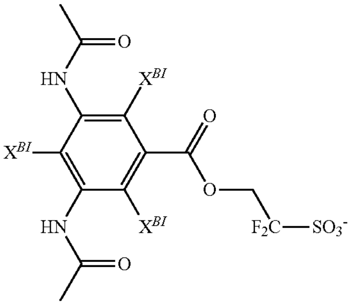
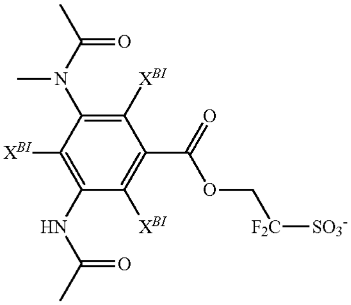
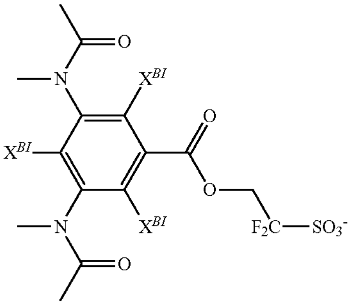
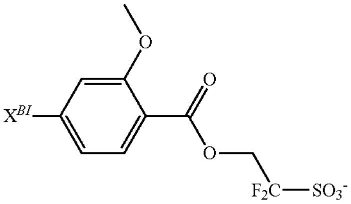
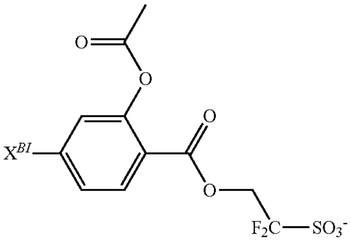
-continued
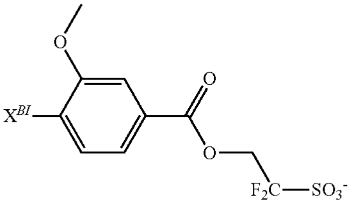
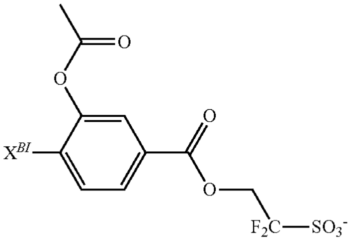
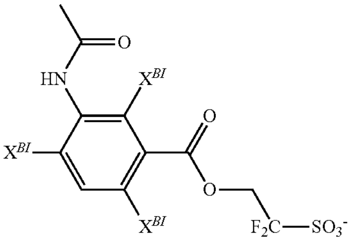
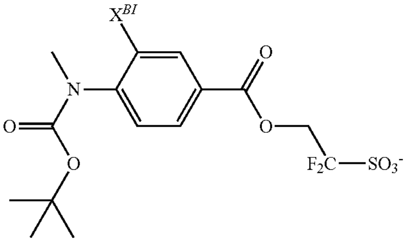
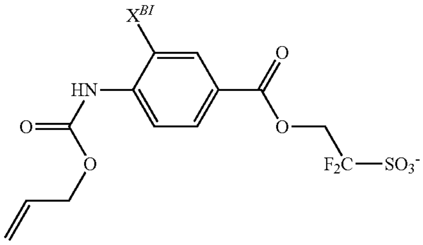
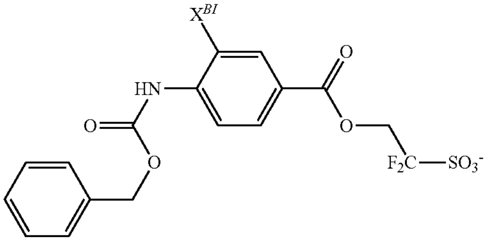
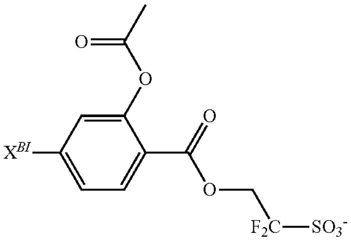

-continued
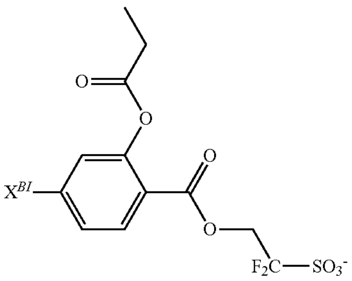
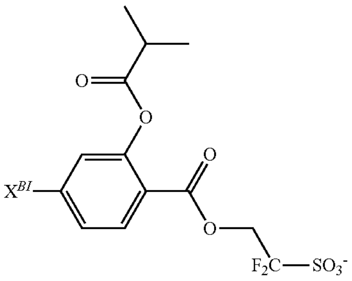
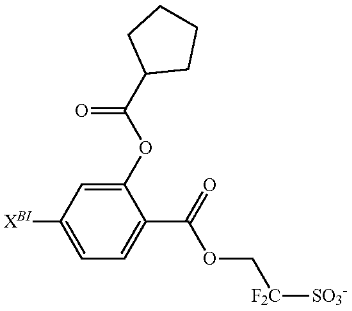
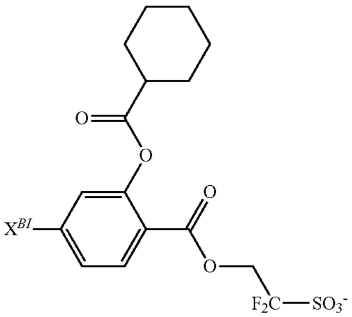
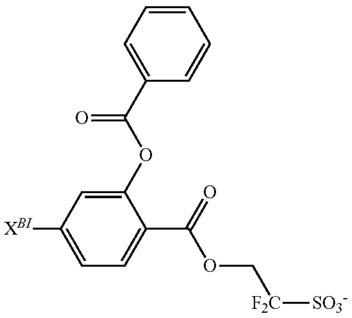
-continued
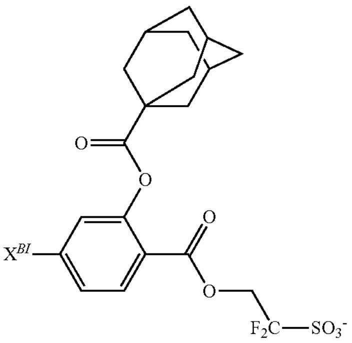
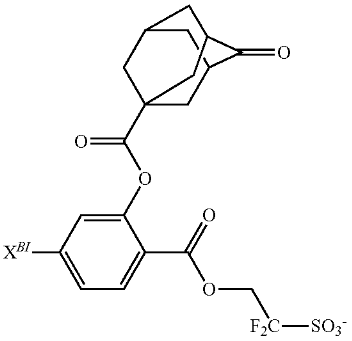
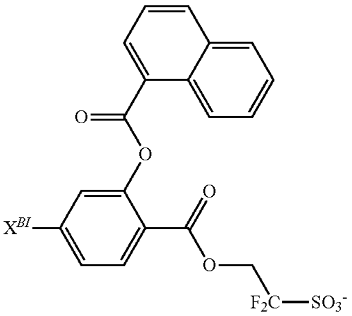
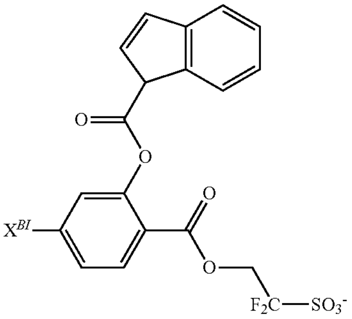
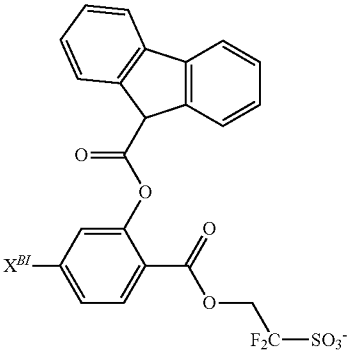

-continued
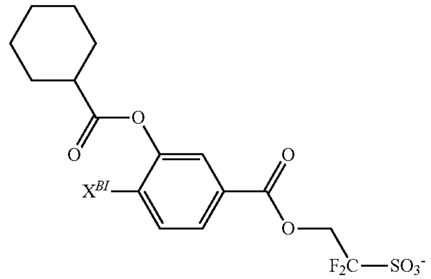
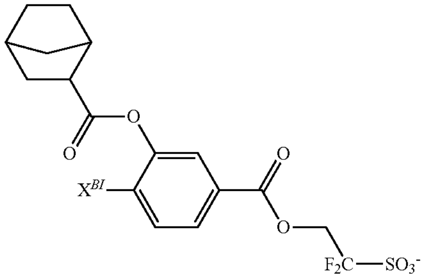
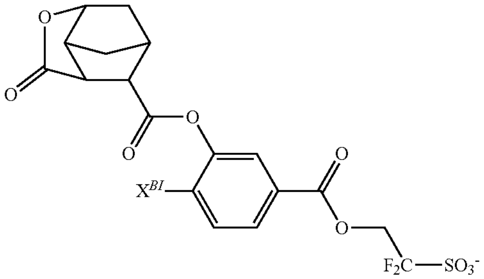
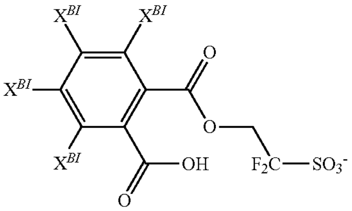
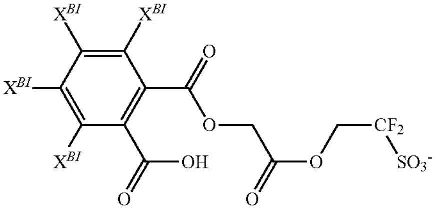
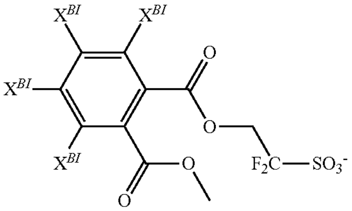
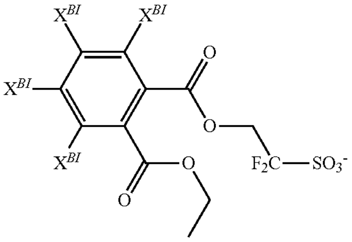
-continued
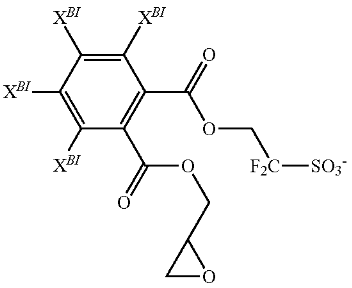
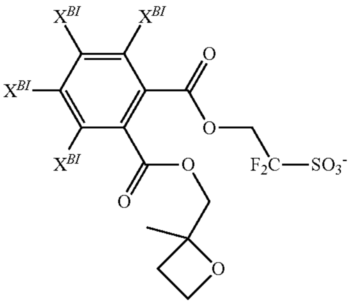
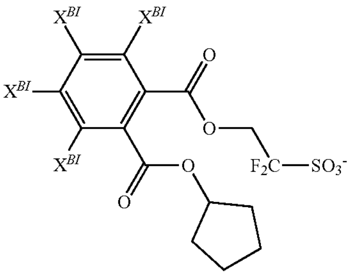
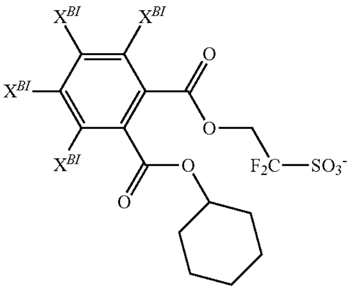
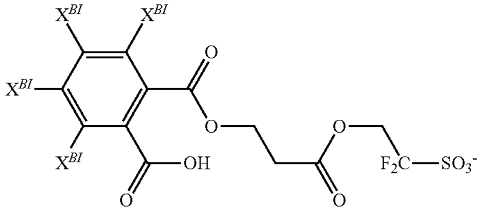
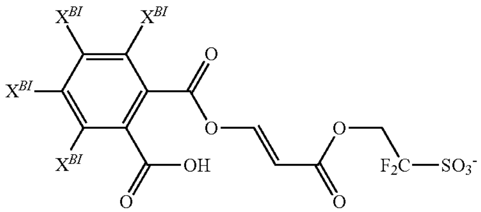

-continued
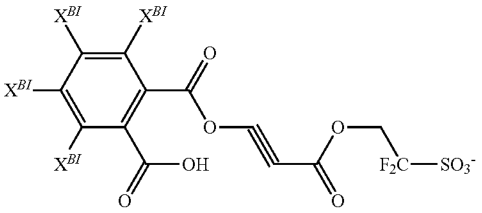
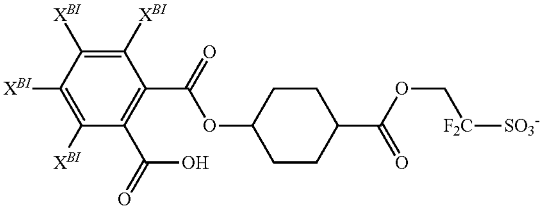
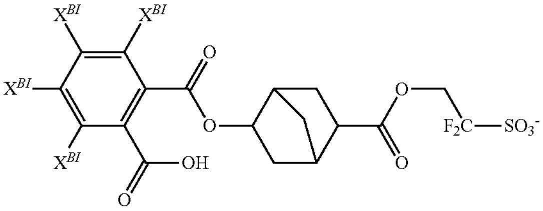
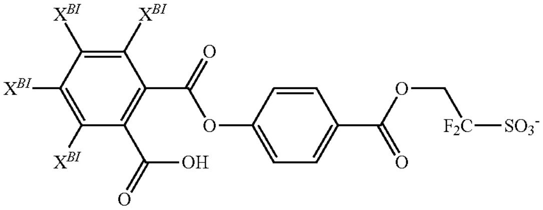
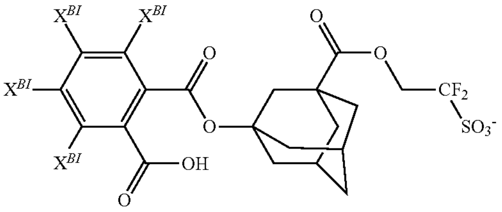
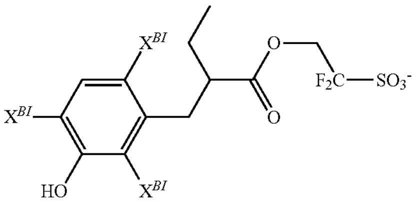
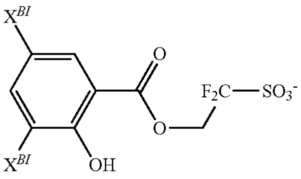
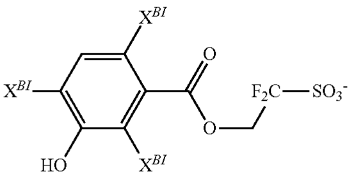
-continued
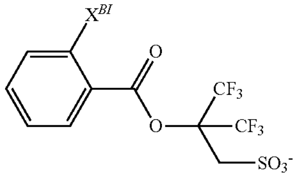
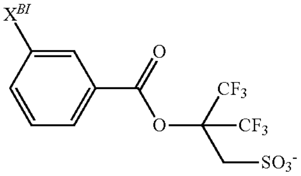
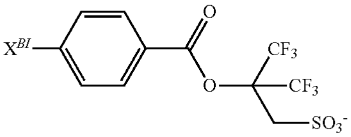
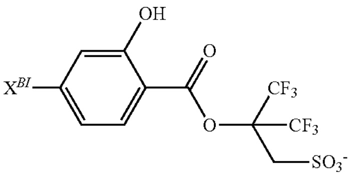
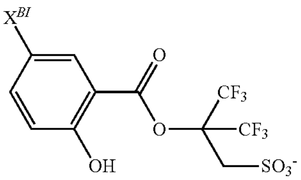
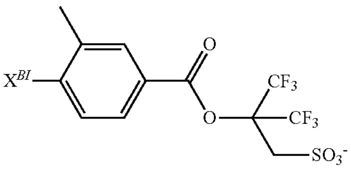
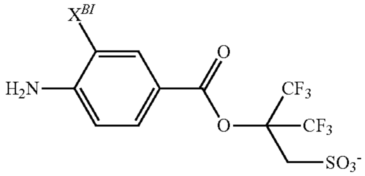
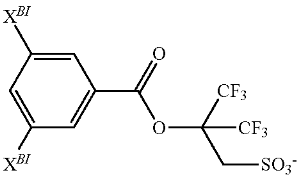
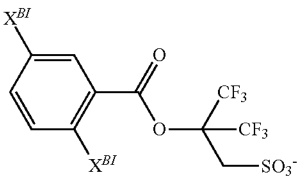
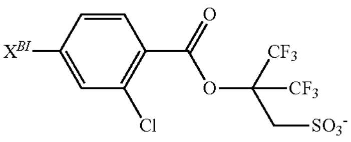

-continued
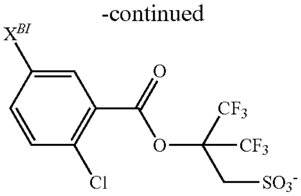
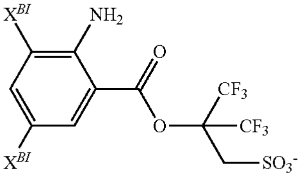
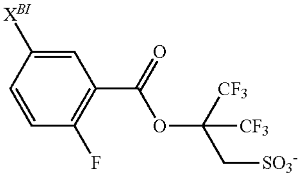
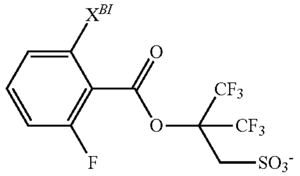
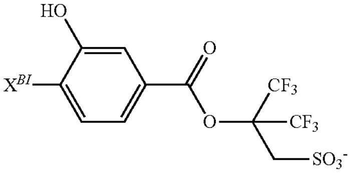
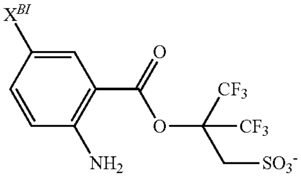
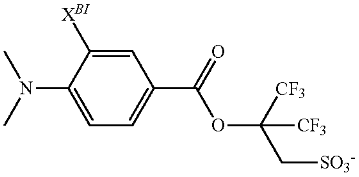
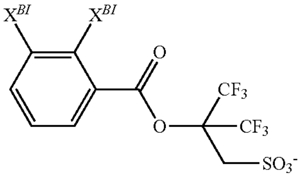
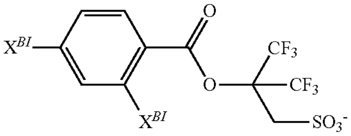
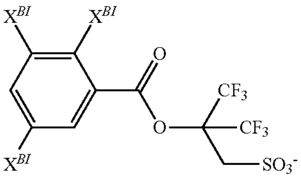
-continued
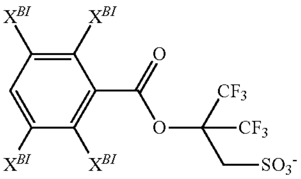
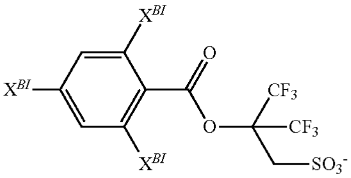
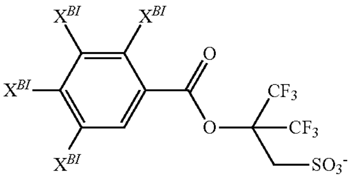
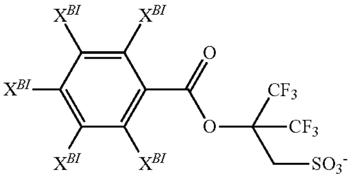
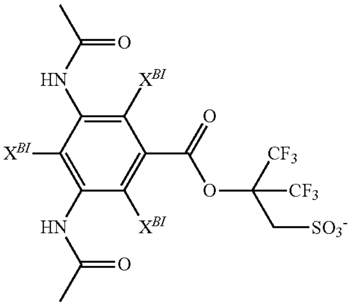
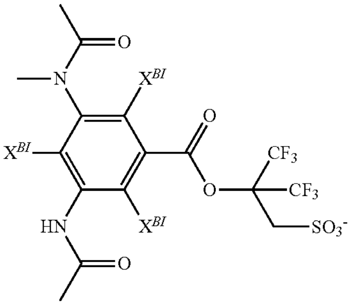
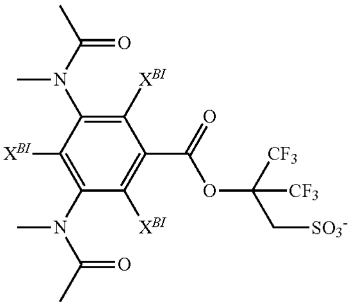

-continued
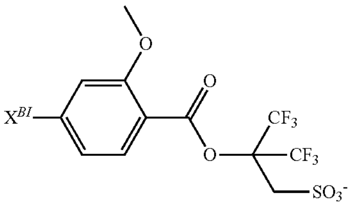
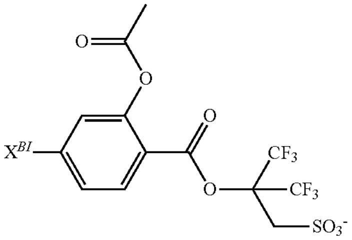
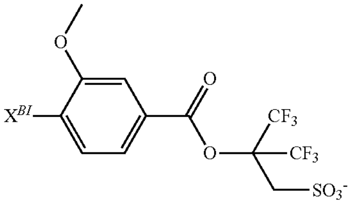
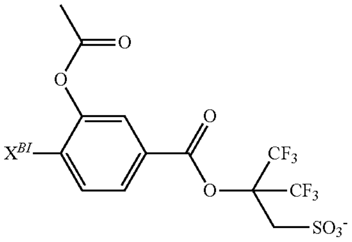
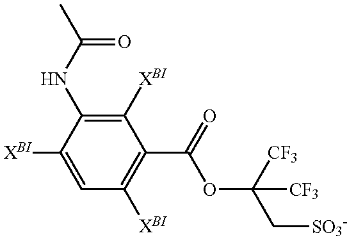
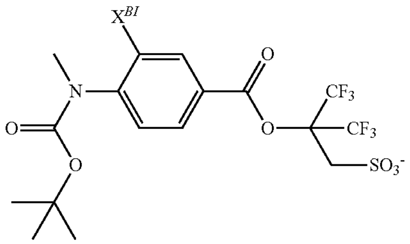
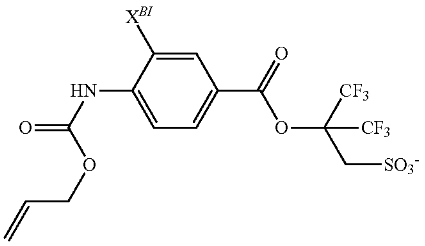
-continued
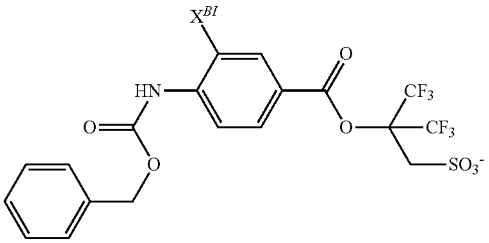
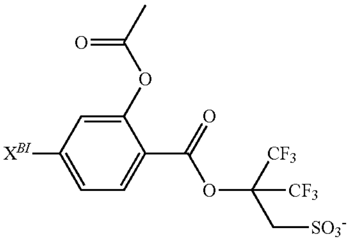
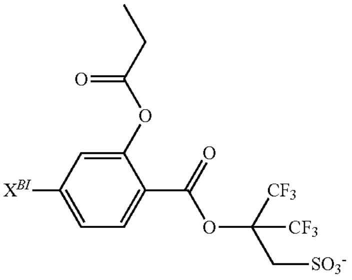
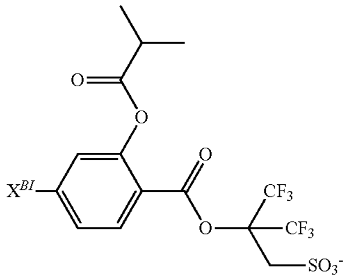
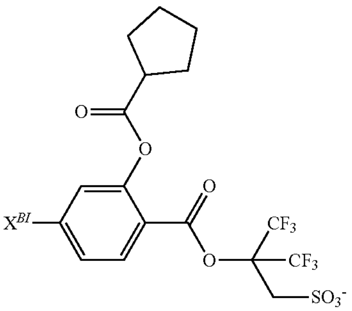
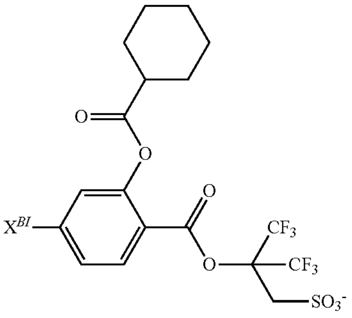

-continued
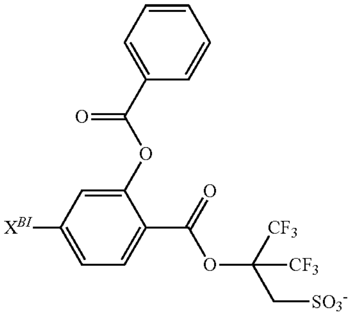
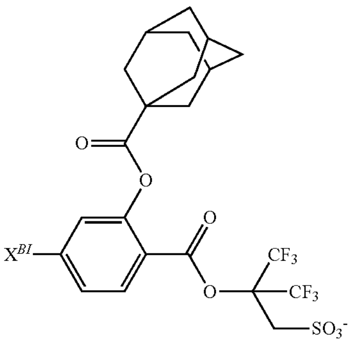
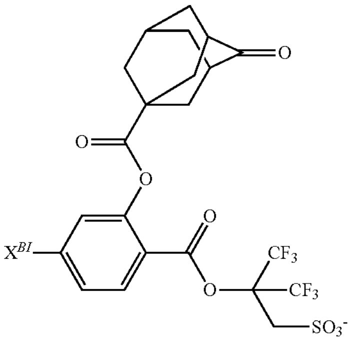
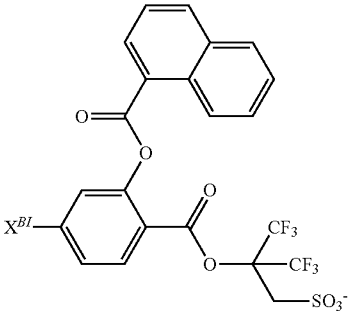
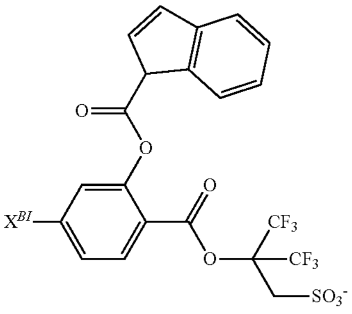
-continued
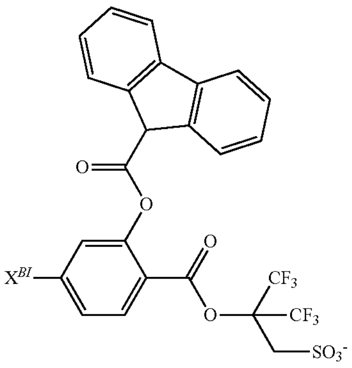
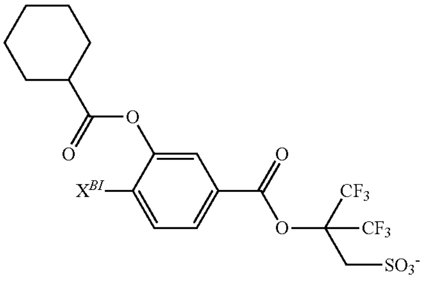
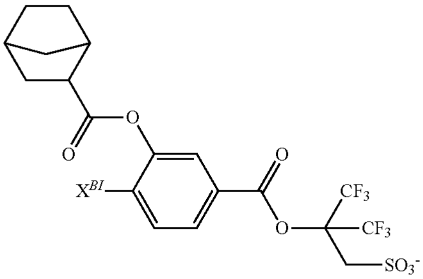
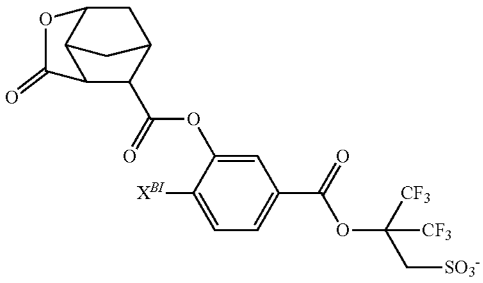
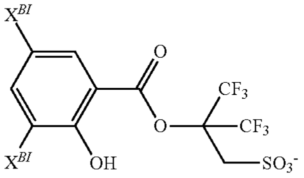
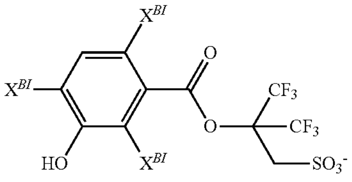

-continued
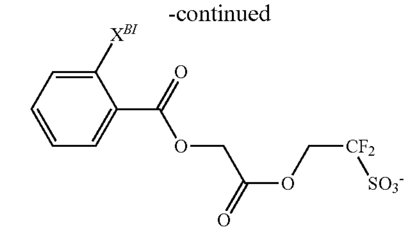
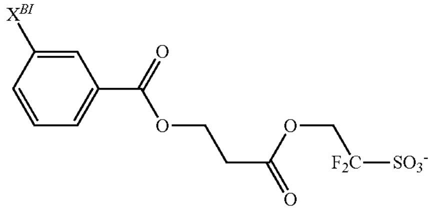
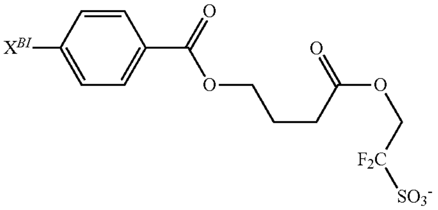
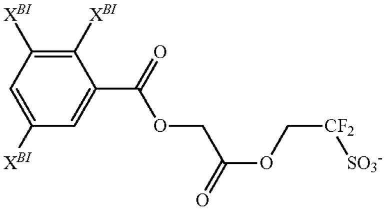
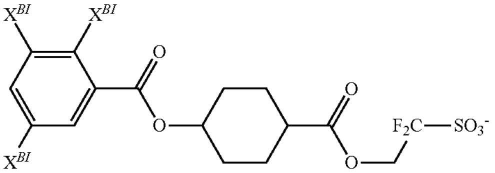
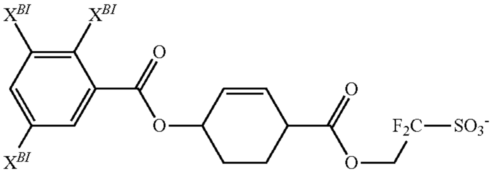
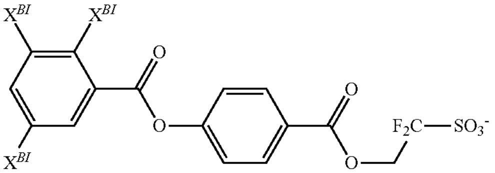
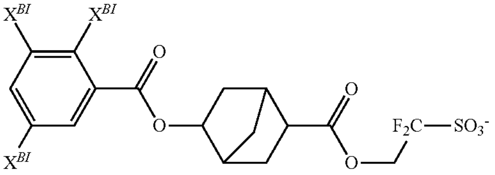
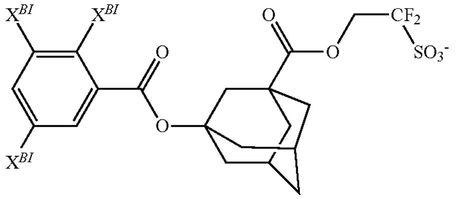
-continued
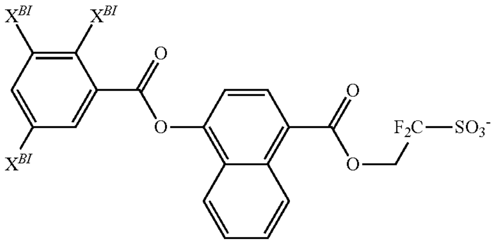
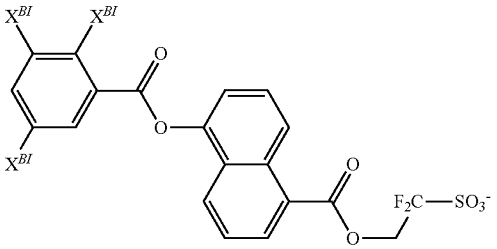
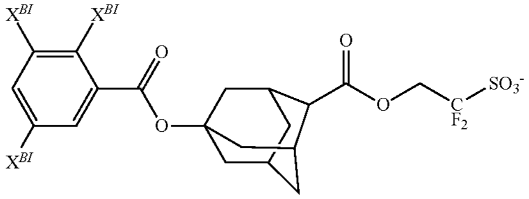
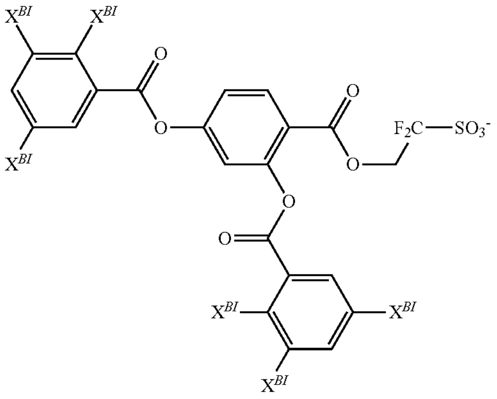
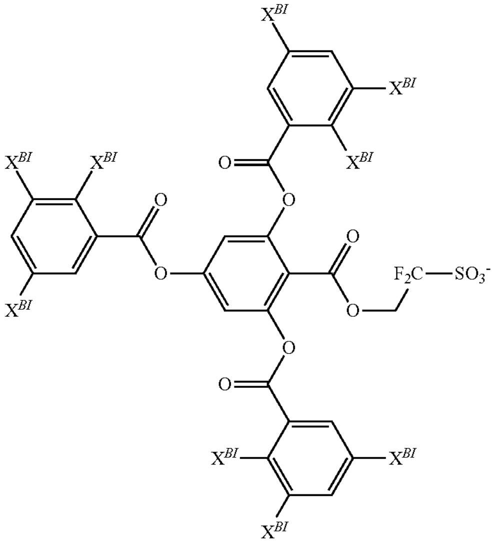

-continued
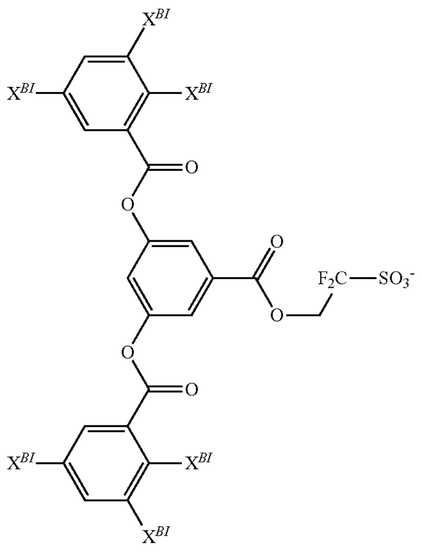
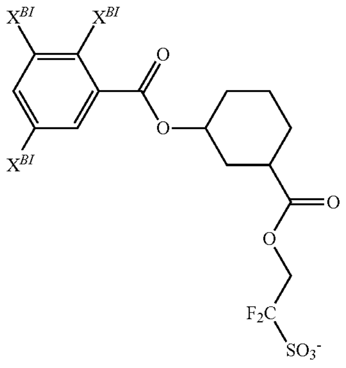
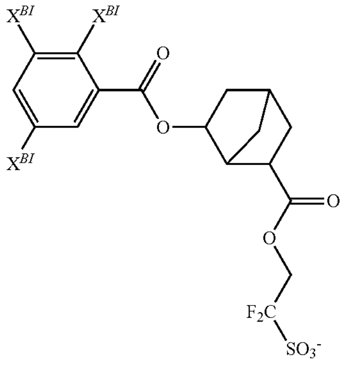
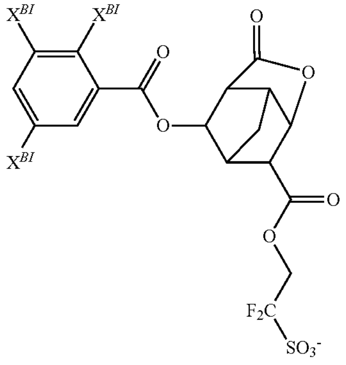
-continued
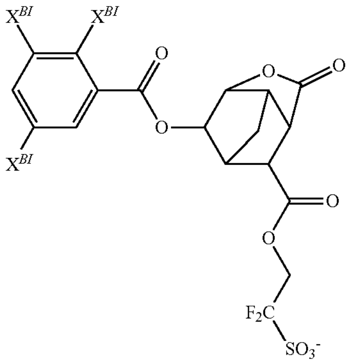
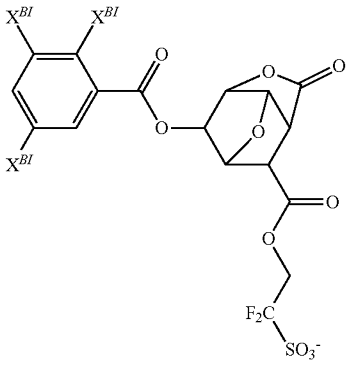
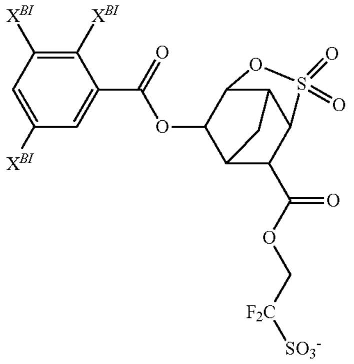
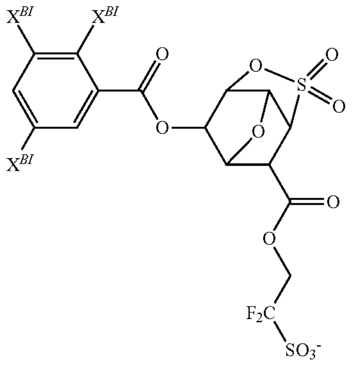

-continued
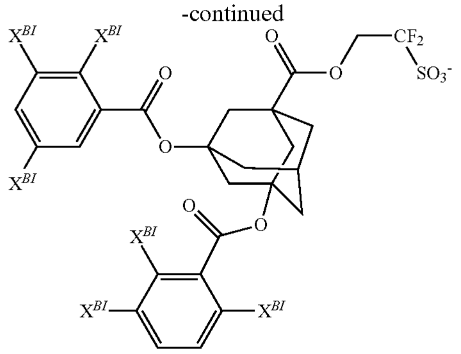
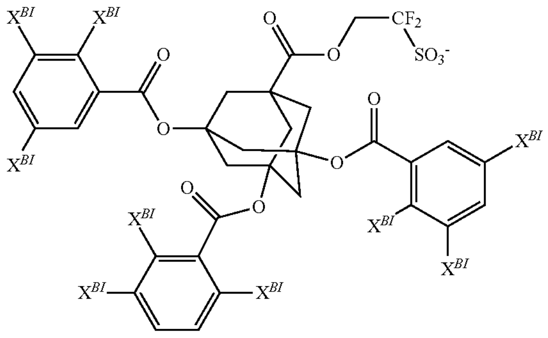
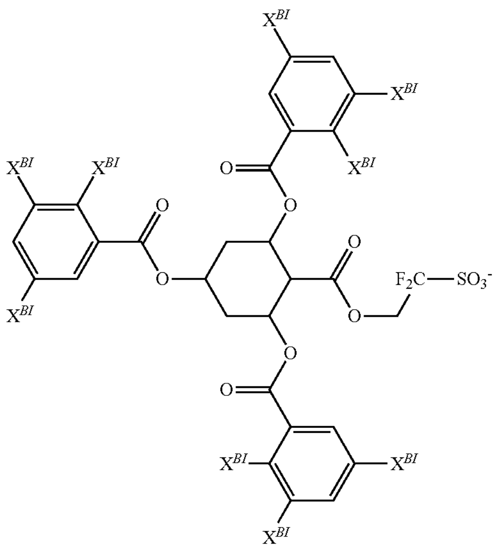
-continued
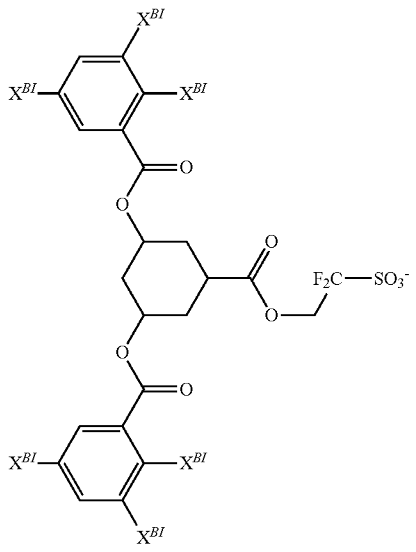
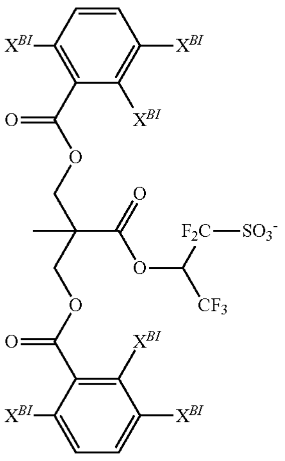
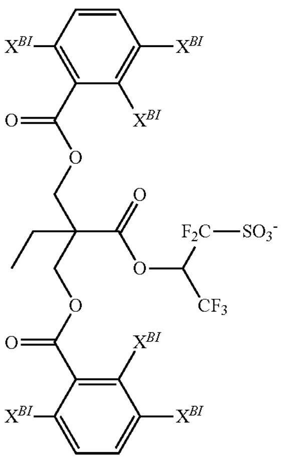

-continued
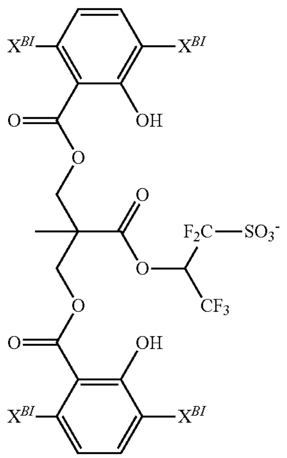
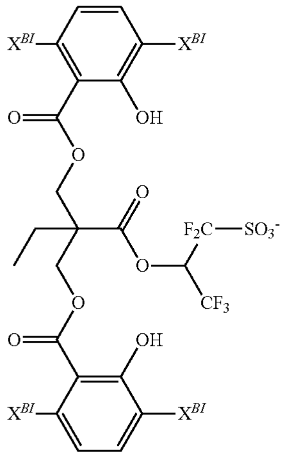
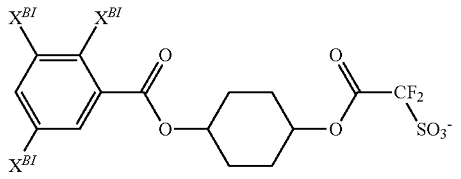
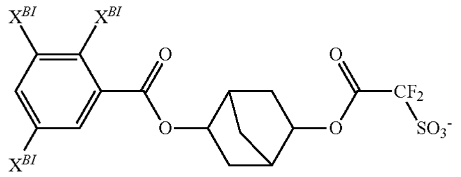
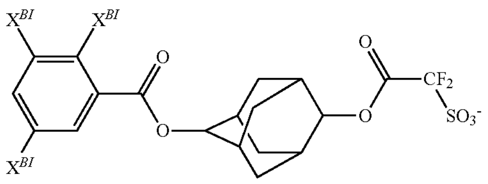
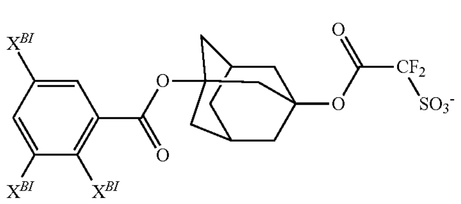
-continued
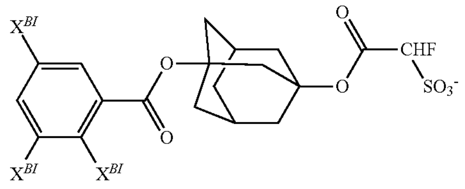
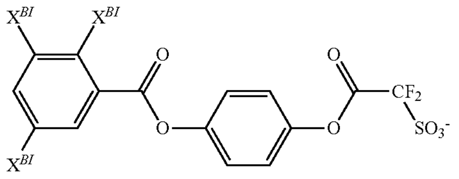
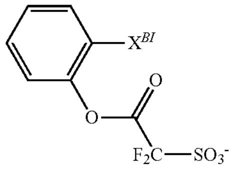
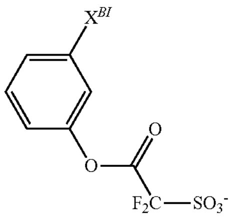
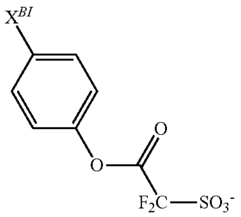
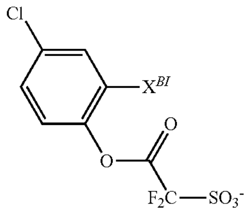
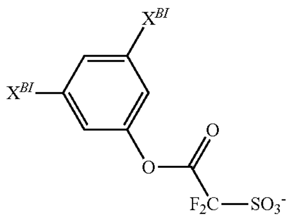
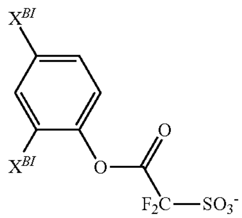
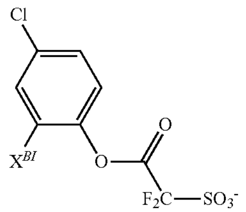
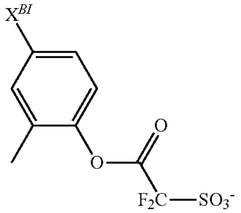
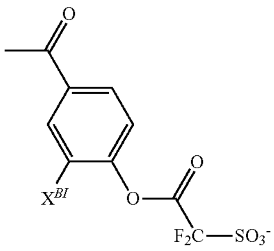
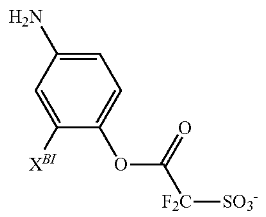

-continued
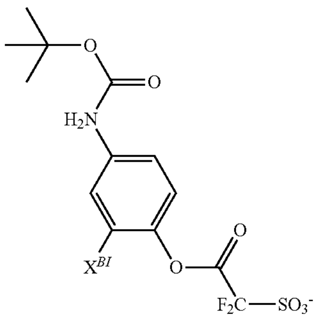
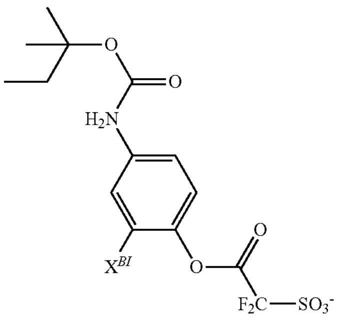
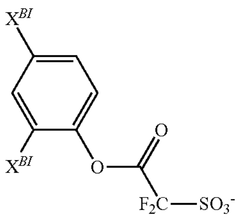
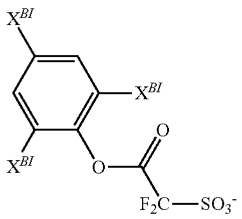
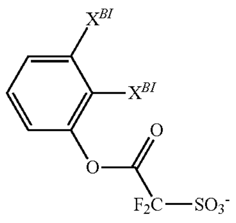
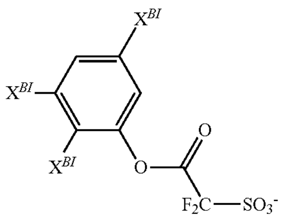
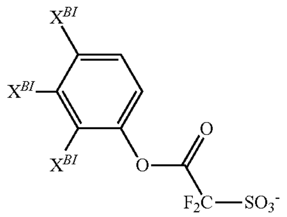
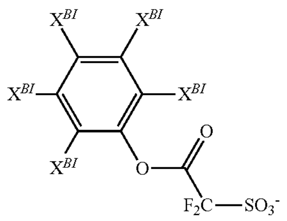
-continued
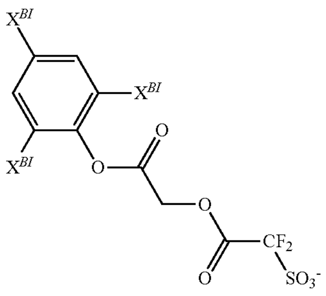
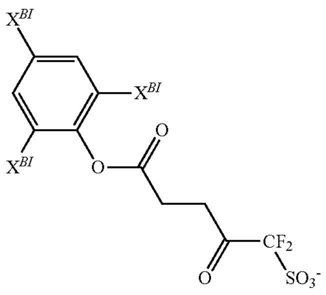
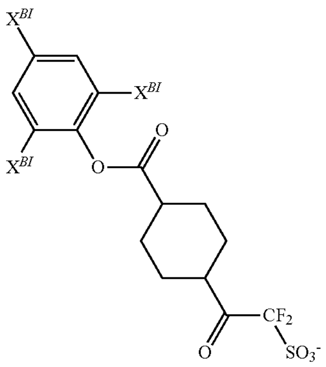
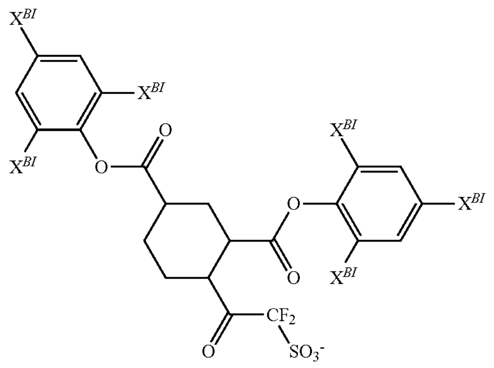
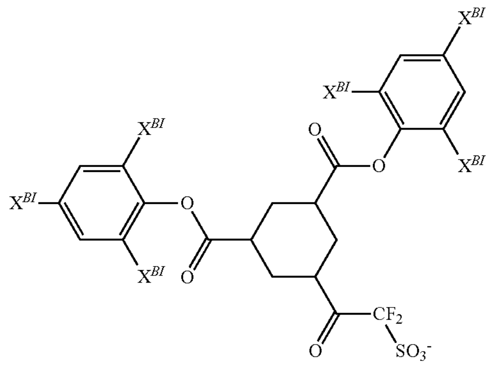

-continued
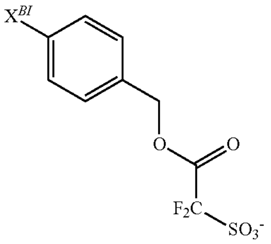
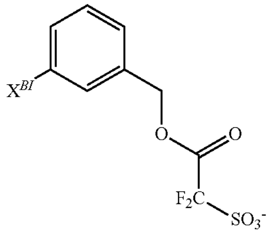
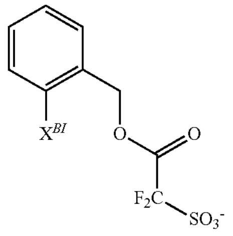
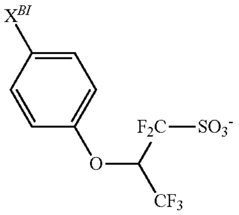
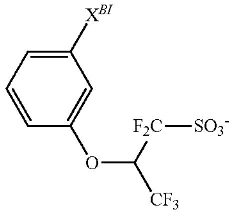
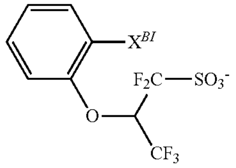
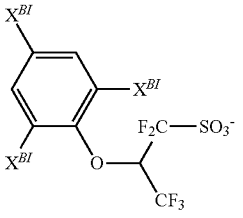
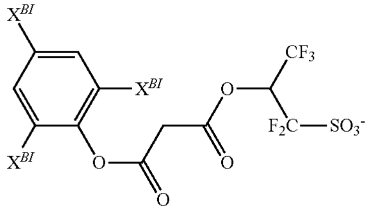
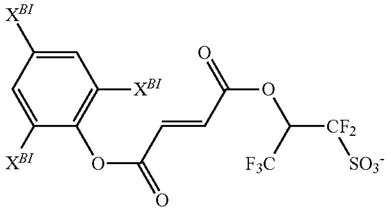
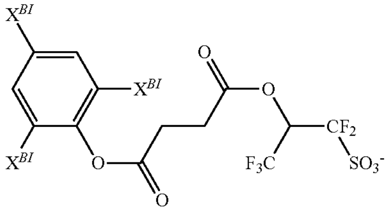
-continued
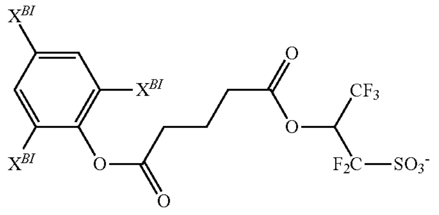
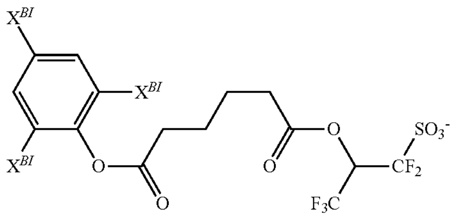
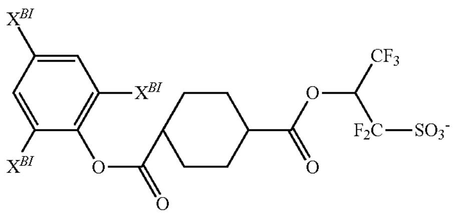
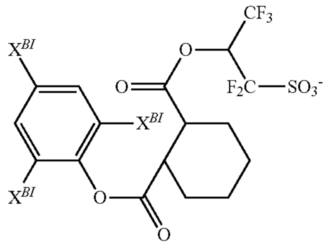
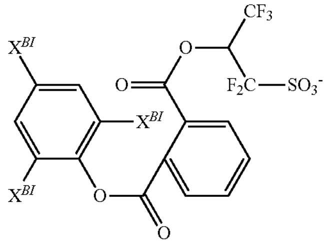
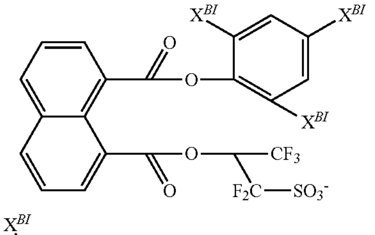
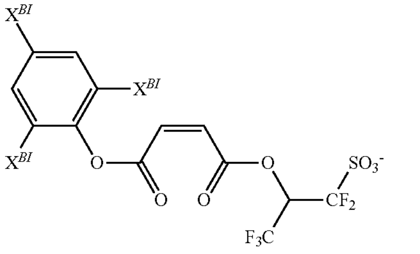

-continued
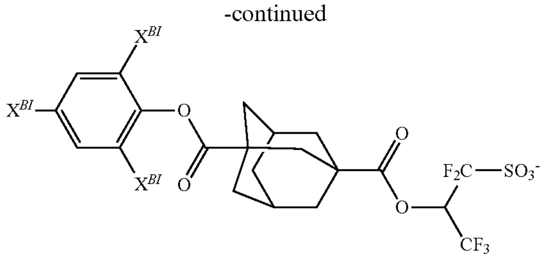
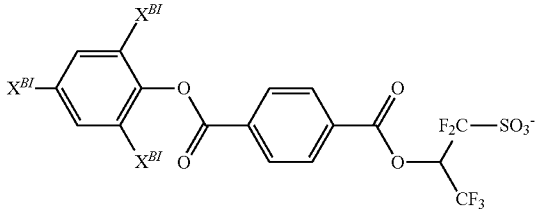
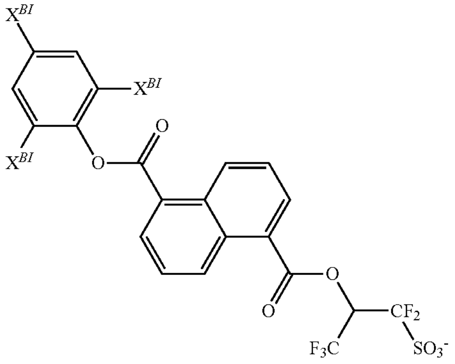
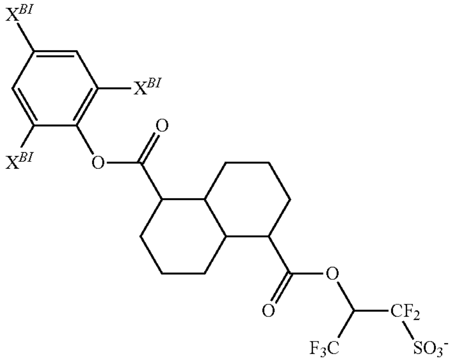
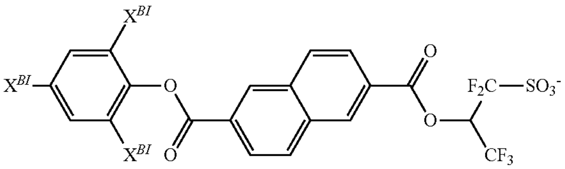
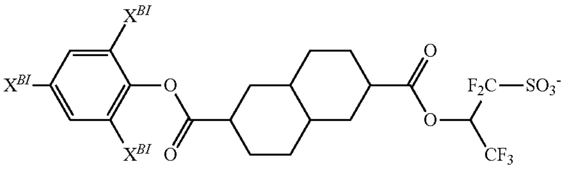
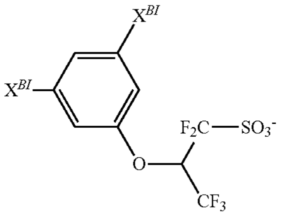
-continued
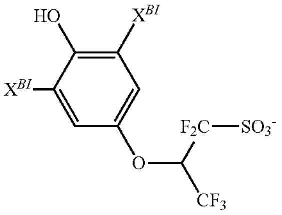
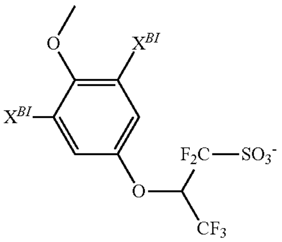
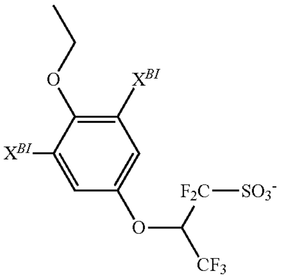
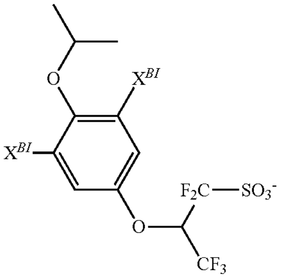
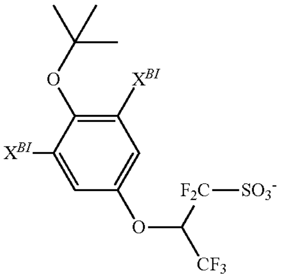
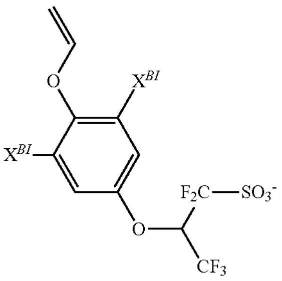

-continued
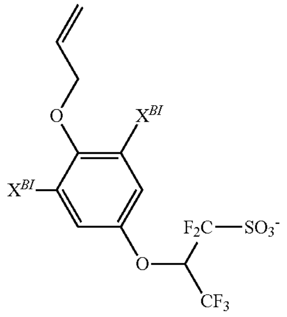
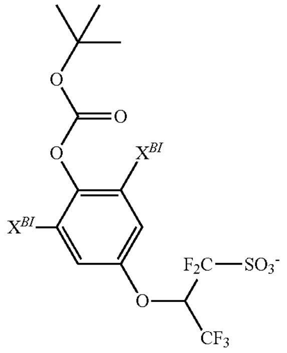
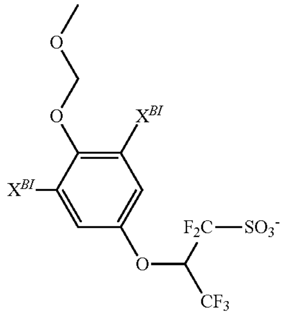
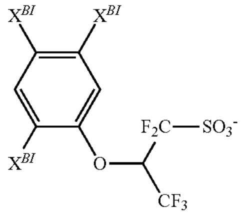
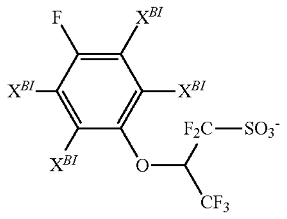
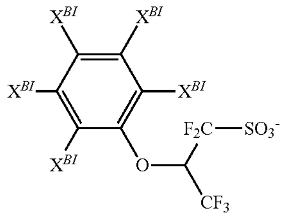
-continued
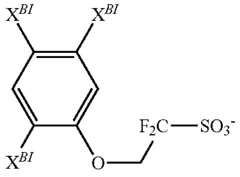
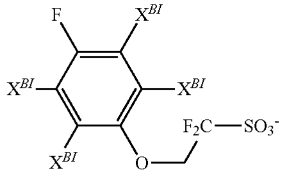
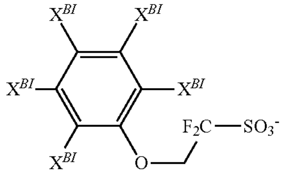
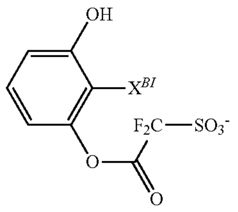
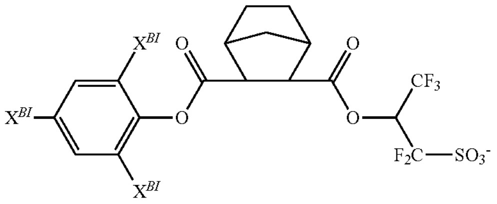
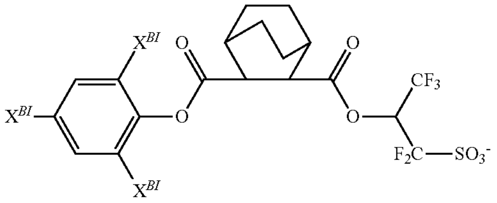
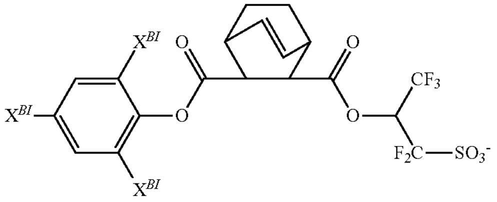
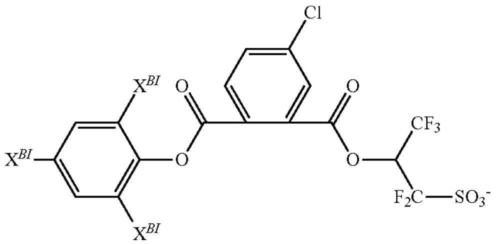
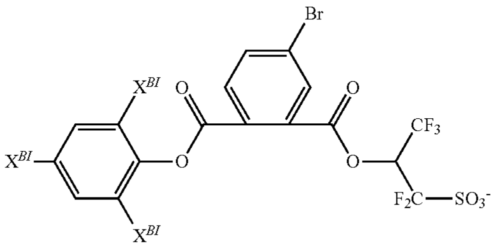
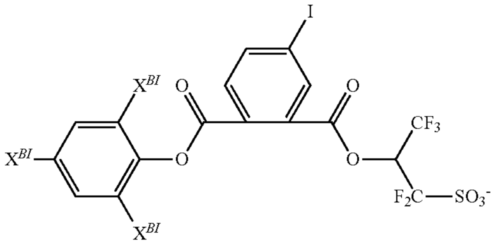

-continued
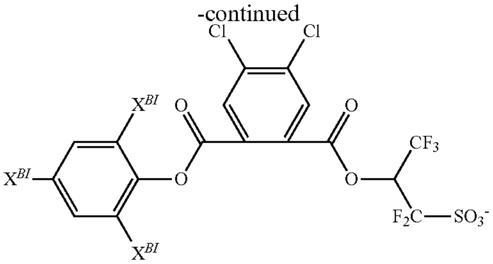
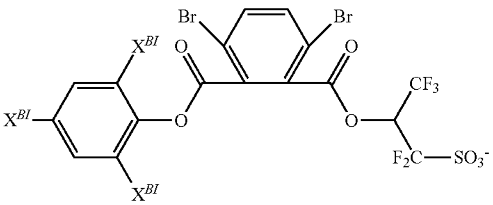
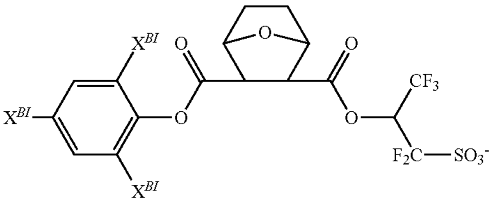
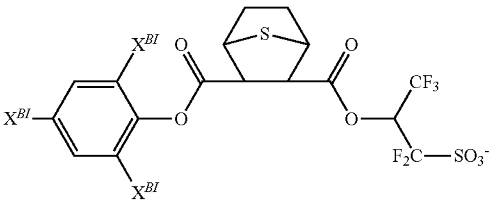
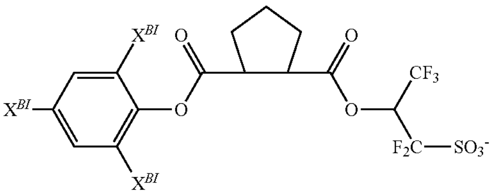
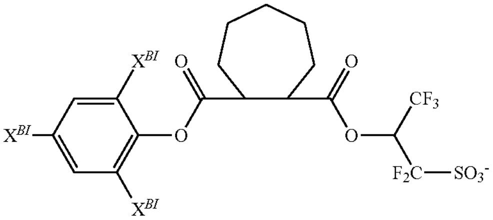
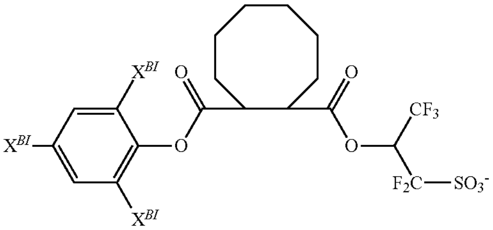
-continued
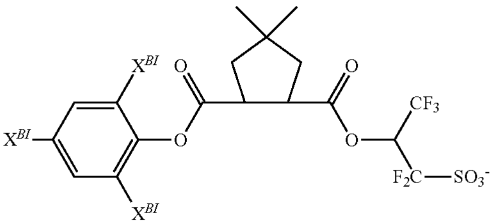
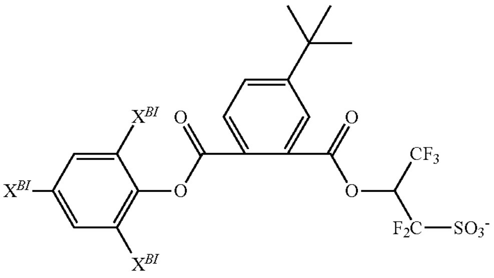
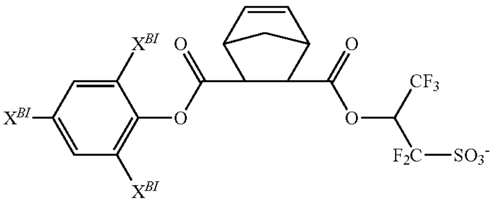
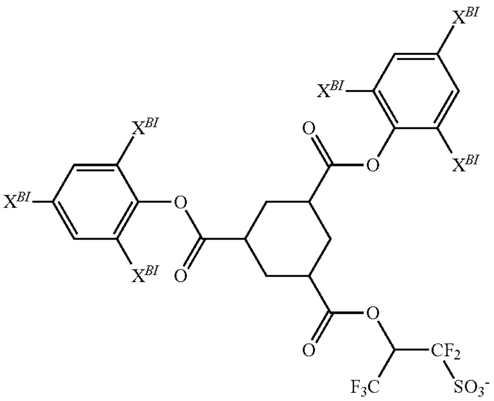
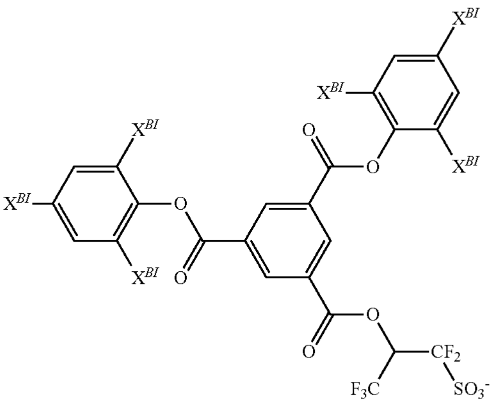

-continued
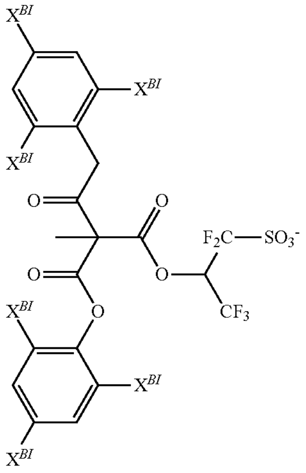
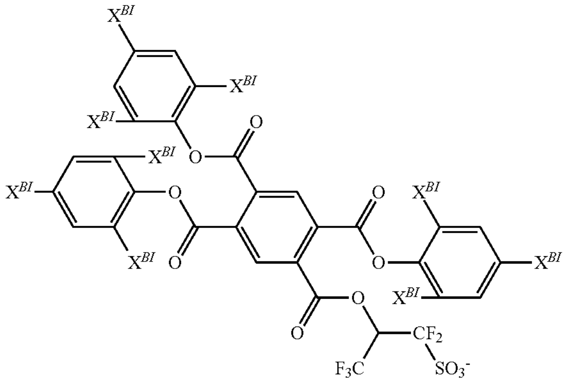
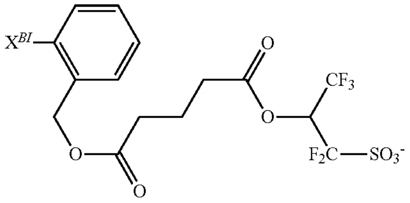
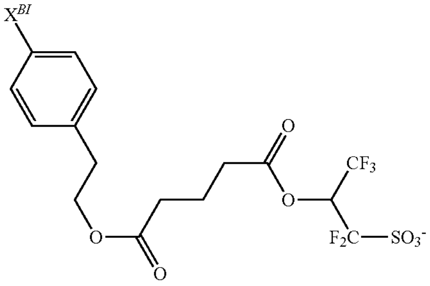
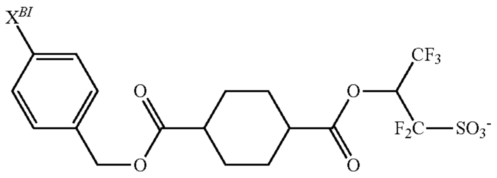
-continued
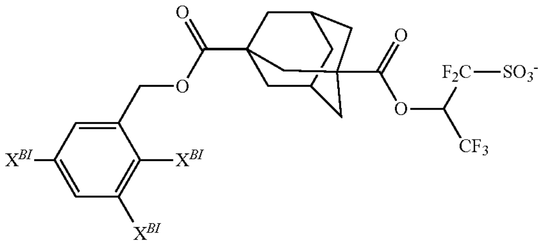
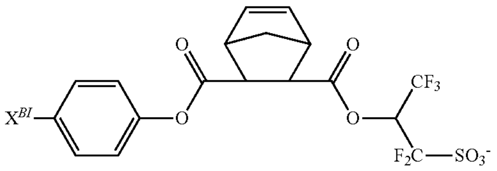
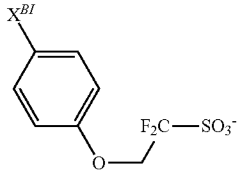
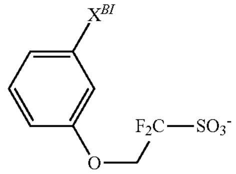
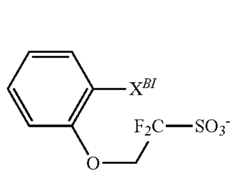
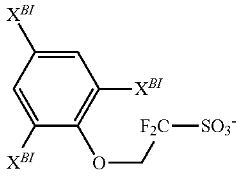
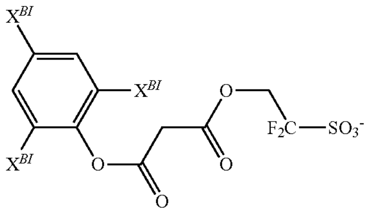
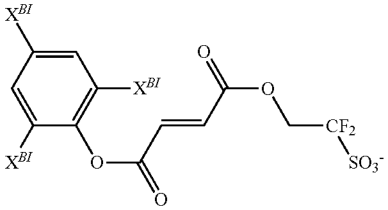
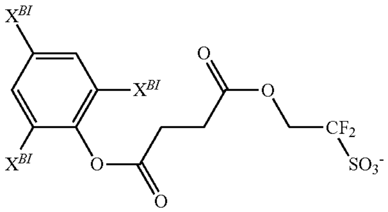
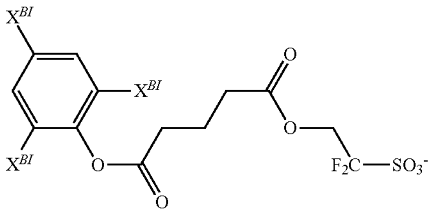

-continued
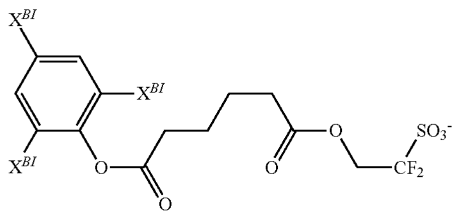
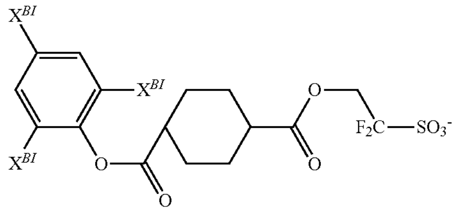
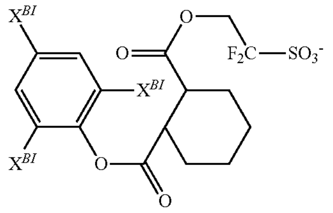
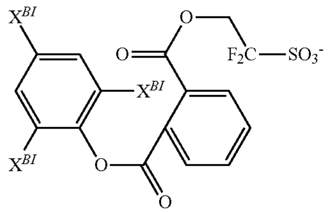
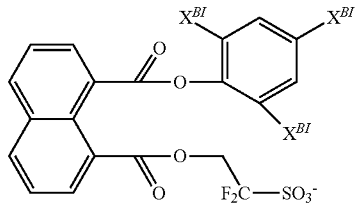
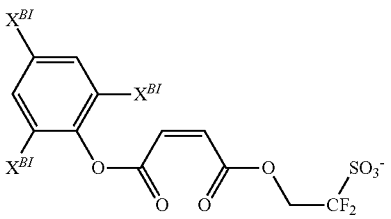
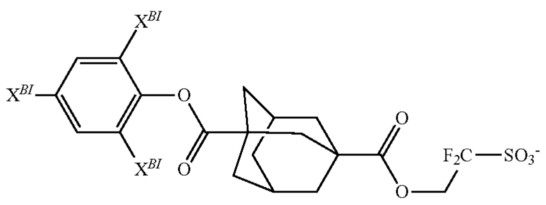
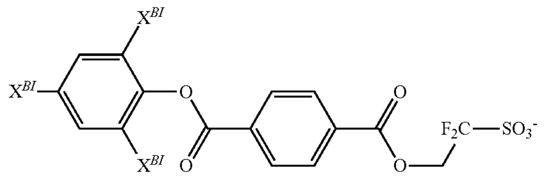
-continued
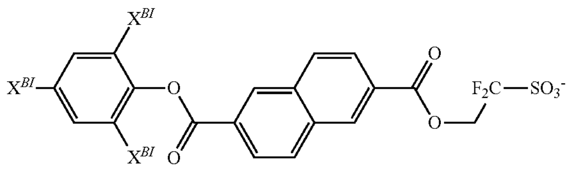
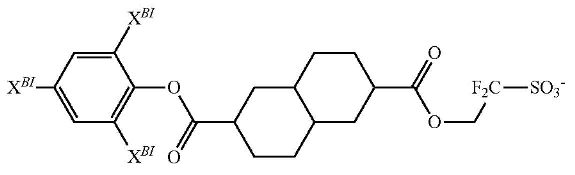
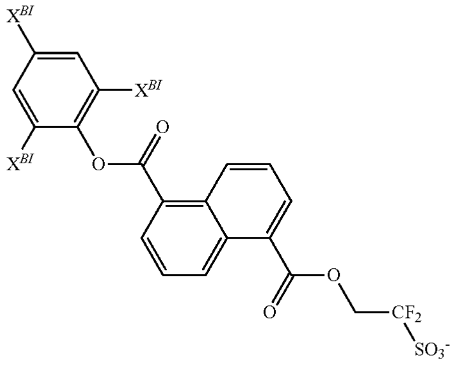
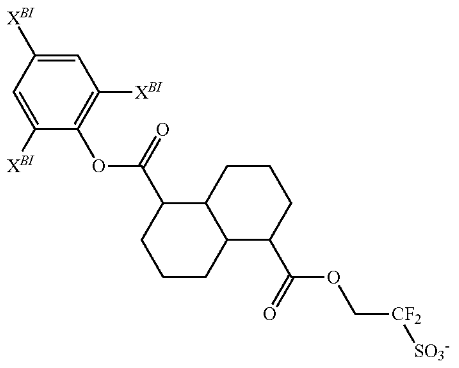
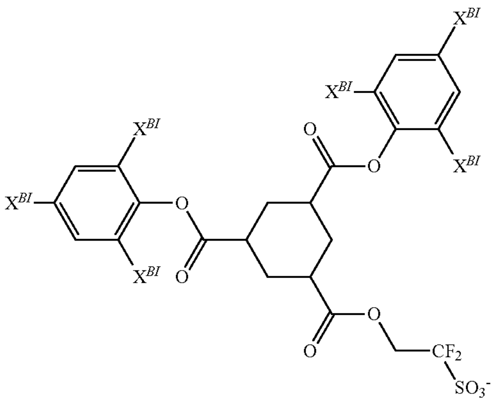

-continued
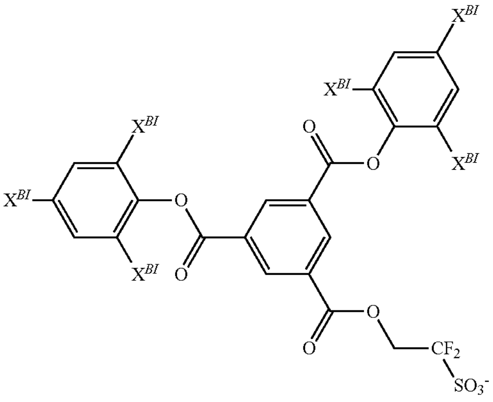
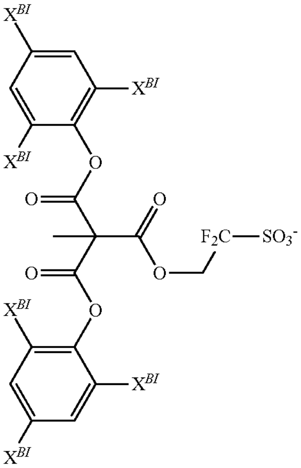
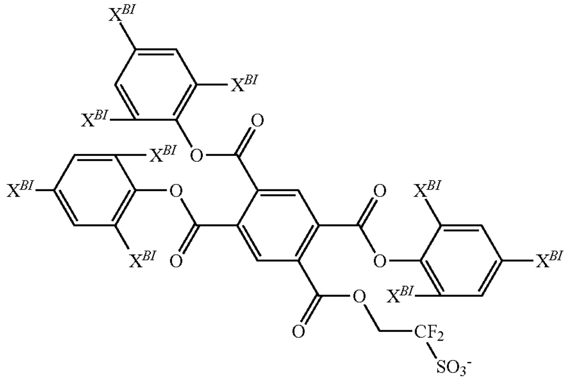
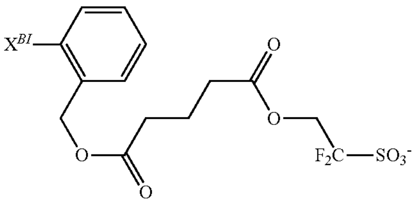
-continued
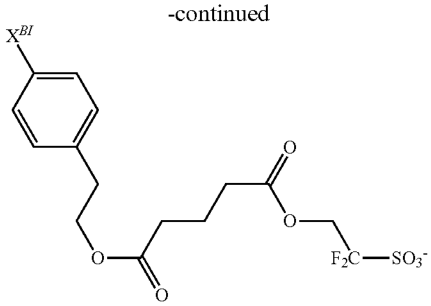
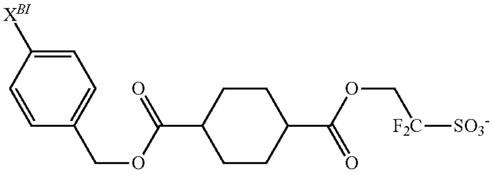
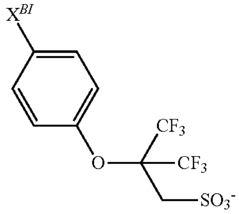
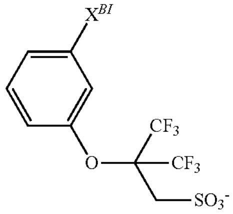
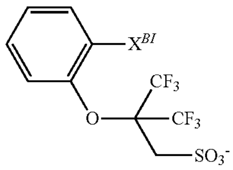
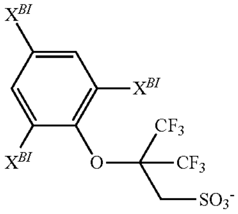
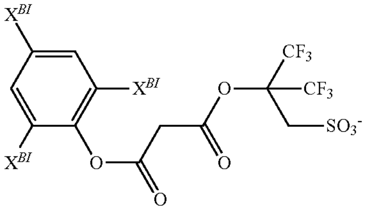
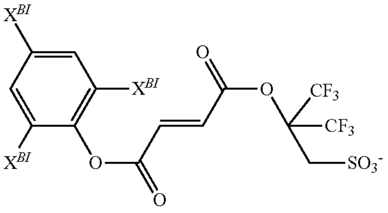
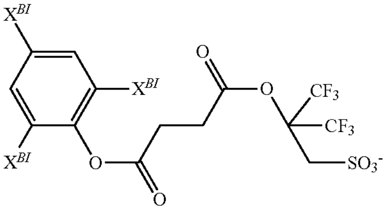
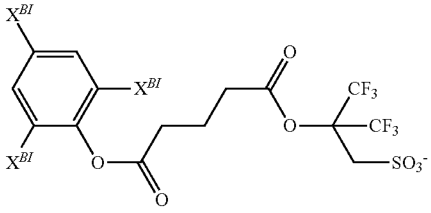

-continued
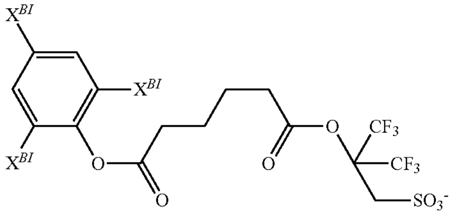
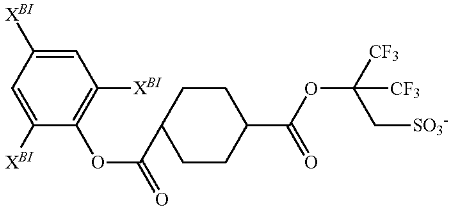
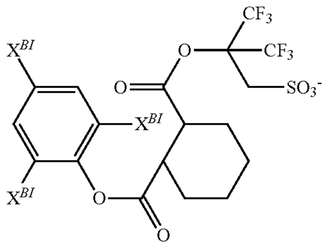
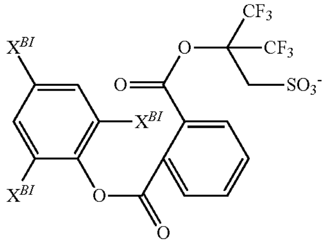
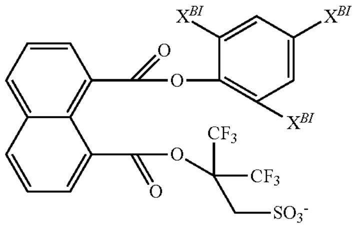
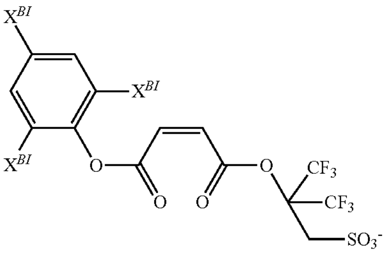
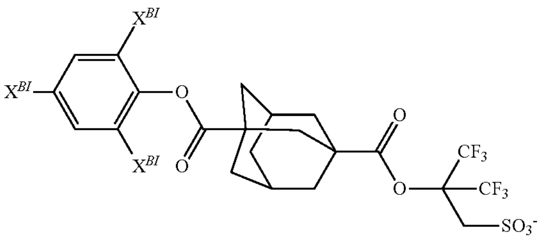
-continued
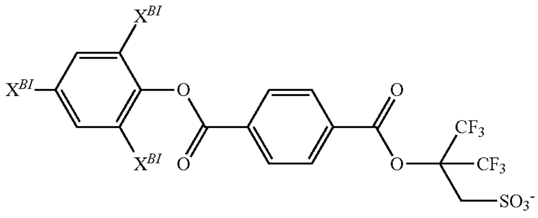
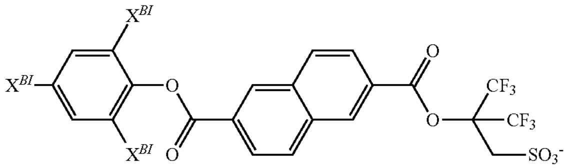
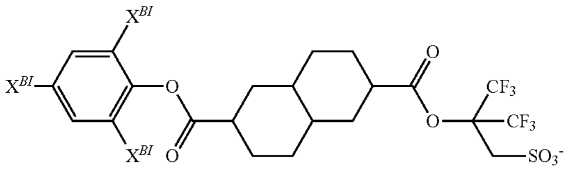
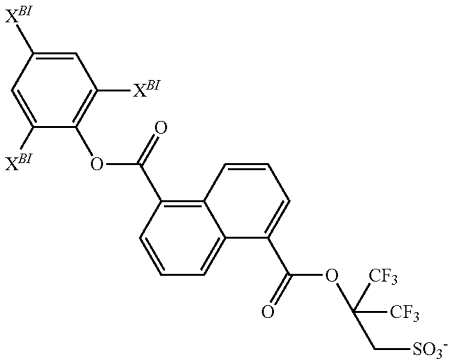
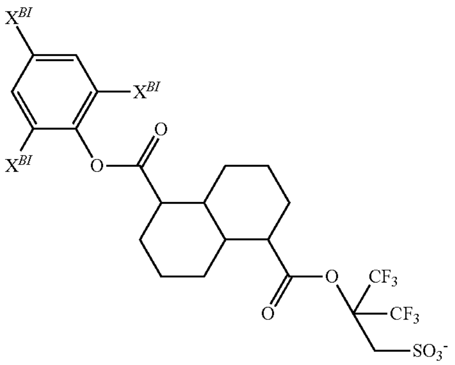
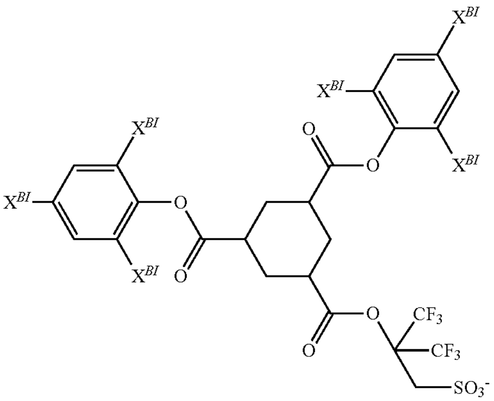

-continued

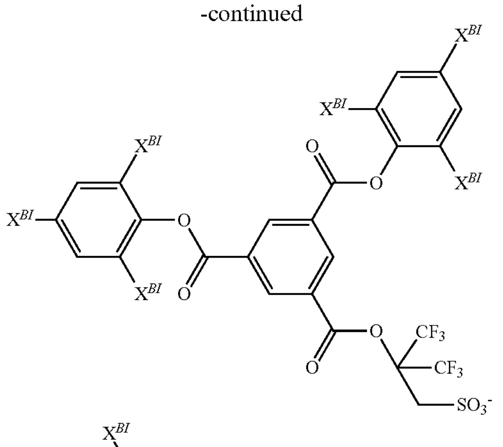

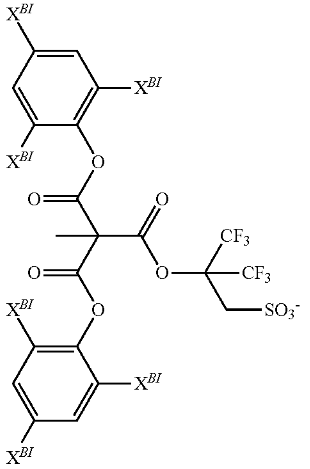

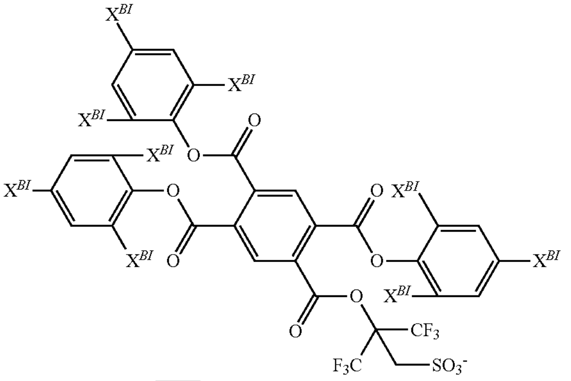

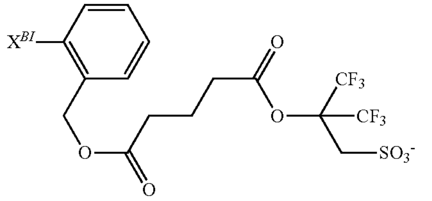

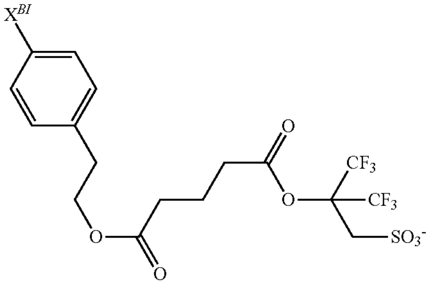

-continued

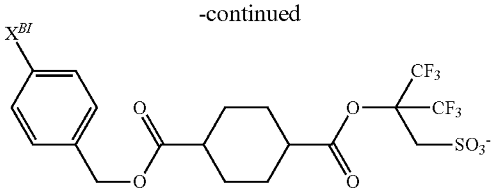

When used, the acid generator of addition type is preferably added in an amount of 0.1 to 50 parts, and more preferably 1 to 40 parts by weight per 100 parts by weight of the base polymer. The acid generator may be used alone or in admixture. The resist composition functions as a chemically amplified positive resist composition when the base polymer includes repeat units (d) and/or the resist composition contains the acid generator of addition type.

Organic Solvent

An organic solvent may be added to the resist composition. The organic solvent used herein is not particularly limited as long as the foregoing and other components are soluble therein. Examples of the organic solvent are described in JP-A 2008-111103, paragraphs [0144]-[0145] (U.S. Pat. No. 7,537,880). Exemplary solvents include ketones such as cyclohexanone, cyclopentanone, methyl-2 n-pentyl ketone and 2-heptanone; alcohols such as 3-methoxybutanol, 3-methyl-3-methoxybutanol, 1-methoxy-2-propanol, 1-ethoxy-2-propanol and diacetone alcohol (DAA): ethers such as propylene glycol monomethyl ether (PGME), ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate (L-, D- or DL-form), ethyl pyruvate, butyl acetate, methyl 3-methoxypropionate, ethyl 3-ethoxypropionate, tert-butyl acetate, tert-butyl propionate, and propylene glycol mono-tert-butyl ether acetate: and lactones such as γ-butyrolactone.

The organic solvent is preferably added in an amount of 100 to 10,000 parts, and more preferably 200 to 8,000 parts by weight per 100 parts by weight of the base polymer. The organic solvent may be used alone or in admixture.

Quencher

While the positive resist composition contains a base polymer having a quencher of sulfonium salt type at the end, it may additionally contain a quencher. As used herein, the quencher refers to a compound capable of trapping the acid generated by the acid generator in the resist composition to prevent the acid from diffusing to the unexposed region.

The quencher is typically selected from conventional basic compounds. Conventional basic compounds include primacy, secondary, and tertiary aliphatic amines, mixed amines, aromatic amines, heterocyclic amines, nitrogen-containing compounds with carboxy group, nitrogen-containing compounds with sulfonyl group, nitrogen-containing compounds with hydroxy group, nitrogen-containing compounds with hydroxyphenyl group, alcoholic nitrogen-containing compounds, amide derivatives, imide derivatives, and carbamate derivatives. Also included are primary, secondary, and tertiary amine compounds, specifically amine compounds having a hydroxy group, ether bond, ester bond, lactone ring, cyano group, or sulfonic ester bond as described in JP-A 2008-111103, paragraphs [0146]-[0164], and compounds having a carbamate group as described in JP 3790649. Addition of a basic compound may be effective for further suppressing the diffusion rate of acid in the resist film or correcting the pattern profile.

Onium salts such as sulfonium, iodonium and ammonium salts of sulfonic acids which are not fluorinated at α-position, carboxylic acids or fluorinated alkoxides as described in U.S. Pat. No. 8,795,942 (JP-A 2008-158339) may also be used as the quencher. While an α-fluorinated sulfonic acid, imide acid, and methide acid are necessary to deprotect the acid labile group of carboxylic acid ester, an α-non-fluorinated sulfonic acid, carboxylic acid or fluorinated alcohol is released by salt exchange with an α-non-fluorinated onium salt. An α-non-fluorinated sulfonic acid, carboxylic acid and fluorinated alcohol function as a quencher because they do not induce deprotection reaction.

Examples of the quencher include a compound (onium salt of α-non-fluorinated sulfonic acid) having the formula (4), a compound (onium salt of carboxylic acid) having the formula (5), and a compound (onium salt of alkoxide) having the formula (6).

$$R^{501}—SO_3^- \ Mq^+ \quad (4)$$

$$R^{502}—CO_2^- \ Mq^+ \quad (5)$$

$$R^{503}—O^- \ Mq^+ \quad (6)$$

In formula (4), $R^{501}$ is hydrogen or a $C_1$-$C_{40}$ hydrocarbyl group which may contain a heteroatom, exclusive of the hydrocarbyl group in which the hydrogen bonded to the carbon atom at α-position of the sulfo group is substituted by fluorine or fluoroalkyl moiety.

The hydrocarbyl group may be saturated or unsaturated and straight, branched or cyclic. Examples thereof include $C_1$-$C_{40}$ alkyl groups such as methyl, ethyl, n-propyl, isopropyl, n-butyl, isobutyl, sec-butyl, tert-butyl, tert-pentyl, n-pentyl, n-hexyl, n-octyl, 2-ethylhexyl, n-nonyl, n-decyl; $C_3$-$C_{40}$ cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl; $C_2$-$C_{40}$ alkenyl groups such as vinyl, allyl, propenyl, butenyl and hexenyl; $C_3$-$C_{40}$ cyclic unsaturated aliphatic hydrocarbyl groups such as cyclohexenyl; $C_6$-$C_{40}$ aryl groups such as phenyl, naphthyl, alkylphenyl groups (e.g., 2-methylphenyl, 3-methylphenyl, 4-methylphenyl, 4-ethylphenyl, 4-tert-butylphenyl, 4-n-butylphenyl), dialkylphenyl groups (e.g., 2,4-dimethylphenyl and 2,4,6-triisopropylphenyl), alkylnaphthyl groups (e.g., methylnaphthyl and ethylnaphthyl), dialkylnaphthyl groups (e.g., dimethylnaphthyl and diethylnaphthyl); and $C_2$-$C_{40}$ aralkyl groups such as benzyl, 1-phenylethyl and 2-phenylethyl.

In the hydrocarbyl group, some hydrogen may be substituted by a moiety containing a heteroatom such as oxygen, sulfur, nitrogen or halogen, and some constituent —$CH_2$— may be replaced by a moiety containing a heteroatom such as oxygen, sulfur or nitrogen, so that the group may contain a hydroxy moiety, cyano moiety, carbonyl moiety, ether bond, ester bond, sulfonic ester bond, carbonate bond, lactone ring, sultone ring, carboxylic anhydride, or haloalkyl moiety. Suitable heteroatom-containing hydrocarbyl groups include heteroaryl groups such as thienyl and indolyl; alkoxyphenyl groups such as 4-hydroxyphenyl, 4-methoxyphenyl, 3-methoxyphenyl, 2-methoxyphenyl, 4-ethoxyphenyl, 4-tert-butoxyphenyl, 3-tert-butoxyphenyl: alkoxynaphthyl groups such as methoxynaphthyl, ethoxynaphthyl, n-propoxynaphthyl and n-butoxynaphthyl; dialkoxynaphthyl groups such as dimethoxynaphthyl and diethoxynaphthyl; and aryloxoalkyl groups, typically 2-aryl-2-oxoethyl groups such as 2-phenyl-2-oxoethyl, 2-(1-naphthyl)-2-oxoethyl and 2-(2-naphthyl)-2-oxoethyl.

In formula (5), $R^{502}$ is a $C_1$-$C_{40}$ hydrocarbyl group which may contain a heteroatom. Examples of the hydrocarbyl group $R^{502}$ are as exemplified above for the hydrocarbyl group $R^{501}$. Also included are fluorinated alkyl groups such as trifluoromethyl, trifluoroethyl, 2,2,2-trifluoro-1-methyl-1-hydroxyethyl, 2,2,2-trifluoro-1-(trifluoromethyl)-1-hydroxyethyl, and fluorinated aryl groups such as pentafluorophenyl and 4-trifluoromethylphenyl.

In formula (6), $R^{563}$ is a $C_1$-$C_8$ saturated hydrocarbyl group having at least 3 fluorine atoms or a $C_6$-$C_{10}$ aryl group having at least 3 fluorine atoms. The hydrocarbyl and aryl groups may contain a nitro moiety.

In formulae (4) to (6), $Mq^+$ is an onium cation. The onium cation is preferably selected from sulfonium, iodonium and ammonium cations, more preferably sulfonium and iodonium cations. Exemplary sulfonium cations are as exemplified above for the cation in the sulfonium salt having formula (1-1). Exemplary iodonium cations are as exemplified above for the cation in the iodonium salt having formula (1-2).

A sulfonium salt of iodized benzene ring-containing carboxylic acid having the formula (7) is also useful as the quencher.

(7)

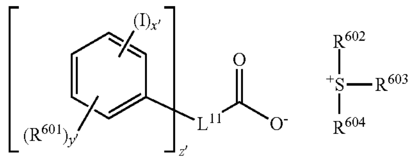

In formula (7), $R^{601}$ is hydroxy, fluorine, chlorine, bromine, amino, nitro, cyano, or a $C_1$-$C_6$ saturated hydrocarbyl, $C_1$-$C_6$ saturated hydrocarbyloxy, $C_2$-$C_6$ saturated hydrocarbylcarbonyloxy or $C_1$-$C_4$ saturated hydrocarbylsulfonyloxy group, in which some or all hydrogen may be substituted by halogen, or —$N(R^{601A})$—C(═O)—$R^{601B}$, or —$N(R^{601A})$—C(═O)—O—$R^{601B}$, $R^{601A}$ is hydrogen or a $C_1$-$C_6$ saturated hydrocarbyl group. $R^{601B}$ is a $C_1$-$C_6$ saturated hydrocarbyl or $C_2$-$C_6$ unsaturated aliphatic hydrocarbyl group.

In formula (7), x' is an integer of 1 to 5, y' is an integer of 0 to 3, and z' is an integer of 1 to 3. $L^{11}$ is a single bond, or a $C_1$-$C_{20}$ (z'+1)-valent linking group which may contain at least one moiety selected from ether bond carbonyl moiety, ester bond, amide bond, sultone ring, lactam ring, carbonate bond, halogen, hydroxy moiety, and carboxy moiety. The saturated hydrocarbyl, saturated hydrocarbyloxy, saturated hydrocarbylcarbonyloxy, and saturated hydrocarbylsulfonyloxy groups may be straight, branched or cyclic. Groups $R^{601}$ may be the same or different when y' and/or z' is 2 or 3.

In formula (7), $R^{602}$, $R^{603}$ and $R^{604}$ are each independently halogen or a $C_1$-$C_{20}$ hydrocarbyl group which may contain a heteroatom. The hydrocarbyl group may be saturated or unsaturated and straight, branched or cyclic. Examples thereof are as exemplified above for the hydrocarbyl groups $R^{101}$ to $R^{105}$ in formulae (1-1) and (1-2). In the hydrocarbyl group, some or all hydrogen may be substituted by hydroxy, carboxy, halogen, oxo, cyano, nitro, sultone, sulfo, or sulfonium salt-containing moiety, or some constituent —$CH_2$— may be replaced by an ether bond, ester bond, carbonyl moiety, amide bond, carbonate bond or sulfonic ester bond. Also $R^{602}$ and $R^{603}$ may bond together to form a ring with the sulfur atom to which they are attached.

Examples of the compound having formula (7) include those described in U.S. Pat. No. 10,295,904 (JP-A 2017-219836).

Also useful are quenchers of polymer type as described in U.S. Pat. No. 7,598,016 (JP-A 2008-239918). The polymeric quencher segregates at the resist surface and thus enhances the rectangularity of resist pattern. When a protective film is applied as is often the case in the immersion lithography, the polymeric quencher is also effective for preventing a film thickness loss of resist pattern or rounding of pattern top.

When used, the quencher is preferably added in an amount of 0 to 5 parts, more preferably 0 to 4 parts by weight per 100 parts by weight of the base polymer. The quencher may be used alone or in admixture.

Other Components

With the foregoing components, other components such as a surfactant, dissolution inhibitor, water repellency improver, and acetylene alcohol may be blended in any desired combination to formulate a positive resist composition.

Exemplary surfactants are described in JP A 2008-111103, paragraphs [0165]-[0166]. Inclusion of a surfactant may improve or control the coating characteristics of the resist composition. When used, the surfactant is preferably added in an amount of 0.0001 to 10 parts by weight per 100 parts by weight of the base polymer. The surfactant may be used alone or in admixture.

The inclusion of a dissolution inhibitor in the positive resist composition may lead to an increased difference in dissolution rate between exposed and unexposed areas and a further improvement in resolution. The dissolution inhibitor which can be used herein is a compound having at least two phenolic hydroxy groups on the molecule, in which an average of from 0 to 100 mol % of all the hydrogen atoms on the phenolic hydroxy groups are replaced by acid labile groups or a compound having at least one carboxy group on the molecule, in which an average of 50 to 100 mol % of all the hydrogen atoms on the carboxy groups are replaced by acid labile groups, both the compounds having a molecular weight of 100 to 1.000, and preferably 150 to 800. Typical are bisphenol A, trisphenol, phenolphthalein, cresol novolac, naphthalenecarboxylic acid, adamantanecarboxylic acid, and cholic acid derivatives in which the hydrogen atom on the hydroxy or carboxy group is substituted by an acid labile group, as described in LISP 7,771,914 (JP-A 2008-122932, paragraphs [0155]-[0178]).

When the positive resist composition contains a dissolution inhibitor, the dissolution inhibitor is preferably added in an amount of 0 to 50 parts, more preferably 5 to 40 parts by weight per 100 parts by weight of the base polymer. The dissolution inhibitor may be used alone or in admixture.

A water repellency improver may be added to the resist composition for improving the water repellency on surface of a resist film. The water repellency improver may be used in the topcoatless immersion lithography. Suitable water repellency improvers include polymers having a fluoroalkyl group and polymers having a specific structure with a 1,1,1,3,3,3-hexafluoro-2-propanol residue and are described in JP-A 2007-297590 and JP-A 2008-111103, for example. The water repellency improver to be added to the resist composition should be soluble in the alkaline developer and organic solvent developer. The water repellency improver of specific structure with a 1,1,1,3,3,3-hexafluoro-2-propanol residue is well soluble in the developer. A polymer having an amino group or amine salt copolymerized as repeat units may serve as the water repellent additive and is effective for preventing evaporation of acid during PEB, thus preventing any hole pattern opening failure after development. An appropriate amount of the water repellency improver is 0 to 20 parts, more preferably 0.5 to 10 parts by weight per 100 parts by weight of the base polymer. The water repellency improver may be used alone or in admixture.

Also, an acetylene alcohol may be blended in the resist composition. Suitable acetylene alcohols are described in JP-A 2008-122932, paragraphs [0179]-[0182]. An appropriate amount of the acetylene alcohol blended is 0 to 5 parts by weight per 100 parts by weight of the base polymer. The acetylene alcohols may be used alone or in admixture.

Pattern Forming Process

The positive resist composition is used in the fabrication of various integrated circuits. Pattern formation using the resist composition may be performed by well-known lithography processes. The process generally involves the steps of applying the resist composition onto a substrate to form a resist film thereon, exposing the resist film to high-energy radiation, and developing the exposed resist film in a developer. If necessary, any additional steps may be added.

The positive resist composition is first applied onto a substrate on which an integrated circuit is to be formed (e.g., Si, $SiO_2$, SiN, SiON, TIN, WSi, BPSG, SOG, or organic antireflective coating) or a substrate on which a mask circuit is to be formed (e.g., Cr, CrO, CrON, $MoSi_2$, or $SiO_2$) by a suitable coating technique such as spin coating, roll coating, flow coating, dipping, spraying or doctor coating. The coating is prebaked on a hot plate at a temperature of 60 to 150° C. for 10 seconds to 30 minutes, preferably at 80 to 120° C. for 30 seconds to 20 minutes. The resulting resist film is generally 0.01 to 2 μm thick.

The resist film is then exposed to a desired pattern of high-energy radiation such as UV, deep-UV, EB, EUV of wavelength 3-15 nm, i-line, x-ray, soft x-ray, excimer laser light, γ-ray or synchrotron radiation. When UV, deep-UV, EUV, x-ray, soft x-ray, excimer laser light, γ-ray or synchrotron radiation is used as the high-energy radiation, the resist film is exposed thereto directly or through a mask having a desired pattern in a dose of preferably about 1 to 200 $mJ/cm^2$, more preferably about 10 to 100 $mg/cm^2$. When EB is used as the high-energy radiation, the resist film is exposed thereto directly or through a mask having a desired pattern in a dose of preferably about 0.1 to 100 $\mu C/cm^2$, more preferably about 0.5 to 50 $\mu C/cm^2$. It is appreciated that the positive resist composition is suited in micropatterning using KrF excimer laser, ArF excimer laser, EB, EUV, i-line, x-ray, soft x-ray, γ-ray or synchrotron radiation, especially in micropatterning using EB or EUV.

After the exposure, the resist film may be baked (PEB) on a hotplate or in an oven at 50 to 150° C. for 10 seconds to 30 minutes, preferably at 60 to 120° C. for 30 seconds to 20 minutes.

After the exposure or PEB, the resist film is developed in a developer in the form of an aqueous base solution for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). The resist film in the exposed area is dissolved in the developer whereas the resist film in the unexposed area is not dissolved. In this way, the desired positive pattern is formed on the substrate.

In an alternative embodiment, a negative pattern may be formed via organic solvent development using the positive resist composition. The developer used herein is preferably selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, t-butyl alcohol, 1-pentanol, 2 pentanol, 3-pentanol, t-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-s-butyl ether, di-n-pentyl ether, diisopentyl ether, di-s-pentyl ether, di-t-pentyl ether, and di n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable aromatic solvents include toluene, xylene, ethylbenzene, isopropylbenzene, t-butylbenzene and mesitylene. The solvents may be used alone or in admixture.

Rinsing is effective for minimizing the risks of resist pattern collapse and defect formation. However, rinsing is not essential. If rinsing is omitted, the amount of solvent used may be reduced.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLES

Examples of the invention are given below by way of illustration and not by way of limitation. The abbreviation "pbw" is parts by weight.

Chain transfer agents CTA-1 to CTA-16 used in the synthesis of base polymers have the structure shown below.

CTA-1

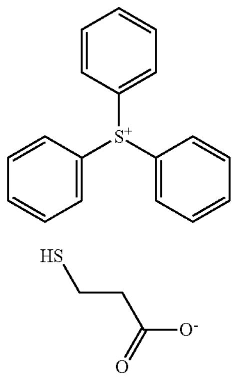

CTA-2

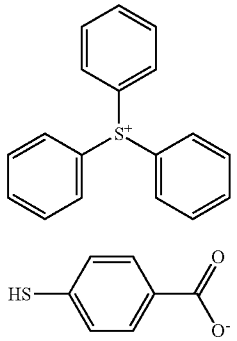

CTA-3

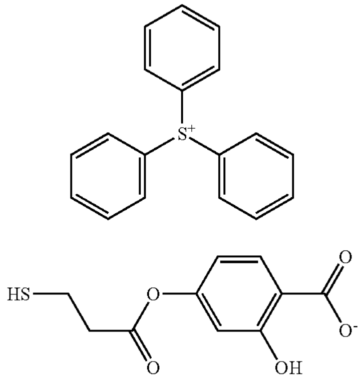

-continued
CTA-4
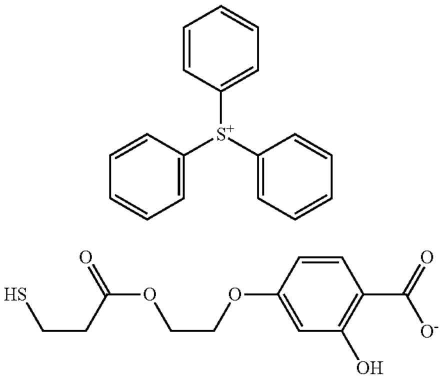
CTA-5
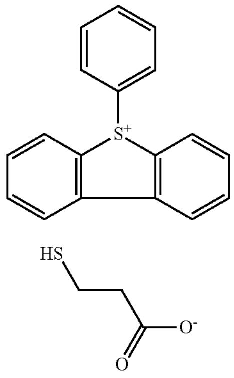
CTA-6
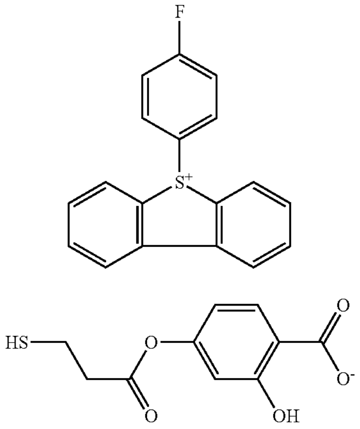
CTA-7
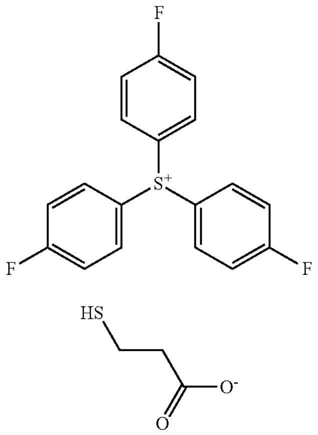
-continued
CTA-8
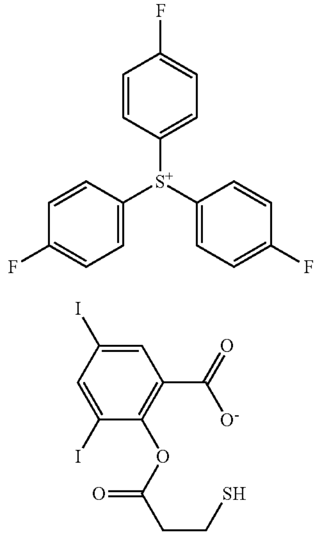
CTA-9
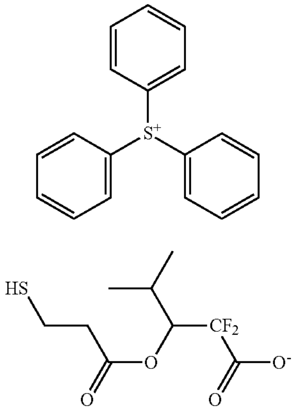
CTA-10
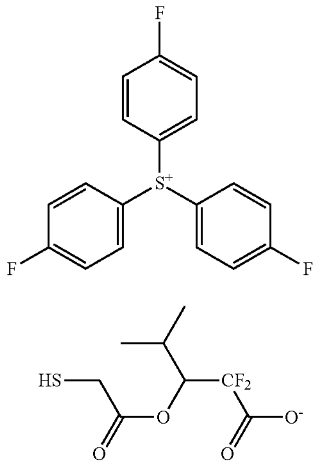

-continued
CTA-11
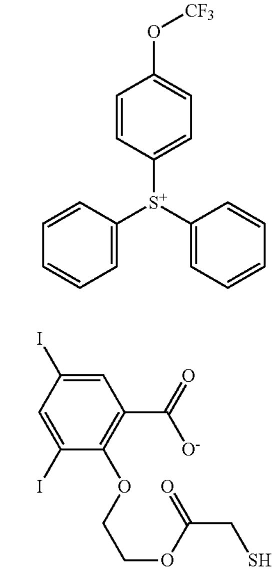
CTA-12
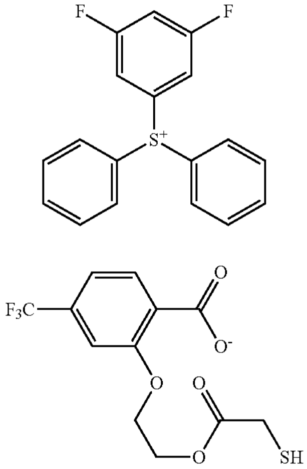
CTA-13
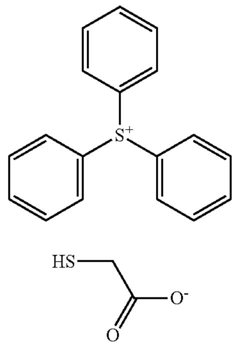
-continued
CTA-14
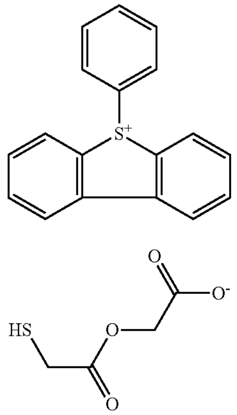
CTA-15
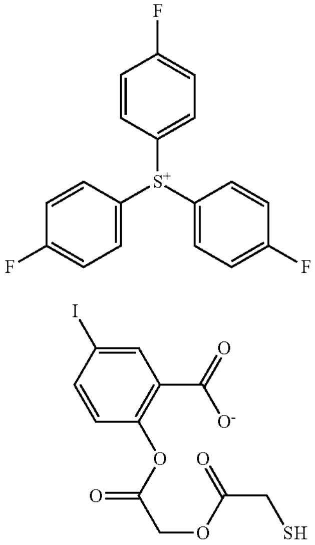
CTA-16
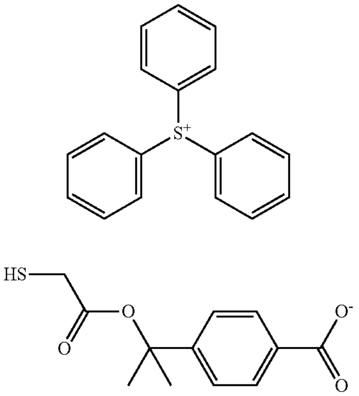
[1] Synthesis of Base Polymers
Monomers PM-1 to PM-3, AM-1 to AM-10, FM-1 and FM-2 used in the synthesis of base polymers have the structure shown below. The polymer is analyzed for composition by $^{13}C$— and $^{1}H$ NMR spectroscopy and for Mw and Mw/Mn by GPC versus polystyrene standards using tetrahydrofuran (THF) solvent.

PM-1
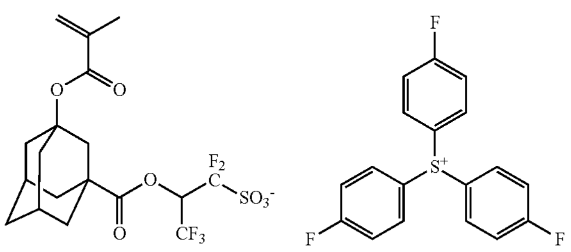
PM-2
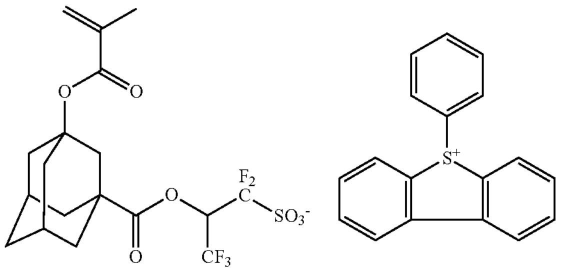
PM-3
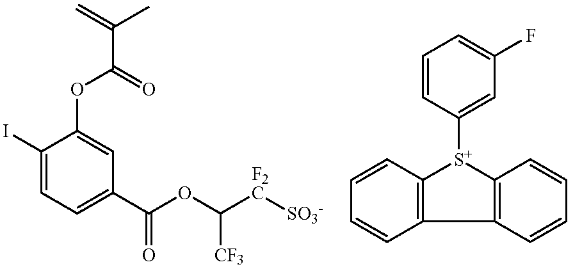
AM-1
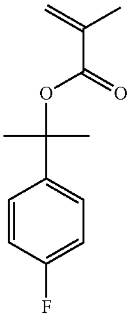
AM-2
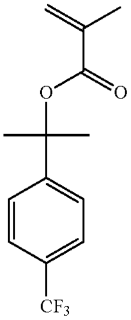
-continued
AM-3
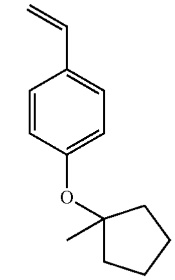
AM-4
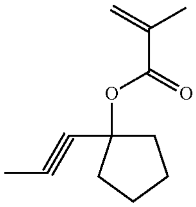
AM-5
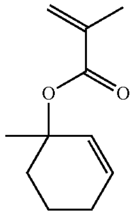
AM-6
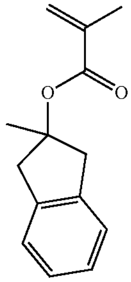
AM-7
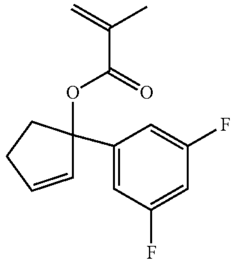
AM-8
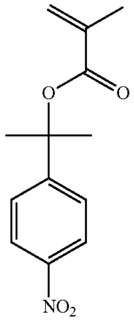

-continued

AM-9

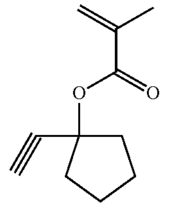

AM-10

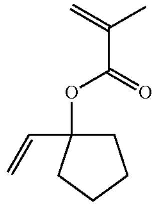

FM-1

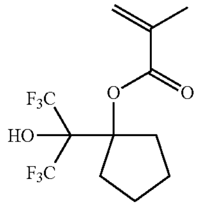

FM-2

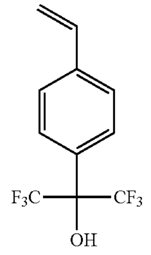

Synthesis Example 1

Synthesis of Polymer P-1

A 2-L flask was charged with 8.4 g of 1-methyl-1-cyclopentyl methacrylate, 6.0 g of 4-hydroxystyrene, and 40 g of THE solvent. The reactor was cooled at −70° C. in nitrogen atmosphere, after which vacuum pumping and nitrogen blow were repeated three times. The reactor was warmed up to room temperature, whereupon 1.2 g of dimethyl 2,2'-azobis(isobutyrate) as polymerization initiator and 2.2 g of CTA-1 were added. The reactor was heated at 60° C. and held at the temperature for 15 hours for reaction. The reaction solution was poured into 1 L of isopropyl alcohol (IPA) for precipitation. The resulting white solid was collected by filtration and dried in vacuum at 60° C., obtaining Polymer P-1. The polymer was analyzed by NMR spectroscopy and GPC.

P-1

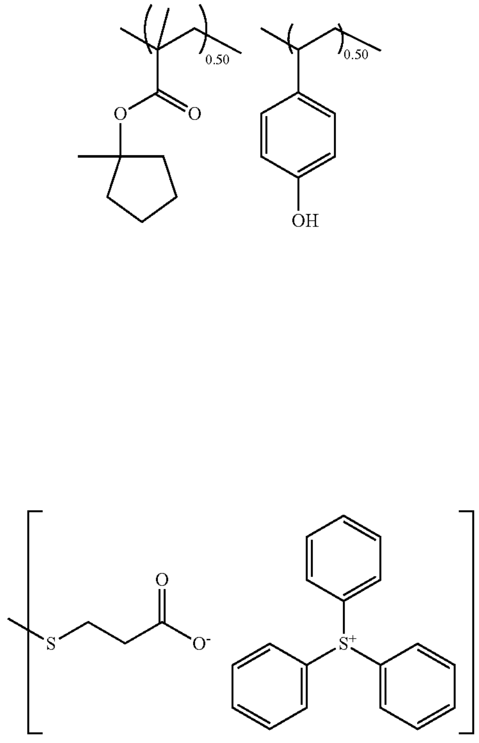

Mw = 5,200
Mw/Mn = 1.42

Synthesis Example 2

Synthesis of Polymer P-2

A 2-L flask was charged with 8.4 g of 1-methyl-1-cyclopentyl methacrylate, 4.2 g of 4-hydroxystyrene, 11.9 g of monomer PM-1, and 40 g of THF solvent. The reactor was cooled at −70° C. in nitrogen atmosphere, after which vacuum pumping and nitrogen blow were repeated three times. The reactor was warned up to room temperature, whereupon 1.2 g of dimethyl 2,2'-azobis(isobutyrate) as polymerization initiator and 2.5 g of CTA-2 were added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer P-2. The polymer was analyzed by NMR spectroscopy and GPC.

P-2

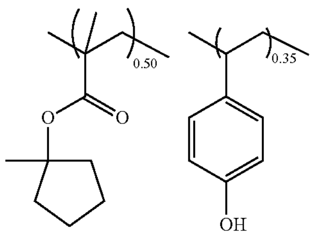

-continued

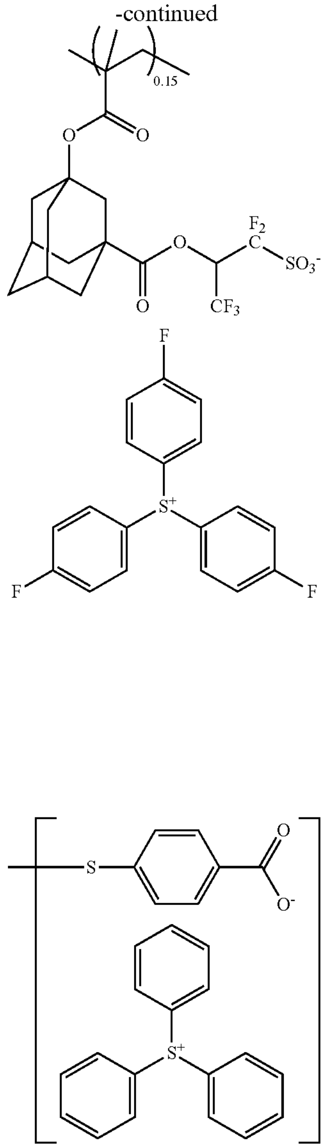

Mw = 7,300
Mw/Mn = 1.76

P-3

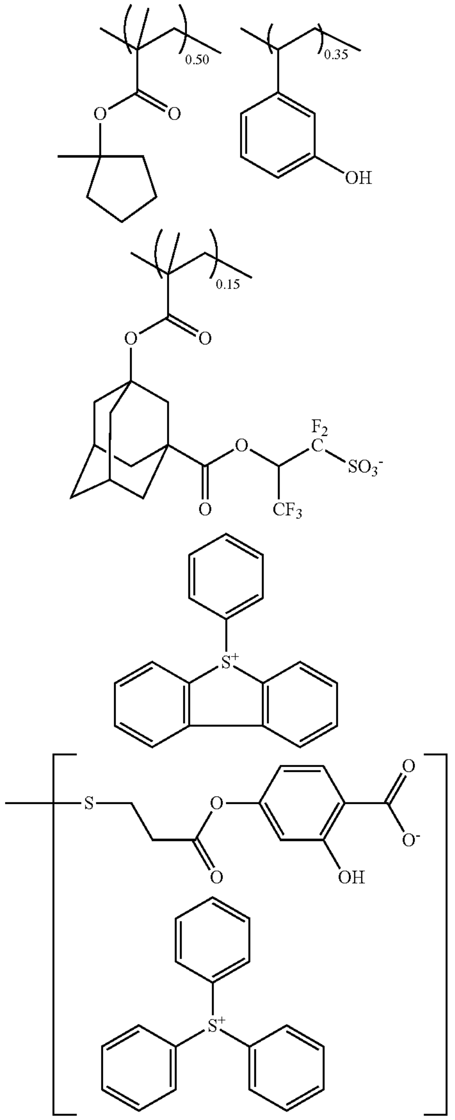

Mw = 7,300
Mw/Mn = 1.48

Synthesis Example 3

Synthesis of Polymer P-3

A 2-L flask was charged with 8.4 g of 1-methyl-1-cyclopentyl methacrylate, 4.2 g of 3-hydroxystyrene, 11.0 g of monomer PM-2, and 40 g of THE solvent. The reactor was cooled at −70° C. in nitrogen atmosphere, after which vacuum pumping and nitrogen blow were repeated three times. The reactor was warned up to room temperature, whereupon 1.2 g of dimethyl 2,2'-azobis(isobutyrate) as polymerization initiator and 3.0 g of CTA-3 were added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer P-3. The polymer was analyzed by NMR spectroscopy and GPC.

Synthesis Example 4

Synthesis of Polymer P-4

A 2-L flask was charged with 8.4 g of 1-methyl-1-cyclopentyl methacrylate, 4.8 g of 3-hydroxystyrene, 8.2 g of monomer PM-3, and 40 g of THE solvent. The reactor was cooled at −70° C. in nitrogen atmosphere, after which vacuum pumping and nitrogen blow were repeated three times. The reactor was warmed up to room temperature, whereupon 1.2 g of dimethyl 2,2'-azobis(isobutyrate) as polymerization initiator and 3.1 g of CTA-6 were added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer P-4. The polymer was analyzed by NMR spectroscopy and GPC.

P-4

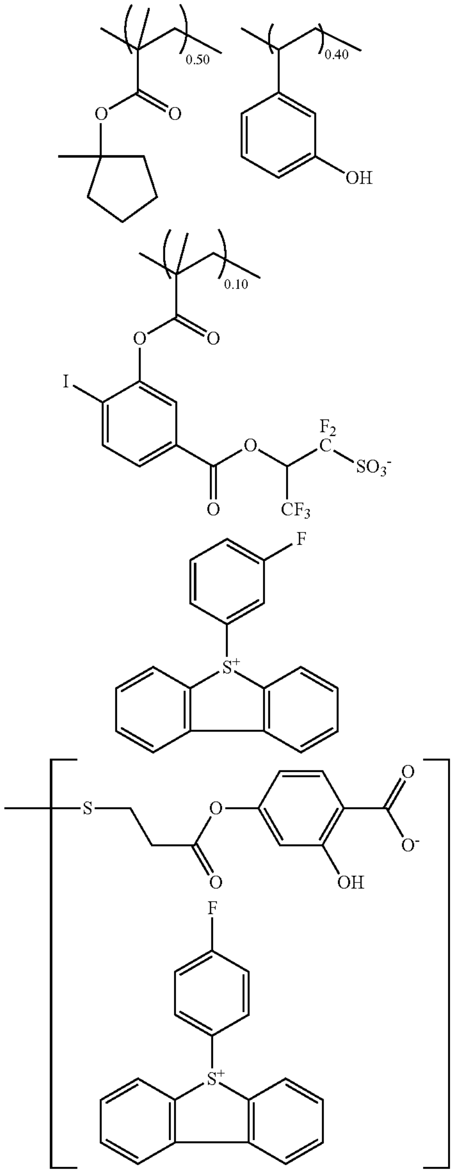

Mw = 8,100
Mw/Mn = 1.50

P-5

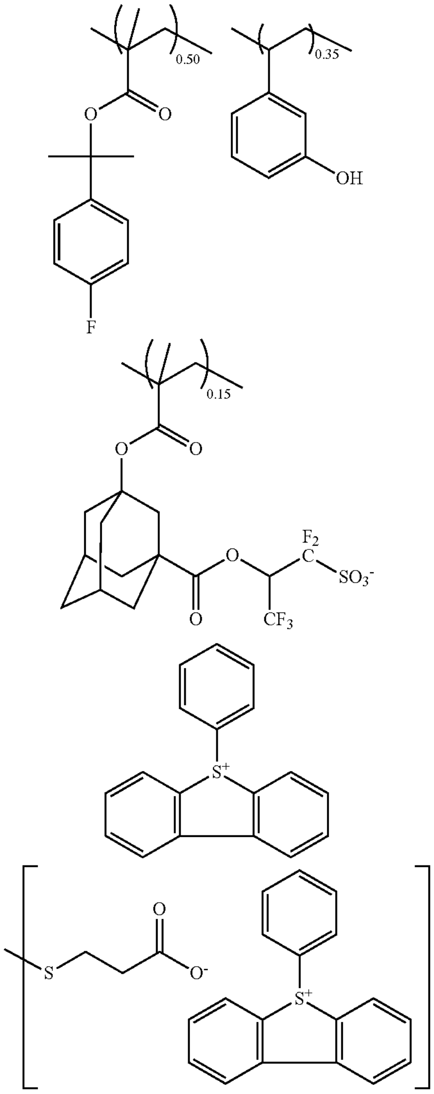

Mw = 7,400
Mw/Mn = 1.60

Synthesis Example 5

Synthesis of Polymer P-5

A 2-L flask was charged with 11.1 g of monomer AM-1, 4.2 g of 3-hydroxystyrene, 11.0 g of monomer PM 2, and 40 g of THE solvent. The reactor was cooled at −70° C. in nitrogen atmosphere, after which vacuum pumping and nitrogen blow were repeated three times. The reactor was warmed up to room temperature, whereupon 1.2 g of dimethyl 2,2'-azobis(isobutyrate) as polymerization initiator and 2.2 g of CTA-5 were added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer P-5. The polymer was analyzed by NMR spectroscopy and GPC.

Synthesis Example 6

Synthesis of Polymer P-6

A 2-L flask was charged with 8.2 g of monomer AM-2, 4.0 g of monomer AM-3, 4.2 g of 3-hydroxystyrene, 11.0 g of monomer PM-2, and 40 g of THE solvent. The reactor was cooled at −70° C. in nitrogen atmosphere, after which vacuum pumping and nitrogen blow were repeated three times. The reactor was warmed up to room temperature, whereupon 1.2 g of dimethyl 2,2'-azobis(isobutyrate) as polymerization initiator and 3.3 g of CTA-4 were added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer P-6. The polymer was analyzed by NMR spectroscopy and GPC.

P-6

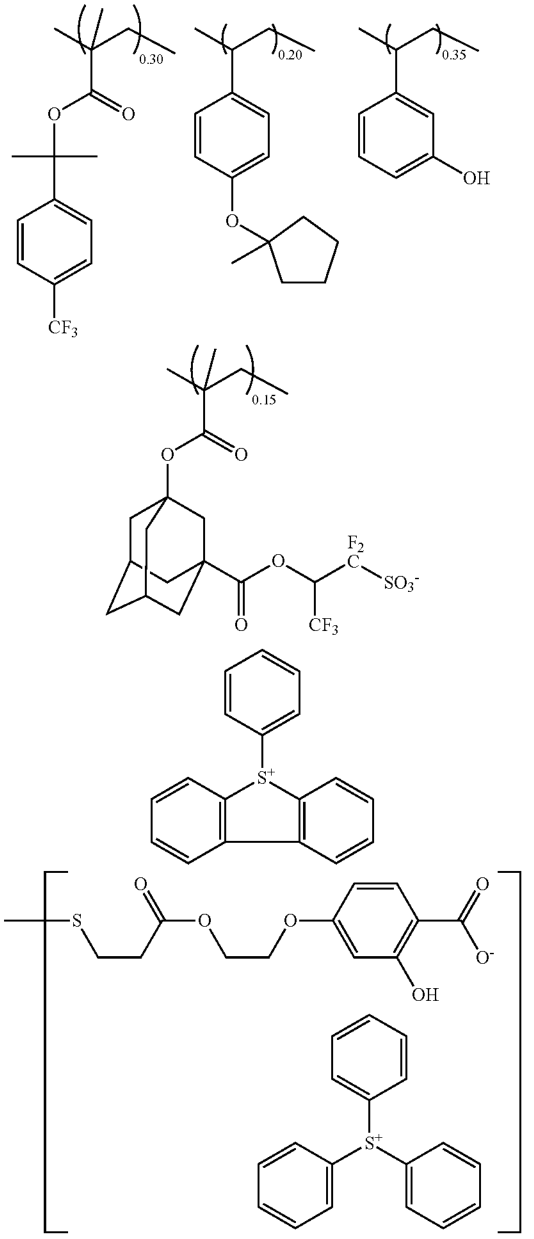

Mw = 7,600
Mw/Mn = 1.52

Synthesis Example 7

Synthesis of Polymer P-7

A 2-L flask was charged with 6.7 g of monomer AM-1, 3.8 g of monomer AM-4, 4.2 g of 3-hydroxystyrene, 11.9 g of monomer PM-1, and 40 g of THE solvent. The reactor was cooled at −70° C. in nitrogen atmosphere, after which vacuum pumping and nitrogen blow were repeated three times. The reactor was warmed up to room temperature, whereupon 1.2 g of dimethyl 2,2'-azobis(isobutyrate) as polymerization initiator and 2.5 g of CTA-7 were added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer P-7. The polymer was analyzed by NMR spectroscopy and GPC.

P-7

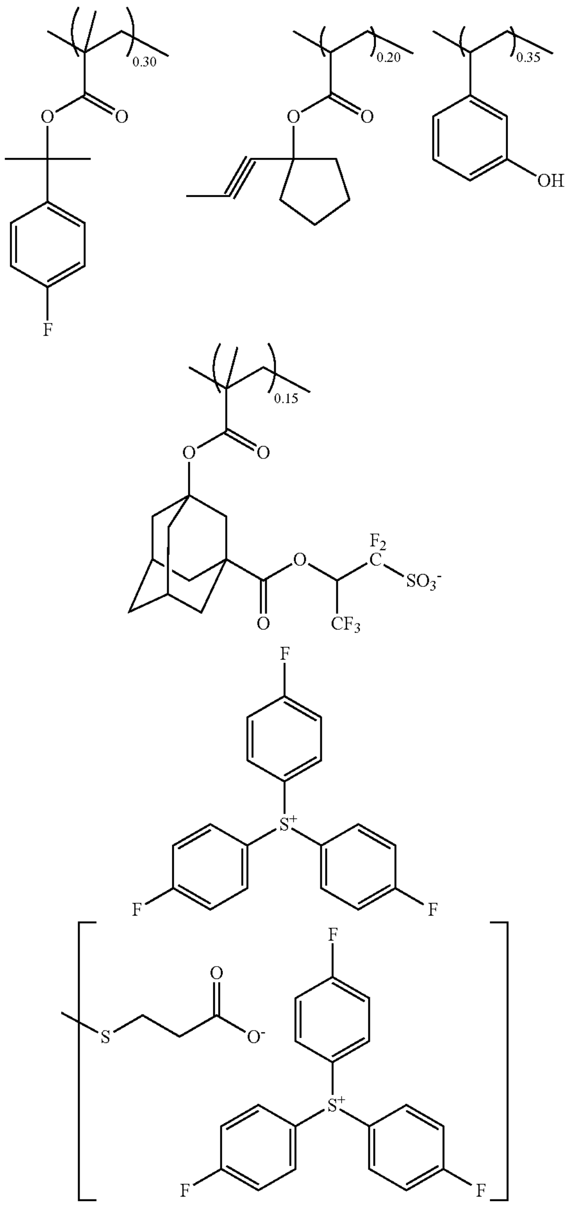

Mw = 7,600
Mw/Mn = 1.52

Synthesis Example 8

Synthesis of Polymer P-8

A 2-L flask was charged with 9.0 g of monomer AM-5, 4.2 g of 3-hydroxystyrene, 11.9 g of monomer PM 1, and 40 g of THE solvent. The reactor was cooled at −70° C. in nitrogen atmosphere, after which vacuum pumping and nitrogen blow were repeated three times. The reactor was warmed up to room temperature, whereupon 1.2 g of dimethyl 2,2'-azobis(isobutyrate) as polymerization initiator and 4.8 g of CTA-8 were added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer P-8. The polymer was analyzed by NMR spectroscopy and GPC.

P-8

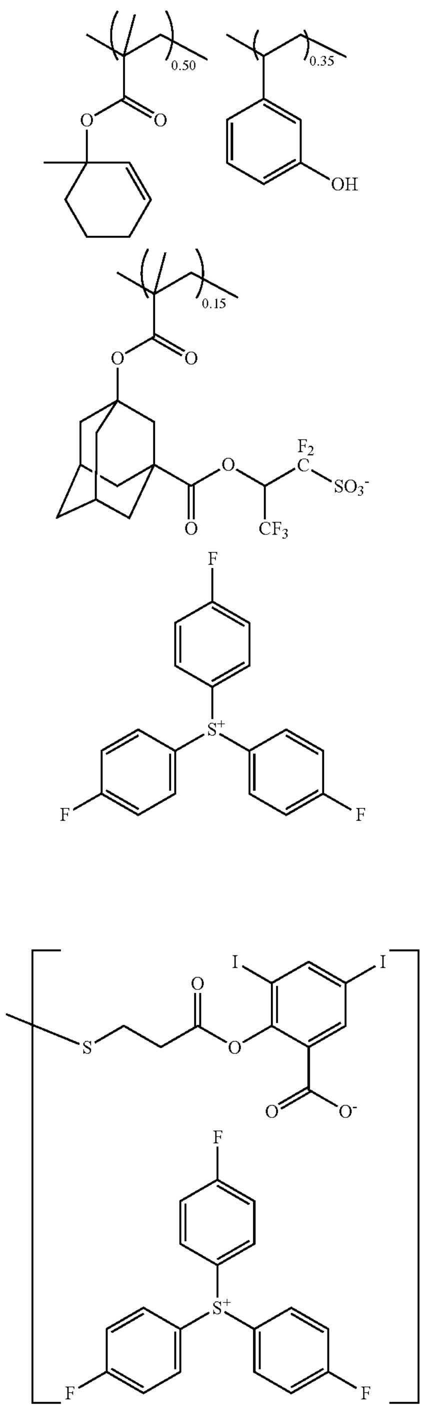

Mw = 7,500
Mw/Mn = 1.51

Synthesis Example 9

Synthesis of Polymer P-9

A 2-L flask was charged with 10.8 g of monomer AM-6, 4.2 g of 3-hydroxystyrene, 11.0 g of monomer PM 2, and 40 g of THE solvent. The reactor was cooled at −70° C. in nitrogen atmosphere, after which vacuum pumping and nitrogen blow were repeated three times. The reactor was warmed up to room temperature, whereupon 1.2 g of dimethyl 2,2'-azobis(isobutyrate) as polymerization initiator and 3.1 g of CTA-9 were added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer P-9. The polymer was analyzed by NMR spectroscopy and GPC.

P-9

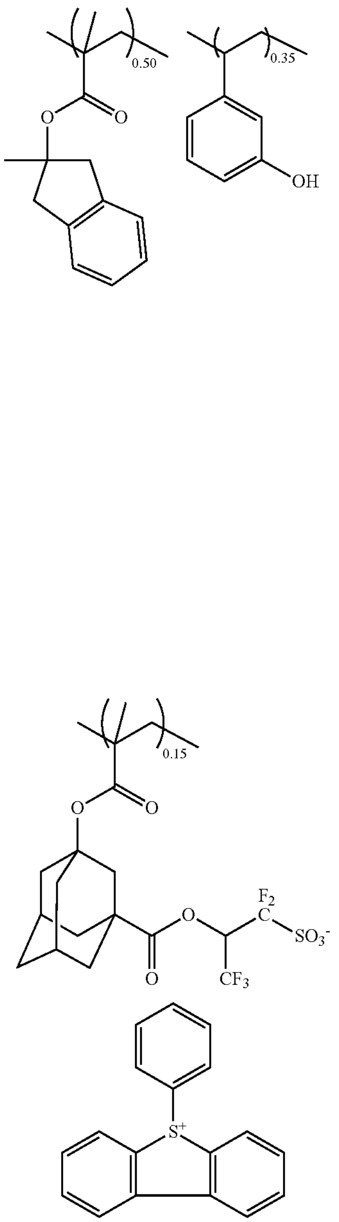

-continued

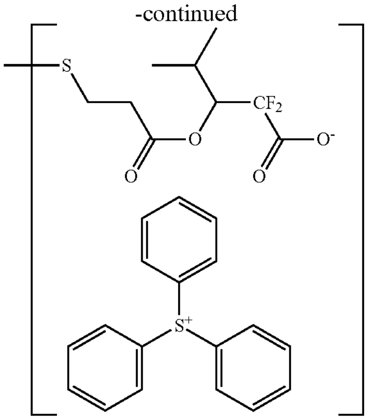

Mw = 7,400
Mw/Mn = 1.49

-continued

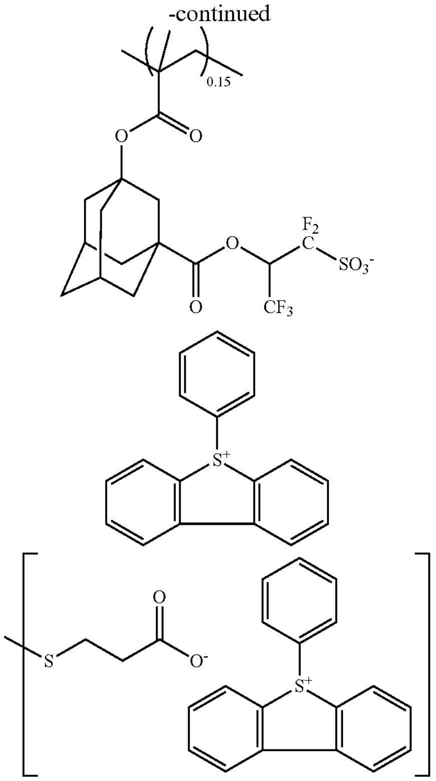

Mw = 7,700
Mw/Mn = 1.41

Synthesis Example 10

Synthesis of Polymer P-10

A 2-L flask was charged with 8.4 g of 1-methyl-1-cyclopentyl methacrylate, 3.0 g of 3-hydroxystyrene, 3.2 g of monomer FM-1, 11.0 g of monomer PM-2, and 40 g of THF solvent. The reactor was cooled at −70° C. in nitrogen atmosphere, after which vacuum pumping and nitrogen blow were repeated three times. The reactor was warmed up to room temperature, whereupon 1.2 g of dimethyl 2,2'-azobis(isobutyrate) as polymerization initiator and 2.2 g of CTA-5 were added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer P-10. The polymer was analyzed by NMR spectroscopy and GPC.

Synthesis Example 11

Synthesis of Polymer P-11

A 2-L flask was charged with 8.4 g of 1-methyl-1-cyclopentyl methacrylate, 3.0 g of 3-hydroxystyrene, 2.7 g of monomer FM-2, 11.0 g of monomer PM-2, and 40 g of THF solvent. The reactor was cooled at −70° C. in nitrogen atmosphere, after which vacuum pumping and nitrogen blow were repeated three times. The reactor was warmed up to room temperature, whereupon 1.2 g of dimethyl 2,2'-azobis(isobutyrate) as polymerization initiator and 2.2 g of CTA-5 were added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer P-11. The polymer was analyzed by NMR spectroscopy and GPC.

P-10

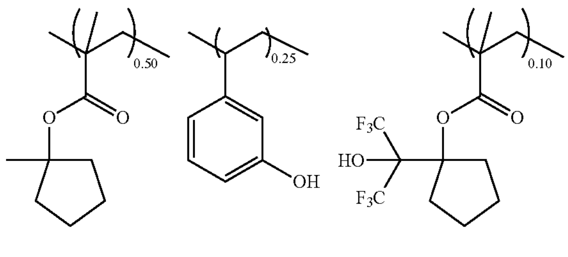

P-11

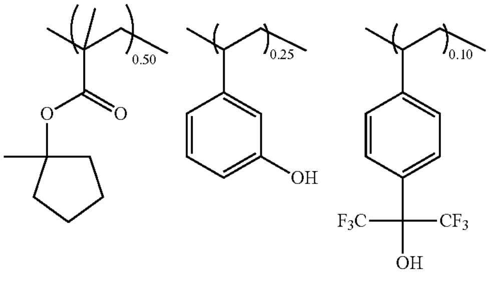

-continued

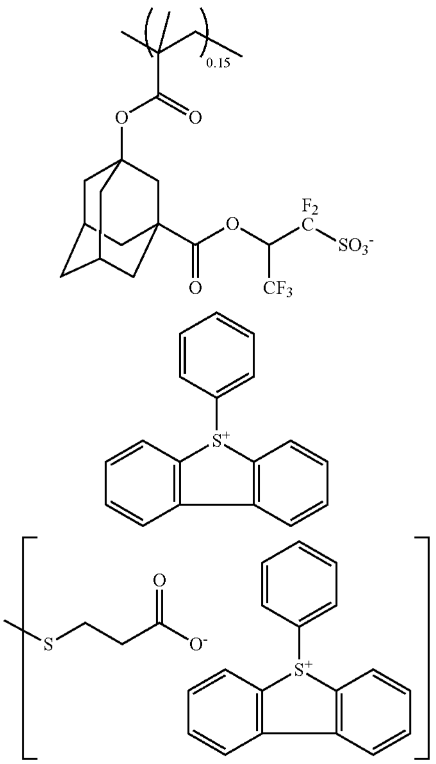

Mw = 7,400
Mw/Mn = 1.40

Synthesis Example 12

Synthesis of Polymer P-12

A 2-L flask was charged with 8.4 g of 1-methyl-1-cyclopentyl methacrylate, 4.2 g of 3-hydroxystyrene, 11.9 g of monomer PM-1, and 40 g of THE solvent. The reactor was cooled at −70° C. in nitrogen atmosphere, after which vacuum pumping and nitrogen blow were repeated three times. The reactor was warmed up to room temperature, whereupon 1.2 g of dimethyl 2,2'-azobis(isobutyrate) as polymerization initiator and 3.3 g of CTA-10 were added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer P-12. The polymer was analyzed by NMR spectroscopy and GPC.

P-12

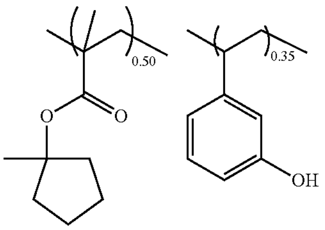

-continued

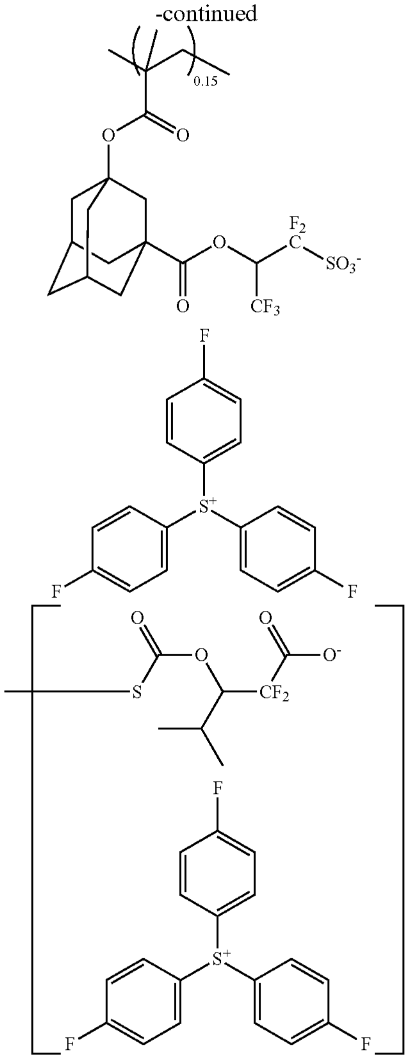

Mw = 7,500
Mw/Mn = 1.77

Synthesis Example 13

Synthesis of Polymer P-13

A 2-L flask was charged with 8.4 g of 1-methyl-1-cyclopentyl methacrylate, 4.2 g of 3-hydroxystyrene, 11.9 g of monomer PM-1, and 40 g of THE solvent. The reactor was cooled at −70° C. in nitrogen atmosphere, after which vacuum pumping and nitrogen blow were repeated three times. The reactor was warmed up to room temperature, whereupon 1.2 g of dimethyl 2,2'-azobis(isobutyrate) as polymerization initiator and 4.5 g of CTA-11 were added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer P-13. The polymer was analyzed by NMR spectroscopy and GPC.

P-13

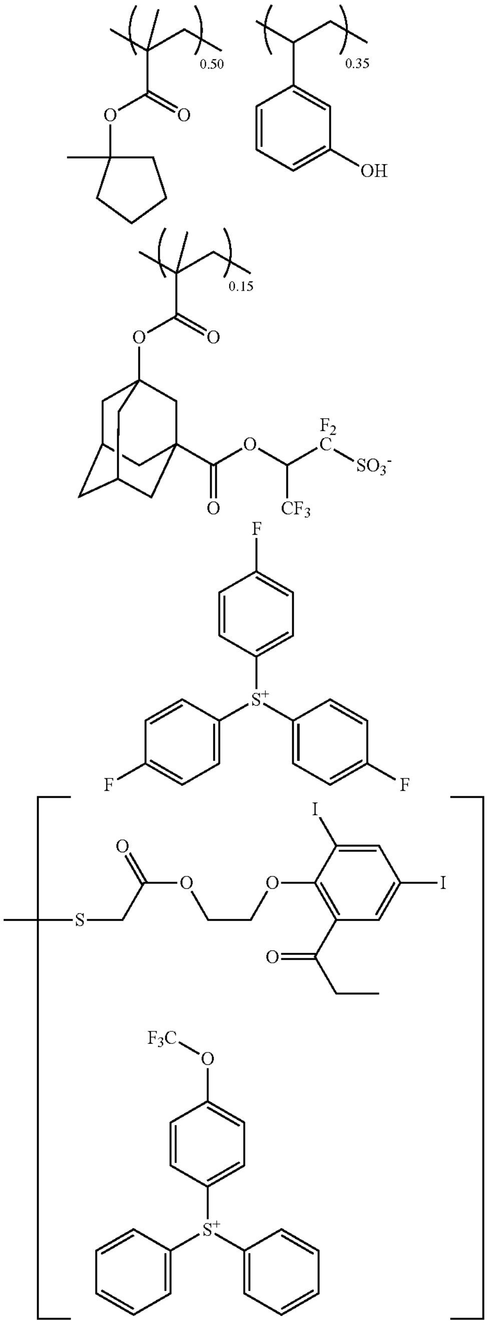

Mw = 8,600
Mw/Mn = 1.71

Synthesis Example 14

Synthesis of Polymer P-14

A 2-L flask was charged with 8.4 g of 1-methyl-1-cyclopentyl methacrylate, 4.2 g of 3-hydroxystyrene, 11.9 g of monomer PM-1, and 40 g of THF solvent. The reactor was cooled at −70° C. in nitrogen atmosphere, after which vacuum pumping and nitrogen blow were repeated three times. The reactor was warmed up to room temperature, whereupon 1.2 g of dimethyl 2,2'-azobis(isobutyrate) as polymerization initiator and 3.3 g of CTA-12 were added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer P-14. The polymer was analyzed by NMR spectroscopy and GPC.

P-14

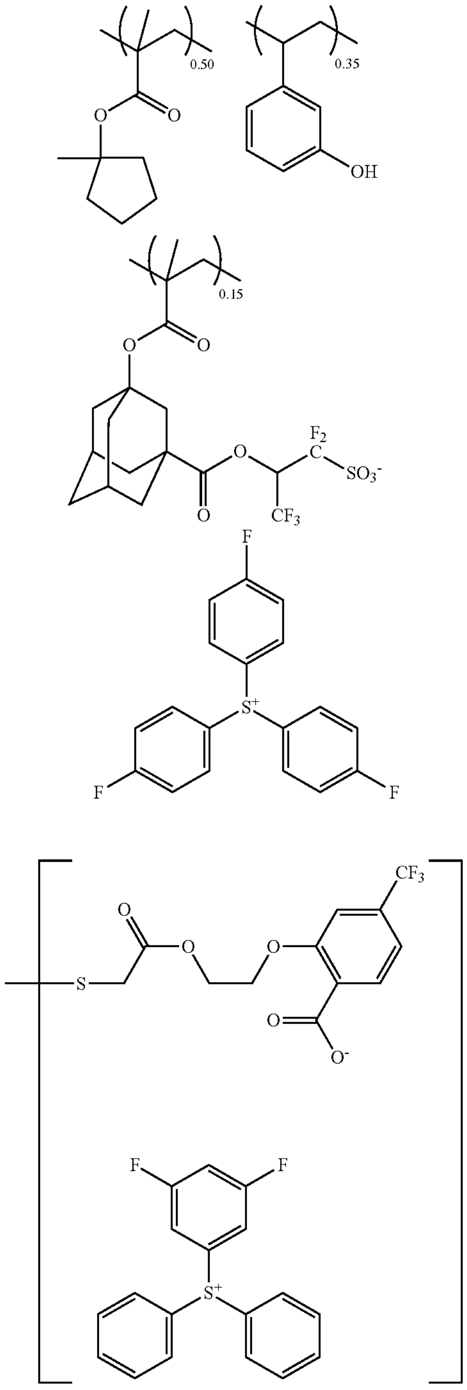

Mw = 8,100
Mw/Mn = 1.75

Synthesis Example 15

Synthesis of Polymer P-15

A 2-L flask was charged with 8.4 g of 1-methyl-1-cyclopentyl methacrylate, 4.2 g of 3-hydroxystyrene, 11.9 g of monomer PM-1, and 40 g of THE solvent. The reactor was cooled at −70'C in nitrogen atmosphere, after which vacuum pumping and nitrogen blow were repeated three times. The reactor was warmed up to room temperature, whereupon 1.2 g of dimethyl 2,2'-azobis(isobutyrate) as polymerization initiator and 1.9 g of CTA-13 were added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer P-15. The polymer was analyzed by NMR spectroscopy and GPC.

P-15

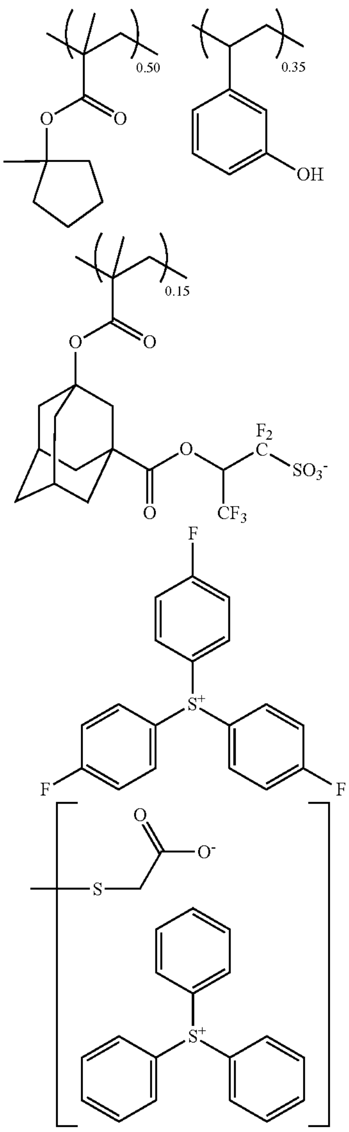

Mw = 7,200
Mw/Mn = 1.64

Synthesis Example 16

Synthesis of Polymer P-16

A 2-L flask was charged with 13.2 g of monomer AM-7, 4.2 g of 3-hydroxystyrene, 11.9 g of monomer PM 1, and 40 g of THE solvent. The reactor was cooled at −70° C. in nitrogen atmosphere, after which vacuum pumping and nitrogen blow were repeated three times. The reactor was warmed up to room temperature, whereupon 1.2 g of dimethyl 2,2'-azobis(isobutyrate) as polymerization initiator and 2.2 g of CTA-14 were added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer P-16. The polymer was analyzed by NMR spectroscopy and GPC.

P-16

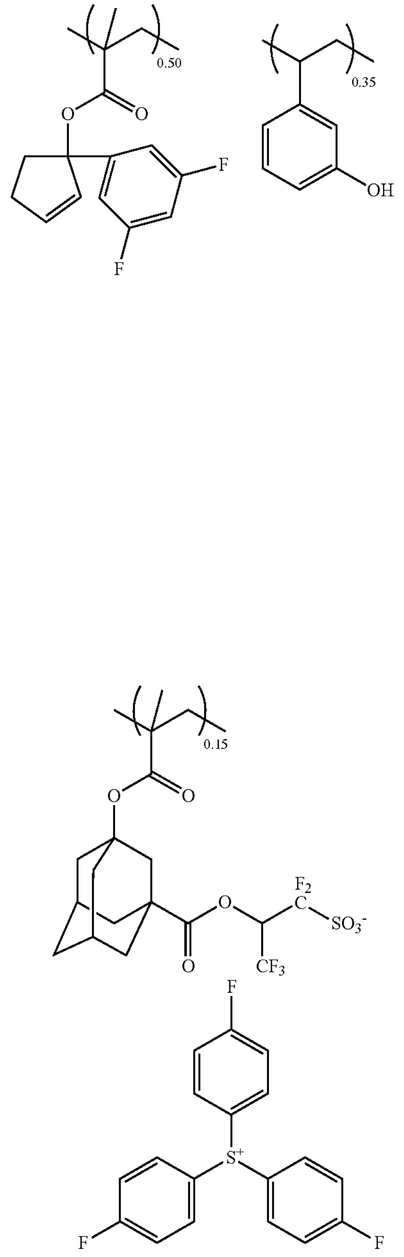

-continued

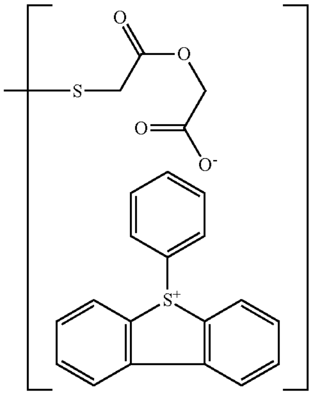

Mw = 7,300
Mw/Mn = 1.65

Synthesis Example 17

Synthesis of Polymer P-17

A 2-L flask was charged with 12.4 g of monomer AM-8, 4.2 g of 3-hydroxystyrene, 11.9 g of monomer PM 1, and 40 g of THE solvent. The reactor was cooled at −70° C. in nitrogen atmosphere, after which vacuum pumping and nitrogen blow were repeated three times. The reactor was warmed up to room temperature, whereupon 1.2 g of dimethyl 2,2'-azobis(isobutyrate) as polymerization initiator and 4.4 g of CTA-15 were added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer P-17. The polymer was analyzed by NMR spectroscopy and GPC.

P-17

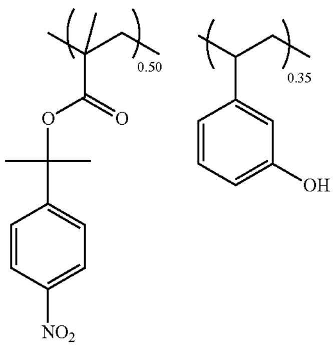

-continued

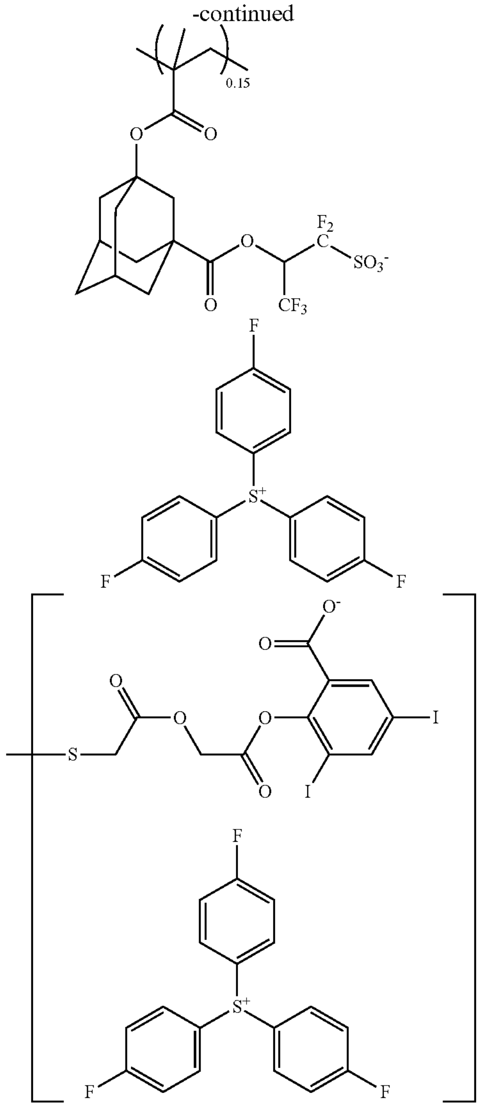

Mw = 8,500
Mw/Mn = 1.72

Synthesis Example 18

Synthesis of Polymer P-18

A 2-L flask was charged with 3.6 g of 1-methyl-1-cyclopentyl methacrylate, 5.8 g of monomer AM-4, 3.6 g of 3-hydroxystyrene, 2.4 g of 2-hydroxystyrene, and 40 g of THE solvent. The reactor was cooled at −70° C. in nitrogen atmosphere, after which vacuum pumping and nitrogen blow were repeated three times. The reactor was warmed up to room temperature, whereupon 1.2 g of dimethyl 2,2'-azobis(isobutyrate) as polymerization initiator and 1.9 g of CTA-14 were added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer P-18. The polymer was analyzed by NMR spectroscopy and GPC.

P-18

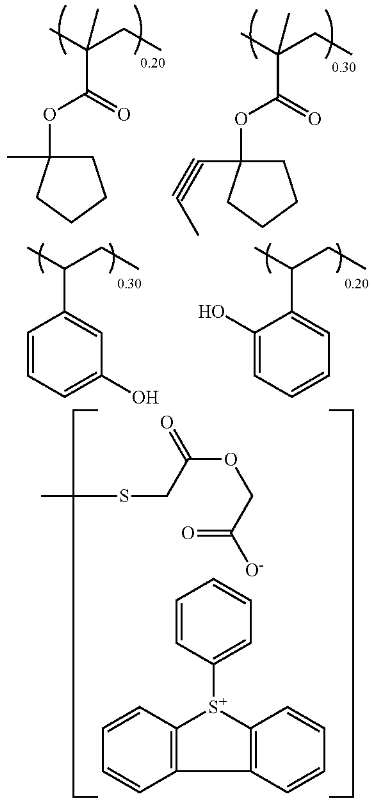

Mw = 5,300
Mw/Mn = 1.41

Synthesis Example 19

Synthesis of Polymer P-19

A 2-L flask was charged with 3.6 g of 1-methyl-1-cyclopentyl methacrylate, 5.3 g of monomer AM-9, 4.8 g of 4-hydroxystyrene, 1.0 g of styrene, and 40 g of THF solvent. The reactor was cooled at −70° C. in nitrogen atmosphere, after which vacuum pumping and nitrogen blow were repeated three times. The reactor was warmed up to room temperature, whereupon 1.2 g of dimethyl 2,2'-azobis(isobutyrate) as polymerization initiator and 1.9 g of CTA-14 were added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer P-19. The polymer was analyzed by HAIR spectroscopy and GPC.

P-19

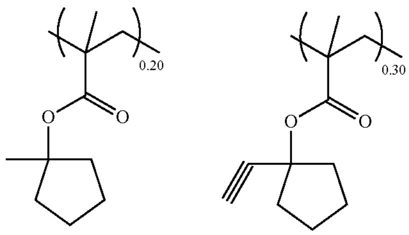

-continued

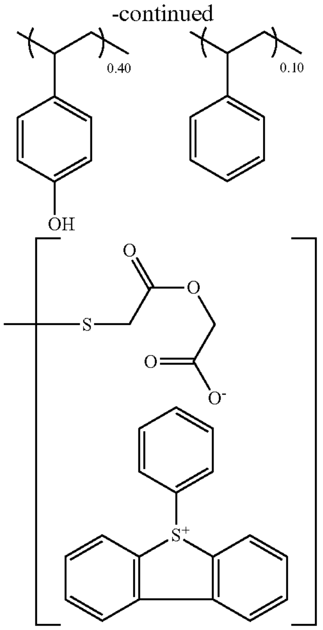

Mw = 5,000
Mw/Mn = 1.40

Synthesis Example 20

Synthesis of Polymer P-20

A 2-L flask was charged with 3.6 g of 1-methyl-1-cyclopentyl methacrylate, 5.4 g of monomer AM-10, 3.0 g of 3-hydroxystyrene, 3.0 g of 2-hydroxystyrene, and 40 g of THE solvent. The reactor was cooled at −70° C. in nitrogen atmosphere, after which vacuum pumping and nitrogen blow were repeated three times. The reactor was warmed up to room temperature, whereupon 1.2 g of dimethyl 2,2'-azobis(isobutyrate) as polymerization initiator and 2.7 g of CTA-16 were added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer P-20. The polymer was analyzed by NMR spectroscopy and GPC.

P-20

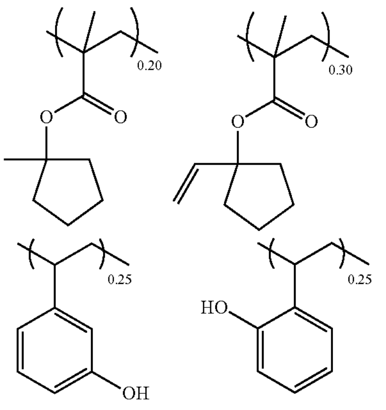

-continued

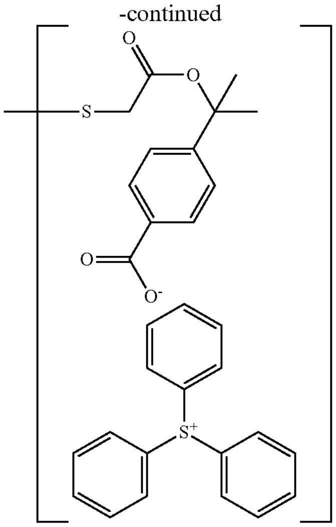

Mw = 5,100
Mw/Mn = 1.42

Comparative Synthesis Example 1

Synthesis of Comparative Polymer cP-1

Comparative Polymer cP-1 was synthesized by the same procedure as in Synthesis Example 1 aside from omitting CFA-1. The polymer was analyzed by NMR spectroscopy and GPC.

cP-1

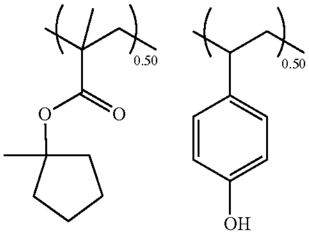

Mw = 8,900
Mw/Mn = 1.79

Comparative Synthesis Example 2

Synthesis of Comparative Polymer cP-2

Comparative Polymer cP-2 was synthesized by the same procedure as in Synthesis Example 1 aside from using 2-mercaptoethanol as chain transfer agent instead of CTA-1. The polymer was analyzed by NMR spectroscopy and GPC.

cP-2

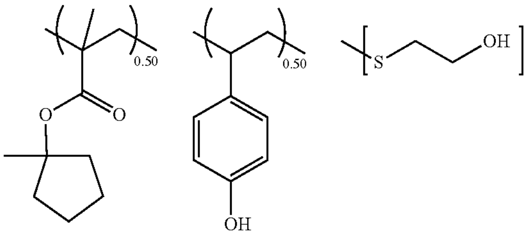

Mw = 6,600
Mw/Mn = 1.62

Comparative Synthesis Example 3

Synthesis of Comparative Polymer cP-3

Comparative Polymer cP-3 was synthesized by the same procedure as in Synthesis Example 2 aside from omitting CTA-2. The polymer was analyzed by NMR spectroscopy and GPC.

cP-3

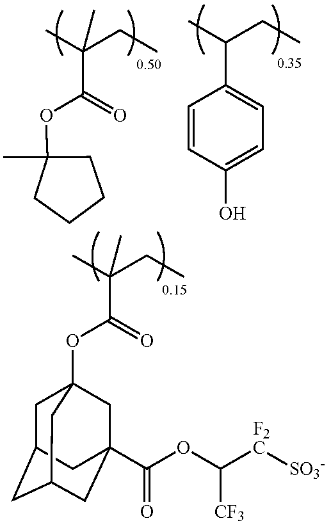

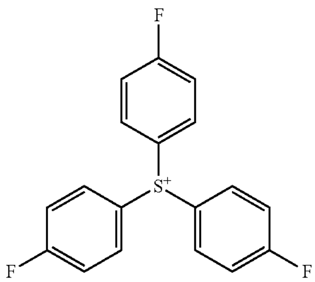

Mw = 10,800
Mw/Mn = 1.93

[2] Preparation and Evaluation of Positive Resist Compositions

Examples 1 to 22 and Comparative Examples 1 to 3

(1) Preparation of Positive Resist Compositions

Positive resist compositions were prepared by dissolving the selected components in a solvent in accordance with the recipe shown in Table 1, and filtering through a high-density polyethylene filter having a pore size of 0.02 μm. The solvent contained 50 ppm of surfactant PolyFox PF-636 (Omnova Solutions Inc.).

The components in Table 1 are as identified below.

Organic Solvents:

PGMEA (propylene glycol monomethyl ether acetate)

DAA (diacetone alcohol)

EL (L-form ethyl lactate)

Acid generators PAG-1, PAG-2

PAG-1

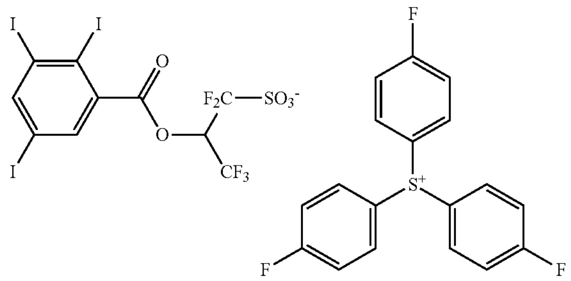

PAG-2

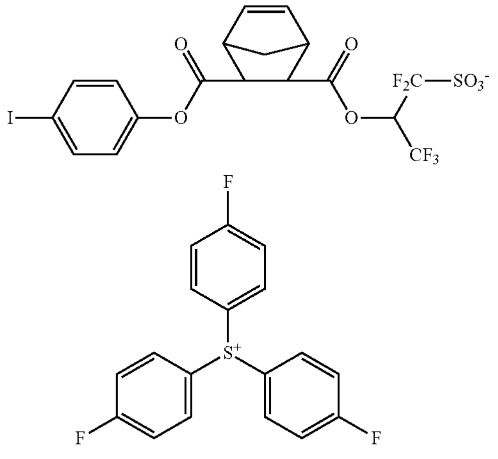

-continued

Quenchers Q-1 to Q-3

Q-1

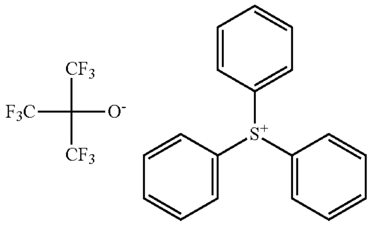

Q-2

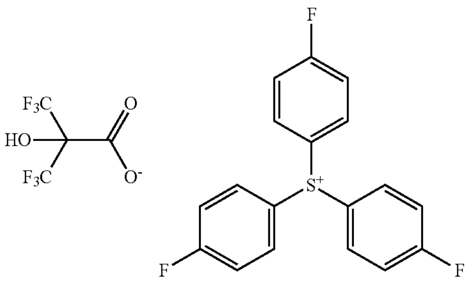

Q-3

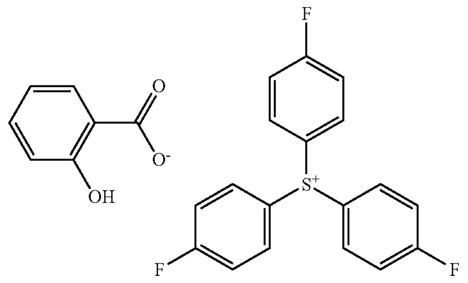

(2) EUV Lithography Test

Each of the positive resist compositions in Table 1 was spin coated on a silicon substrate having a 20 nm coating of silicon-containing spin-on hard mask SHB-A940 (Shin-Etsu Chemical Co., Ltd., silicon content 43 wt %) and prebaked on a hotplate at 105° C. for 60 seconds to form a resist film of 60 nm thick Using an EUV scanner NXE3400 (ASML, NA 0.33, σ0.9/0.6, quadrupole illumination), the resist film was exposed to EUV through a mask bearing a hole pattern having a pitch (on-wafer size) of 46 nm+20% bias. The resist film was baked (PEB) on a hotplate at the temperature shown in Table 1 for 60 seconds and developed in a 2.38 wt % TMAH aqueous solution for 30 seconds to form a hole pattern having a size of 23 nm.

The resist pattern was observed under CD-SEM (CG-6300, Hitachi High-Technologies Corp.). The exposure dose that provides a hole pattern of 23 nm size is reported as sensitivity. The size of 50 holes was measured, from which a 3-fold value (3σ) of standard deviation (σ) was computed and reported as CDU.

The resist composition is shown in Table 1 together with the sensitivity and CDU of EUV lithography.

TABLE 1

| | | Base polymer (pbw) | Acid generator (pbw) | Quencher (pbw) | Organic solvent (pbw) | PEB temp (° C.) | Sensitivity ($mJ/cm^2$) | CDU (nm) |
|---|---|---|---|---|---|---|---|---|
| Example | 1 | P-1 (100) | PAG-1 (25.0) | Q-1 (3.50) | PGMEA (2,000) DAA (500) | 80 | 28 | 2.6 |
| | 2 | P-1 (100) | PAG-2 (25.0) | Q-1 (3.50) | PGMEA (2,000) DAA (500) | 80 | 29 | 2.5 |

TABLE 1-continued

| | | Base polymer (pbw) | Acid generator (pbw) | Quencher (pbw) | Organic solvent (pbw) | PEB temp (° C.) | Sensitivity (mJ/cm$^2$) | CDU (nm) |
|---|---|---|---|---|---|---|---|---|
| | 3 | P-2 (100) | — | Q-1 (3.50) | PGMEA (2,000) DAA (500) | 80 | 26 | 2.4 |
| | 4 | P-3 (100) | — | Q-1 (3.50) | PGMEA (2,000) DAA (500) | 85 | 25 | 2.3 |
| | 5 | P-4 (100) | — | Q-2 (4.00) | PGMEA (2,000) DAA (500) | 85 | 27 | 2.3 |
| | 6 | P-5 (100) | — | Q-2 (4.00) | PGMEA (2,000) DAA (500) | 85 | 25 | 2.2 |
| | 7 | P-6 (100) | — | Q-2 (4.00) | PGMEA (2,000) DAA (500) | 80 | 24 | 2.2 |
| | 8 | P-7 (100) | — | Q-2 (4.00) | PGMEA (2,000) DAA (500) | 80 | 26 | 2.4 |
| | 9 | P-8 (100) | — | Q-2 (4.00) | PGMEA (2,000) DAA (500) | 80 | 25 | 2.5 |
| | 10 | P-9 (100) | — | Q-2 (4.00) | PGMEA (2,000) DAA (500) | 80 | 25 | 2.4 |
| | 11 | P-10 (100) | — | Q-2 (4.00) | PGMEA (1,500) EL (1,000) | 80 | 27 | 2.3 |
| | 12 | P-11 (100) | — | Q-3 (3.18) | PGMEA (1,000) EL (1,000) DAA (500) | 80 | 28 | 2.3 |
| | 13 | P-12 (100) | — | Q-2 (4.00) | PGMEA (2,000) DAA (500) | 80 | 26 | 2.3 |
| | 14 | P-13 (100) | — | Q-2 (4.00) | PGMEA (2,000) DAA (500) | 80 | 25 | 2.5 |
| | 15 | P-14 (100) | — | Q-2 (4.00) | PGMEA (2,000) DAA (500) | 80 | 29 | 2.4 |
| | 16 | P-15 (100) | — | Q-2 (4.00) | PGMEA (1,500) EL (1,000) | 80 | 28 | 2.3 |
| | 17 | P-16 (100) | — | Q-3 (3.18) | PGMEA (1,000) EL (1,000) DAA (500) | 80 | 26 | 2.4 |
| | 18 | P-17 (100) | — | Q-3 (3.18) | PGMEA (1,000) EL (1,000) DAA (500) | 80 | 26 | 2.5 |
| | 19 | P-18 (100) | PAG-1 (25.0) | Q-1 (3.50) | PGMEA (2,000) DAA (500) | 80 | 27 | 2.5 |
| | 20 | P-19 (100) | PAG-1 (25.0) | Q-1 (3.50) | PGMEA (2,000) DAA (500) | 80 | 28 | 2.5 |
| | 21 | P-20 (100) | PAG-1 (25.0) | Q-1 (3.50) | PGMEA (2,000) DAA (500) | 80 | 29 | 2.5 |
| | 22 | P-5 (100) | — | — | PGMEA (2,000) DAA (500) | 80 | 18 | 2.8 |
| Comparative Example | 1 | cP-1 (100) | PAG-1 (25.0) | Q-1 (4.98) | PGMEA (2,000) DAA (500) | 80 | 33 | 4.2 |
| | 2 | cP-2 (100) | PAG-1 (25.0) | Q-1 (4.98) | PGMEA (2,000) DAA (500) | 80 | 30 | 3.9 |
| | 3 | cP-3 (100) | — | Q-1 (4.98) | PGMEA (2,000) DAA (500) | 80 | 28 | 3.0 |

It is demonstrated in Table 1 that positive resist compositions comprising a base polymer which is end-capped with a sulfonium salt containing a carboxylate anion linked to a sulfide group form patterns with improved CDU.

Japanese Patent Application Nos. 2021-187306 and 2022-12.5391 are incorporated herein by reference.

Although some preferred embodiments have been described many modifications and variations may be made thereto in light of the above teachings. It is therefore to be understood that the invention may be practiced otherwise than as specifically described without departing from the scope of the appended claims.

The invention claimed is:

1. A positive resist composition comprising a base polymer end-capped with a suilfonium salt containing a carboxylate anion having a sulfide group linked thereto.

2. The positive resist composition of claim 1 wherein the base polymer has a terminal structure represented by the formula (a):

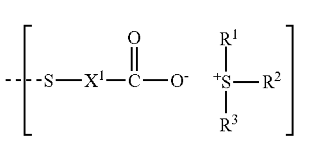

(a)

wherein $X^1$ is a $C_1$-$C_{20}$ hydrocarbylene group which may contain at least one moiety selected from hydroxy, ether bond, sulfide, ester bond, carbonate bond, urethane bond, lactone ring, sultone ring, and halogen, $R^1$ to $R^3$ are each independently a $C_1$-$C_{20}$ hydrocarbyl group which may contain at least one atom selected from oxygen, sulfur, nitrogen and halogen, $R^1$ and $R^2$ may bond together to form a ring with the sulfur atom to which they are attached, the broken line designates a valence bond.

3. The positive resist composition of claim 1 wherein the base polymer comprises repeat units (b1) having a carboxy group whose hydrogen is substituted by an acid labile group or repeat units (b2) having a phenolic hydroxy group whose hydrogen is substituted by an acid labile group.

4. The positive resist composition of claim 3 wherein the repeat units (b1) are represented by the formula (b1) and the repeat units (b2) are represented by the formula (b2):

(b1)

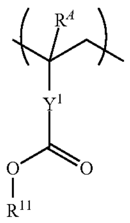

(b2)

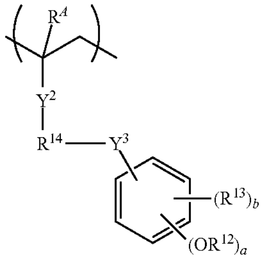

wherein $R^A$ is each independently hydrogen or methyl, $Y^1$ is a single bond, phenylene group, naphthylene group, or a $C_1$-$C_{12}$ linking group containing at least one moiety selected from an ester bond, ether bond and lactone ring, $Y^2$ is a single bond, ester bond or amide bond, $Y^3$ is a single bond, ether bond or ester bond, $R^{11}$ and $R^{12}$ are each independently an acid labile group, $R^{13}$ is fluorine, trifluoromethyl, cyano or a $C_1$-$C_6$ saturated hydrocarbyl group, $R^{14}$ is a single bond or a $C_1$-$C_6$ alkanediyl group which may contain an ether bond or ester bond, a is 1 or 2, b is an integer of 0 to 4, and the stun of a+b is from 1 to 5.

5. The positive resist composition of claim 1 wherein the base polymer further comprises repeat units (c) having an adhesive group which is selected from a hydroxy moiety, carboxy moiety, lactone ring, carbonate bond, thiocarbonate bond, carbonyl moiety, cyclic acetal moiety, ether bond, ester bond, sulfonic ester bond, cyano moiety, amide bond, —O—C(═O)—S—, and —O—C(═O)—NH—.

6. The positive resist composition of claim 1 wherein the base polymer further comprises repeat units having the formula (d1), (d2) or (d3):

(d1)

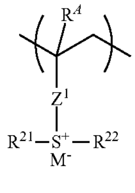

-continued (d2)

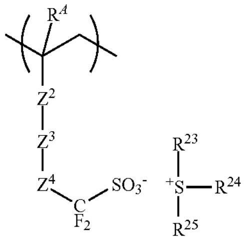

(d3)

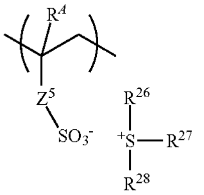

wherein $R^A$ is each independently hydrogen or methyl, $Z^1$ is a single bond, a $C_1$-$C_6$ aliphatic hydrocarbylene group, phenylene group, naphthylene group, or $C_7$-$C_{18}$ is group obtained by combining the foregoing, or —O—$Z^{11}$, —C(═O)—O—$Z^{11}$— or —C(═O)—NH—$Z^{11}$—, $Z^{11}$ is a $C_1$-$C_6$ aliphatic hydrocarbylene group, phenylene group, naphthylene group, or $C_7$-$C_{18}$ group obtained by combining the foregoing, which may contain a carbonyl moiety, ester bond, ether bond or hydroxy moiety, $Z^2$ is a single bond or ester bond, $Z^3$ is a single bond, —$Z^{31}$—C(═O)—O—, —$Z^{31}$—O—, or —$Z^{31}$—O—C(═O)—, $Z^{31}$ is a $C_1$-$C_{12}$ aliphatic hydrocarbylene group, phenylene group, or $C_7$-$C_{18}$ group obtained by combining the foregoing, which may contain a carbonyl moiety, ester bond, ether bond, brome or iodine, $Z^4$ is methylene, 2,2,2-trifluoro-1,1-ethanediyl, or carbonyl, $Z^5$ is a single bond, methylene, ethylene, phenylene, fluorinated phenylene, trifluoromethyl-substituted phenylene group, —O—$Z^{51}$—, —C(═O)—O—$Z^{51}$—, or —C(═O)—NH—$Z^{51}$—, $Z^{51}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond, halogen or hydroxy moiety, $R^{21}$ to $R^{28}$ are each independently halogen or a $C_1$-$C_{20}$ hydrocarbyl group which may contain a heteroatom, a pair of $R^{23}$ and $R^{24}$ or $R^{26}$ and $R^{27}$ may bond together to form a ring with the sulfur atom to which they are attached, and $M^-$ is a non-nucleophilic counter ion.

7. The positive resist composition of claim 1, further comprising an acid generator.

8. The positive resist composition of claim 1, further comprising an organic solvent.

9. The positive resist composition of claim 1, further comprising a quencher.

10. The positive resist composition of claim 1, further comprising a surfactant.

11. A pattern forming process comprising the steps of applying the positive resist composition of claim 1 onto a substrate to form a resist film thereon, exposing the resist film to high-energy radiation, and developing the exposed resist film in a developer.

12. The process of claim 11 wherein the high-energy radiation is i-line, KrF excimer laser, ArF excimer laser, EB, or ET of wavelength 3 to 15 nm.

* * * * *